US009988455B2

(12) United States Patent
Heldwein et al.

(10) Patent No.: US 9,988,455 B2
(45) Date of Patent: Jun. 5, 2018

(54) METHODS OF TREATING CARDIOVASCULAR DISORDERS WITH LECTIN-LIKE OXIDIZED LDL RECEPTOR 1 ANTIBODIES

(71) Applicant: NOVARTIS AG, Basel (CH)

(72) Inventors: Kurt Alex Heldwein, Belmont, MA (US); Jennifer Brogdon, Sudbury, MA (US); William Dole, Ipswich, MA (US); John Trauger, Cambridge, MA (US); Yuting Tang, Lexington, MA (US); Julia Neugebauer, Munich (DE); Annika Schmid, Neuried (DE)

(73) Assignee: NOVARTIS AG, Basel (CH)

(*) Notice: Subject to any disclaimer, the term of this patent is extended or adjusted under 35 U.S.C. 154(b) by 0 days. days.

(21) Appl. No.: 15/390,067

(22) Filed: Dec. 23, 2016

(65) Prior Publication Data
US 2017/0260272 A1   Sep. 14, 2017

Related U.S. Application Data

(62) Division of application No. 14/307,519, filed on Jun. 18, 2014, now Pat. No. 9,562,101.

(60) Provisional application No. 61/837,765, filed on Jun. 21, 2013.

(51) Int. Cl.
| A61P 9/08 | (2006.01) |
| A61P 9/04 | (2006.01) |
| A61P 9/10 | (2006.01) |
| A61P 9/12 | (2006.01) |
| A61K 39/395 | (2006.01) |
| C07K 16/28 | (2006.01) |
| C07K 14/47 | (2006.01) |

(52) U.S. Cl.
CPC ...... *C07K 16/2851* (2013.01); *C07K 2317/21* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,197,937 | B1 | 3/2001 | Sawamura et al. |
| 7,993,643 | B2 | 8/2011 | Kobayashi et al. |
| 8,481,314 | B2 | 7/2013 | Banchereau et al. |
| 9,339,556 | B2 | 5/2016 | Banchereau et al. |
| 9,512,222 | B2 | 12/2016 | Heldwein et al. |
| 9,562,101 | B2 | 2/2017 | Heldwein et al. |
| 2003/0143226 | A1 | 7/2003 | Kobayashi et al. |
| 2008/0152657 | A1 | 6/2008 | Horowitz et al. |
| 2008/0267984 | A1 | 10/2008 | Banchereau et al. |
| 2009/0311270 | A1 | 12/2009 | Allen et al. |
| 2012/0087926 | A1 | 4/2012 | Matsuda et al. |
| 2014/0120617 | A1 | 5/2014 | Banchereau et al. |
| 2014/0377281 | A1 | 12/2014 | Heldwein et al. |
| 2015/0004168 | A1 | 1/2015 | Heldwein et al. |
| 2015/0150945 | A1 | 6/2015 | Francois et al. |
| 2016/0024593 | A1 | 1/2016 | Zheng et al. |
| 2017/0015744 | A1 | 1/2017 | Sawamura et al. |
| 2017/0152313 | A1 | 6/2017 | Heldwein et al. |

FOREIGN PATENT DOCUMENTS

| EP | 1 418 234 A1 | 5/2004 |
| EP | 2 048 161 A1 | 4/2009 |
| EP | 2 444 492 A1 | 4/2012 |
| EP | 2444492 A9 | 7/2012 |
| JP | 2000109435 A | 4/2000 |
| JP | 4497586 B2 | 7/2010 |
| JP | 2010180212 A | 8/2010 |
| JP | 2012100585 A | 5/2012 |
| JP | 5232818 B2 | 7/2013 |
| JP | 5706669 B2 | 4/2015 |
| JP | 2015127309 | 7/2015 |
| WO | 2008103953 A2 | 8/2008 |
| WO | 2010147171 A1 | 12/2010 |
| WO | 2012009709 A1 | 1/2012 |
| WO | 2013063095 A1 | 5/2013 |
| WO | 2014039840 A1 | 3/2014 |
| WO | 2014144666 A2 | 9/2014 |
| WO | 2014205300 A2 | 12/2014 |
| WO | 2014205302 A2 | 12/2014 |
| WO | 2015098901 A1 | 7/2015 |
| WO | 2016050889 A1 | 4/2016 |

OTHER PUBLICATIONS

Mehta et al, 2011. Cardiovasc Drugs Ther. 25:495-500.*
Sakamoto et al., "Role of LOX-1 in monocyte adhesion-triggered redox, AKT/eNOS and Ca2+ signaling pathways in endothelial cells," J Cell Physiol. Sep. 2009;220(3):706-15.
Tickle et al., "High-Throughput Screening for High Affinity Antibodies," JALA Oct. 2009; 14:303-7.
Rudikoff et al., "Single amino acid substitution altering antigen-binding specificity," Proc Natl Acad Sci U S A. Mar. 1982;79(6):1979-83.
MacCallum et al., "Antibody-antigen interactions: contact analysis and binding site topography," J Mol Biol. Oct. 11, 1996;262(5):732-45.
De Pascalis et al., "Grafting of "abbreviated" complementarity-determining regions containing specificity-determining residues essential for ligand contact to engineer a less immunogenic humanized monoclonal antibody," J Immunol. Sep. 15, 2002;169(6):3076-84.
Casset et al., "A peptide mimetic of an anti-CD4 monoclonal antibody by rational design," Biochem Biophys Res Commun. Jul. 18, 2003;307(1):198-205.

(Continued)

*Primary Examiner* — Zachary Howard
(74) *Attorney, Agent, or Firm* — Sherwin Y. Chan

(57) ABSTRACT

The present invention relates to monoclonal antibodies binding to human lectin-like oxidized LDL (low density lipoprotein) receptor 1 (hereinafter, sometimes referred to as "LOX-1"), and pharmaceutical compositions and methods of treatment comprising the same.

28 Claims, 7 Drawing Sheets

(56) References Cited

OTHER PUBLICATIONS

Vajdos et al., "Comprehensive functional maps of the antigen-binding site of an anti-ErbB2 antibody obtained with shotgun scanning mutagenesis," J Mol Biol. Jul. 5, 2002;320(2):415-28.

Holm et al., "Functional mapping and single chain construction of the anti-cytokeratin 8 monoclonal antibody TS1," Mol Immunol. Feb. 2007;44(6):1075-84.

Chen et al., "Selection and analysis of an optimized anti-VEGF antibody: crystal structure of an affinity-matured Fab in complex with antigen," J Mol Biol. Nov. 5, 1999;293(4):865-81.

Wu et al., "Humanization of a murine monoclonal antibody by simultaneous optimization of framework and CDR residues," J Mol Biol. Nov. 19, 1999;294(1)151-62.

Brown et al., "Tolerance of single, but not multiple, amino acid replacements in antibody VH CDR 2: a means of minimizing B cell wastage from somatic hypermutation?" J Immunol. May 1, 1996;156(9):3285-91.

Ohki et al., "Crystal structure of human lectin-like, oxidized low-density lipoprotein receptor 1 ligand binding domain and its ligand recognition mode to OxLDL," Structure. Jun. 2005;13(6):905-17.

Wark et al., "Latest technologies for the enhancement of antibody affinity," Adv Drug Deliv Rev. Aug. 7, 2006;58(5-6):657-70.

Xu et al., "Anti-LOX-1 rescues endothelial function in coronary arterioles in atherosclerotic ApoE knockout mice," Arterioscler Thromb Vasc Biol. Apr. 2007;27(4):871-7.

"Francone, et al., ""The hydrophobic tunnel present in LOX-1 is essential for oxidized LDL recognition and binding"", Journal of Lipid Research 50(3):546-555 (2009)."

* cited by examiner

SEQUENCE LISTING

<160> NUMBER OF SEQ ID NOS: 422

<210> SEQ ID NO 1
<211> LENGTH: 273
<212> TYPE: PRT
<213> ORGANISM: Homo sapiens

<400> SEQUENCE: 1

Met Thr Phe Asp Asp Leu Lys Ile Gln Thr Val Lys Asp Gln Pro Asp
1               5                   10                  15

Glu Lys Ser Asn Gly Lys Lys Ala Lys Gly Leu Gln Phe Leu Tyr Ser
            20                  25                  30

Pro Trp Trp Cys Leu Ala Ala Ala Thr Leu Gly Val Leu Cys Leu Gly
        35                  40                  45

Leu Val Val Thr Ile Met Val Leu Gly Met Gln Leu Ser Gln Val Ser
    50                  55                  60

Asp Leu Leu Thr Gln Glu Gln Ala Asn Leu Thr His Gln Lys Lys Lys
65                  70                  75                  80

Leu Glu Gly Gln Ile Ser Ala Arg Gln Gln Ala Glu Glu Ala Ser Gln
                85                  90                  95

Glu Ser Glu Asn Glu Leu Lys Glu Met Ile Glu Thr Leu Ala Arg Lys
            100                 105                 110

Leu Asn Glu Lys Ser Lys Glu Gln Met Glu Leu His His Gln Asn Leu
        115                 120                 125

Asn Leu Gln Glu Thr Leu Lys Arg Val Ala Asn Cys Ser Ala Pro Cys
    130                 135                 140

Pro Gln Asp Trp Ile Trp His Gly Glu Asn Cys Tyr Leu Phe Ser Ser
145                 150                 155                 160

Gly Ser Phe Asn Trp Glu Lys Ser Gln Glu Lys Cys Leu Ser Leu Asp
                165                 170                 175

Ala Lys Leu Leu Lys Ile Asn Ser Thr Ala Asp Leu Asp Phe Ile Gln
            180                 185                 190

Gln Ala Ile Ser Tyr Ser Ser Phe Pro Phe Trp Met Gly Leu Ser Arg
        195                 200                 205

Arg Asn Pro Ser Tyr Pro Trp Leu Trp Glu Asp Gly Ser Pro Leu Met
    210                 215                 220

Pro His Leu Phe Arg Val Arg Gly Ala Val Ser Gln Thr Tyr Pro Ser
225                 230                 235                 240

Gly Thr Cys Ala Tyr Ile Gln Arg Gly Ala Val Tyr Ala Glu Asn Cys
                245                 250                 255

Ile Leu Ala Ala Phe Ser Ile Cys Gln Lys Lys Ala Asn Leu Arg Ala
            260                 265                 270

Gln

<210> SEQ ID NO 2
<211> LENGTH: 819
<212> TYPE: DNA
<213> ORGANISM: Homo sapiens

<400> SEQUENCE: 2 atgactttg atgacctaaa gatccagact gtgaaggacc agcctgatga gaagtcaaat      60
ggaaaaaaag ctaaaggtct tcagtttctt tactctccat ggtggtgcct ggctgctgcg    120
actctagggg tcctttgcct gggattagta gtgaccatta tggtgctggg catgcaatta    180
tcccaggtgt ctgacctcct aacacaagag caagcaaacc taactcacca gaaaaagaaa    240

```
ctggagggac agatctcagc ccggcaacaa gcagaagaag cttcacagga gtcagaaaac    300
gaactcaagg aaatgataga aacccttgct cggaagctga atgagaaatc caaagagcaa    360
atggaacttc accaccagaa tctgaatctc caagaaacac tgaagagagt agcaaattgt    420
tcagctcctt gtccgcaaga ctggatctgg catggagaaa actgttacct attttcctcg    480
ggctcattta actgggaaaa gagccaagag aagtgcttgt ctttggatgc caagttgctg    540
aaaattaata gcacagctga tctggacttc atccagcaag caatttccta ttccagtttt    600
ccattctgga tggggctgtc tcggaggaac cccagctacc catggctctg ggaggacggt    660
tctcctttga tgccccactt atttagagtc cgaggcgctg tctcccagac atacccttca    720
ggtacctgtg catatataca acgaggagct gtttatgcgg aaaactgcat tttagctgcc    780
ttcagtatat gtcagaagaa ggcaaaccta agagcacag                            819
```

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Asp Tyr Ala Ile Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Gly Ile Val Pro Ile Val Gly Thr Ala Asn Tyr Ala Gln Lys Phe Gln
1               5                   10                  15

Gly

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Asp Ser Ser Thr Ser Tyr Tyr Tyr Tyr Phe Asp Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Gly Gly Thr Phe Ser Asp Tyr
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Pro Ile Val Gly Thr
1               5

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Ser Ser Thr Ser Tyr Tyr Tyr Tyr Phe Asp Tyr
1               5                   10

<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Val Pro Ile Val Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Thr Ser Tyr Tyr Tyr Tyr Phe Asp Tyr Trp Gly
            100                 105                 110

Gln Gly Thr Leu Val Thr Val Ser Ser
        115                 120

<210> SEQ ID NO 10
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
caggtgcaat tggtgcagag cggtgccgaa gtgaaaaaac cgggcagcag cgtgaaagtt      60
agctgcaaag catccggagg gacgtttttct gactacgcta tctcttgggt gcgccaggcc    120
ccgggccagg gcctcgagtg gatgggcggt atcgttccga tcgttggcac tgcgaactac    180

```
gcccagaaat tcagggccg ggtgaccatt accgccgatg aaagcaccag caccgcctat      240
atggaactga gcagcctgcg cagcgaagat acggccgtgt attattgcgc gcgtgactct      300
tctacttctt actactacta cttcgattac tggggccaag gcaccctggt gactgttagc      360
tca                                                                   363
```

<210> SEQ ID NO 11
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Val Pro Ile Val Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Thr Ser Tyr Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
            325                 330                 335
Glu Lys Thr Ile Ser Lys Ala Lys Gly Gln Pro Arg Glu Pro Gln Val
        340                 345                 350
Tyr Thr Leu Pro Pro Ser Arg Glu Glu Met Thr Lys Asn Gln Val Ser
    355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 12
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
caggtgcaat tggtgcagag cggtgccgaa gtgaaaaaac cgggcagcag cgtgaaagtt     60
agctgcaaag catccggagg gacgttttct gactacgcta tctcttgggt gcgccaggcc    120
ccgggccagg gcctcgagtg gatgggcggt atcgttccga tcgttggcac tgcgaactac    180
gcccagaaat tcagggccg gtgaccatt accgccgatg aaagcaccag caccgcctat     240
atggaactga gcagcctgcg cagcgaagat acggcgtgt attattgcgc gcgtgactct    300
tctacttctt actactacta cttcgattac tggggccaag gcaccctggt gactgttagc    360
tcagcctcca ccaagggtcc atcggtcttc cccctggcac cctcctccaa gagcacctct    420
gggggcacag cggccctggg ctgcctggtc aaggactact ccccgaacc ggtgacggtg     480 tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga gcagcgggg    720 ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgggtggt cagcgtcctc accgtcctgc accaggactg gctgaatggc    960
aaggagtaca agtgcaaggt ctccaacaaa gccctcccag cccccatcga gaaaccatc    1020 tccaaagcca agggcagcc cgagaaccca ggtgtaca cctgcccc atccgggag        1080 gagatgacca gaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
```

```
tggcagcagg ggaacgtctt ctcatgctcc gtgatgcatg aggctctgca caaccactac   1320
acgcagaaga gcctctccct gtctccgggt aaa                                1353
```

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Ser Gln Asp Ile Asn Ser Trp Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ala Ser Asn Leu Gln Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Met Trp Gln Phe Pro Ile Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gln Asp Ile Asn Ser Trp
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ala Ser
1

<210> SEQ ID NO 18
<211> LENGTH: 6
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 18

Met Trp Gln Phe Pro Ile
1               5

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Trp
            20                  25                  30

Leu Ala Trp Tyr Gln Gln Lys Pro Gly Lys Ala Pro Lys Leu Leu Ile
        35                  40                  45

Tyr Gln Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met Trp Gln Phe Pro Ile
                85                  90                  95

Thr Phe Gly Gln Gly Thr Lys Val Glu Ile Lys
            100                 105

<210> SEQ ID NO 20
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gatatccaga tgacccagag cccgagcagc ctgagcgcca gcgtgggcga tcgcgtgacc      60
attacctgca gagccagcca ggacattaac tcttggctgg cttggtacca gcagaaaccg    120
ggcaaagcgc cgaaactatt aatctaccag gcttctaacc tgcaaagcgg cgtgccgagc    180
cgctttagcg gcagcggatc cggcaccgat ttcaccctga ccattagctc tctgcaaccg    240
gaagactttg cgacctatta ttgccagcag atgtggcagt tcccgatcac ctttggccag    300
ggcacgaaag ttgaaattaa a                                              321

<210> SEQ ID NO 21
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Ile Asn Ser Trp
         20                  25                  30

Leu Ala Trp Tyr Gln Gln Lys Pro Gly Lys Ala Pro Lys Leu Leu Ile
         35                  40                  45

Tyr Gln Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met Trp Gln Phe Pro Ile
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gatatccaga tgacccagag cccgagcagc ctgagcgcca gcgtgggcga tcgcgtgacc      60
attacctgca gagccagcca ggacattaac tcttggctgg cttggtacca gcagaaaccg     120
ggcaaagcgc cgaaactatt aatctaccag gcttctaacc tgcaaagcgg cgtgccgagc     180
cgctttagcg gcagcggatc cggcaccgat ttcaccctga ccattagctc tctgcaaccg     240
gaagactttg cgacctatta ttgccagcag atgtggcagt tcccgatcac ctttggccag     300
ggcacgaaag ttgaaattaa acgtacggtg gccgctccca gcgtgttcat cttcccccca     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag caccctgacc     540
ctgagcaagg ccgactacga gaagcacaag gtgtacgcct gcgaggtgac ccaccagggc     600
ctgtccagcc ccgtgaccaa gagcttcaac cggggcgagt gt                       642

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 23

Asp Tyr Ala Ile Ser
1               5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ile Val Pro Ile Val Gly Thr Ala Asn Tyr Ala Gln Lys Phe Gln
1               5                   10                  15

Gly

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Ser Ser Thr Ser Tyr Tyr Tyr Tyr Phe Asp Tyr
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Thr Phe Ser Asp Tyr
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Pro Ile Val Gly Thr
1               5

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Ser Ser Thr Ser Tyr Tyr Tyr Tyr Phe Asp Tyr
1               5                   10

<210> SEQ ID NO 29
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Val Pro Ile Val Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Thr Ser Tyr Tyr Tyr Phe Asp Tyr Trp Gly
            100                 105                 110

Gln Gly Thr Leu Val Thr Val Ser Ser
        115                 120

<210> SEQ ID NO 30
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
caggtgcaat tggtgcagag cggtgccgaa gtgaaaaaac cgggcagcag cgtgaaagtt     60
agctgcaaag catccggagg gacgtttttct gactacgcta tctcttgggt gcgccaggcc   120
ccgggccagg gcctcgagtg gatgggcggt atcgttccga tcgttggcac tgcgaactac   180
gcccagaaat ttcagggccg ggtgaccatt accgccgatg aaagcaccag caccgcctat   240
atggaactga gcagcctgcg cagcgaagat acggccgtgt attattgcgc gcgtgactct   300
tctacttctt actactacta cttcgattac tggggccaag gcaccctggt gactgttagc   360
tca                                                                  363

<210> SEQ ID NO 31
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

-continued

```
Gly Gly Ile Val Pro Ile Val Gly Thr Ala Asn Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Ser Ser Thr Ser Tyr Tyr Tyr Phe Asp Tyr Trp Gly
                100                 105                 110
Gln Gly Thr Leu Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Arg Val Glu Pro Lys Ser Cys
210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys
        450
```

<210> SEQ ID NO 32
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
caggtgcaat tggtgcagag cggtgccgaa gtgaaaaaac cgggcagcag cgtgaaagtt      60
agctgcaaag catccggagg gacgttttct gactacgcta tctcttgggt gcgccaggcc     120
ccgggccagg gcctcgagtg gatgggcggt atcgttccga tcgttggcac tgcgaactac     180
gcccagaaat tcagggccg gtgaccatt accgccgatg aaagcaccag caccgcctat      240
atggaactga gcagcctgcg cagcgaagat acggccgtgt attattgcgc gcgtgactct     300
tctacttctt actactacta cttcgattac tggggccaag caccctggt gactgttagc      360 tcagcctcca ccaagggtcc atcggtcttc cccctggcac cctcctccaa gagcacctct     420
gggggcacag cggccctggg ctgcctggtc aaggactact ccccgaacc ggtgacggtg      480 tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga gcagcgggg      720 ggaccgtcag tcttcctctt cccccccaaaa cccaaggaca ccctcatgat ctcccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgggtggt cagcgtcctc accgtcctgc accaggactg gctgaatggc     960
aaggagtaca agtgcaaggt ctccaacaaa gccctcccag cccccatcga gaaaaccatc    1020
tccaaagcca agggcagcc ccgagaacca caggtgtaca ccctgccccc atcccgggag    1080
gagatgacca gaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                  1353
```

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ser Gln Asp Ile Asn Ser Trp Leu Ala
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ala Ser Asn Leu Gln Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gln Ile Asp His Thr Pro Phe Thr
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Gln Asp Ile Asn Ser Trp
1               5

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ala Ser
1

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Asp His Thr Pro Phe
1               5

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Trp
            20                  25                  30

Leu Ala Trp Tyr Gln Gln Lys Pro Gly Lys Ala Pro Lys Leu Leu Ile
            35                  40                  45

Tyr Gln Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Asp His Thr Pro Phe
                 85                  90                  95

Thr Phe Gly Gln Gly Thr Lys Val Glu Ile Lys
            100                 105

<210> SEQ ID NO 40
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gatatccaga tgacccagag cccgagcagc ctgagcgcca gcgtgggcga tcgcgtgacc      60
attacctgca gagccagcca ggacattaac tcttggctgg cttggtacca gcagaaaccg     120
ggcaaagcgc cgaaactatt aatctaccag gcttctaacc tgcaaagcgg cgtgccgagc     180
cgctttagcg gcagcggatc cggcaccgat ttcaccctga ccattagctc tctgcaaccg     240
gaagactttg cgacctatta ttgccagcag atcgaccata ctccgttcac ctttggccag     300
ggcacgaaag ttgaaattaa a                                               321

<210> SEQ ID NO 41
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Asn Ser Trp
             20                  25                  30

Leu Ala Trp Tyr Gln Gln Lys Pro Gly Lys Ala Pro Lys Leu Leu Ile
         35                  40                  45

Tyr Gln Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Asp His Thr Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

-continued

```
Glu Ser Val Thr Glu Gln Asp Ser Lys Asp Ser Thr Tyr Ser Leu Ser
            165                 170                 175
Ser Thr Leu Thr Leu Ser Lys Ala Asp Tyr Glu Lys His Lys Val Tyr
        180                 185                 190
Ala Cys Glu Val Thr His Gln Gly Leu Ser Ser Pro Val Thr Lys Ser
    195                 200                 205
Phe Asn Arg Gly Glu Cys
    210
```

<210> SEQ ID NO 42
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
gatatccaga tgacccagag cccgagcagc ctgagcgcca gcgtgggcga tcgcgtgacc     60
attacctgca gagccagcca ggacattaac tcttggctgg cttggtacca gcagaaaccg    120
ggcaaagcgc cgaaactatt aatctaccag gcttctaacc tgcaaagcgg cgtgccgagc    180
cgctttagcg gcagcggatc cggcaccgat ttcaccctga ccattagctc tctgcaaccg    240
gaagactttg cgacctatta ttgccagcag atcgaccata ctccgttcac ctttggccag    300
ggcacgaaag ttgaaattaa acgtacggtg gccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gaaagcgtca ccgagcagga cagcaaggac tccacctaca gcctgagcag caccctgacc    540
ctgagcaagg ccgactacga aagcacaag gtgtacgcct gcgaggtgac ccaccagggc    600
ctgtccagcc ccgtgaccaa gagcttcaac cggggcgagt gt                      642
```

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

```
Asp Tyr Ala Ile Ser
1               5
```

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

```
Gly Ile Met Pro Ile Ser Gly Ala Pro Tyr Tyr Ala Gln Lys Phe Gln
1               5                   10                  15
Gly
```

<210> SEQ ID NO 45
<211> LENGTH: 12
<212> TYPE: PRT

<213> ORGANISM: Artificial Sequence
<220> FEATURE:
<223> OTHER INFORMATION: Description of Artificial Sequence: Synthetic peptide

<400> SEQUENCE: 45

Asp Ser Ser Thr Ser Tyr Tyr Tyr Tyr Phe Asp Tyr
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Gly Gly Thr Phe Ser Asp Tyr
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Met Pro Ile Ser Gly Ala
1               5

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Asp Ser Ser Thr Ser Tyr Tyr Tyr Tyr Phe Asp Tyr
1               5                   10

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Met Pro Ile Ser Gly Ala Pro Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys

```
                    85                  90                  95
Ala Arg Asp Ser Ser Thr Ser Tyr Tyr Tyr Tyr Phe Asp Tyr Trp Gly
                100                 105                 110

Gln Gly Thr Leu Val Thr Val Ser Ser
            115                 120

<210> SEQ ID NO 50
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
caggtgcaat tggtgcagag cggtgccgaa gtgaaaaaac cgggcagcag cgtgaaagtt        60
agctgcaaag catccggagg gacgttttct gactacgcta tctcttgggt gcgccaggcc       120
ccgggccagg gcctcgagtg gatgggcggt atcatgccga tctctggcgc tccgtactac       180
gcccagaaat tcagggccgg ggtgaccatt accgccgatg aaagcaccag caccgcctat       240
atggaactga gcagcctgcg cagcgaagat acggccgtgt attattgcgc gcgtgactct       300
tctacttctt actactacta cttcgattac tggggccaag caccctggt gactgttagc       360 tca                                                                     363

<210> SEQ ID NO 51
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Ala Ile Ser Trp Val Arg Gln Ala Pro Gly Gln Gly Leu Glu Trp Met
            35                  40                  45

Gly Gly Ile Met Pro Ile Ser Gly Ala Pro Tyr Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Thr Ser Tyr Tyr Tyr Tyr Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 52
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
caggtgcaat tggtgcagag cggtgccgaa gtgaaaaaac cgggcagcag cgtgaaagtt      60
agctgcaaag catccggagg gacgttttct gactacgcta tctcttgggt gcgccaggcc     120
ccgggccagg gcctcgagtg gatgggcggt atcatgccga tctctggcgc tccgtactac     180
gcccagaaat ttcagggccg ggtgaccatt accgccgatg aaagcaccag caccgcctat     240
atggaactga gcagcctgcg cagcgaagat acggccgtgt attattgcgc gcgtgactct     300
tctacttctt actactacta cttcgattac tggggccaag caccctggt  gactgttagc     360 tcagcctcca ccaagggtcc atcggtcttc cccctggcac cctcctccaa gagcacctct     420
gggggcacag cggccctggg ctgcctggtc aaggactact ccccgaacc  ggtgacggtg     480
```

```
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga agcagcgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgggtggt cagcgtcctc accgtcctgc accaggactg gctgaatggc    960
aaggagtaca agtgcaaggt ctccaacaaa gccctcccag cccccatcga gaaaaccatc   1020
tccaaagcca agggcagccc cgagaaccac aggtgtaca ccctgccccc atcccgggag   1080
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Ala Ser Gln Asp Ile Ser Ser Trp Leu Ala
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Ala Ser Asn Leu Gln Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Gln Ile Asp His Thr Pro Phe Thr
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Ser Gln Asp Ile Ser Ser Trp
1               5

<210> SEQ ID NO 57
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ala Ser
1

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Asp His Thr Pro Phe
1               5

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Gln Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Asp His Thr Pro Phe
                85                  90                  95

Thr Phe Gly Gln Gly Thr Lys Val Glu Ile Lys
            100                 105

<210> SEQ ID NO 60
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gatatccaga tgacccagag cccgagcagc ctgagcgcca gcgtgggcga tcgcgtgacc      60

```
attacctgca gagccagcca ggacattagc tcttggctgg cttggtacca gcagaaaccg    120
ggcaaagcgc cgaaactatt aatctaccag gcttctaacc tgcaaagcgg cgtgccgagc    180
cgctttagcg gcagcggatc cggcaccgat tcaccctga ccattagctc tctgcaaccg     240
gaagactttg cgacctatta ttgccagcag atcgaccata ctccgttcac ctttggccag    300
ggcacgaaag ttgaaattaa a                                              321
```

<210> SEQ ID NO 61
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Gln Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Asp His Thr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 62
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

```
gatatccaga tgacccagag cccgagcagc ctgagcgcca gcgtgggcga tcgcgtgacc    60
attacctgca gagccagcca ggacattagc tcttggctgg cttggtacca gcagaaaccg    120
```

```
ggcaaagcgc cgaaactatt aatctaccag gcttctaacc tgcaaagcgg cgtgccgagc    180
cgctttagcg gcagcggatc cggcaccgat tcaccctga ccattagctc tctgcaaccg     240
gaagactttg cgacctatta ttgccagcag atcgaccata ctccgttcac ctttggccag    300
ggcacgaaag ttgaaattaa acgtacggtg gccgctccca gcgtgttcat cttcccccc     360 agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gaaagcgtca ccgagcagga cagcaaggac tccacctaca gcctgagcag caccctgacc    540
ctgagcaagg ccgactacga aagcacaag gtgtacgcct gcgaggtgac ccaccagggc     600
ctgtccagcc ccgtgaccaa gagcttcaac cggggcgagt gt                       642
```

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Tyr Ala Ile Ser
1               5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Ile Val Pro Ile Val Gly Thr Ala Asn Tyr Ala Gln Lys Phe Gln
1               5                   10                  15

Gly

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Ser Ser Thr Ser Tyr Tyr Tyr Tyr Phe Asp Tyr
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Thr Phe Ser Asp Tyr
1               5

<210> SEQ ID NO 67
<211> LENGTH: 6

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Pro Ile Val Gly Thr
1               5

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ser Ser Thr Ser Tyr Tyr Tyr Tyr Phe Asp Tyr
1               5                   10

<210> SEQ ID NO 69
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Val Pro Ile Val Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Thr Ser Tyr Tyr Tyr Tyr Phe Asp Tyr Trp Gly
            100                 105                 110

Gln Gly Thr Leu Val Thr Val Ser Ser
        115                 120

<210> SEQ ID NO 70
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
caggtgcaat tggtgcagag cggtgccgaa gtgaaaaaac cgggcagcag cgtgaaagtt      60
agctgcaaag catccggagg acgttttctg actacgctat ctcttgggt gcgccaggcc     120 ccgggccagg gcctcgagtg gatgggcggt atcgttccga tcgttggcac tgcgaactac     180
gcccagaaat tcagggccgg ggtgaccatt accgccgatg aaagcaccag caccgcctat     240

-continued

```
atggaactga gcagcctgcg cagcgaagat acggccgtgt attattgcgc gcgtgactct    300
tctacttctt actactacta cttcgattac tggggccaag gcaccctggt gactgttagc    360
tca                                                                  363
```

<210> SEQ ID NO 71
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Val Pro Ile Val Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Thr Ser Tyr Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 72
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
caggtgcaat tggtgcagag cggtgccgaa gtgaaaaaac cgggcagcag cgtgaaagtt      60
agctgcaaag catccggagg acgtttcct gactacgcta tctcttgggt cgccaggcc      120 ccgggccagg gcctcgagtg gatgggcggt atcgttccga tcgttggcac tgcgaactac     180
gcccagaaat tcagggccg gtgaccatt accgccgatg aaagcaccag caccgcctat      240
atggaactga gcagcctgcg cagcgaagat acggccgtgt attattgcgc gcgtgactct     300
tctacttctt actactacta cttcgattac tggggccaag gcaccctggt gactgttagc     360
tcagcctcca ccaagggtcc atcggtcttc cccctggcac cctcctccaa gagcacctct     420 ggggggcacag cggccctggg ctgcctggtc aaggactact ccccgaaccc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga agcagcgggg     720
ggaccgtcag tcttcctctt ccccccaaaa cccaaggaca cctcatgat ctcccggacc      780 cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgggtggt cagcgtcctc accgtcctgc accaggactg gctgaatggc     960
aaggagtaca agtgcaaggt ctccaacaaa gccctcccag ccccatcga gaaaaccatc    1020 tccaaagcca aagggcagcc ccgagaacca caggtgtaca ccctgccccc atcccgggag    1080
gagatgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
```
acgcagaaga gcctctccct gtctccgggt aaa                                          1353

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ala Ser Gln Asp Ile Ser Ser Trp Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Ala Ser Asn Leu Gln Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Gln Met Trp Gln Phe Pro Ile Thr
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Gln Asp Ile Ser Ser Trp
1               5

<210> SEQ ID NO 77
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ala Ser
1

<210> SEQ ID NO 78
<211> LENGTH: 6
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 78

Met Trp Gln Phe Pro Ile
1               5

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
                20                  25                  30

Leu Ala Trp Tyr Gln Gln Lys Pro Gly Lys Ala Pro Lys Leu Leu Ile
            35                  40                  45

Tyr Gln Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met Trp Gln Phe Pro Ile
                85                  90                  95

Thr Phe Gly Gln Gly Thr Lys Val Glu Ile Lys
            100                 105

<210> SEQ ID NO 80
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gatatccaga tgacccagag cccgagcagc ctgagcgcca gcgtgggcga tcgcgtgacc      60
attacctgca gagccagcca ggacattagc tcttggctgg cttggtacca gcagaaaccg     120
ggcaaagcgc cgaaactatt aatctaccag gcttctaacc tgcaaagcgg cgtgccgagc     180
cgctttagcg gcagcggatc cggcaccgat ttcaccctga ccattagctc tctgcaaccg     240
gaagactttg cgacctatta ttgccagcag atgtggcagt tcccgatcac ctttggccag     300
ggcacgaaag ttgaaattaa a                                               321

<210> SEQ ID NO 81
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
                20                  25                  30

```
Leu Ala Trp Tyr Gln Gln Lys Pro Gly Lys Ala Pro Lys Leu Leu Ile
         35                  40                  45
Tyr Gln Ala Ser Asn Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Met Trp Gln Phe Pro Ile
                 85                  90                  95
Thr Phe Gly Gln Gly Thr Lys Val Glu Ile Lys Arg Thr Val Ala Ala
             100                 105                 110
Pro Ser Val Phe Ile Phe Pro Pro Ser Asp Glu Gln Leu Lys Ser Gly
         115                 120                 125
Thr Ala Ser Val Val Cys Leu Leu Asn Asn Phe Tyr Pro Arg Glu Ala
     130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 82
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
gatatccaga tgacccagag cccgagcagc ctgagcgcca gcgtgggcga tcgcgtgacc    60
attacctgca gagccagcca ggacattagc tcttggctgg cttggtacca gcagaaaccg   120
ggcaaagcgc cgaaactatt aatctaccag gcttctaacc tgcaaagcgg cgtgccgagc   180
cgctttagcg gcagcggatc cggcaccgat ttcaccctga ccattagctc tctgcaaccg   240
gaagactttg cgacctatta ttgccagcag atgtggcagt tcccgatcac ctttggccag   300
ggcacgaaag ttgaaattaa acgtacggtg gccgctccca gcgtgttcat cttcccccca   360
agcgacgagc agctgaagag cggcaccgcc agcgtggtgt gcctgctgaa caacttctac   420
cccgggagg ccaaggtgca gtggaaggtg gacaacgccc tgcagagcgg caacagccag   480
gaaagcgtca ccgagcagga cagcaaggac tccacctaca gcctgagcag cacctgacc   540
ctgagcaagg ccgactacga gaagcacaag gtgtacgcct gcgaggtgac ccaccagggc   600
ctgtccagcc ccgtgaccaa gagcttcaac cggggcgagt gt                      642
```

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 83

Asp Tyr Ala Ile Ser
1               5

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ile Met Pro Ile Ser Gly Ala Pro Tyr Tyr Ala Gln Lys Phe Gln
1               5                   10                  15

Gly

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Ser Ser Thr Ser Tyr Tyr Tyr Tyr Phe Asp Tyr
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Gly Thr Phe Ser Asp Tyr
1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Met Pro Ile Ser Gly Ala
1               5

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Ser Ser Thr Ser Tyr Tyr Tyr Phe Asp Tyr
1               5                   10

<210> SEQ ID NO 89
```

```
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Met Pro Ile Ser Gly Ala Pro Tyr Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Thr Ser Tyr Tyr Tyr Phe Asp Tyr Trp Gly
            100                 105                 110

Gln Gly Thr Leu Val Thr Val Ser Ser
        115                 120

```
<210> SEQ ID NO 90
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 90
caggtgcaat tggtgcagag cggtgccgaa gtgaaaaaac cgggcagcag cgtgaaagtt      60
agctgcaaag catccggagg gacgttttct gactacgcta tctcttgggt gcgccaggcc     120
ccgggccagg gcctcgagtg gatgggcggt atcatgccga tctctggcgc tccgtactac     180
gcccagaaat tcagggccgg ggtgaccatt accgccgatg aaagcaccag caccgcctat     240
atggaactga gcagcctgcg cagcgaagat acggccgtgt attattgcgc gcgtgactct     300
tctacttctt actactacta cttcgattac tggggccaag caccctggt gactgttagc     360
tca                                                                  363

<210> SEQ ID NO 91
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Met Pro Ile Ser Gly Ala Pro Tyr Tyr Ala Gln Lys Phe

```
            50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Ser Thr Ser Tyr Tyr Tyr Phe Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 92
```

```
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
caggtgcaat tggtgcagag cggtgccgaa gtgaaaaaac cgggcagcag cgtgaaagtt    60
agctgcaaag catccggagg gacgttttct gactacgcta tctcttgggt gcgccaggcc   120
ccgggccagg gcctcgagtg gatgggcggt atcatgccga tctctggcgc tccgtactac   180
gcccagaaat ttcagggccg ggtgaccatt accgccgatg aaagcaccag caccgcctat   240
atggaactga gcagcctgcg cagcgaagat acggccgtgt attattgcgc gcgtgactct   300
tctacttctt actactacta cttcgattac tggggccaag gcaccctggt gactgttagc   360
tcagcctcca ccaagggtcc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gagagttgag   660
cccaaatctt gtgacaaaac tcacacatgc ccaccgtgcc cagcacctga gcagcgggg   720 ggaccgtcag tcttcctctt ccccccaaaa cccaaggaca ccctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgggtggt cagcgtcctc accgtcctgc accaggactg gctgaatggc   960
aaggagtaca agtgcaaggt ctccaacaaa gccctcccag cccccatcga gaaaaccatc  1020
tccaaagcca aagggcagcc ccgagaacca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                               1353

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Ala Ser Gln Asp Ile Asn Ser Trp Leu Ala
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94
```

```
Gln Ala Ser Asn Leu Gln Ser
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Ile Asp His Thr Pro Phe Thr
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Gln Asp Ile Asn Ser Trp
1               5

<210> SEQ ID NO 97
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Ala Ser
1

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ile Asp His Thr Pro Phe
1               5

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Asn Ser Trp
            20                  25                  30

Leu Ala Trp Tyr Gln Gln Lys Pro Gly Lys Ala Pro Lys Leu Leu Ile
        35                  40                  45
```

```
Tyr Gln Ala Ser Asn Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Asp His Thr Pro Phe
                 85                  90                  95

Thr Phe Gly Gln Gly Thr Lys Val Glu Ile Lys
            100                 105
```

<210> SEQ ID NO 100
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
gatatccaga tgacccagag cccgagcagc ctgagcgcca gcgtgggcga tcgcgtgacc      60
attacctgca gagccagcca ggacattaac tcttggctgg cttggtacca gcagaaaccg     120
ggcaaagcgc cgaaactatt aatctaccag gcttctaacc tgcaaagcgg cgtgccgagc     180
cgctttagcg gcagcggatc cggcaccgat ttcaccctga ccattagctc tctgcaaccg     240
gaagactttg cgacctatta ttgccagcag atcgaccata ctccgttcac ctttggccag     300
ggcacgaaag ttgaaattaa a                                               321
```

<210> SEQ ID NO 101
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Asn Ser Trp
             20                  25                  30

Leu Ala Trp Tyr Gln Gln Lys Pro Gly Lys Ala Pro Lys Leu Leu Ile
         35                  40                  45

Tyr Gln Ala Ser Asn Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Asp His Thr Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 102
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gatatccaga tgacccagag cccgagcagc ctgagcgcca gcgtgggcga tcgcgtgacc      60
attacctgca gagccagcca ggacattaac tcttggctgg cttggtacca gcagaaaccg     120
ggcaaagcgc cgaaactatt aatctaccag gcttctaacc tgcaaagcgg cgtgccgagc     180
cgctttagcg gcagcggatc cggcaccgat ttcaccctga ccattagctc tctgcaaccg     240
gaagactttg cgacctatta ttgccagcag atcgaccata ctccgttcac ctttggccag     300
ggcacgaaag ttgaaattaa acgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg acaacgcccc tgcagagcgg caacagccag     480
gaaagcgtca ccgagcagga cagcaaggac tccacctaca gcctgagcag caccctgacc     540
ctgagcaagg ccgactacga gaagcacaag gtgtacgcct gcgaggtgac ccaccagggc     600
ctgtccagcc ccgtgaccaa gagcttcaac cggggcgagt gt                       642

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Tyr Ala Leu Ser
1               5

<210> SEQ ID NO 104
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Thr Lys His Glu Asn Glu Gly Tyr Thr Thr Trp Tyr Ala Ala Ser
1               5                   10                  15

Val Lys Gly

<210> SEQ ID NO 105
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 105

Asp Phe Trp Ala Asp His Tyr Tyr Tyr Phe Asp Tyr
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Phe Thr Phe Ser Ser Tyr
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys His Glu Asn Glu Gly Tyr Thr
1               5

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Phe Trp Ala Asp His Tyr Tyr Tyr Phe Asp Tyr
1               5                   10

<210> SEQ ID NO 109
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Thr Lys His Glu Asn Glu Gly Tyr Thr Thr Trp Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

```
Tyr Cys Ala Arg Asp Phe Trp Ala Asp His Tyr Tyr Phe Asp Tyr
            100                 105                 110

Trp Gly Gln Gly Thr Leu Val Thr Val Ser Ser
        115                 120
```

<210> SEQ ID NO 110
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
caggtgcaat tggtggaaag cggcggtggc ctggtgaaac caggcggcag cctgcgcctg    60
agctgcgccg cctccggatt cacctttct tcttacgctc tgtcttgggt gcgccaggcc   120
ccgggcaaag gtctcgagtg ggtgggccgt actaaacatg aaacgaagg ctacactact   180 tggtatgccg cctctgtgaa aggccgcttt accattagcc gcgatgattc gaaaaacacc   240
ctgtatctgc aaatgaacag cctgaaaacc gaagatacgg ccgtgtatta ttgcgcgcgt   300
gacttctggg ctgaccatta ctactacttc gattactggg gccaaggcac cctggtgact   360
gttagctca                                                           369
```

<210> SEQ ID NO 111
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Thr Lys His Glu Asn Glu Gly Tyr Thr Thr Trp Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Trp Ala Asp His Tyr Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
```

```
            195                 200                 205
Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 112
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
caggtgcaat tggtggaaag cggcggtggc ctggtgaaac aggcggcag cctgcgcctg    60 agctgcgccg cctccggatt cacctttct tcttacgctc tgtcttgggt gcgccaggcc   120
ccgggcaaag gtctcgagtg gtgggccgt actaaacatg aaaacgaagg ctacactact   180
tggtatgccg cctctgtgaa aggccgcttt accattagcc gcgatgattc gaaaaacacc   240
ctgtatctgc aaatgaacag cctgaaaacc gaagatacgg ccgtgtatta ttgcgcgcgt   300
gacttctggg ctgaccatta ctactactc gattactggg gccaaggcac cctggtgact   360
gttagctcag cctccaccaa gggtccatcg gtcttccccc tggcaccctc ctccaagagc   420
acctctgggg gcacagcggc cctgggctgc ctggtcaagg actacttccc cgaaccggtg   480
acggtgtcgt ggaactcagg cgccctgacc agcggcgtgc acaccttccc ggctgtccta   540
```

```
cagtcctcag gactctactc cctcagcagc gtggtgaccg tgccctccag cagcttgggc    600
acccagacct acatctgcaa cgtgaatcac aagcccagca acaccaaggt ggacaagaga    660
gttgagccca atcttgtga caaaactcac acatgcccac cgtgcccagc acctgaagca    720
gcggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcggaggag    900 cagtacaaca gcacgtaccg ggtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
cgggaggaga tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaa                          1359
```

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Thr Gly Thr Ser Ser Asp Val Gly Tyr Ile Asn Tyr Val Asn
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Glu Val Ser Asn Arg Pro Ser
1               5

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Ser Trp Asp Trp Tyr Asp Asn Val Val
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Ser Ser Asp Val Gly Tyr Ile Asn Tyr
1               5                   10

<210> SEQ ID NO 117
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Glu Val Ser
1

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Asp Trp Tyr Asp Asn Val
1               5

<210> SEQ ID NO 119
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Ile
            20                  25                  30

Asn Tyr Val Asn Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Trp Asp Trp Tyr
                85                  90                  95

Asp Asn Val Val Phe Gly Gly Gly Thr Lys Leu Thr Val Leu
            100                 105                 110

<210> SEQ ID NO 120
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
gatatcgcgc tgacccagcc ggcgagcgtg agcggtagcc cgggccagag cattaccatt      60
agctgcaccg gcaccagcag cgatgtgggc tacatcaact acgtgaactg gtaccagcag     120

```
catccgggca aggcgccgaa actgatgatc tacgaagttt ctaaccgtcc gagcggcgtg    180
agcaaccgtt ttagcggatc caaaagcggc aacaccgcga gcctgaccat tagcggcctg    240
caagcggaag acgaagcgga ttattactgc gcttcttggg actggtacga caacgttgtg    300
tttggcggcg gcacgaagtt aaccgtccta                                     330
```

<210> SEQ ID NO 121
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Ile
            20                  25                  30

Asn Tyr Val Asn Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Trp Asp Trp Tyr
                85                  90                  95

Asp Asn Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 122
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
gatatcgcgc tgacccagcc ggcgagcgtg agcggtagcc cgggccagag cattaccatt    60
agctgcaccg gcaccagcag cgatgtgggc tacatcaact acgtgaactg gtaccagcag    120
catccgggca aggcgccgaa actgatgatc tacgaagttt ctaaccgtcc gagcggcgtg    180
```

```
agcaaccgtt ttagcggatc caaaagcggc aacaccgcga gcctgaccat tagcggcctg      240
caagcggaag acgaagcgga ttattactgc gcttcttggg actggtacga caacgttgtg      300
tttggcggcg gcacgaagtt aaccgtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac accctccaaa caaagcaaca caagtacgc ggccagcagc       540 tatctgagcc tgacgcctga gcagtggaag tcccacagaa gctacagctg ccaggtcacg      600
catgaaggga gcaccgtgga agacagtg gcccctacag aatgttca                    648
```

```
<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Tyr Ala Leu Ser
1               5

<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ile Lys Leu Ile Asn Lys Gly Tyr Thr Thr Trp Tyr Ala Ala Ser
1               5                   10                  15

Val Lys Gly

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asp Phe Trp Ala Asp His Tyr Tyr Tyr Phe Asp Tyr
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Phe Thr Phe Ser Ser Tyr
1               5

<210> SEQ ID NO 127
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 127

Lys Leu Ile Asn Lys Gly Tyr Thr
1               5

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asp Phe Trp Ala Asp His Tyr Tyr Tyr Phe Asp Tyr
1               5                   10

<210> SEQ ID NO 129
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Lys Leu Ile Asn Lys Gly Tyr Thr Thr Trp Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Trp Ala Asp His Tyr Tyr Tyr Phe Asp Tyr
            100                 105                 110

Trp Gly Gln Gly Thr Leu Val Thr Val Ser Ser
        115                 120

<210> SEQ ID NO 130
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
caggtgcaat tggtggaaag cggcggtggc ctggtgaaac caggcggcag cctgcgcctg      60
agctgcgccg cctccggatt cacctttct tcttacgctc tgtcttgggt gcgccaggcc     120
ccgggcaaag gtctcgagtg ggtgggccgt atcaaactga tcaacaaagg ctacactact     180
tggtatgccg cctctgtgaa aggccgcttt accattagcc gcgatgattc gaaaaacacc     240
ctgtatctgc aaatgaacag cctgaaaacc gaagatacgg ccgtgtatta ttgcgcgcgt     300
```

-continued

```
gacttctggg ctgaccatta ctactacttc gattactggg gccaaggcac cctggtgact    360
gttagctca                                                            369
```

<210> SEQ ID NO 131
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Lys Leu Ile Asn Lys Gly Tyr Thr Thr Trp Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Trp Ala Asp His Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
```

```
                    340                 345                 350
Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 132
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
caggtgcaat tggtggaaag cggcggtggc ctggtgaaac aggcggcag cctgcgcctg        60 agctgcgccg cctccggatt caccttttct tcttacgctc tgtcttgggt gcgccaggcc      120
ccgggcaaag gtctcgagtg ggtgggccgt atcaaactga tcaacaaagg ctacactact      180
tggtatgccg cctctgtgaa aggccgcttt accattagcc gcgatgattc gaaaaacacc      240
ctgtatctgc aaatgaacag cctgaaaacc gaagatacgg ccgtgtatta ttgcgcgcgt      300
gacttctggg ctgaccatta ctactacttc gattactggg gccaaggcac cctggtgact      360
gttagctcag cctccaccaa gggtccatcg gtcttccccc tggcaccctc ctccaagagc      420
acctctgggg gcacagcggc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acccagacct acatctgcaa cgtgaatcac aagcccagca caccaaggt ggacaagaga       660 gttgagccca aatcttgtga caaaactcac acatgcccac cgtgcccagc acctgaagca      720
gcggggggac cgtcagtctt cctcttcccc ccaaaaccca aggacaccct catgatctcc      780
cggacccctg aggtcacatg cgtggtggtg gacgtgagcc acgaagaccc tgaggtcaag      840
ttcaactggt acgtggacgg cgtggaggtg cataatgcca agacaaagcc gcgggaggag      900
cagtacaaca gcacgtaccg ggtggtcagc gtcctcaccg tcctgcacca ggactggctg      960
aatggcaagg agtacaagtg caaggtctcc aacaaagccc tcccagcccc catcgagaaa     1020
accatctcca aagccaaagg gcagccccga gaaccacagg tgtacaccct gcccccatcc     1080
cgggaggaga tgaccaagaa ccaggtcagc ctgacctgcc tggtcaaagg cttctatccc     1140
agcgacatcg ccgtggagtg ggagagcaat gggcagccgg agaacaacta caagaccacg     1200
cctcccgtgc tggactccga cggctccttc ttcctctaca gcaagctcac cgtggacaag     1260
agcaggtggc agcaggggaa cgtcttctca tgctccgtga tgcatgaggc tctgcacaac     1320
cactacacgc agaagagcct ctccctgtct ccgggtaaa                            1359
```

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Gly Thr Ser Ser Asp Val Gly Tyr Ile Asn Tyr Val Asn
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Glu Val Ser Asn Arg Pro Ser
1               5

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Ser Trp Asp Trp Tyr Asp Asn Val Val
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Ser Ser Asp Val Gly Tyr Ile Asn Tyr
1               5                   10

<210> SEQ ID NO 137
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Glu Val Ser
1

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Trp Asp Trp Tyr Asp Asn Val
1               5

<210> SEQ ID NO 139
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Ile
            20                  25                  30

Asn Tyr Val Asn Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Trp Asp Trp Tyr
                85                  90                  95

Asp Asn Val Val Phe Gly Gly Gly Thr Lys Leu Thr Val Leu
            100                 105                 110

<210> SEQ ID NO 140
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
gatatcgcgc tgacccagcc ggcgagcgtg agcggtagcc cgggccagag cattaccatt    60
agctgcaccg gcaccagcag cgatgtgggc tacatcaact acgtgaactg gtaccagcag   120
catccgggca aggcgccgaa actgatgatc tacgaagttt ctaaccgtcc gagcggcgtg   180
agcaaccgtt ttagcggatc caaaagcggc aacaccgcga gcctgaccat tagcggcctg   240
caagcggaag acgaagcgga ttattactgc gcttcttggg actggtacga caacgttgtg   300
tttggcggcg gcacgaagtt aaccgtccta                                    330

<210> SEQ ID NO 141
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Ile
            20                  25                  30

Asn Tyr Val Asn Trp Tyr Gln Gln His Pro Gly Lys Ala Pro Lys Leu

```
                 35                  40                  45
Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Trp Asp Trp Tyr
                 85                  90                  95

Asp Asn Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 142
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
gatatcgcgc tgacccagcc ggcgagcgtg agcggtagcc cgggccagag cattaccatt      60
agctgcaccg gcaccagcag cgatgtgggc tacatcaact acgtgaactg gtaccagcag     120
catccgggca aggcgccgaa actgatgatc tacgaagttt ctaaccgtcc gagcggcgtg     180
agcaaccgtt ttagcggatc caaaagcggc aacaccgcga gcctgaccat tagcggcctg     240
caagcggaag acgaagcgga ttattactgc gcttcttggg actggtacga caacgttgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
tatctgagcc tgacgcctga gcagtggaag tcccacagaa gctacagctg ccaggtcacg     600
catgaaggga gcaccgtgga agacagtg gcccctacag aatgttca                    648

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143
```

```
Asp Tyr Ala Leu His
1               5

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Val Ile Ser Tyr Gln Gly Gly Phe Ile Tyr Tyr Ala Asp Ser Val Lys
1               5                   10                  15

Gly

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Pro Gly Leu Thr Ser Tyr His Asp Ser
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Phe Thr Phe Ser Asp Tyr
1               5

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Tyr Gln Gly Gly Phe
1               5

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Pro Gly Leu Thr Ser Tyr His Asp Ser
1               5                   10

<210> SEQ ID NO 149
<211> LENGTH: 119
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 149

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu His Trp Val Arg Gln Ala Pro Gly Lys Gly Leu Glu Trp Val
        35                  40                  45

Ser Val Ile Ser Tyr Gln Gly Gly Phe Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Gly Leu Thr Ser Tyr His Asp Ser Trp Gly Gln Gly
            100                 105                 110

Thr Leu Val Thr Val Ser Ser
        115

<210> SEQ ID NO 150
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 150
caggtgcaat tgctggaaag cggcggtggc ctggtgcagc cgggtggcag cctgcgtctg        60
agctgcgcgg cgtccggatt cacctttct gactacgctc tgcattgggt gcgccaggcc       120
ccgggcaaag gtctcgagtg gtttccgtt atctcttacc agggcggttt catctactat       180
gcggatagcg tgaaaggccg ctttaccatc agccgcgata attcgaaaaa caccctgtat       240
ctgcaaatga acagcctgcg tgcggaagat acggccgtgt attattgcgc gcgttctccg       300
ggtctgactt cttaccatga ttcttggggc caaggcaccc tggtgactgt tagctca         357

<210> SEQ ID NO 151
<211> LENGTH: 449
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 151

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu His Trp Val Arg Gln Ala Pro Gly Lys Gly Leu Glu Trp Val
        35                  40                  45

Ser Val Ile Ser Tyr Gln Gly Gly Phe Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Ser Pro Gly Leu Thr Ser Tyr His Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 152
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 152

```
caggtgcaat tgctggaaag cggcggtggc ctggtgcagc cgggtggcag cctgcgtctg      60
agctgcgcgg cgtccggatt cacctttct gactacgctc tgcattgggt gcgccaggcc     120
ccgggcaaag gtctcgagtg ggtttccgtt atctcttacc agggcggttt catctactat    180
gcggatagcg tgaaaggccg ctttaccatc agccgcgata attcgaaaaa caccctgtat    240
ctgcaaatga acagcctgcg tgcggaagat acggccgtgt attattgcgc gcgttctccg    300
ggtctgactt cttaccatga ttcttggggc caaggcaccc tggtgactgt tagctcagcc    360
tccaccaagg gtccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaagcagc ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccggg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                      1347
```

<210> SEQ ID NO 153
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Ser Gly Ser Ser Ser Asn Ile Gly Ser Asn Tyr Val Ser
1               5                   10

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Ser Asn Ser His Arg Pro Ser
1               5

-continued

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gln Ser Trp Asp Tyr Glu Ser Glu Arg Val Val
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ser Ser Ser Asn Ile Gly Ser Asn Tyr
1               5

<210> SEQ ID NO 157
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Asn Ser
1

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Trp Asp Tyr Glu Ser Glu Arg Val
1               5

<210> SEQ ID NO 159
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile His Ser Asn Ser His Arg Pro Ser Gly Val Pro Asp Arg Phe Ser
    50                  55                  60

Gly Ser Lys Ser Gly Thr Ser Ala Ser Leu Ala Ile Thr Gly Leu Gln

```
                65                  70                  75                  80
Ala Glu Asp Glu Ala Asp Tyr Tyr Cys Gln Ser Trp Asp Tyr Glu Ser
                    85                  90                  95

Glu Arg Val Val Phe Gly Gly Gly Thr Lys Leu Thr Val Leu
                    100                 105                 110

<210> SEQ ID NO 160
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
gatatcgtgc tgacccagcc gccgagcgtg agcggtgcac cgggccagcg cgtgaccatt     60
agctgtagcg gcagcagcag caacattggt tctaactacg tgtcttggta ccagcagctg    120
ccgggcacgg cgccgaaact gctgatccat tctaactctc atcgcccgag cggcgtgccg    180
gatcgcttta gcggatccaa aagcggcacc agcgccagcc tggcgattac cggcctgcaa    240
gcagaagacg aagcggatta ttactgccag tcttgggact acgaatctga acgtgttgtg    300
tttggcggcg gcacgaagtt aaccgtccta                                      330

<210> SEQ ID NO 161
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
                20                  25                  30

Tyr Val Ser Trp Tyr Gln Gln Leu Pro Gly Thr Ala Pro Lys Leu Leu
            35                  40                  45

Ile His Ser Asn Ser His Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Tyr Glu Ser
                    85                  90                  95

Glu Arg Val Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
```

Thr Val Ala Pro Thr Glu Cys Ser
          210              215

<210> SEQ ID NO 162
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162

```
gatatcgtgc tgacccagcc gccgagcgtg agcggtgcac cgggccagcg cgtgaccatt    60
agctgtagcg gcagcagcag caacattggt tctaactacg tgtcttggta ccagcagctg   120
ccgggcacgg cgccgaaact gctgatccat tctaactctc atcgcccgag cggcgtgccg   180
gatcgcttta gcggatccaa agcggcacc agcgccagcc tggcgattac cggcctgcaa   240
gcagaagacg aagcggatta ttactgccag tcttgggact acgaatctga acgtgttgtg   300
tttggcggcg gcacgaagtt aaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac acctccaaa caaagcaaca caagtacgc ggccagcagc   540
tatctgagcc tgacgcctga cagtggaag tcccacagaa gctacagctg ccaggtcacg   600
catgaaggga gcaccgtgga agacagtg gcccctacag aatgttca                  648
```

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Tyr Ala Leu His
1               5

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Val Ile Ser Tyr Ala Gly Gly Phe Lys Phe Tyr Ala Asp Ser Val Lys
1               5                   10                  15

Gly

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

```
Ser Pro Gly Leu Thr Ser Tyr His Asp Ser
1               5                   10
```

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

```
Gly Phe Thr Phe Ser Asp Tyr
1               5
```

<210> SEQ ID NO 167
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

```
Ser Tyr Ala Gly Gly Phe
1               5
```

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

```
Ser Pro Gly Leu Thr Ser Tyr His Asp Ser
1               5                   10
```

<210> SEQ ID NO 169
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

```
Gln Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Ala Leu His Trp Val Arg Gln Ala Pro Gly Lys Gly Leu Glu Trp Val
            35                  40                  45

Ser Val Ile Ser Tyr Ala Gly Gly Phe Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Gly Leu Thr Ser Tyr His Asp Ser Trp Gly Gln Gly
                100                 105                 110

Thr Leu Val Thr Val Ser Ser
            115
```

<210> SEQ ID NO 170
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
caggtgcaat tgctggaaag cggcggtggc ctggtgcagc cgggtggcag cctgcgtctg    60
agctgcgcgg cgtccggatt caccttttct gactacgctc tgcattgggt gcgccaggcc   120
ccgggcaaag gtctcgagtg ggtttccgtt atctcttacg ctggcggttt caaattctat   180
gcggatagcg tgaaaggccg ctttaccatc agccgcgata attcgaaaaa cacccctgtat  240 ctgcaaatga acagcctgcg tgcggaagat acggccgtgt attattgcgc gcgttctccg   300
ggtctgactt cttaccatga ttcttggggc caaggcaccc tggtgactgt tagctca      357

<210> SEQ ID NO 171
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu His Trp Val Arg Gln Ala Pro Gly Lys Gly Leu Glu Trp Val
        35                  40                  45

Ser Val Ile Ser Tyr Ala Gly Gly Phe Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Gly Leu Thr Ser Tyr His Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 172
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
caggtgcaat tgctggaaag cggcggtggc ctggtgcagc cgggtggcag cctgcgtctg     60
agctgcgcgg cgtccggatt caccttttct gactacgctc tgcattgggt gcgccaggcc    120
ccgggcaaag gtctcgagtg gtttccgtt atctcttacg ctggcggttt caaattctat    180
gcggatagcg tgaaaggccg ctttaccatc agccgcgata ttcgaaaaa caccctgtat    240 ctgcaaatga acagcctgcg tgcggaagat acggccgtgt attattgcgc gcgttctccg    300
ggtctgactt cttaccatga ttcttgggc aaggcaccc tggtgactgt agctcagcc    360 tccaccaagg gtccatcggt cttccccctg gcaccctcct ccaagagcac ctctggggggc    420 acagcggccc tgggctgcct ggtcaaggac tacttcccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaagcagc ggggggaccg    720
tcagtcttcc tcttcccccc aaaacccaag gacaccctca tgatctcccg gacccctgag    780

```
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccggg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Gly Ser Ser Ser Asn Ile Gly Ser Asn Tyr Val Ser
1               5                   10

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Asn Ser His Arg Pro Ser
1               5

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Ser Trp Asp Tyr Glu Ser Glu Arg Val Val
1               5                   10

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Ser Ser Asn Ile Gly Ser Asn Tyr
1               5

<210> SEQ ID NO 177
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Asn Ser
1

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Trp Asp Tyr Glu Ser Glu Arg Val
1               5

<210> SEQ ID NO 179
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile His Ser Asn Ser His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Tyr Glu Ser
                85                  90                  95

Glu Arg Val Val Phe Gly Gly Gly Thr Lys Leu Thr Val Leu
            100                 105                 110

<210> SEQ ID NO 180
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
gatatcgtgc tgacccagcc gccgagcgtg agcggtgcac cgggccagcg cgtgaccatt      60
agctgtagcg gcagcagcag caacattggt tctaactacg tgtcttggta ccagcagctg     120
ccgggcacgg cgccgaaact gctgatccat tctaactctc atcgcccgag cggcgtgccg     180
gatcgcttta gcggatccaa aagcggcacc agcgccagcc tggcgattac cggcctgcaa     240
gcagaagacg aagcggatta ttactgccag tcttgggact acgaatctga acgtgttgtg     300
tttggcggcg gcacgaagtt aaccgtccta                                      330
```

<210> SEQ ID NO 181
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile His Ser Asn Ser His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Tyr Glu Ser
                85                  90                  95

Glu Arg Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 182
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182
gatatcgtgc tgacccagcc gccgagcgtg agcggtgcac cgggccagcg cgtgaccatt     60
agctgtagcg gcagcagcag caacattggt tctaactacg tgtcttggta ccagcagctg    120
ccgggcacgg cgccgaaact gctgatccat tctaactctc atcgcccgag cggcgtgccg    180
gatcgcttta gcggatccaa aagcggcacc agcgccagcc tggcgattac cggcctgcaa    240
gcagaagacg aagcggatta ttactgccag tcttgggact acgaatctga acgtgttgtg    300
tttggcggcg gcacgaagtt aaccgtccta ggtcagccca aggctgcccc ctcggtcact    360
ctgttcccgc cctcctctga ggagcttcaa gccaacaagg ccacactggt gtgtctcata    420

```
agtgacttct acccgggagc cgtgacagtg gcctggaagg cagatagcag ccccgtcaag    480
gcgggagtgg agaccaccac accctccaaa caaagcaaca acaagtacgc ggccagcagc    540
tatctgagcc tgacgcctga gcagtggaag tcccacagaa gctacagctg ccaggtcacg    600
catgaaggga gcaccgtgga agacagtg gcccctacag aatgttca                   648
```

```
<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asp Tyr Ala Ile Ser
1               5

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Ile Ile Pro Gly Phe Gly Gln Ala Asn Tyr Ala Gln Lys Phe Gln
1               5                   10                  15

Gly

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Glu Pro Ser Pro Leu Tyr Gly Pro Tyr Ser Asp Tyr Val Met Asp Pro
1               5                   10                  15

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Gly Thr Phe Ser Asp Tyr
1               5

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ile Pro Gly Phe Gly Gln
1               5
```

<210> SEQ ID NO 188
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Glu Pro Ser Pro Leu Tyr Gly Pro Tyr Ser Asp Tyr Val Met Asp Pro
1               5                   10                  15

<210> SEQ ID NO 189
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 189

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Ala Ile Ser Trp Val Arg Gln Ala Pro Gly Gln Gly Leu Glu Trp Met
            35                  40                  45

Gly Gly Ile Ile Pro Gly Phe Gly Gln Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Pro Ser Pro Leu Tyr Gly Pro Tyr Ser Asp Tyr Val Met
            100                 105                 110

Asp Pro Trp Gly Gln Gly Thr Leu Val Thr Val Ser Ser
        115                 120                 125

<210> SEQ ID NO 190
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 190
caggtgcaat tggtgcagag cggtgccgaa gtgaaaaaac cgggcagcag cgtgaaagtt      60
agctgcaaag catccggagg acgttttcct gactacgcta tctcttgggt gcgccaggcc     120
ccgggccagg gcctcgagtg gatgggcggt atcatcccgg gtttcggcca ggcgaactac     180
gcccagaaat tcagggccgg ggtgaccatt accgccgatg aaagcaccag caccgcctat     240
atggaactga gcagcctgcg cagcgaagat acggccgtgt attattgcgc gcgtgaaccg     300
tctccgctgt acggtccgta ctctgactac gttatggatc gtggggcca aggcaccctg      360 gtgactgtta gctca                                                      375

<210> SEQ ID NO 191
<211> LENGTH: 455
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 191

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Gly Ile Ile Pro Gly Phe Gly Gln Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Pro Ser Pro Leu Tyr Gly Pro Tyr Ser Asp Tyr Val Met
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro Gly Lys
    450                 455

<210> SEQ ID NO 192
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
caggtgcaat tggtgcagag cggtgccgaa gtgaaaaaac cgggcagcag cgtgaaagtt      60
agctgcaaag catccggagg gacgttttct gactacgcta tctcttgggt gcgccaggcc     120
ccgggccagg gcctcgagtg gatgggcggt atcatcccgg gtttcggcca ggcgaactac     180
gcccagaaat tcagggccgg ggtgaccatt accgccgatg aaagcaccag caccgcctat     240
atggaactga gcagcctgcg cagcgaagat acggccgtgt attattgcgc gcgtgaaccg     300
tctccgctgt acggtccgta ctctgactac gttatggatc gtggggcca aggcaccctg     360 gtgactgtta gctcagcctc caccaagggt ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagagagttg agcccaaatc ttgtgacaaa actcacacat gcccaccgtg cccagcacct     720
gaagcagcgg ggggaccgtc agtcttcctc ttccccccaa aacccaagga caccctcatg     780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgggtg gtcagcgtcc tcaccgtcct gcaccaggac     960
tggctgaatg gcaaggagta caagtgcaag gtctccaaca aagccctccc agcccccatc    1020
gagaaaacca tctccaaagc caagggcag ccccgagaac acaggtgta cccctgccc    1080 ccatcccggg aggagatgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaa                    1365

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic

```
                          peptide

<400> SEQUENCE: 193

Thr Gly Thr Ser Ser Asp Val Gly Tyr Phe Asn Phe Val Ser
1               5                   10

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asp Val Ser Asn Arg Pro Ser
1               5

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ala Ser Tyr Gly Trp Asp Ser Ser Trp Val
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Thr Ser Ser Asp Val Gly Tyr Phe Asn Phe
1               5                   10

<210> SEQ ID NO 197
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Asp Val Ser
1

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Tyr Gly Trp Asp Ser Ser Trp
1               5

<210> SEQ ID NO 199
```

<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 199

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Phe
            20                  25                  30

Asn Phe Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Gly Trp Asp
                85                  90                  95

Ser Ser Trp Val Phe Gly Gly Gly Thr Lys Leu Thr Val Leu
            100                 105                 110
```

<210> SEQ ID NO 200
<211> LENGTH: 330
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 200

```
gatatcgcgc tgacccagcc ggcgagcgtg agcggtagcc cgggccagag cattaccatt    60
agctgcaccg gcaccagcag cgatgtgggc tacttcaact cgtgtcttg gtaccagcag   120
catccgggca aggcgccgaa actgatgatc tacgacgttt ctaaccgtcc gagcggcgtg   180
agcaaccgtt ttagcggatc caaaagcggc aacaccgcga gcctgaccat tagcggcctg   240
caagcggaag acgaagcgga ttattactgc gcttcttacg gttgggactc ttcttgggtg   300
tttggcggcg gcacgaagtt aaccgtccta                                     330
```

<210> SEQ ID NO 201
<211> LENGTH: 216
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 201

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Phe
            20                  25                  30

Asn Phe Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Tyr Cys Ala Ser Tyr Gly Trp Asp
             85                  90                  95

Ser Ser Trp Val Phe Gly Gly Thr Lys Leu Thr Val Leu Gly Gln
        100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215
```

<210> SEQ ID NO 202
<211> LENGTH: 648
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 202

```
gatatcgcgc tgacccagcc ggcgagcgtg agcggtagcc cgggccagag cattaccatt      60
agctgcaccg gcaccagcag cgatgtgggc tacttcaact tcgtgtcttg gtaccagcag     120
catccgggca aggcgccgaa actgatgatc tacgacgttt ctaaccgtcc gagcggcgtg     180
agcaaccgtt ttagcggatc caaaagcggc aacaccgcga gcctgaccat tagcggcctg     240
caagcggaag acgaagcgga ttattactgc gcttcttacg gttgggactc ttcttgggtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc      540
tatctgagcc tgacgcctga gcagtggaag tcccacagaa gctacagctg ccaggtcacg     600
catgaaggga gcaccgtgga agacagtg gccccctacag aatgttca                    648
```

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 203

```
Asn Tyr Trp Ile Ala
1               5
```

<210> SEQ ID NO 204
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 204

Arg Ile Phe Pro Gly Asp Ser Thr Thr Thr Tyr Ser Pro Ser Phe Gln
1               5                   10                  15

Gly

<210> SEQ ID NO 205
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Lys Arg Gly Ala Thr His Pro Thr Gln Tyr Glu Gly Trp Glu Val
1               5                   10                  15

Tyr Gly Phe Asp Pro
            20

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Tyr Ser Phe Thr Asn Tyr
1               5

<210> SEQ ID NO 207
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Phe Pro Gly Asp Ser Thr
1               5

<210> SEQ ID NO 208
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Lys Arg Gly Ala Thr His Pro Thr Gln Tyr Glu Gly Trp Glu Val
1               5                   10                  15

Tyr Gly Phe Asp Pro
            20

<210> SEQ ID NO 209
<211> LENGTH: 130
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 209

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ala Trp Val Arg Gln Met Pro Gly Lys Gly Leu Glu Trp Met
        35                  40                  45

Gly Arg Ile Phe Pro Gly Asp Ser Thr Thr Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Lys Arg Gly Ala Thr His Pro Thr Gln Tyr Glu Gly Trp
            100                 105                 110

Glu Val Tyr Gly Phe Asp Pro Trp Gly Gln Gly Thr Leu Val Thr Val
        115                 120                 125

Ser Ser
    130

<210> SEQ ID NO 210
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210
caggtgcaat tggtgcagag cggtgcggaa gtgaaaaaac cgggcgaaag cctgaaaatt      60
agctgcaaag gctccggata tagcttcact aactactgga ttgcttgggt gcgccagatg     120
ccgggcaaag gtctcgagtg gatgggccgt atcttcccgg gtgacagcac taccacttat     180
agcccgagct ttcagggcca ggtgaccatt agcgcggata aaagcatcag caccgcgtat     240
ctgcaatgga gcagcctgaa agcgagcgat accgcgatgt attattgcgc gcgtggtaaa     300
cgtggtgcta ctcatccgac tcagtacgaa ggttgggaag tttacggttt cgatccgtgg     360
ggccaaggca ccctggtgac tgttagctca                                      390

<210> SEQ ID NO 211
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ala Trp Val Arg Gln Met Pro Gly Lys Gly Leu Glu Trp Met
        35                  40                  45

Gly Arg Ile Phe Pro Gly Asp Ser Thr Thr Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Gly Lys Arg Gly Ala Thr His Pro Thr Gln Tyr Glu Gly Trp
        100                 105                 110

Glu Val Tyr Gly Phe Asp Pro Trp Gly Gln Gly Thr Leu Val Thr Val
    115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Ala Ala Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 212
<211> LENGTH: 1380

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
caggtgcaat tggtgcagag cggtgcggaa gtgaaaaaac cgggcgaaag cctgaaaatt      60
agctgcaaag ctccggata tagcttcact aactactgga ttgcttgggt gcgccagatg     120
ccgggcaaag gtctcgagtg gatgggccgt atcttcccgg gtgacagcac taccacttat    180
agcccgagct ttcagggcca ggtgaccatt agcgcggata aaagcatcag caccgcgtat    240
ctgcaatgga gcagcctgaa agcgagcgat accgcgatgt attattgcgc gcgtggtaaa    300
cgtggtgcta ctcatccgac tcagtacgaa ggttgggaag tttacggttt cgatccgtgg    360
ggccaaggca ccctggtgac tgttagctca gcctccacca gggtccatc ggtcttcccc     420
ctggcaccct cctccaagag cacctctggg ggcacagcgg ccctgggctg cctggtcaag    480
gactacttcc ccgaaccggt gacggtgtcg tggaactcag cgccctgac cagcggcgtg     540
cacaccttcc cggctgtcct acagtcctca ggactctact ccctcagcag cgtggtgacc    600
gtgccctcca gcagcttggg cacccagacc tacatctgca acgtgaatca caagcccagc    660
aacaccaagg tggacaagag agttgagccc aaatcttgtg acaaaactca cacatgccca    720
ccgtgcccag cacctgaagc agcggggga ccgtcagtct tcctcttccc cccaaaaccc     780
aaggacaccc tcatgatctc ccggaccct gaggtcacat gcgtggtggt ggacgtgagc     840
cacgaagacc ctgaggtcaa gttcaactgg tacgtggacg gcgtggaggt gcataatgcc    900
aagacaaagc cgcgggagga gcagtacaac agcacgtacc gggtggtcag cgtcctcacc    960
gtcctgcacc aggactggct gaatggcaag gagtacaagt gcaaggtctc caacaaagcc   1020
ctcccagccc ccatcgagaa aaccatctcc aaagccaaag gcagccccg agaaccacag    1080
gtgtacaccc tgcccccatc ccgggaggag atgaccaaga accaggtcag cctgacctgc   1140
ctggtcaaag gcttctatcc cagcgacatc gccgtggagt gggagagcaa tgggcagccg   1200
gagaacaact acaagaccac gcctcccgtg ctggactccg acggctcctt cttcctctac   1260
agcaagctca ccgtggacaa gagcaggtgg cagcagggga acgtcttctc atgctccgtg   1320
atgcatgagg ctctgcacaa ccactacacg cagaagagcc tctccctgtc tccgggtaaa   1380

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Gly Asp Ala Leu Gly Gly Lys Tyr Ala Ser
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214
```

```
Asp Asp Asn Lys Arg Pro Ser
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Ser Trp Ala Phe Tyr Ser Gly Val
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Asp Ala Leu Gly Gly Lys Tyr
1               5

<210> SEQ ID NO 217
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asp Asp Asn
1

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Trp Ala Phe Tyr Ser Gly
1               5

<210> SEQ ID NO 219
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Asp Ile Glu Leu Thr Gln Pro Pro Ser Val Ser Val Ser Pro Gly Gln
1               5                   10                  15

Thr Ala Ser Ile Thr Cys Ser Gly Asp Ala Leu Gly Gly Lys Tyr Ala
            20                  25                  30

Ser Trp Tyr Gln Gln Lys Pro Gly Gln Ala Pro Val Leu Val Ile Tyr
        35                  40                  45
```

```
Asp Asp Asn Lys Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Trp Ala Phe Tyr Ser Gly Val
                 85                  90                  95

Phe Gly Gly Gly Thr Lys Leu Thr Val Leu
                100                 105
```

<210> SEQ ID NO 220
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220

```
gatatcgaac tgacccagcc gccgagcgtg agcgtgagcc cgggccagac cgcgagcatt      60
acctgtagcg gcgatgctct gggtggtaaa tacgcttctt ggtaccagca gaaaccgggc     120
caggcgccgg tgctggtgat ctacgacgac aacaaacgtc cgagcggcat cccggaacgt     180
tttagcggat ccaacagcgg caacaccgcg accctgacca ttagcggcac ccaggcggaa     240
gacgaagcgg attattactg ccagtcttgg gctttctact ctggtgtgtt tggcggcggc     300
acgaagttaa ccgtcccta                                                  318
```

<210> SEQ ID NO 221
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

```
Asp Ile Glu Leu Thr Gln Pro Pro Ser Val Ser Val Ser Pro Gly Gln
 1               5                  10                  15

Thr Ala Ser Ile Thr Cys Ser Gly Asp Ala Leu Gly Gly Lys Tyr Ala
             20                  25                  30

Ser Trp Tyr Gln Gln Lys Pro Gly Gln Ala Pro Val Leu Val Ile Tyr
         35                  40                  45

Asp Asp Asn Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Trp Ala Phe Tyr Ser Gly Val
                 85                  90                  95

Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175
```

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 222
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
gatatcgaac tgacccagcc gccgagcgtg agcgtgagcc cgggccagac cgcgagcatt    60
acctgtagcg gcgatgctct gggtggtaaa tacgcttctt ggtaccagca gaaaccgggc   120
caggcgccgg tgctggtgat ctacgacgac aacaaacgtc cgagcggcat cccggaacgt   180
tttagcggat ccaacagcgg caacaccgcg accctgacca ttagcggcac ccaggcggaa   240
gacgaagcgg attattactg ccagtcttgg gctttctact ctggtgtgtt tggcggcggc   300
acgaagttaa ccgtcctagg tcagcccaag gctgcccct cggtcactct gttcccgccc    360
tcctctgagg agcttcaagc caacaaggcc acactggtgt gtctcataag tgacttctac   420
ccgggagccg tgacagtggc ctggaaggca gatagcagcc cgtcaaggc gggagtggag    480 accaccacac cctccaaaca aagcaacaac aagtacgcgg ccagcagcta tctgagcctg   540
acgcctgagc agtggaagtc ccacagaagc tacagctgcc aggtcacgca tgaagggagc   600
accgtggaga agacagtggc ccctacagaa tgttca                             636

<210> SEQ ID NO 223
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Asp Tyr Ala Leu His
1               5

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Val Ile Ser Tyr Ser Gly Gly Tyr Thr Tyr Tyr Ala Asp Ser Val Lys
1               5                   10                  15

Gly

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Ser Pro Gly Leu Thr Ser Tyr His Asp Ser
1               5                   10

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Phe Thr Phe Ser Asp Tyr
1               5

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ser Tyr Ser Gly Gly Tyr
1               5

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ser Pro Gly Leu Thr Ser Tyr His Asp Ser
1               5                   10

<210> SEQ ID NO 229
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu His Trp Val Arg Gln Ala Pro Gly Lys Gly Leu Glu Trp Val
        35                  40                  45

Ser Val Ile Ser Tyr Ser Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Gly Leu Thr Ser Tyr His Asp Ser Trp Gly Gln Gly

Thr Leu Val Thr Val Ser Ser
        115

<210> SEQ ID NO 230
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
caggtgcaat tgctggaaag cggcggtggc ctggtgcagc cgggtggcag cctgcgtctg    60
agctgcgcgg cgtccggatt cacctttttct gactacgctc tgcattgggt gcgccaggcc   120
ccgggcaaag gtctcgagtg gtttccgtt atctcttact ctggtggtta cacctactat    180
gcggatagcg tgaaaggccg ctttaccatc agccgcgata attcgaaaaa caccctgtat   240
ctgcaaatga acagcctgcg tgcggaagat acggccgtgt attattgcgc gcgttctccg   300
ggtctgactt cttaccatga ttcttggggc caaggcaccc tggtgactgt tagctca      357

<210> SEQ ID NO 231
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu His Trp Val Arg Gln Ala Pro Gly Lys Gly Leu Glu Trp Val
        35                  40                  45

Ser Val Ile Ser Tyr Ser Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Gly Leu Thr Ser Tyr His Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys

```
                210               215                 220
Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 232
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
caggtgcaat tgctggaaag cggcggtggc ctggtgcagc cgggtggcag cctgcgtctg    60
agctgcgcgg cgtccggatt cacctttctt gactacgctc tgcattgggt gcgccaggcc   120
ccgggcaaag gtctcgagtg gtttccgtt atctcttact ctggtggtta cacctactat   180
gcggatagcg tgaaaggccg ctttaccatc agccgcgata ttcgaaaaa caccctgtat   240 ctgcaaatga acagcctgcg tgcggaagat acggccgtgt attattgcgc cgttctcccg   300
ggtctgactt cttaccatga ttcttggggc caaggcaccc tggtgactgt tagctcagcc   360
tccaccaagg gtccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagagagt tgagcccaaa   660
```

```
tcttgtgaca aaactcacac atgcccaccg tgcccagcac ctgaagcagc ggggggaccg    720
tcagtcttcc tcttccccc aaacccaag acacccctca tgatctcccg accccctgag     780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccggg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 233
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Gly Ser Ser Ser Asn Ile Gly Ser Asn Tyr Val Ser
1               5                   10

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Asn Ser His Arg Pro Ser
1               5

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gln Ser Trp Asp Tyr Glu Ser Glu Arg Val Val
1               5                   10

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Ser Ser Asn Ile Gly Ser Asn Tyr
1               5

```
<210> SEQ ID NO 237
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Asn Ser
1

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Trp Asp Tyr Glu Ser Glu Arg Val
1               5

<210> SEQ ID NO 239
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile His Ser Asn Ser His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Tyr Glu Ser
                85                  90                  95

Glu Arg Val Val Phe Gly Gly Gly Thr Lys Leu Thr Val Leu
            100                 105                 110

<210> SEQ ID NO 240
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 240
gatatcgtgc tgacccagcc gccgagcgtg agcggtgcac cgggccagcg cgtgaccatt      60
agctgtagcg gcagcagcag caacattggt tctaactacg tgtcttggta ccagcagctg     120
ccgggcacgg cgccgaaact gctgatccat tctaactctc atcgcccgag cggcgtgccg     180
gatcgcttta gcggatccaa aagcggcacc agcgccagcc tggcgattac cggcctgcaa     240
```
gcagaagacg aagcggatta ttactgccag tcttgggact acgaatctga acgtgttgtg    300
tttggcggcg gcacgaagtt aaccgtccta                                      330

<210> SEQ ID NO 241
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile His Ser Asn Ser His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Tyr Glu Ser
                85                  90                  95

Glu Arg Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 242
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 242
gatatcgtgc tgacccagcc gccgagcgtg agcggtgcac cgggccagcg cgtgaccatt    60
agctgtagcg gcagcagcag caacattggt tctaactacg tgtcttggta ccagcagctg    120
ccgggcacgg cgccgaaact gctgatccat tctaactctc atcgcccgag cggcgtgccg    180
gatcgcttta gcggatccaa aagcggcacc agcgccagcc tggcgattac cggcctgcaa    240
gcagaagacg aagcggatta ttactgccag tcttgggact acgaatctga acgtgttgtg    300

```
tttggcggcg gcacgaagtt aaccgtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca acaagtacgc ggccagcagc    540
tatctgagcc tgacgcctga gcagtggaag tcccacagaa gctacagctg ccaggtcacg    600
catgaaggga gcaccgtgga agacagtgtg cccctacag aatgttca                 648
```

```
<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ser Gly Ala Ala Met His
1               5

<210> SEQ ID NO 244
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Ile Ser Ser Phe Ser Ser Ser Thr Asp Tyr Ala Asp Ser Val Lys
1               5                   10                  15
Gly

<210> SEQ ID NO 245
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asn Phe Lys Tyr Ala Met Asp Tyr
1               5

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Phe Thr Phe Arg Ser Gly Ala
1               5

<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 247

Ser Ser Phe Ser Ser Ser
1               5

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asn Phe Lys Tyr Ala Met Asp Tyr
1               5

<210> SEQ ID NO 249
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gln Val Gln Leu Leu Glu Ser Gly Gly Gly Leu Val Gln Ser Gly Gly
1               5                   10                  15

Ser Leu Arg Leu Ser Cys Ala Ala Ser Gly Phe Thr Phe Arg Ser Gly
            20                  25                  30

Ala Ala Met His Trp Val Arg Gln Ala Pro Gly Lys Gly Leu Glu Trp
        35                  40                  45

Val Ser Gly Ile Ser Ser Phe Ser Ser Thr Asp Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Phe Lys Tyr Ala Met Asp Tyr Trp Gly Gln Gly Thr
            100                 105                 110

Leu Val Thr Val Ser Ser
        115

<210> SEQ ID NO 250
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250
caggtgcaat tgctggaaag cggcggtggc ctggtgcagt cgggtggcag cctgcgtctg      60
agctgcgcgg cgtccggatt cacctttcgt tctggtgctg ctatgcattg ggtgcgccag     120
gccccgggca aggtctcga gtgggtttcc ggtatctctt ctttctcttc ttctaccgac     180
tatgcggata gcgtgaaagg ccgctttacc atcagccgcg ataattcgaa aaacaccctg     240
tatctgcaaa tgaacagcct gcgtgcggaa gatacggccg tgtattattg cgcgcgtaac     300
ttcaaatacg ctatggatta ctggggccaa ggcacccctgg tgactgttag ctca          354

<210> SEQ ID NO 251

```
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gln Val Gln Leu Leu Glu Ser Gly Gly Gly Leu Val Gln Ser Gly Gly
1               5                   10                  15

Ser Leu Arg Leu Ser Cys Ala Ala Ser Gly Phe Thr Phe Arg Ser Gly
            20                  25                  30

Ala Ala Met His Trp Val Arg Gln Ala Pro Gly Lys Gly Leu Glu Trp
        35                  40                  45

Val Ser Gly Ile Ser Ser Phe Ser Ser Ser Thr Asp Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Phe Lys Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
```

```
                370              375              380
Asn Gly Gln Pro Glu Asn Asn Tyr Lys Thr Thr Pro Pro Val Leu Asp
385              390              395              400

Ser Asp Gly Ser Phe Phe Leu Tyr Ser Lys Leu Thr Val Asp Lys Ser
            405              410              415

Arg Trp Gln Gln Gly Asn Val Phe Ser Cys Ser Val Met His Glu Ala
        420              425              430

Leu His Asn His Tyr Thr Gln Lys Ser Leu Ser Leu Ser Pro Gly Lys
        435              440              445

<210> SEQ ID NO 252
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
```

| | | | | | |
|---|---|---|---|---|---|
| caggtgcaat | tgctggaaag | cggcggtggc | ctggtgcagt | cgggtggcag | cctgcgtctg | 60 |
| agctgcgcgg | cgtccggatt | cacctttcgt | tctggtgctg | ctatgcattg | ggtgcgccag | 120 |
| gccccgggca | aggtctcga | gtgggtttcc | ggtatctctt | ctttctcttc | ttctaccgac | 180 |
| tatgcggata | gcgtgaaagg | ccgctttacc | atcagccgcg | ataattcgaa | aaacaccctg | 240 |
| tatctgcaaa | tgaacagcct | gcgtgcggaa | gatacggccg | tgtattattg | cgcgcgtaac | 300 |
| ttcaaatacg | ctatggatta | ctggggccaa | ggcaccctgg | tgactgttag | ctcagcctcc | 360 |
| accaagggtc | atcggtctt | cccctggca | ccctcctcca | gagcacctc | tgggggcaca | 420 |
| gcggccctgg | gctgcctggt | caaggactac | ttccccgaac | cggtgacggt | gtcgtggaac | 480 |
| tcaggcgccc | tgaccagcgg | cgtgcacacc | ttcccggctg | tcctacagtc | ctcaggactc | 540 |
| tactccctca | gcagcgtggt | gaccgtgccc | tccagcagct | gggcaccca | gacctacatc | 600 |
| tgcaacgtga | atcacaagcc | cagcaacacc | aaggtggaca | agagagttga | gcccaaatct | 660 |
| tgtgacaaaa | ctcacacatg | cccaccgtgc | ccagcacctg | aagcagcggg | ggaccgtca | 720 |
| gtcttcctct | tccccccaaa | acccaaggac | accctcatga | tctcccggac | ccctgaggtc | 780 |
| acatgcgtgg | tggtggacgt | gagccacgaa | gaccctgagg | tcaagttcaa | ctggtacgtg | 840 |
| gacggcgtgg | aggtgcataa | tgccaagaca | aagccgcggg | aggagcagta | caacagcacg | 900 |
| taccgggtgg | tcagcgtcct | caccgtcctg | caccaggact | ggctgaatgg | caaggagtac | 960 |
| aagtgcaagg | tctccaacaa | agccctccca | gcccccatcg | agaaaaccat | ctccaaagcc | 1020 |
| aaagggcagc | cccgagaacc | acaggtgtac | accctgcccc | catcccggga | ggagatgacc | 1080 |
| aagaaccagg | tcagcctgac | ctgcctggtc | aaaggcttct | atcccagcga | catcgccgtg | 1140 |
| gagtgggaga | gcaatgggca | gccggagaac | aactacaaga | ccacgcctcc | cgtgctggac | 1200 |
| tccgacggct | ccttcttcct | ctacagcaag | ctcaccgtgg | acaagagcag | gtggcagcag | 1260 |
| gggaacgtct | tctcatgctc | cgtgatgcat | gaggctctgc | acaaccacta | cacgcagaag | 1320 |
| agcctctccc | tgtctccggg | taaa | | | | 1344 |

```
<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 253

Thr Gly Thr Ser Ser Asp Val Gly Ser Ile Asn Tyr Val Ser
1               5                   10

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ala Val Ser Tyr Arg Pro Ser
1               5

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gln Val Trp Asp Trp Arg Ser Asp Ser Arg Val
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Thr Ser Ser Asp Val Gly Ser Ile Asn Tyr
1               5                   10

<210> SEQ ID NO 257
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ala Val Ser
1

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Trp Asp Trp Arg Ser Asp Ser Arg
1               5

<210> SEQ ID NO 259
<211> LENGTH: 110

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Ile
            20                  25                  30

Asn Tyr Val Ser Trp Tyr Gln Gln His Pro Gly Lys Ala Pro Lys Met
        35                  40                  45

Ile Tyr Ala Val Ser Tyr Arg Pro Ser Gly Val Ser Asn Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Gln Val Trp Asp Trp Arg Ser
                85                  90                  95

Asp Ser Arg Val Phe Gly Gly Gly Thr Lys Leu Thr Val Leu
                100                 105                 110

<210> SEQ ID NO 260
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260
gatatcgcgc tgacccagcc ggcgagcgtg agcggtagcc cgggccagag cattaccatt    60
agctgcaccg gcaccagcag cgatgtgggc tctatcaact acgtgtcttg gtaccagcag   120
catccgggca aggcgccgaa aatgatctac gctgtttctt accgtccgag cggcgtgagc   180
aaccgtttta gcggatccaa aagcggcaac accgcgagcc tgaccattag cggcctgcaa   240
gcggaagacg aagcggatta ttactgccag gtttgggact ggcgttctga ctctcgtgtg   300
tttggcggcg gcacgaagtt aaccgtccta                                    330

<210> SEQ ID NO 261
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Ile
            20                  25                  30

Asn Tyr Val Ser Trp Tyr Gln Gln His Pro Gly Lys Ala Pro Lys Met
        35                  40                  45

Ile Tyr Ala Val Ser Tyr Arg Pro Ser Gly Val Ser Asn Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Gln Val Trp Asp Trp Arg Ser
```

```
                    85                  90                  95
Asp Ser Arg Val Phe Gly Gly Gly Thr Lys Leu Thr Val Leu Gly Gln
            100                 105                 110
Pro Lys Ala Ala Pro Ser Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser
    210                 215

<210> SEQ ID NO 262
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 262
gatatcgcgc tgacccagcc ggcgagcgtg agcggtagcc cgggccagag cattaccatt      60
agctgcaccg gcaccagcag cgatgtgggc tctatcaact acgtgtcttg gtaccagcag     120
catccgggca aggcgccgaa aatgatctac gctgtttctt accgtccgag cggcgtgagc     180 aaccgttttta gcggatccaa aagcggcaac accgcgagcc tgaccattag cggcctgcaa     240
gcggaagacg aagcggatta ttactgccag gtttgggact ggcgttctga ctctcgtgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc     540 tatctgagcc tgacgcctga gcagtggaag tcccacagaa gctacagctg ccaggtcacg     600
catgaaggga gcaccgtgga agacagtgtg cccctacag aatgttca                    648

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Tyr Ala Leu Ser
1               5

<210> SEQ ID NO 264
<211> LENGTH: 19
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 264

Arg Ile Lys Ser Lys Thr Met Gly Gly Thr Ser Asp Tyr Ala Ala Pro
1               5                   10                  15

Val Lys Gly

<210> SEQ ID NO 265
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Asp Phe Trp Ala Asp His Tyr Tyr Tyr Phe Asp Tyr
1               5                   10

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gly Phe Thr Phe Ser Ser Tyr
1               5

<210> SEQ ID NO 267
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Lys Ser Lys Thr Met Gly Gly Thr
1               5

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asp Phe Trp Ala Asp His Tyr Tyr Tyr Phe Asp Tyr
1               5                   10

<210> SEQ ID NO 269
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Gln Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Lys Ser Lys Thr Met Gly Gly Thr Ser Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Trp Ala Asp His Tyr Tyr Phe Asp Tyr
            100                 105                 110

Trp Gly Gln Gly Thr Leu Val Thr Val Ser Ser
        115                 120
```

<210> SEQ ID NO 270
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 270

```
caggtgcaat tggtggaaag cggcggtggc ctggtgaaac aggcggcag cctgcgcctg      60 agctgcgccg cctccggatt caccttttct tcttacgctc tgtcttgggt gcgccaggcc    120
ccgggcaaag gtctcgagtg ggtgggccgt atcaaatcta aaactatggg tggtacttct    180
gactatgccg ccccagtgaa aggccgcttt accattagcc gcgatgattc gaaaaacacc    240
ctgtatctgc aaatgaacag cctgaaaacc gaagatacgg ccgtgtatta ttgcgcgcgt    300
gacttctggg ctgaccatta ctactacttc gattactggg gccaaggcac cctggtgact    360
gttagctca                                                            369
```

<210> SEQ ID NO 271
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 271

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Lys Ser Lys Thr Met Gly Gly Thr Ser Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Trp Ala Asp His Tyr Tyr Phe Asp Tyr
            100                 105                 110
```

-continued

```
Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 272
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 272
caggtgcaat tggtggaaag cggcggtggc ctggtgaaac aggcggcag cctgcgcctg      60
```

```
agctgcgccg cctccggatt caccttttct tcttacgctc tgtcttgggt gcgccaggcc    120
ccgggcaaag gtctcgagtg ggtgggccgt atcaaatcta aaactatggg tggtacttct    180
gactatgccg ccccagtgaa aggccgcttt accattagcc gcgatgattc gaaaaacacc    240
ctgtatctgc aaatgaacag cctgaaaacc gaagatacgg ccgtgtatta ttgcgcgcgt    300
gacttctggg ctgaccatta ctactacttc gattactggg gccaaggcac cctggtgact    360
gttagctcag cctccaccaa gggtccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca caccaaggt ggacaagaga     660
gttgagccca atcttgtga caaaactcac acatgcccac cgtgcccagc acctgaagca    720
gcgggggac cgtcagtctt cctcttcccc ccaaaaccca aggacaccct catgatctcc     780
cggacccctg aggtcacatg cgtggtggtg gacgtgagcc acgaagaccc tgaggtcaag    840
ttcaactggt acgtggacgg cgtggaggtg cataatgcca agacaaagcc gcggaggag     900
cagtacaaca gcacgtaccg ggtggtcagc gtcctcaccg tcctgcacca ggactggctg    960
aatggcaagg agtacaagtg caaggtctcc aacaaagccc tcccagcccc catcgagaaa    1020
accatctcca agccaaagg gcagccccga gaaccacagg tgtacaccct gcccccatcc     1080
cgggaggaga tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaa                          1359
```

<210> SEQ ID NO 273
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Thr Gly Thr Ser Ser Asp Val Gly Tyr Ile Asn Tyr Val Asn
1               5                   10

<210> SEQ ID NO 274
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Glu Val Ser Asn Arg Pro Ser
1               5

<210> SEQ ID NO 275
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Ala Ser Trp Asp Trp Tyr Asp Asn Val Val
1               5                   10

<210> SEQ ID NO 276
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Thr Ser Ser Asp Val Gly Tyr Ile Asn Tyr
1               5                   10

<210> SEQ ID NO 277
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Glu Val Ser
1

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Trp Asp Trp Tyr Asp Asn Val
1               5

<210> SEQ ID NO 279
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Ile
                20                  25                  30

Asn Tyr Val Asn Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Trp Asp Trp Tyr
                85                  90                  95

Asp Asn Val Val Phe Gly Gly Gly Thr Lys Leu Thr Val Leu

<210> SEQ ID NO 280
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 280

```
gatatcgcgc tgacccagcc ggcgagcgtg agcggtagcc cgggccagag cattaccatt      60
agctgcaccg gcaccagcag cgatgtgggc tacatcaact acgtgaactg gtaccagcag     120
catccgggca aggcgccgaa actgatgatc tacgaagttt ctaaccgtcc gagcggcgtg     180
agcaaccgtt ttagcggatc caaaagcggc aacaccgcga gcctgaccat tagcggcctg     240
caagcggaag acgaagcgga ttattactgc gcttcttggg actggtacga caacgttgtg     300
tttggcggcg gcacgaagtt aaccgtccta                                      330
```

<210> SEQ ID NO 281
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 281

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Ile
            20                  25                  30

Asn Tyr Val Asn Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Trp Asp Trp Tyr
                85                  90                  95

Asp Asn Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

```
<210> SEQ ID NO 282
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 282
gatatcgcgc tgacccagcc ggcgagcgtg agcggtagcc cgggccagag cattaccatt     60
agctgcaccg gcaccagcag cgatgtgggc tacatcaact acgtgaactg gtaccagcag    120
catccgggca aggcgccgaa actgatgatc tacgaagttt ctaaccgtcc gagcggcgtg    180
agcaaccgtt ttagcggatc caaaagcggc aacaccgcga gcctgaccat tagcggcctg    240
caagcggaag acgaagcgga ttattactgc gcttcttggg actggtacga caacgttgtg    300
tttggcggcg gcacgaagtt aaccgtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca acaagtacgc ggccagcagc    540
tatctgagcc tgacgcctga gcagtggaag tcccacagaa gctacagctg ccaggtcacg    600
catgaaggga gcaccgtgga agacagtg gcccctacag aatgttca                   648

<210> SEQ ID NO 283
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ser Tyr Ala Ile Ser
1               5

<210> SEQ ID NO 284
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Ile Ile Pro Ile Phe Gly Gly Ala Asn Tyr Ala Gln Lys Phe Gln
1               5                   10                  15

Gly

<210> SEQ ID NO 285
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Asp Pro Leu Tyr Arg Ser Asp Tyr Tyr Tyr His Trp Phe Asp Phe
1               5                   10                  15

<210> SEQ ID NO 286
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gly Gly Thr Phe Ser Ser Tyr
1               5

<210> SEQ ID NO 287
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ile Pro Ile Phe Gly Gly
1               5

<210> SEQ ID NO 288
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Asp Pro Leu Tyr Arg Ser Asp Tyr Tyr His Trp Phe Asp Phe
1               5                   10                  15

<210> SEQ ID NO 289
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Leu Tyr Arg Ser Asp Tyr Tyr His Trp Phe Asp
            100                 105                 110

Phe Trp Gly Gln Gly Thr Leu Val Thr Val Ser Ser
        115                 120

<210> SEQ ID NO 290
<211> LENGTH: 372
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 290
caggtgcaat tggtgcagag cggtgccgaa gtgaaaaaac cgggcagcag cgtgaaagtt    60
agctgcaaag catccggagg gacgtttttct tcttacgcta tctcttgggt gcgccaggcc  120
ccgggccagg gcctcgagtg gatgggccgt atcatcccga tcttcggcgg tgcgaactac  180
gcccagaaat tcagggccgg ggtgaccatt accgccgatg aaagcaccag caccgcctat  240
atggaactga gcagcctgcg cagcgaagat acggccgtgt attattgcgc gcgtgacccg  300
ctgtaccgtt ctgactacta ctaccattgg ttcgatttct ggggccaagg caccctggtg  360
actgttagct ca                                                       372

<210> SEQ ID NO 291
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Phe Gly Gly Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Leu Tyr Arg Ser Asp Tyr Tyr Tyr His Trp Phe Asp
            100                 105                 110

Phe Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

```
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 292
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 292
caggtgcaat tggtgcagag cggtgccgaa gtgaaaaaac cgggcagcag cgtgaaagtt      60
agctgcaaag catccggagg gacgttttct tcttacgcta tctcttgggt gcgccaggcc     120
ccgggccagg gcctcgagtg gatgggccgt atcatcccga tcttcggcgg tgcgaactac     180
gcccagaaat ttcagggccg ggtgaccatt accgccgatg aaagcaccag caccgcctat     240
atggaactga gcagcctgcg cagcgaagat acggccgtgt attattgcgc gcgtgacccg     300
ctgtaccgtt ctgactacta ctaccattgg ttcgatttct ggggccaagg caccctggtg     360
actgttagct cagcctccac caagggtcca tcggtcttcc ccctggcacc ctcctccaag     420
agcacctctg ggggcacagc ggccctgggc tgcctggtca aggactactt ccccgaaccg     480
gtgacggtgt cgtggaactc aggcgccctg accagcggcg tgcacacctt ccggctgtc      540 ctacagtcct caggactcta ctccctcagc agcgtggtga ccgtgccctc agcagcttg      600 ggcacccaga cctacatctg caacgtgaat cacaagccca gcaacaccaa ggtgacaag      660 agagttgagc ccaaatcttg tgacaaaact cacacatgcc caccgtgccc agcacctgaa     720
gcagcggggg gaccgtcagt cttcctcttc ccccaaaac ccaaggacac cctcatgatc      780
tcccggaccc ctgaggtcac atgcgtggtg gtggacgtga gccacgaaga ccctgaggtc     840
aagttcaact ggtacgtgga cggcgtggag gtgcataatg ccaagacaaa gccgcgggag     900
```

```
gagcagtaca acagcacgta ccgggtggtc agcgtcctca ccgtcctgca ccaggactgg    960
ctgaatggca aggagtacaa gtgcaaggtc tccaacaaag ccctcccagc ccccatcgag   1020
aaaaccatct ccaaagccaa agggcagccc cgagaaccac aggtgtacac cctgccccca   1080
tcccgggagg agatgaccaa gaaccaggtc agcctgacct gcctggtcaa aggcttctat   1140
cccagcgaca tcgccgtgga gtgggagagc aatgggcagc cggagaacaa ctacaagacc   1200
acgcctcccg tgctggactc cgacggctcc ttcttcctct acagcaagct caccgtggac   1260
aagagcaggt ggcagcaggg gaacgtcttc tcatgctccg tgatgcatga ggctctgcac   1320
aaccactaca cgcagaagag cctctccctg tctccgggta aa                      1362
```

<210> SEQ ID NO 293
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Thr Gly Thr Ser Ser Asp Val Gly Asn Phe Asn Tyr Val Ser
1               5                   10

<210> SEQ ID NO 294
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Val Asn Asn Arg Pro Ser
1               5

<210> SEQ ID NO 295
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ala Ala Tyr Gly Trp Ala Leu Asp Glu Val Val
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Thr Ser Ser Asp Val Gly Asn Phe Asn Tyr
1               5                   10

<210> SEQ ID NO 297
<211> LENGTH: 3
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 297

Gly Val Asn
1

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Tyr Gly Trp Ala Leu Asp Glu Val
1               5

<210> SEQ ID NO 299
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asn Phe
            20                  25                  30

Asn Tyr Val Ser Trp Tyr Gln Gln His Pro Gly Lys Ala Pro Lys Leu
        35                  40                  45

Met Ile Tyr Gly Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ala Tyr Gly Trp Ala
                85                  90                  95

Leu Asp Glu Val Val Phe Gly Gly Gly Thr Lys Leu Thr Val Leu
            100                 105                 110

<210> SEQ ID NO 300
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 300
gatatcgcgc tgacccagcc ggcgagcgtg agcggtagcc cgggccagag cattaccatt     60
agctgcaccg gcaccagcag cgatgtgggc aacttcaact acgtgtcttg gtaccagcag    120
catccgggca aggcgccgaa actgatgatc tacggtgtca acaaccgtcc gagcggcgtg    180
agcaaccgtt ttagcggatc caaaagcggc aacaccgcga gcctgaccat tagcggcctg    240
caagcggaag acgaagcgga ttattactgc gctgcttacg gttgggctct ggacgaagtt    300
gtgtttggcg gcggcacgaa gttaaccgtc cta                                 333

<210> SEQ ID NO 301

<211> LENGTH: 217
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 301

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asn Phe
            20                  25                  30

Asn Tyr Val Ser Trp Tyr Gln Gln His Pro Gly Lys Ala Pro Lys Leu
        35                  40                  45

Met Ile Tyr Gly Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ala Tyr Gly Trp Ala
                85                  90                  95

Leu Asp Glu Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 302
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 302
gatatcgcgc tgacccagcc ggcgagcgtg agcggtagcc cgggccagag cattaccatt      60
agctgcaccg gcaccagcag cgatgtgggc aacttcaact acgtgtcttg gtaccagcag     120
catccgggca aggcgccgaa actgatgatc tacggtgtca acaaccgtcc gagcggcgtg     180
agcaaccgtt ttagcggatc caaaagcggc aacaccgcga gcctgaccat tagcggcctg     240
caagcggaag acgaagcgga ttattactgc gctgcttacg gttgggctct ggacgaagtt     300
gtgtttggcg gcggcacgaa gttaaccgtc ctaggtcagc ccaaggctgc ccctcggtc      360 actctgttcc cgccctcctc tgaggagctt caagccaaca ggccacact ggtgtgtctc      420 ataagtgact tctacccggg agccgtgaca gtggcctgga aggcagatag cagccccgtc     480
aaggcgggag tggagaccac cacacccctcc aaacaaagca acaacaagta cgcggccagc     540

```
agctatctga gcctgacgcc tgagcagtgg aagtcccaca gaagctacag ctgccaggtc    600
acgcatgaag ggagcaccgt ggagaagaca gtggccccta cagaatgttc a            651
```

<210> SEQ ID NO 303
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

```
Asp Tyr Ala Leu His
1               5
```

<210> SEQ ID NO 304
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

```
Val Ile Ser Tyr Gln Gly Gly Phe Ile Tyr Tyr Ala Asp Ser Val Lys
1               5                   10                  15

Gly
```

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

```
Ser Pro Gly Leu Thr Ser Tyr His Asp Ser
1               5                   10
```

<210> SEQ ID NO 306
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

```
Gly Phe Thr Phe Ser Asp Tyr
1               5
```

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

```
Ser Tyr Gln Gly Gly Phe
1               5
```

<210> SEQ ID NO 308

<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Ser Pro Gly Leu Thr Ser Tyr His Asp Ser
1               5                   10

<210> SEQ ID NO 309
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 309

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu His Trp Val Arg Gln Ala Pro Gly Lys Gly Leu Glu Trp Val
        35                  40                  45

Ser Val Ile Ser Tyr Gln Gly Gly Phe Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Gly Leu Thr Ser Tyr His Asp Ser Trp Gly Gln Gly
            100                 105                 110

Thr Leu Val Thr Val Ser Ser
        115

<210> SEQ ID NO 310
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 310
caggtgcaat tgctggaaag cggcggtggc ctggtgcagc cgggtggcag cctgcgtctg    60
agctgcgcgg cgtccggatt cacctttct gactacgctc tgcattgggt gcgccaggcc   120
ccgggcaaag gtctcgagtg ggtttccgtt atctcttacc agggcggttt catctactat   180
gcggatagcg tgaaaggccg ctttaccatc agccgcgata attcgaaaaa caccctgtat   240
ctgcaaatga acagcctgcg tgcggaagat acggccgtgt attattgcgc gcgttctccg   300
ggtctgactt cttaccatga ttcttggggc caaggcaccc tggtgactgt tagctca      357

<210> SEQ ID NO 311
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 311

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu His Trp Val Arg Gln Ala Pro Gly Lys Gly Leu Glu Trp Val
        35                  40                  45

Ser Val Ile Ser Tyr Gln Gly Gly Phe Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Gly Leu Thr Ser Tyr His Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 312
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 312
caggtgcaat tgctggaaag cggcggtggc ctggtgcagc cgggtggcag cctgcgtctg     60
agctgcgcgg cgtccggatt cacctttct gactacgctc tgcattgggt cgcgccaggcc   120 ccgggcaaag gtctcgagtg gtttccgtt atctcttacc agggcggttt catctactat    180
gcggatagcg tgaaaggccg ctttaccatc agccgcgata attcgaaaaa caccctgtat   240
ctgcaaatga acagcctgcg tgcggaagat acggccgtgt attattgcgc gcgttctccg   300
ggtctgactt cttaccatga ttcttggggc caaggcaccc tggtgactgt tagctcagcc   360
tccaccaagg gtccatcggt cttccccctg caccctcct ccaagagcac ctctgggggc    420
acagcggccc tgggctgcct ggtcaaggac tacttcccg aaccggtgac ggtgtcgtgg    480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagagagt tgagcccaaa   660
tcttgtgaca aaactcacac atgcccaccg tgcccagcac ctgaagcagc ggggggaccg   720
tcagtcttcc tcttcccccc aaaacccaag gacaccctca tgatctcccg gacccctgag   780
gtcacatgcg tggtggtgga cgtgagccac gaagaccctg aggtcaagtt caactggtac   840
gtggacggcg tggaggtgca taatgccaag acaaagccgc gggaggagca gtacaacagc   900
acgtaccggg tggtcagcgt cctcaccgtc ctgcaccagg actggctgaa tggcaaggag   960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaa                                       1347

<210> SEQ ID NO 313
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ser Gly Ser Ser Ser Asn Ile Gly Ser Asn Tyr Val Ser
1               5                   10

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ser Thr Ser His Arg Pro Ser
1               5

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gln Ser Trp Asp Tyr Glu Ser Glu Arg Val Val
1               5                   10

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Ser Ser Ser Asn Ile Gly Ser Asn Tyr
1               5

<210> SEQ ID NO 317
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Ser Thr Ser
1

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Trp Asp Tyr Glu Ser Glu Arg Val
1               5

<210> SEQ ID NO 319
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Gln Ser Val Leu Thr Gln Pro Pro Ser Val Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile His Ser Thr Ser His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Tyr Glu Ser
                85                  90                  95

Glu Arg Val Val Phe Gly Gly Gly Thr Lys Leu Thr Val Leu
            100                 105                 110

<210> SEQ ID NO 320
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 320
cagagcgtgc tgacccagcc gccgagcgtg agcggtgcac cgggccagcg cgtgaccatt      60
agctgtagcg gcagcagcag caacattggt tctaactacg tgtcttggta ccagcagctg     120
ccgggcacgg cgccgaaact gctgatccat tctacctctc atcgcccgag cggcgtgccg     180
gatcgcttta gcggatccaa aagcggcacc agcgccagcc tggcgattac cggcctgcaa     240
gcagaagacg aagcggatta ttactgccag tcttgggact acgaatctga acgtgttgtg     300
tttggcggcg gcacgaagtt aaccgtccta                                      330

<210> SEQ ID NO 321
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Gln Ser Val Leu Thr Gln Pro Pro Ser Val Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile His Ser Thr Ser His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Tyr Glu Ser
                85                  90                  95

Glu Arg Val Val Phe Gly Gly Gly Thr Lys Leu Thr Val Leu Gly Gln
            100                 105                 110

```
Pro Lys Ala Ala Pro Ser Val Thr Leu Phe Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 322
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 322

```
cagagcgtgc tgacccagcc gccgagcgtg agcggtgcac cgggccagcg cgtgaccatt      60
agctgtagcg gcagcagcag caacattggt tctaactacg tgtcttggta ccagcagctg     120
ccgggcacgg cgccgaaact gctgatccat tctacctctc atcgcccgag cggcgtgccg     180
gatcgcttta gcggatccaa agcggcacc agcgccagcc tggcgattac cggcctgcaa      240
gcagaagacg aagcggatta ttactgccag tcttgggact acgaatctga acgtgttgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc     540
tatctgagcc tgacgcctga gcagtggaag tcccacagaa gctacagctg ccaggtcacg     600
catgaaggga gcaccgtgga agacagtgt gcccctacag aatgttca                  648
```

<210> SEQ ID NO 323
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 323

```
Asp Tyr Ala Leu His
1               5
```

<210> SEQ ID NO 324
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

```
Val Ile Ser Tyr Ala Gly Gly Phe Lys Phe Tyr Ala Asp Ser Val Lys
1               5                   10                  15

Gly

<210> SEQ ID NO 325
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ser Pro Gly Leu Thr Ser Tyr His Asp Ser
1               5                   10

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Phe Thr Phe Ser Asp Tyr
1               5

<210> SEQ ID NO 327
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Ser Tyr Ala Gly Gly Phe
1               5

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Ser Pro Gly Leu Thr Ser Tyr His Asp Ser
1               5                   10

<210> SEQ ID NO 329
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu His Trp Val Arg Gln Ala Pro Gly Lys Gly Leu Glu Trp Val
```

```
                35                  40                  45
Ser Val Ile Ser Tyr Ala Gly Gly Phe Lys Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Pro Gly Leu Thr Ser Tyr His Asp Ser Trp Gly Gln Gly
                100                 105                 110

Thr Leu Val Thr Val Ser Ser
            115

<210> SEQ ID NO 330
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 330
caggtgcaat tgctggaaag cggcggtggc ctggtgcagc cgggtggcag cctgcgtctg      60
agctgcgcgg cgtccggatt caccttttct gactacgctc tgcattgggt gcgccaggcc    120
ccgggcaaag gtctcgagtg gtttccgtta tctcttacg ctggcggttt caaattctat      180
gcggatagcg tgaaaggccg ctttaccatc agccgcgata attcgaaaaa caccctgtat    240
ctgcaaatga acagcctgcg tgcggaagat acggccgtgt attattgcgc gcgttctccg    300
ggtctgactt cttaccatga ttcttggggc caaggcaccc tggtgactgt tagctca      357

<210> SEQ ID NO 331
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Gln Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Ala Leu His Trp Val Arg Gln Ala Pro Gly Lys Gly Leu Glu Trp Val
             35                  40                  45

Ser Val Ile Ser Tyr Ala Gly Gly Phe Lys Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Pro Gly Leu Thr Ser Tyr His Asp Ser Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
```

```
                145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Arg Val Glu Pro Lys Ser Cys Asp Lys
                210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys
```

<210> SEQ ID NO 332
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 332

| | | |
|---|---|---|
| caggtgcaat tgctggaaag cggcggtggc ctggtgcagc cgggtggcag cctgcgtctg | | 60 |
| agctgcgcgg cgtccggatt cacctttcct gactacgctc tgcattgggt gcgccaggcc | | 120 |
| ccgggcaaag gtctcgagtg ggtttccgtt atctcttacg ctggcggttt caaattctat | | 180 |
| gcggatagcg tgaaaggccg ctttaccatc agccgcgata ttcgaaaaa caccctgtat | | 240 |
| ctgcaaatga acagcctgcg tgcggaagat acggccgtgt attattgcgc gcgttctccg | | 300 |

```
ggtctgactt cttaccatga ttcttggggc caaggcaccc tggtgactgt tagctcagcc    360
tccaccaagg gtccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaagcagc ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccggg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 333
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ser Gly Ser Ser Ser Asn Ile Gly Ser Asn Tyr Val Ser
1               5                   10

<210> SEQ ID NO 334
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Ser Ser Ser His Arg Pro Ser
1               5

<210> SEQ ID NO 335
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gln Ser Trp Asp Tyr Glu Ser Glu Arg Val Val
1               5                   10

```
<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ser Ser Ser Asn Ile Gly Ser Asn Tyr
1               5

<210> SEQ ID NO 337
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ser Ser Ser
1

<210> SEQ ID NO 338
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Trp Asp Tyr Glu Ser Glu Arg Val
1               5

<210> SEQ ID NO 339
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
                20                  25                  30

Tyr Val Ser Trp Tyr Gln Gln Leu Pro Gly Thr Ala Pro Lys Leu Leu
            35                  40                  45

Ile His Ser Ser His Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Tyr Glu Ser
                85                  90                  95

Glu Arg Val Val Phe Gly Gly Gly Thr Lys Leu Thr Val Leu
            100                 105                 110

<210> SEQ ID NO 340
<211> LENGTH: 330
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 340

```
cagagcgtgc tgacccagcc gccgagcgtg agcggtgcac cgggccagcg cgtgaccatt    60
agctgtagcg gcagcagcag caacattggt tctaactacg tgtcttggta ccagcagctg   120
ccgggcacgg cgccgaaact gctgatccat tctagctctc atcgcccgag cggcgtgccg   180
gatcgcttta gcggatccaa aagcggcacc agcgccagcc tggcgattac cggcctgcaa   240
gcagaagacg aagcggatta ttactgccag tcttgggact acgaatctga acgtgttgtg   300
tttggcggcg gcacgaagtt aaccgtccta                                    330
```

<210> SEQ ID NO 341
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Gln Ser Val Leu Thr Gln Pro Pro Ser Val Ser Gly Ala Pro Gly Gln
1               5                   10                  15
Arg Val Thr Ile Ser Cys Ser Gly Ser Ser Ser Asn Ile Gly Ser Asn
            20                  25                  30
Tyr Val Ser Trp Tyr Gln Gln Leu Pro Gly Thr Ala Pro Lys Leu Leu
        35                  40                  45
Ile His Ser Ser Ser His Arg Pro Ser Gly Val Pro Asp Arg Phe Ser
    50                  55                  60
Gly Ser Lys Ser Gly Thr Ser Ala Ser Leu Ala Ile Thr Gly Leu Gln
65                  70                  75                  80
Ala Glu Asp Glu Ala Asp Tyr Tyr Cys Gln Ser Trp Asp Tyr Glu Ser
                85                  90                  95
Glu Arg Val Val Phe Gly Gly Gly Thr Lys Leu Thr Val Leu Gly Gln
            100                 105                 110
Pro Lys Ala Ala Pro Ser Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser
    210                 215

<210> SEQ ID NO 342
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 342

```
cagagcgtgc tgacccagcc gccgagcgtg agcggtgcac cgggccagcg cgtgaccatt    60
agctgtagcg gcagcagcag caacattggt tctaactacg tgtcttggta ccagcagctg   120
ccgggcacgg cgccgaaact gctgatccat tctagctctc atcgcccgag cggcgtgccg   180
gatcgcttta gcggatccaa aagcggcacc agcgccagcc tggcgattac cggcctgcaa   240
gcagaagacg aagcggatta ttactgccag tcttgggact acgaatctga acgtgttgtg   300
tttggcggcg gcacgaagtt aaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca caagtacgc ggccagcagc    540
tatctgagcc tgacgcctga gcagtggaag tcccacagaa gctacagctg ccaggtcacg   600
catgaaggga gcaccgtgga agacagtg gcccctacag aatgttca                  648
```

<210> SEQ ID NO 343
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Ser Tyr Ala Leu Ser
1               5

<210> SEQ ID NO 344
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Arg Thr Lys His Glu Asn Glu Gly Tyr Thr Thr Trp Tyr Ala Ala Ser
1               5                   10                  15

Val Lys Gly

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

Asp Phe Trp Ala Asp His Tyr Tyr Tyr Phe Asp Tyr
1               5                   10

<210> SEQ ID NO 346
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Gly Phe Thr Phe Ser Ser Tyr
1               5

<210> SEQ ID NO 347
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Lys His Glu Asn Glu Gly Tyr Thr
1               5

<210> SEQ ID NO 348
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Asp Phe Trp Ala Asp His Tyr Tyr Tyr Phe Asp Tyr
1               5                   10

<210> SEQ ID NO 349
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Thr Lys His Glu Asn Glu Gly Tyr Thr Thr Trp Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Trp Ala Asp His Tyr Tyr Tyr Phe Asp Tyr
            100                 105                 110

Trp Gly Gln Gly Thr Leu Val Thr Val Ser Ser
        115                 120

<210> SEQ ID NO 350
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 350
caggtgcaat tggtggaaag cggcggtggc ctggtgaaac caggcggcag cctgcgcctg      60

```
agctgcgccg cctccggatt cacctttct tcttacgctc tgtcttgggt gcgccaggcc    120
ccgggcaaag gtctcgagtg ggtgggccgt actaaacatg aaaacgaagg ctacactact    180
tggtatgccg cctctgtgaa aggccgcttt accattagcc gcgatgattc gaaaaacacc    240
ctgtatctgc aaatgaacag cctgaaaacc gaagatacgg ccgtgtatta ttgcgcgcgt    300
gacttctggg ctgaccatta ctactacttc gattactggg gccaaggcac cctggtgact    360
gttagctca                                                            369
```

<210> SEQ ID NO 351
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Thr Lys His Glu Asn Glu Gly Tyr Thr Thr Trp Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Trp Ala Asp His Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 352
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 352
caggtgcaat tggtggaaag cggcggtggc ctggtgaaac aggcggcag cctgcgcctg      60 agctgcgccg cctccggatt caccttttct tcttacgctc tgtcttgggt gcgccaggcc    120
ccgggcaaag gtctcgagtg ggtgggccgt actaaacatg aaaacgaagg ctacactact    180
tggtatgccg cctctgtgaa aggccgcttt accattagcc gcgatgattc gaaaaacacc    240
ctgtatctgc aaatgaacag cctgaaaacc gaagatacgg ccgtgtatta ttgcgcgcgt    300
gacttctggg ctgaccatta ctactacttc gattactggg gccaaggcac cctggtgact    360
gttagctcag cctccaccaa gggtccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca caccaaggt ggacaagaga    660 gttgagccca aatcttgtga caaaactcac acatgcccac cgtgcccagc acctgaagca    720
gcggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcggaggag    900 cagtacaaca gcacgtaccg ggtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagcccga gaaccacagg tgtacaccct gcccccatcc   1080
cgggaggaga tgaccaagaa ccaggtcagc ctgacctgcc tggtcaaagg cttctatccc   1140

```
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaa                           1359
```

```
<210> SEQ ID NO 353
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Thr Gly Thr Ser Ser Asp Val Gly Tyr Ile Asn Tyr Val Asn
1               5                   10

<210> SEQ ID NO 354
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Glu Val Ser Asn Arg Pro Ser
1               5

<210> SEQ ID NO 355
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Ala Ser Trp Asp Trp Tyr Asp Asn Val Val
1               5                   10

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Thr Ser Ser Asp Val Gly Tyr Ile Asn Tyr
1               5                   10

<210> SEQ ID NO 357
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Glu Val Ser
1
```

<210> SEQ ID NO 358
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Trp Asp Trp Tyr Asp Asn Val
1               5

<210> SEQ ID NO 359
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Ile
            20                  25                  30

Asn Tyr Val Asn Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Trp Asp Trp Tyr
                85                  90                  95

Asp Asn Val Val Phe Gly Gly Gly Thr Lys Leu Thr Val Leu
            100                 105                 110

<210> SEQ ID NO 360
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 360
cagagcgcgc tgacccagcc ggcgagcgtg agcggtagcc cgggccagag cattaccatt     60
agctgcaccg gcaccagcag cgatgtgggc tacatcaact acgtgaactg gtaccagcag    120
catccgggca aggcgccgaa actgatgatc tacgaagttt ctaaccgtcc gagcggcgtg    180
agcaaccgtt ttagcggatc caaaagcggc aacaccgcga gcctgaccat tagcggcctg    240
caagcggaag acgaagcgga ttattactgc gcttcttggg actggtacga caacgttgtg    300
tttggcggcg gcacgaagtt aaccgtccta                                     330

<210> SEQ ID NO 361
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Tyr Ile
             20                  25                  30

Asn Tyr Val Asn Trp Tyr Gln Gln His Pro Gly Lys Ala Pro Lys Leu
         35                  40                  45

Met Ile Tyr Glu Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Trp Asp Trp Tyr
                 85                  90                  95

Asp Asn Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 362
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 362
cagagcgcgc tgacccagcc ggcgagcgtg agcggtagcc cgggccagag cattaccatt      60
agctgcaccg gcaccagcag cgatgtgggc tacatcaact acgtgaactg gtaccagcag     120
catccgggca aggcgccgaa actgatgatc tacgaagttt ctaaccgtcc gagcggcgtg     180
agcaaccgtt ttagcggatc caaaagcggc aacaccgcga gcctgaccat tagcggcctg     240
caagcggaag acgaagcgga ttattactgc gcttcttggg actggtacga caacgttgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
tatctgagcc tgacgcctga gcagtggaag tcccacagaa gctacagctg ccaggtcacg     600
catgaaggga gcaccgtgga agacagtgtg ccctacagaa tgttca                    648

<210> SEQ ID NO 363
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ser Tyr Ala Leu Ser
1               5

<210> SEQ ID NO 364
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Arg Ile Lys Leu Ile Asn Lys Gly Tyr Thr Thr Trp Tyr Ala Ala Ser
1               5                   10                  15

Val Lys Gly

<210> SEQ ID NO 365
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Asp Phe Trp Ala Asp His Tyr Tyr Tyr Phe Asp Tyr
1               5                   10

<210> SEQ ID NO 366
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gly Phe Thr Phe Ser Ser Tyr
1               5

<210> SEQ ID NO 367
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Lys Leu Ile Asn Lys Gly Tyr Thr
1               5

<210> SEQ ID NO 368
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368
```

Asp Phe Trp Ala Asp His Tyr Tyr Phe Asp Tyr
1               5                   10

<210> SEQ ID NO 369
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Lys Leu Ile Asn Lys Gly Tyr Thr Thr Trp Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Trp Ala Asp His Tyr Tyr Phe Asp Tyr
            100                 105                 110

Trp Gly Gln Gly Thr Leu Val Thr Val Ser Ser
        115                 120

<210> SEQ ID NO 370
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 370
caggtgcaat tggtggaaag cggcggtggc ctggtgaaac caggcggcag cctgcgcctg     60
agctgcgccg cctccggatt cacctttttct tcttacgctc tgtcttgggt gcgccaggcc    120
ccgggcaaag gtctcgagtg ggtgggccgt atcaaactga tcaacaaagg ctacactact    180
tggtatgccg cctctgtgaa aggccgcttt accattagcc gcgatgattc gaaaaacacc    240
ctgtatctgc aaatgaacag cctgaaaacc gaagatacgg ccgtgtatta ttgcgcgcgt    300
gacttctggg ctgaccatta ctactacttc gattactggg gccaaggcac cctggtgact    360
gttagctca                                                            369

<210> SEQ ID NO 371
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr

```
            20                  25                  30
Ala Leu Ser Trp Val Arg Gln Ala Pro Gly Lys Gly Leu Glu Trp Val
        35                  40                  45
Gly Arg Ile Lys Leu Ile Asn Lys Gly Tyr Thr Thr Trp Tyr Ala Ala
 50                  55                  60
Ser Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Val Tyr
                85                  90                  95
Tyr Cys Ala Arg Asp Phe Trp Ala Asp His Tyr Tyr Phe Asp Tyr
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Ser Ser Lys Ser Thr Ser Gly Gly
                130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Arg Val Glu Pro Lys
                210                 215                 220
Ser Cys Asp Lys Thr His Thr Cys Pro Pro Cys Pro Ala Pro Glu Ala
225                 230                 235                 240
Ala Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn Ser
                290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
                355                 360                 365
Val Ser Leu Thr Cys Leu Val Lys Gly Phe Tyr Pro Ser Asp Ile Ala
                370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
                435                 440                 445
```

Leu Ser Pro Gly Lys
    450

<210> SEQ ID NO 372
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 372

| caggtgcaat tggtggaaag cggcggtggc ctggtgaaac caggcggcag cctgcgcctg | 60 |
| agctgcgccg cctccggatt caccttttct tcttacgctc tgtcttgggt gcgccaggcc | 120 |
| ccgggcaaag gtctcgagtg gtgggccgt atcaaactga tcaacaaagg ctacactact | 180 |
| tggtatgccg cctctgtgaa aggccgcttt accattagcc gcgatgattc gaaaaacacc | 240 |
| ctgtatctgc aaatgaacag cctgaaaacc gaagatacgg ccgtgtatta ttgcgcgcgt | 300 |
| gacttctggg ctgaccatta ctactacttc gattactggg gccaaggcac cctggtgact | 360 |
| gttagctcag cctccaccaa gggtccatcg gtcttccccc tggcaccctc ctccaagagc | 420 |
| acctctgggg gcacagcggc cctgggctgc ctggtcaagg actacttccc cgaaccggtg | 480 |
| acggtgtcgt ggaactcagg cgccctgacc agcggcgtgc acaccttccc ggctgtccta | 540 |
| cagtcctcag gactctactc cctcagcagc gtggtgaccg tgccctccag cagcttgggc | 600 |
| acccagacct acatctgcaa cgtgaatcac aagcccagca caccaaggt ggacaagaga | 660 |
| gttgagccca atcttgtga caaaactcac acatgcccac cgtgcccagc acctgaagca | 720 |
| gcggggggac cgtcagtctt cctcttcccc ccaaaaccca aggacaccct catgatctcc | 780 |
| cggacccctg aggtcacatg cgtggtggtg gacgtgagcc acgaagaccc tgaggtcaag | 840 |
| ttcaactggt acgtggacgg cgtggaggtg cataatgcca agacaaagcc gcgggaggag | 900 |
| cagtacaaca gcacgtaccg ggtggtcagc gtcctcaccg tcctgcacca ggactggctg | 960 |
| aatggcaagg agtacaagtg caaggtctcc aacaaagccc tcccagcccc catcgagaaa | 1020 |
| accatctcca aagccaaagg gcagccccga gaaccacagg tgtacaccct gcccccatcc | 1080 |
| cgggaggaga tgaccaagaa ccaggtcagc ctgacctgcc tggtcaaagg cttctatccc | 1140 |
| agcgacatcg ccgtggagtg ggagagcaat gggcagccgg agaacaacta caagaccacg | 1200 |
| cctcccgtgc tggactccga cggctccttc ttcctctaca gcaagctcac cgtggacaag | 1260 |
| agcaggtggc agcaggggaa cgtcttctca tgctccgtga tgcatgaggc tctgcacaac | 1320 |
| cactacacgc agaagagcct ctccctgtct ccgggtaaa | 1359 |

<210> SEQ ID NO 373
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Thr Gly Thr Ser Ser Asp Val Gly Tyr Ile Asn Tyr Val Asn
1               5                   10

<210> SEQ ID NO 374
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 374

Glu Val Ser Asn Arg Pro Ser
1               5

<210> SEQ ID NO 375
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ala Ser Trp Asp Trp Tyr Asp Asn Val Val
1               5                   10

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Thr Ser Ser Asp Val Gly Tyr Ile Asn Tyr
1               5                   10

<210> SEQ ID NO 377
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Glu Val Ser
1

<210> SEQ ID NO 378
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Trp Asp Trp Tyr Asp Asn Val
1               5

<210> SEQ ID NO 379
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Gln Ser Ala Leu Thr Gln Pro Ala Ser Val Ser Gly Ser Pro Gly Gln
1               5                   10                  15
```

```
Ser Ile Thr Ile Ser Cys Thr Gly Thr Ser Ser Asp Val Gly Tyr Ile
            20                  25                  30

Asn Tyr Val Asn Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Trp Asp Trp Tyr
                85                  90                  95

Asp Asn Val Val Phe Gly Gly Gly Thr Lys Leu Thr Val Leu
            100                 105                 110

<210> SEQ ID NO 380
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 380
cagagcgcgc tgacccagcc ggcgagcgtg agcggtagcc cgggccagag cattaccatt    60
agctgcaccg gcaccagcag cgatgtgggc tacatcaact acgtgaactg gtaccagcag   120
catccgggca aggcgccgaa actgatgatc tacgaagttt ctaaccgtcc gagcggcgtg   180
agcaaccgtt ttagcggatc caaaagcggc aacaccgcga gcctgaccat tagcggcctg   240
caagcggaag acgaagcgga ttattactgc gcttcttggg actggtacga caacgttgtg   300
tttggcggcg gcacgaagtt aaccgtccta                                    330

<210> SEQ ID NO 381
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Ile
            20                  25                  30

Asn Tyr Val Asn Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Trp Asp Trp Tyr
                85                  90                  95

Asp Asn Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140
```

```
Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 382
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 382

```
cagagcgcgc tgacccagcc ggcgagcgtg agcggtagcc cgggccagag cattaccatt      60
agctgcaccg gcaccagcag cgatgtgggc tacatcaact acgtgaactg gtaccagcag     120
catccgggca aggcgccgaa actgatgatc tacgaagttt ctaaccgtcc gagcggcgtg     180
agcaaccgtt ttagcggatc caaaagcggc aacaccgcga gcctgaccat tagcggcctg     240
caagcggaag acgaagcgga ttattactgc gcttcttggg actggtacga caacgttgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
tatctgagcc tgacgcctga gcagtggaag tcccacagaa gctacagctg ccaggtcacg     600
catgaaggga gcaccgtgga agacagtgcc ccctacagaa atgttca                  648
```

<210> SEQ ID NO 383
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 383

```
His His His His His His
1               5
```

<210> SEQ ID NO 384
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 384

```
Gly Leu Asn Asp Ile Phe Glu Ala Gln Lys Ile Glu Trp His Glu
1               5                   10                  15
```

<210> SEQ ID NO 385

<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Glu Phe Arg His Gly Leu Asn Asp Ile Phe Glu Ala Gln Lys Ile Glu
1               5                   10                  15

Trp His Glu Ser Gln Val Ser Asn Leu Leu Lys Gln Gln Thr Asn
            20                  25                  30

Leu Thr His Gln Lys Asn Lys Leu Glu Gly Gln Ile Ser Ala Arg Gln
        35                  40                  45

Gln Ala Glu Glu Ala Ser Gln Glu Ser Gln Asn Glu Leu Lys Glu Met
    50                  55                  60

Ile Glu Thr Leu Ala Trp Lys Leu Asn Glu Lys Ser Lys Glu Gln Met
65                  70                  75                  80

Glu Leu His His Gln Asn Leu Asn Leu Gln Glu Thr Leu Lys Arg Val
                85                  90                  95

Ala Asn Cys Ser Ala Pro Cys Pro Gln Asp Trp Ile Trp His Glu Glu
            100                 105                 110

Asn Cys Tyr Leu Phe Ser Thr Gly Ser Phe Asn Trp Glu Lys Ser Gln
        115                 120                 125

Glu Lys Cys Leu Ser Leu Asp Ala Lys Leu Leu Lys Ile Asn Ser Thr
    130                 135                 140

Ala Asp Leu Asp Phe Ile Gln Gln Ala Ile Ser Tyr Ser Ser Phe Pro
145                 150                 155                 160

Phe Trp Met Gly Leu Ser Arg Arg Asn Pro Ser Tyr Pro Trp Leu Trp
                165                 170                 175

Glu Asp Gly Ser Pro Leu Met Pro His Leu Phe Arg Ile Arg Gly Ala
            180                 185                 190

Val Ser Gln Thr Tyr Pro Ser Gly Thr Cys Ala Tyr Ile Gln Arg Gly
        195                 200                 205

Ala Val Tyr Ala Glu Asn Cys Ile Leu Ala Ala Phe Ser Ile Cys Gln
    210                 215                 220

Lys Lys Ala Asn Leu Arg Ala Gln
225                 230

<210> SEQ ID NO 386
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Met Gly Arg Val Ile Arg Pro Tyr Tyr Gly Trp Thr Glu Tyr Ala Gln
1               5                   10                  15

Lys Phe Gln Gly
            20

<210> SEQ ID NO 387
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Met Gly Gly Ile Gln Pro Gly Phe Ala Gly Ala Trp Tyr Ala Gln Lys
1               5                   10                  15

Phe Gln Gly

<210> SEQ ID NO 388
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Met Gly Ala Ile Met Pro Lys Phe Ala Gly Trp Pro Gln Tyr Ala Gln
1               5                   10                  15

Lys Phe Gln Gly
            20

<210> SEQ ID NO 389
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Met Gly Arg Ile Phe Pro Gly Lys Ser Glu Thr Ser Tyr Ser Pro Ser
1               5                   10                  15

Phe Gln Gly

<210> SEQ ID NO 390
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Met Gly Arg Ile Glu Pro Leu Ser Ser Thr Thr Glu Tyr Ser Pro Ser
1               5                   10                  15

Phe Gln Gly

<210> SEQ ID NO 391
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Met Gly Ala Ile Arg Pro Glu Trp Ser Glu Thr Lys Tyr Ser Pro Ser
1               5                   10                  15

Phe Gln Gly

<210> SEQ ID NO 392
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 392

Val Ser Ser Ile Ser Tyr Val Gly Gly Phe Ile Tyr Tyr Ala Asp Ser
1               5                   10                  15

Val Lys Gly

<210> SEQ ID NO 393
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Val Ser Val Ile Ser Tyr Val Gly Gly Phe Lys Phe Tyr Ala Asp Ser
1               5                   10                  15

Val Lys Gly

<210> SEQ ID NO 394
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Val Ser Val Ile Ser Tyr Gln Gly Gly Phe Ile Tyr Tyr Ala Asp Ser
1               5                   10                  15

Val Lys Gly

<210> SEQ ID NO 395
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Val Ser Val Ile Ser Tyr Ala Gly Gly Phe Thr Tyr Tyr Ala Asp Ser
1               5                   10                  15

Val Lys Gly

<210> SEQ ID NO 396
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Val Ser Gly Ile Ser Tyr Gln Gly Gly Phe Ile Phe Tyr Ala Asp Ser
1               5                   10                  15

Val Lys Gly

<210> SEQ ID NO 397
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 397

Val Ser Val Ile Ser Tyr Met Gly Gly Phe Lys Tyr Tyr Ala Asp Ser
1               5                   10                  15

Val Lys Gly

<210> SEQ ID NO 398
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Val Ser Leu Ile Ser Tyr Gln Gly Gly Phe Lys Tyr Tyr Ala Asp Ser
1               5                   10                  15

Val Lys Gly

<210> SEQ ID NO 399
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Val Ser Val Ile Ser Tyr Gln Gly Ala Phe Ile Tyr Tyr Ala Asp Ser
1               5                   10                  15

Val Lys Gly

<210> SEQ ID NO 400
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Val Ser Val Ile Ser Tyr Met Gly Gly Phe Lys Phe Tyr Ala Asp Ser
1               5                   10                  15

Val Lys Gly

<210> SEQ ID NO 401
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Val Ser Val Ile Ser Tyr Gln Gly Gly Phe Thr Phe Tyr Ala Asp Ser
1               5                   10                  15

Val Lys Gly

<210> SEQ ID NO 402
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 402

Val Ser Val Ile Ser Tyr Ala Gly Gly Phe Lys Phe Tyr Ala Asp Ser
1               5                   10                  15

Val Lys Gly

<210> SEQ ID NO 403
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Val Ser Ala Ile Ser Tyr Gln Gly Gly Phe Ile Phe Tyr Ala Asp Ser
1               5                   10                  15

Val Lys Gly

<210> SEQ ID NO 404
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Val Ser Val Ile Ser Tyr Ala Gly Ala Phe Thr Tyr Tyr Ala Asp Ser
1               5                   10                  15

Val Lys Gly

<210> SEQ ID NO 405
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Val Ser Ser Ile Glu Tyr Phe Gly Ser Ala Thr Leu Tyr Ala Asp Ser
1               5                   10                  15

Val Lys Gly

<210> SEQ ID NO 406
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Val Gly Arg Thr Lys His Glu Asn Glu Gly Tyr Thr Thr Trp Tyr Ala
1               5                   10                  15

Ala Ser Val Lys Gly
            20

<210> SEQ ID NO 407
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Val Gly Arg Ile Lys Leu Ile Asn Lys Gly Tyr Thr Thr Trp Tyr Ala
1               5                   10                  15

Ala Ser Val Lys Gly
            20

<210> SEQ ID NO 408
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Val Gly Arg Ile Arg His Tyr Lys Trp Gly Gly Thr Thr Glu Tyr Ala
1               5                   10                  15

Ala Pro Val Lys Gly
            20

<210> SEQ ID NO 409
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Val Gly Arg Ile Arg Tyr Trp Pro Asp Gly Tyr Thr Thr His Tyr Ala
1               5                   10                  15

Ala Ser Val Lys Gly
            20

<210> SEQ ID NO 410
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Val Gly Arg Thr Arg Met Trp Thr Val Gly Tyr Thr Thr His Tyr Ala
1               5                   10                  15

Ala Ser Val Lys Gly
            20

<210> SEQ ID NO 411
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Met Gly Arg Ile Val Pro Gly Phe Val Tyr Thr Ser Tyr Ala Gln Lys
1               5                   10                  15
```

Phe Gln Gly

<210> SEQ ID NO 412
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Met Gly Arg Ile Ile Pro Gln Trp Ala Gly Thr Pro Glu Tyr Ala Gln
1               5                   10                  15

Lys Phe Gln Gly
            20

<210> SEQ ID NO 413
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Met Gly Gly Ile Met Pro Ile Ser Gly Ala Pro Tyr Tyr Ala Gln Lys
1               5                   10                  15

Phe Gln Gly

<210> SEQ ID NO 414
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Met Gly Gly Ile Val Pro Ile Leu Gly Ala Ala Asn Tyr Ala Gln Lys
1               5                   10                  15

Phe Gln Gly

<210> SEQ ID NO 415
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Gln Gln Met Trp Gln Phe Pro Ile
1               5

<210> SEQ ID NO 416
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gln Gln Met Gln Thr Ser Leu Ile
1               5

```
<210> SEQ ID NO 417
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Gln Gln Met Lys Ile Ser Leu Ile
1               5

<210> SEQ ID NO 418
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Gln Gln Met His Arg His Pro Ile
1               5

<210> SEQ ID NO 419
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Gln Gln Met His Arg Phe Pro Met
1               5

<210> SEQ ID NO 420
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Gln Gln Met Gln Glu Ser Leu Leu
1               5

<210> SEQ ID NO 421
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gln Gln Met Lys Thr Phe Pro Ile
1               5

<210> SEQ ID NO 422
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 422

Gln Gln Met His Arg Leu Pro Val
1               5
```

METHODS OF TREATING CARDIOVASCULAR DISORDERS WITH LECTIN-LIKE OXIDIZED LDL RECEPTOR 1 ANTIBODIES

BACKGROUND OF THE INVENTION

Vascular disease remains one of the leading causes of morbidity and mortality worldwide. Drugs targeting conventional risk factors lower part of the vascular risk. However, experimental and clinical data suggest that other novel factors may explain the greater part of the risk for coronary, cerebral and peripheral arterial diseases and their clinical manifestations.

Dysregulated uptake of oxidatively modified low density lipoprotein (LDL) particles (oxLDL) by vascular cells mediated by scavenger receptors is considered to be a crucial step in atherogenesis. In addition to mediating the uptake of oxidized lipids, the scavenger receptors can mediate activation of pro-oxidant and pro-inflammatory signaling pathways which are involved in activation of endothelial cells and macrophages, and which lead to progression of atherosclerosis and plaque erosion/rupture as well as to microvascular dysfunction with impaired tissue perfusion and oxygen delivery/utilization, resulting in myocardial or lower limb ischemia.

The lectin-like oxidized low density lipoprotein receptor 1 (LOX-1) is a multifunctional scavenger receptor which is expressed on vascular endothelial cells, monocytes and macrophages, vascular smooth muscle cells, and platelets. LOX-1 binds oxLDL and other oxidized lipids, resulting in activation of NADPH oxidase and generation of reactive oxygen species including superoxide anion. Superoxide anion inactivates endothelial nitric oxide and activates MAP kinase and NF-κB. This in turn induces expression of inflammatory adhesion molecules, cytokines and chemokines, as well as matrix metalloproteinases and pro-apoptotic mediators.

The pro-inflammatory, pro-oxidant and pro-apoptotic consequences of oxLDL-LOX-1 mediated signaling in endothelial cells, smooth muscle cells, and macrophages are thought to play a key role in progression of atherosclerosis and plaque instability and may also play a role in impaired tissue perfusion and oxygen delivery, resulting in ischemia. The clinical consequences of advanced atherosclerosis and organ ischemia include: acute coronary syndromes, myocardial infarction, unstable angina, stroke, angina, claudication and critical limb ischemia. In addition, oxidative stress, vascular inflammation and resulting microvascular dysfunction are thought to contribute to diabetic vascular disease, including nephropathy and retinopathy.

While basal LOX-1 endothelial expression levels are relatively low under normal physiological conditions, vascular LOX-1 expression is upregulated in conditions associated with vascular disease. Endothelial LOX-1 levels have been shown to be increased by oxidative stress, pro-inflammatory cytokines, C-reactive protein (CRP) and angiotensin II. LOX-1 is also upregulated in the endothelium of atherosclerotic and diabetic animals and in monocytes/macrophages isolated from patients with vascular disease. Hyperglycemia, advanced glycated end products and atherogenic lipoproteins also upregulate LOX-1 expression, providing a specific molecular mechanistic link between diabetes and vascular complications.

The upregulation of LOX-1 by cytokines and CRP also suggests a link between conventional vascular risk factors and accelerated vascular disease in high risk patients and diabetics. Both CRP and soluble LOX-1 are elevated in patients with acute coronary syndromes. In vitro data have shown that anti-LOX-1 antibodies prevent CRP mediated monocyte adhesion to human aortic endothelial cells, further supporting a role for LOX-1 as an adhesion molecule relevant to vascular inflammation (Li et al., Circulation Research 2004, 95: 877-883).

Increased expression of LOX-1 coupled to elevated levels of oxLDL and other oxidized lipoproteins induces endothelial dysfunction, in part, by activating NADPH oxidase and generation of reactive oxygen species. Experimentally, oxidant stress induced endothelial dysfunction can be reversed with a neutralizing anti-LOX-1 antibody in ApoE-knockout mice (Xu at al., Arteriosclerosis, Thrombosis and Vascular Biology 2007, 27:871-877). In this study, anti-LOX-1 antibody increased both bioavailable nitric oxide and eNOS protein expression.

Experimental in vivo data indicate that overexpression of vascular and macrophage LOX-1 in the presence of oxidized lipids contributes to atherosclerosis and microvascular dysfunction by activating pro-oxidant and pro-inflammatory signaling pathways. Thus, inhibition of LOX-1 is expected to prevent development and progression of atherosclerosis and its acute complications such as acute coronary syndromes, myocardial infarction and unstable angina. In addition LOX-1 inhibition is also expected to ameliorate microvascular dysfunction, preventing clinical manifestations of tissue ischemia such as chronic angina, refractory angina, claudication and critical limb ischemia.

LOX-1 inhibition is useful not only in the treatment and prevention of atherosclerotic vascular disease, but also in treatment of other pathologic conditions characterized by oxidative stress and inflammation such as rheumatoid arthritis, various forms of vasculitis, uveitis, age related macular degeneration, and prevention of cardiovascular events in autoimmune diseases (e.g. lupus erythematosis, psoriasis).

In summary, experimental and clinical data suggest that LOX-1 may be the critical oxidized lipid receptor linking oxidative stress, inflammation and vascular disease. The anti-LOX-1 antibodies and antigen binding fragments described in this invention inhibit binding of oxLDL and other oxidized lipids/lipoproteins to LOX-1, preventing activation of LOX-1, thereby reducing vascular oxidative stress and inflammation. These antibodies are expected to prevent and ameliorate the acute and chronic manifestations of vascular disease and to prevent and ameliorate other diseases characterized by oxidative stress and inflammation.

SUMMARY OF THE INVENTION

The present invention relates to monoclonal antibodies binding to human lectin-like oxidized LDL (low density lipoprotein) receptor 1 (hereinafter, sometimes referred to as "LOX-1"), and pharmaceutical compositions and methods of treatment comprising the same.

The isolated anti-LOX-1 antibodies, or antigen binding fragments, described herein bind LOX-1, with an equilibrium dissociation constant ($K_D$) of less than or equal to 100 pM. For example, the isolated antibodies or antigen binding fragments described herein may bind to human LOX-1 with a $K_D$ of less than or equal to 100 pM, less than or equal to 50 pM, less than or equal to 45 pM, less than or equal to 40 pM, less than or equal to 35 pM. More specifically, the isolated antibodies or antigen binding fragments described herein may also bind human LOX-1 with a $K_D$ of less than or equal to 34 pM, as measured by BIACORE™, or less than or equal to 4 pM, as measured by solution equilibrium titration assay (SET); and may also bind cynomolgus monkey LOX-1 with a $K_D$ of less than or equal to 53 pM, as measured by BIACORE™, or less than or equal to 4 pM, as measured by SET.

The present invention relates to an isolated antibody, or antigen binding fragments thereof, that binds to human and cynomolgus monkey LOX-1. The invention also relates to an isolated antibody, or antigen binding fragments thereof, that binds to the LOX-1 C-terminal lectin-like domain (oxLDL binding domain).

The present invention also relates to an isolated antibody, or antigen binding fragments thereof, that binds LOX-1 and further competes for binding with an antibody as described in Table 1. The present invention also further relates to an isolated antibody, or antigen binding fragments thereof, that binds the same epitope as an antibody as described in Table 1.

The binding affinity of isolated antibodies and antigen binding fragments described herein can be determined by solution equilibrium titration (SET). Methods for SET are known in the art and are described in further detail below. Alternatively, binding affinity of the isolated antibodies, or fragments, described herein can be determined by BIACORE™ assay. Methods for BIACORE™ kinetic assays are known in the art and are described in further detail below.

The isolated anti-LOX-1 antibodies and antigen binding fragments described herein can be used to inhibit LOX-1 binding to oxLDL (also known as modified LDL).

The isolated anti-LOX-1 antibodies and antigen binding fragments described herein can be used to inhibit LOX-1 binding to multiple forms of modified LDL (low density lipoproteins) with an $IC_{50}$ of less than or equal to 100 nM, less than or equal to 50 nM, less than or equal to 35 nM, less than or equal to 25 nM, less than or equal to 10 nM, or less than or equal to 5.2 nM. More specifically, an isolated antibody or antigen binding fragments thereof as described herein can inhibit LOX-1 binding to copper sulfate oxidatively modified LDL (ox-LDLs) with an $IC_{50}$ of less than or equal to 100 nM, less than or equal to 50 nM, less than or equal to 35 nM, less than or equal to 25 nM, less than or equal to 10 nM, or less than or equal to 5.2 nM. More specifically, an isolated antibody or antigen binding fragments thereof as described herein can inhibit LOX-1 binding to malondialdehyde modified LDL with an $IC_{50}$ of less than or equal to 100 nM, less than or equal to 50 nM, less than or equal to 35 nM, less than or equal to 25 nM, less than or equal to 20 nM, or less than or equal to 18 nM. More specifically, an isolated antibody or antigen binding fragments thereof as described herein can inhibit LOX-1 binding to hypochlorite modified LDL with an $IC_{50}$ of less than or equal to 100 nM, less than or equal to 50 nM, less than or equal to 35 nM, less than or equal to 25 nM, less than or equal to 10 nM, or less than or equal to 5 nM.

The isolated anti-LOX-1 antibodies, or antigen binding fragments thereof, may be used to reduce the expression of LOX-1 and/or NADPH oxidase (NADPH is the reduced form of NADP, or nicotinamide adenine dinucleotide phosphate).

The isolated anti-LOX-1 antibodies, or antigen binding fragments thereof, may be used to inhibit (e.g., block the induction of) oxidative stress, e.g., via inhibiting binding of oxLDLs to LOX-1. The isolated anti-LOX-1 antibodies, or antigen binding fragments thereof, may be used to block oxLDL-stimulated reactive oxygen species (ROS) production. Vascular oxidative stress, which the isolated antibodies, or antigen binding fragments thereof, may be used to prevent, treat, or ameliorate, causes myocardial ischemia by inducing vasoconstriction, impairing vasodilation, and increasing oxygen demand.

The isolated anti-LOX-1 antibodies, or antigen binding fragments thereof, may be used to restore endothelial nitric oxide synthase (eNOS) levels to a healthy, homeostatic state. Endothelial NOS is a nitric oxide synthase that generates nitric oxide (NO) in blood vessels and is involved in regulating vascular tone by inhibiting smooth muscle contraction and platelet aggregation; its downregulation is associated with LOX-1-related endothelial cell dysfunction.

The isolated anti-LOX-1 antibodies, or antigen binding fragments thereof, as described herein can be monoclonal antibodies, human or humanized antibodies, chimeric antibodies, single chain antibodies, Fab fragments, Fv fragments, F(ab')2 fragments, or scFv fragments, and/or IgG isotypes.

The isolated anti-LOX-1 antibodies, or antigen binding fragments thereof, as described herein can also include a framework in which an amino acid has been substituted into the antibody framework from the respective human VH or VL germline sequences.

Another aspect of the invention includes an isolated antibody or antigen binding fragments thereof having the full heavy and light chain sequences of Fabs described in Table 1. More specifically, the isolated antibody or antigen binding fragments thereof can have the heavy and light chain sequences of MOR21435, MOR20159, MOR22031, MOR22034, MOR21433, MOR21452, MOR21453, MOR21460, MOR21468, MOR20052, MOR20133, MOR20144, MOR20148, MOR20151, MOR20152, MOR022025, MOR22028, MOR22029, and MOR22030.

A further aspect of the invention includes an isolated antibody or antigen binding fragments thereof having the heavy and light chain variable domain sequences of Fabs described in Table 1. More specifically, the isolated antibody or antigen binding fragment thereof can have the heavy and light chain variable domain sequence of MOR21435, MOR20159, MOR22031, MOR22034, MOR21433, MOR21452, MOR21453, MOR21460, MOR21468, MOR20052, MOR20133, MOR20144, MOR20148, MOR20151, MOR20152, MOR022025, MOR22028, MOR22029, and MOR22030.

The invention also relates to an isolated antibody or antigen binding fragments thereof that includes a heavy chain CDR1 selected from the group consisting of SEQ ID NOs: 3, 23, 43, 63, 83, 103, 123, 143, 163, 183, 203, 223, 243, 263, 283, 303, 323, 343, and 363; a heavy chain CDR2 selected from the group consisting of SEQ ID NOs: 4, 24, 44, 64, 84, 104, 124, 144, 164, 184, 204, 224, 244, 264, 284, 304, 324, 344, and 364; and a heavy chain CDR3 selected from the group consisting of SEQ ID NOs: 5, 25, 45, 65, 85, 105, 125, 145, 165, 185, 205, 225, 245, 265, 285, 305, 325, 345, and 365, wherein the isolated antibody or antigen binding fragments thereof binds to human LOX-1. In another aspect, such isolated antibody or antigen binding fragments thereof further includes a light chain CDR1 selected from the group consisting of SEQ ID NOs: 13, 33, 53, 73, 93, 113, 133, 153, 173, 193, 213, 233, 253, 273, 293, 313, 333, 353, and 373; a light chain CDR2 selected from the group consisting of SEQ ID NOs: 14, 34, 54, 74, 94, 114, 134, 154, 174, 194, 214, 234, 254, 274, 294, 314, 334, 354, and 374; and a light chain CDR3 selected from the group consisting of SEQ ID NOs: 15, 35, 55, 75, 95, 115, 135, 155, 175, 195, 215, 235, 255, 275, 295, 315, 335, 355, and 375.

The invention also relates to an isolated antibody or antigen binding fragments thereof that includes a light chain CDR1 selected from the group consisting of SEQ ID NOs: 13, 33, 53, 73, 93, 113, 133, 153, 173, 193, 213, 233, 253, 273, 293, 313, 333, 353, and 373; a light chain CDR2 selected from the group consisting of SEQ ID NOs: 14, 34, 54, 74, 94, 114, 134, 154, 174, 194, 214, 234, 254, 274, 294, 314, 334, 354, and 374; and a light chain CDR3 selected from the group consisting of SEQ ID NOs: 15, 35, 55, 75, 95, 115, 135, 155, 175, 195, 215, 235, 255, 275, 295, 315, 335, 355, and 375, wherein the isolated antibody or antigen binding fragments thereof binds to human LOX-1.

The invention also relates to an isolated antibody or antigen binding fragments thereof that binds LOX-1 having HCDR1, HCDR2, and HCDR3 and LCDR1, LCDR2, and LCDR3, wherein HCDR1, HCDR2, and HCDR3 comprises SEQ ID NOs: 3, 4, and 5, and LCDR1, LCDR2, LCDR3 comprises SEQ ID NOs: 13, 14, and 15; or HCDR1, HCDR2, and HCDR3 comprises SEQ ID NOs: 23, 24, and 25, and LCDR1, LCDR2, LCDR3 comprises SEQ ID NOs: 33, 34, and 35; or HCDR1, HCDR2, and HCDR3 comprises SEQ ID NOs: 43, 44, and 45, and LCDR1, LCDR2, LCDR3 comprises SEQ ID NOs: 53, 54, and 55; or HCDR1, HCDR2, and HCDR3 comprises SEQ ID NOs: 63, 64, and 65, and LCDR1, LCDR2, LCDR3 comprises SEQ ID NOs: 73, 74, and 75; or HCDR1, HCDR2, and HCDR3 comprises SEQ ID NOs: 83, 84, and 85, and LCDR1, LCDR2, LCDR3 comprises SEQ ID NOs: 93, 94, and 95.

The invention also relates to an isolated antibody or antigen binding fragments thereof that binds LOX-1 having HCDR1, HCDR2, and HCDR3 and LCDR1, LCDR2, and LCDR3, wherein HCDR1, HCDR2, and HCDR3 comprises SEQ ID NOs: 103, 104, and 105, and LCDR1, LCDR2, LCDR3 comprises SEQ ID NOs: 113, 114, and 115; or HCDR1, HCDR2, and HCDR3 comprises SEQ ID NOs: 123, 124, and 125, and LCDR1, LCDR2, LCDR3 comprises SEQ ID NOs: 133, 134, and 135; or HCDR1, HCDR2, and HCDR3 comprises SEQ ID NOs: 143, 144, and 145, and LCDR1, LCDR2, LCDR3 comprises SEQ ID NOs: 153, 154, and 155; or HCDR1, HCDR2, and HCDR3 comprises SEQ ID NOs: 163, 164, and 165, and LCDR1, LCDR2, LCDR3 comprises SEQ ID NOs: 173, 174, and 175; or HCDR1, HCDR2, and HCDR3 comprises SEQ ID NOs: 183, 184, and 185, and LCDR1, LCDR2, LCDR3 comprises SEQ ID NOs: 193, 194, and 195.

The invention also relates to an isolated antibody or antigen binding fragments thereof that binds LOX-1 having HCDR1, HCDR2, and HCDR3 and LCDR1, LCDR2, and LCDR3, wherein or HCDR1, HCDR2, and HCDR3 comprises SEQ ID NOs: 203, 204, and 205, and LCDR1, LCDR2, LCDR3 comprises SEQ ID NOs: 213, 214, and 215; or HCDR1, HCDR2, and HCDR3 comprises SEQ ID NOs: 223, 224, and 225, and LCDR1, LCDR2, LCDR3 comprises SEQ ID NOs: 233, 234, and 235; or HCDR1, HCDR2, and HCDR3 comprises SEQ ID NOs: 243, 244, and 245, and LCDR1, LCDR2, LCDR3 comprises SEQ ID NOs: 253, 254, and 255; or HCDR1, HCDR2, and HCDR3 comprises SEQ ID NOs: 263, 264, and 265, and LCDR1, LCDR2, LCDR3 comprises SEQ ID NOs: 273, 274, and 275; or HCDR1, HCDR2, and HCDR3 comprises SEQ ID NOs: 283, 284, and 285, and LCDR1, LCDR2, LCDR3 comprises SEQ ID NOs: 293, 294, and 295.

The invention also relates to an isolated antibody or antigen binding fragments thereof that binds LOX-1 having HCDR1, HCDR2, and HCDR3 and LCDR1, LCDR2, and LCDR3, wherein or HCDR1, HCDR2, and HCDR3 comprises SEQ ID NOs: 303, 304, and 305, and LCDR1, LCDR2, LCDR3 comprises SEQ ID NOs: 313, 314, and 315; or HCDR1, HCDR2, and HCDR3 comprises SEQ ID NOs: 323, 324, and 325, and LCDR1, LCDR2, LCDR3 comprises SEQ ID NOs: 333, 334, and 335; or HCDR1, HCDR2, and HCDR3 comprises SEQ ID NOs: 343, 344, and 345, and LCDR1, LCDR2, LCDR3 comprises SEQ ID NOs: 353, 354, and 355; or HCDR1, HCDR2, and HCDR3 comprises SEQ ID NOs: 363, 364, and 365, and LCDR1, LCDR2, LCDR3 comprises SEQ ID NOs: 373, 374, and 375.

The invention also relates to an antibody or antigen binding fragment having HCDR1, HCDR2, and HCDR3 of the variable heavy chain of SEQ ID NOs: 9, 29, 49, 69, 89, 109, 129, 149, 169, 189, 209, 229, 249, 269, 289, 309, 329, 349, and 369, and the LCDR1, LCDR2 and LCDR3 of the variable light chain of SEQ ID NOs: 19, 39, 59, 79, 99, 119, 139, 159, 179, 199, 219, 239, 259, 279, 299, 319, 339, 359, and 379, as defined by Chothia. In another aspect of the invention the antibody or antigen binding fragment may have the HCDR1, HCDR2, and HCDR3 of the heavy chain variable domain sequence of SEQ ID NOs: 9, 29, 49, 69, 89, 109, 129, 149, 169, 189, 209, 229, 249, 269, 289, 309, 329, 349, and 369, and the LCDR1, LCDR2 and LCDR3 of the light chain variable domain sequence of SEQ ID NOs: 19, 39, 59, 79, 99, 119, 139, 159, 179, 199, 219, 239, 259, 279, 299, 319, 339, 359, and 379, as defined by Kabat.

In one aspect of the invention the isolated antibody or antigen binding fragments thereof includes a heavy chain variable domain sequence selected from the group consisting of SEQ ID NOs: 9, 29, 49, 69, 89, 109, 129, 149, 169, 189, 209, 229, 249, 269, 289, 309, 329, 349, and 369. The isolated antibody or antigen binding fragment further can comprise a light chain variable domain sequence wherein the heavy chain variable domain and light chain variable domain combine to form and antigen binding site for LOX-1. In particular the light chain variable domain sequence can be selected from SEQ ID NOs: 24, 44, 64, 84, and 104 wherein said isolated antibody or antigen binding fragments thereof binds LOX-1.

The invention also relates to an isolated antibody or antigen binding fragments thereof that includes a light chain variable domain sequence selected from the group consisting of SEQ ID NOs: 24, 44, 64, 84, and 104, wherein said isolated antibody or antigen binding fragments thereof binds to human LOX-1. The isolated antibody or antigen binding fragment may further comprise a heavy chain variable domain sequence wherein the light chain variable domain and heavy chain variable domain combine to form and antigen binding site for LOX-1.

In particular, the isolated antibody or antigen binding fragments thereof that binds LOX-1, may have heavy and light chain variable domains comprising the sequences of SEQ ID NOs: 14 and 24; 34 and 44; 54 and 64; 74 and 84; or 94 and 104, respectively.

The invention further relates to an isolated antibody or antigen binding fragments thereof, that includes a heavy chain variable domain having at least 90% sequence identity to a sequence selected from the group consisting of SEQ ID NOs: 9, 29, 49, 69, 89, 109, 129, 149, 169, 189, 209, 229, 249, 269, 289, 309, 329, 349, and 369, wherein said antibody binds to LOX-1. In one aspect, the isolated antibody or antigen binding fragments thereof also includes a light chain variable domain having at least 90% sequence identity to a sequence selected from the group consisting of SEQ ID NOs: 24, 44, 64, 84, and 104. In a further aspect of the invention, the isolated antibody or antigen binding fragment has an HCDR1, HCDR2, HCDR3, LCDR1, LCDR2 and LCDR3 as defined by Kabat and as described in Table 1.

The invention also relates to an isolated antibody or antigen binding fragments thereof, having a light chain variable domain having at least 90% sequence identity to a sequence selected from the group consisting of SEQ ID NOs: 24, 44, 64, 84, and 104, wherein said antibody binds LOX-1.

In another aspect of the invention, the isolated antibody, or antigen binding fragments thereof, that binds to LOX-1 may have a heavy chain comprising the sequence of SEQ ID NOs: 11, 31, 51, 71, 91, 111, 131, 151, 171, 191, 211, 231, 251, 271, 291, 311, 331, 351, or 371. The isolated antibody can also include a light chain that can combine with the heavy chain to form an antigen binding site to human LOX-1. In particular, the light chain may have a sequence comprising SEQ ID NOs: 21, 41, 61, 81, 101, 121, 141, 161, 181, 201, 221, 241, 261, 281, 301, 321, 341, 361, or 381. In particular, the isolated antibody or antigen binding fragments thereof that binds LOX-1, may have a heavy chain and a light chain comprising the sequences of SEQ ID NOs: 16 and 26; 36 and 46; 56 and 66; 76 and 86; or 96 and 106, respectively.

The invention still further relates to an isolated antibody or antigen binding fragments thereof that includes a heavy chain having at least 90% sequence identity to a sequence selected from the group consisting of SEQ ID NOs: 11, 31, 51, 71, 91, 111, 131, 151, 171, 191, 211, 231, 251, 271, 291, 311, 331, 351, or 371, wherein said antibody binds to LOX-1. In one aspect, the isolated antibody or antigen binding fragments thereof also includes a light chain having at least 90% sequence identity to a sequence selected from the group consisting of SEQ ID NOs: 21, 41, 61, 81, 101, 121, 141, 161, 181, 201, 221, 241, 261, 281, 301, 321, 341, 361, or 381.

The invention still further relates to an isolated antibody or antigen binding fragments thereof that includes a light chain having at least 90% sequence identity to a sequence selected from the group consisting of SEQ ID NOs: 21, 41, 61, 81, 101, 121, 141, 161, 181, 201, 221, 241, 261, 281, 301, 321, 341, 361, or 381, wherein said antibody binds LOX-1.

The invention also relates to compositions comprising the isolated antibody, or antigen binding fragments thereof, described herein. As well as, antibody compositions in combination with a pharmaceutically acceptable carrier. Specifically, the invention further includes pharmaceutical compositions comprising an antibody or antigen binding fragments thereof of Table 1, such as, for example antibody MOR21435, MOR20159, MOR22031, MOR22034, MOR21433, MOR21452, MOR21453, MOR21460, MOR21468, MOR20052, MOR20133, MOR20144, MOR20148, MOR20151, MOR20152, MOR022025, MOR22028, MOR22029, and MOR22030. The invention also relates to pharmaceutical compositions comprising a combination of two or more of the isolated antibodies or antigen binding fragments thereof of Table 1.

The invention also relates to an isolated nucleic acid sequence encoding the variable heavy chain having a sequence selected from SEQ ID NOs: 9, 29, 49, 69, 89, 109, 129, 149, 169, 189, 209, 229, 249, 269, 289, 309, 329, 349, and 369. In particular the nucleic acid has a sequence at least 90% sequence identity to a sequence selected from the group consisting of SEQ ID NOs: 10, 30, 50, 70, 90, 110, 130, 150, 170, 190, 210, 230, 250, 270, 290, 310, 330, 350, and 370. In a further aspect of the invention the sequence is SEQ ID NOs: 10, 30, 50, 70, 90, 110, 130, 150, 170, 190, 210, 230, 250, 270, 290, 310, 330, 350, and 370.

The invention also relates to an isolated nucleic acid sequence encoding the variable light chain having a sequence selected from SEQ ID NOs: 20, 40, 60, 80, 100, 120, 140, 160, 180, 200, 220, 240, 260, 280, 300, 320, 340, 360, and 380. In particular the nucleic acid has a sequence at least 90% sequence identity to a sequence selected from the group consisting of SEQ ID NOs: 20, 40, 60, 80, 100, 120, 140, 160, 180, 200, 220, 240, 260, 280, 300, 320, 340, 360, and 380. In a further aspect of the invention the sequence is SEQ ID NOs: 20, 40, 60, 80, 100, 120, 140, 160, 180, 200, 220, 240, 260, 280, 300, 320, 340, 360, and 380.

The invention also relates to an isolated nucleic acid comprising a sequence encoding a polypeptide that includes a light chain variable domain having at least 90% sequence identity to a sequence selected from the group consisting of SEQ ID NOs: 20, 40, 60, 80, 100, 120, 140, 160, 180, 200, 220, 240, 260, 280, 300, 320, 340, 360, and 380.

The invention also relates to a vector that includes one or more of the nucleic acid molecules described herein.

The invention also relates to an isolated host cell that includes a recombinant DNA sequence encoding a heavy chain of the antibody described above, and a second recombinant DNA sequence encoding a light chain of the antibody described above, wherein said DNA sequences are operably linked to a promoter and are capable of being expressed in the host cell. It is contemplated that the antibody can be a human monoclonal antibody. It is also contemplated that the host cell is a non-human mammalian cell.

The invention also relates to a method of reducing LOX-1 expression, and/or NADPH oxidase expression, wherein the method includes the step of contacting a cell with an effective amount of a composition comprising the isolated antibody or antigen binding fragments thereof described herein.

The invention also relates to a method of inhibiting the binding of oxidized LDL (oxLDL) to a human oxidized LDL receptor (LOX-1) or to inhibit the human oxidized LDL receptor-mediated incorporation of oxidized LDL into cells, wherein the method includes the step of contacting a cell with an effective amount of a composition comprising the isolated antibody or antigen binding fragments thereof described herein.

It is contemplated that the cell is a human cell. It is further contemplated that the cell is in a subject. In one embodiment, it is contemplated that the cell is an endothelial cell. In other embodiments, the cell may be one or more of macrophages, monocytes, dendritic cells, vascular smooth muscle cells (SMC), chondrocytes, and cardiac myocytes. It is still further contemplated that the subject is human.

The invention also relates to a method of treating, improving, or preventing a LOX-1-associated disorder in a subject, wherein the method includes the step of administering to the subject an effective amount of a composition comprising the antibody or antigen binding fragments thereof described herein. In one aspect, the LOX-1-associated disorder is associated with claudication (e.g., intermittent claudication, Rutherford Class II/III Claudication). In one aspect, the LOX-1-associated disorder is associated with angina (e.g., refractory angina). It is contemplated that the subject is human.

Any of the foregoing isolated antibodies or antigen binding fragments thereof may be a monoclonal antibody or antigen binding fragments thereof.

Definitions

Unless defined otherwise, all technical and scientific terms used herein have the same meaning as commonly understood by those of ordinary skill in the art to which this invention pertains.

The term "LOX-1 protein" or "LOX-1 antigen" or "LOX-1" or "Lox1" are used interchangeably, and refers to the Lectin-Like Oxidized LDL Receptor 1 (LOX-1) protein in different species. For example, human LOX-1 has the sequence as set out in Table 1 (SEQ ID NO:1), and has been described in previous reports and literature (Nature, Vol. 386, p. 73-77, 1997; Genomics, Vol. 54, No. 2, p. 191-199, 1998; Biochem. J., Vol. 339, Part 1, P. 177-184, 1999; Genbank Accession No. NP 002534). It is a class E scavenger receptor that mediates the uptake of oxLDL by vascular cells and oxLDL signaling in vascular cells, and as such, is a mediator of the toxic effects of oxLDL. LOX-1 is expressed on the surface of vascular endothelial cells and has been implicated in the accumulation of monocytes and macrophages on vascular endothelial cells.

In addition, in the context of this invention, the term "LOX-1" includes mutants of the natural human oxidized-LDL receptor, which have substantially the same amino acid sequence as that of the native primary structure (amino acid sequence) described in the above-mentioned reports. Herein, the term "mutants of the natural human oxidized-LDL receptor having substantially the same amino acid sequence" refers to such mutant proteins.

Multiple forms of modified LDL formed in vitro and/or in vivo have been shown to bind to LOX-1. As used herein, the term "modified LDL" and "oxidized LDL" (and "oxLDL") are used interchangeably to describe low density lipoproteins which are oxidized by cells, such as vascular endothelial cells, in combination with various chemical and physical factors (e.g., heat). LDL is oxidized, for example, within the vascular wall under atherogenic conditions to form oxLDL. The term "modified LDL" can encompass the following: oxidized LDL, copper sulfate oxidatively modified LDL, acetyl LDL, chlorinated LDL (e.g., LDL modified via a chemical chlorination reaction), myeloperoxidase modified LDL, hypochlorite modified LDL, succinyl LDL, and malondialdehyde modified LDL (i.e., LDL modified via reaction with malondialdehyde; malondialdehyde is produced in vivo as a consequence of oxidative stress).

The term "antibody" as used herein means a whole antibody and any antigen binding fragment (i.e., "antigen-binding portion") or single chain thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen binding portion" or "antigen binding fragment" of an antibody, as used herein, refers to one or more fragments of an intact antibody that retain the ability to specifically bind to a given antigen (e.g., human oxidized LDL receptor (LOX-1)). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen binding fragments thereof (e.g., a Fab fragment) generally refers to an antibody, or antigen binding fragment, having a KD of $10^{-9}$M or less.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., a LOX-1-binding antibody) refers to a binding reaction that is determinative of the presence of a cognate antigen (e.g., a human LOX-1 or cynomolgus LOX-1) in a heterogeneous population of proteins and other biologics. The phrases "an antibody recognizing an antigen" and "an antibody specific for an antigen" are used interchangeably herein with the term "an antibody which binds specifically to an antigen".

The term "LOX-1 mediated" refers to the fact that the LOX-1 receptor mediates the cellular response upon binding of a LOX-1 ligand, e.g., oxLDL, to LOX-1 on the cell surface, which then triggers the cell to increase production of certain pro-inflammatory molecules. The term "pro-inflammatory gene" refers to a gene encoding any molecule, such as, but not limited to, a cytokine, a chemokine, or a cell-adhesion molecule, which plays a role in an inflammatory process. Exemplary "pro-inflammatory" genes include, but are not limited to, interleukin-8 (IL-8), intercellular adhesion molecule-1 (ICAM-1), vascular cell adhesion molecule-1 (VCAM-1) and monocyte chemotactic protein-1 (MCP-1).

A "LOX-1-associated disorder," "LOX-1-associated condition," "disease or condition associated with elevated levels of LOX-1," or similar terms as used herein, refer to any number of conditions or diseases in which the LOX-1 protein levels are aberrantly high and/or in which a reduction of LOX-1 protein levels is sought. These conditions include but are not limited to cardiovascular disorders, endothelial cell dysfunction, endothelial cell disorders, atherosclerosis, arteriosclerosis, hypertension, hyperlipidemia, hypercholesterolemia, diabetes mellitus, nitric oxide deficiency, myocardial infarction, vascular oxidative stress, myocardial ischemia, ischemia-reperfusion, sepsis, diabetic nephropathy, renal disease, cardiomyopathy, heart failure, peripheral artery disease, coronary heart disease, claudication (e.g., intermittent claudication, Rutherford Class II/III Claudication), peripheral artery disease (PAD), angina (e.g., refractory angina), coronary artery disease (CAD)(e.g., due to atherosclerosis of the arteries feeding the heart), stroke, and abnormal endothelium-dependent vasodilation.

"Endothelial cell dysfunction," as used herein, means the inability of an endothelial cell to maintain its normal function. The endothelium plays a critical role in regulating vascular smooth tone and growth, vascular permeability, the inflammatory response, coagulation, and platelet adhesion. Non-limiting examples of endothelial cell function include maintaining balanced vascular tone, inhibiting thrombosis, inhibiting pro-inflammatory processes, maintaining vascular integrity (e.g., non-leakiness of the vasculature), and maintaining an anti-proliferative state in both the endothelium and smooth muscle cells. Common conditions and risk factors predisposing to atherosclerosis, such as dyslipidemia, hypertension, diabetes, and smoking are all associated with endothelial dysfunction, which promotes the development, progression, and complications of atherosclerosis. Endothelial dysfunction has generally been assessed as impaired endothelium-dependent vasodilation. This assumes that endothelium-dependent vasodilation is a surrogate marker for other important endothelial functions. The basis for this assumption is the observation that endothelium-derived nitric oxide, synthesized by the endothelial NO synthase (eNOS) from L-arginine, mediates endothelium-dependent vasodilation and other endothelial vasculoprotective functions. A growing clinical database suggests that endothelial dysfunction (impaired endothelial dependent vasodilation) is closely associated with major adverse cardiovascular events including myocardial ischemia and infarction, acute coronary syndromes, claudication and critical limb ischemia, transient ischemic attacks and stroke.

Accumulating experimental data also suggests that endothelial and endocardial impaired eNOS-derived NO availability not only may lead to abnormal left ventricular remodeling and dysfunction contributing to development and progression of heart failure.

An "endothelial cell disorder," as used herein, is any disorder that is characterized by endothelial cell dysfunction. Non-limiting examples of diseases or disorders that are characterized by endothelial cell dysfunction include angiogenic disorders such as cancers which require neovascularization to support tumor growth, infectious diseases, autoimmune disorders, vascular malformations, DiGeorge syndrome, HHT, cavernous hemangioma, transplant arteriopathy, vascular access stenosis associated with hemodialysis, vasculitis, vasculitidis, vascular inflammatory disorders, atherosclerosis, obesity, psoriasis, warts, allergic dermatitis, scar keloids, pyogenic granulomas, blistering disease, Kaposi sarcoma, persistent hyperplastic vitreous syndrome, retinopathy of prematurity, choroidal neovascularization, macular degeneration, diabetic retinopathy, ocular neovascularization, primary pulmonary hypertension, asthma, nasal polyps, inflammatory bowel and periodontal disease, ascites, peritoneal adhesions, contraception, endometriosis, uterine bleeding, ovarian cysts, ovarian hyperstimulation, arthritis, rheumatoid arthritis, chronic articular rheumatism, synovitis, osteoarthritis, osteomyelitis, osteophyte formation, sepsis, and vascular leak. Endothelial cell dysfunction can be determined using assays known in the art including detecting the increased expression of endothelial adhesion molecules or decreased expression or biological activity of nitric oxide synthase (eNOS).

"Claudication," as used herein, includes severe claudication and other like terms, and describes a mobility impairment and high unmet medical need. Claudication is a condition characterized by lower extremity ischemia, causing muscle fatigue, pain on exertion relieved by rest, limited mobility, and reduced quality of life, and is caused by atherosclerosis and abnormal (e.g., impaired) endothelium-dependent vasodilation. Its prevalence in the US is 8-12 million patients. Among patients with intermittent claudication, 7% will undergo lower extremity bypass surgery, 4% will require major amputations, and 16% will develop worsening claudication. Cardiovascular events, such as myocardial infarction and stroke, occur in 20% of severe claudication sufferers over 5 years. The current therapy is surgical, and treatment through less invasive means, such as the administration of the anti-LOX-1 antibodies of the invention, would represent an enormous therapeutic breakthrough.

"Refractory angina," as used herein, is a condition marked by chest pain due to ischemia of the heart muscle, generally due to obstruction or spasm of the coronary arteries (e.g., from coronary artery disease), with debilitating symptoms, very limited physical activity and poor quality of life. The 1-1.8 million patients refractory angina sufferers in the US experience increased cardiovascular mortality at a rate of 10% per year; at least 100,000 new refractory angina cases arise per year.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are prepared using phage display methods for screening libraries of human immunoglobulin genes.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et at, J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=-4, and a comparison of both strands.

The BLAST algorithm also performs a statistical analysis of the similarity between two sequences (see, e.g., Karlin and Alschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds LOX-1 is substantially free of antibodies that specifically bind antigens other than LOX-1). An isolated antibody that specifically binds LOX-1 may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. Methods for determining the $K_D$ of an antibody include measuring surface plasmon resonance using a biosensor system such as a BIACORE™ system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g.: mammals and non-mammals) such as, non-human primates (e.g.: cynomolgus monkey), sheep, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*).

As used herein, the term "treating" or "treatment" of any disease or disorder (e.g., LOX-1 associated disorder) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., LOX-1 associated disorder, means any action that prevents or slows a worsening in e.g., LOX-1 associated disease parameters, as described below, in a patient at risk for said worsening.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

BRIEF DESCRIPTION OF THE DRAWINGS

FIG. 4A shows antibody MOR020225, FIG. 4B shows antibody MOR020228, FIG. 4C shows antibody MOR020229, FIG. 4D shows antibody MOR020230, FIG. 4E shows antibody MOR020231, FIG. 4F shows antibody MOR020234, and FIG. 4G shows isotype (hIgG1-LALA) control antibody. The isotype control antibody has no effect on oxLDL induced ROS production in human LOX-1 transfected HEK293 cells.

FIG. 6 depicts LOX-1 antibodies binding to LOX-1 on human neutrophils.

DETAILED DESCRIPTION

Figure 1A:
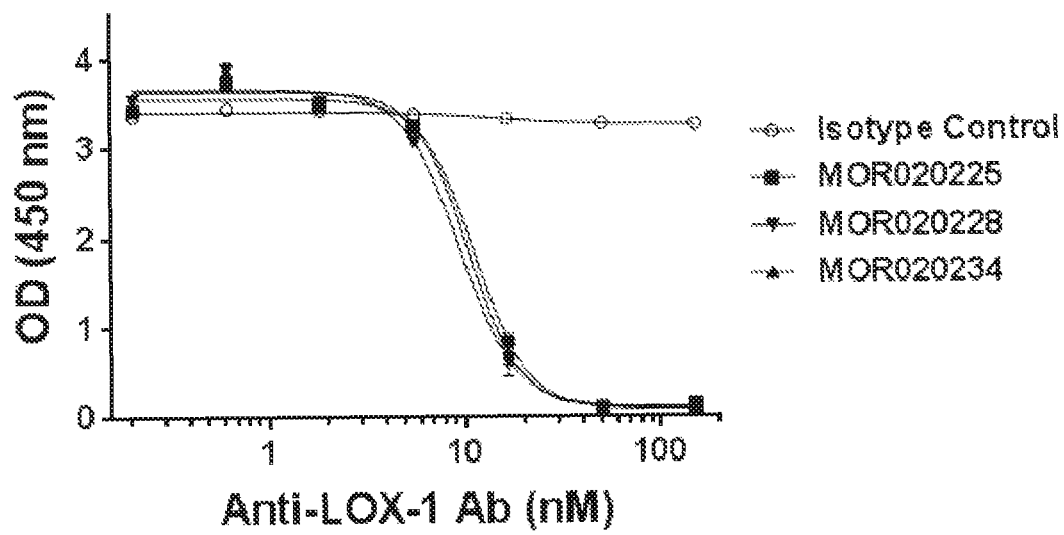
FIGS. 1A-1B depict the inhibition of OxLDL binding to LOX-1 protein by selected LOX-1 antibodies of the invention.

The present invention is based, in part, on the discovery of antibody molecules that specifically bind to LOX-1 and inhibit its biological activities. The invention relates to both full IgG format antibodies as well as antigen binding fragments thereof, such as Fab fragments (e.g., antibodies MOR21435, MOR20159, MOR22031, MOR22034, MOR21433, MOR21452, MOR21453, MOR21460, MOR21468, MOR20052, MOR20133, MOR20144, MOR20148, MOR20151, MOR20152, MOR022025, MOR22028, MOR22029, and MOR22030).

Accordingly, the present invention provides antibodies that specifically bind to LOX-1 (e.g., human LOX-1 and cynomolgus monkey LOX-1), pharmaceutical compositions, production methods, and methods of use of such antibodies and compositions.

LOX-1 Proteins

The present invention provides antibodies that specifically bind to LOX-1 and inhibit its biological activities, including is pro-oxidative and pro-inflammatory activities. LOX-1, a receptor for oxidatively modified LDLs (ox-LDLs), is expressed on the surface of vascular cells (endothelial cells and smooth muscle cells), neutrophils, monocytes and macrophages, and platelets. Furthermore, LOX-1 is upregulated in vascular diseases, including in human and animal atherosclerotic lesions (Kataoka H, et al., Circulation 99; 3110-3117). LOX-1 is also upregulated in systemic inflammatory/autoimmune diseases (e.g., rheumatoid arthritis, uveitis, age-related macular degeneration, and pre-eclampsia). OxLDLs are implicated in the pathogenesis of vascular disease. In addition to oxLDLs, LOX-1 binds other ligands including acetylated LDL, advanced glycation end products (AGEs), heat shock protein 70, (HSP70), apoptotic cells, aged red blood cells, leukocytes, activated platelets, bacteria, phosphatidylserine, and C reactive protein (CRP).

LOX-1 is a type-II membrane protein which belongs to the C-type lectin family. LOX-1 also is classified as a class E scavenger receptor. LOX-1 consists of 4 domains: a short N-terminal cytoplasmic domain, a transmembrane region, a connecting neck, and a lectin-like domain at the C-terminus. The C-terminal lectin-like domain (CTLD; also referred to as the oxLDL binding domain) is the ligand binding domain (Sawamura T, et al., Nature 386; 73-77; Shi X, et al., J Cell Sci. 114; 1273-1282). Human LOX-1 has the sequence as set out in Table 1 (SEQ ID NO:1), and has been described in previous reports and literature (Nature, Vol. 386, p. 73-77, 1997; Genomics, Vol. 54, No. 2, p. 191-199, 1998; Biochem. J., Vol. 339, Part 1, P. 177-184, 1999; Genbank Accession No. NP 002534).

The oxLDL/LOX-1 pathway contributes to oxidative stress, vascular inflammation, atherosclerosis, and impaired tissue blood flow and oxygen delivery. Activation of LOX-1 by binding of LOX-1 ligands (e.g., oxLDLs) results in generation of reactive oxygen species due to activation of NADPH oxidase, and subsequent activation of NFkB and MAP kinase pathways resulting in inflammation. The oxLDL/LOX-1 signaling pathway acts as a positive feedback loop, in that LOX-1 induced reactive oxygen species results in formation of additional oxLDL and upregulates LOX-1 expression. Binding of oxLDLs to LOX-1 expressed on the surface of macrophages also results in uptake of oxLDL which contributes to foam cell formation and atherosclerosis. Importantly, vascular inflammation is thought to be critical to the pathobiology of acute thrombotic complications of atherosclerosis including myocardial infarction and ischemic stroke. LOX-1 activation has also been shown to alter vasomotor function by impairing vasodilation by a mechanism involving NADPH oxidase. Impaired vasodilation has been shown to occur in patients with chronic coronary artery disease and angina, and in patients with peripheral artery disease and claudication.

Studies with LOX-1 knockout mice and LOX-1 antagonist antibodies have shown that inhibition of LOX-1 can have beneficial cardiovascular effects. For example, knocking out LOX-1 prevents oxLDL-mediated impairment of vasorelaxation and reduces atherosclerosis (Mehta et al, Circulation Research 2007, 100: 1634). In addition, anti-LOX-1 antibodies have been shown to (i) block oxLDL-induced oxidative stress in human endothelial cells (Ou et al., J Appl Phys 2010, 108: 1745); and (ii) inhibit superoxide production and restore eNOS expression, resulting in improved NO bioavailability and vasodilation (Xu at al., Arteriosclerosis, Thrombosis and Vascular Biology 2007, 27: 871-877).

We propose that inhibiting LOX-1, for example through administration of the anti-LOX-1 antibodies of the invention, will improve blood flow and oxygen delivery to ischemic tissue, resulting in therapeutic benefit to patients with chronic vascular disease, including angina, claudication, and critical limb ischemia. Inhibiting LOX-1, for example through administration of the anti-LOX-1 antibodies of the invention, may also slow or reverse the progression of atherosclerosis and reduce the incidence of its acute thrombotic complications (e.g., acute coronary syndrome, unstable angina, myocardial infarction, and ischemic stroke).

LOX-1 Antibodies & Antigen Binding Fragments

The present invention provides antibodies that specifically bind to LOX-1. In some embodiments, the present invention provides antibodies that specifically bind to human and cynomolgus monkey LOX-1. Antibodies of the invention include, but are not limited to, the human monoclonal antibodies and Fabs, isolated as described in the Examples.

The present invention provides antibodies that specifically bind a LOX-1 protein (e.g., human and cynomolgus monkey LOX-1), wherein the antibodies comprise a VH domain having an amino acid sequence of SEQ ID NOs: 9, 29, 49, 69, 89, 109, 129, 149, 169, 189, 209, 229, 249, 269, 289, 309, 329, 349, and 369. The present invention also provides antibodies that specifically bind to a LOX-1 protein, wherein the antibodies comprise a VH CDR having an amino acid sequence of any one of the VH CDRs listed in Table 1, Infra. In particular, the invention provides antibodies that specifically bind to an LOX-1 protein (e.g., human and cynomolgus monkey LOX-1), wherein the antibodies comprise (or alternatively, consist of) one, two, three, or more VH CDRs having an amino acid sequence of any of the VH CDRs listed in Table 1, infra.

The present invention provides antibodies that specifically bind to a LOX-1 protein, said antibodies comprising a VL domain having an amino acid sequence of SEQ ID NOs: 19, 39, 59, 79, 99, 119, 139, 159, 179, 199, 219, 239, 259, 279, 299, 319, 339, 359, and 379. The present invention also provides antibodies that specifically bind to an LOX-1 protein (e.g., human and cynomolgus monkey LOX-1), said antibodies comprising a VL CDR having an amino acid sequence of any one of the VL CDRs listed in Table 1, Infra. In particular, the invention provides antibodies that specifically bind to an LOX-1 protein (e.g., human and cynomolgus monkey LOX-1), said antibodies comprising (or alternatively, consisting of) one, two, three or more VL CDRs having an amino acid sequence of any of the VL CDRs listed in Table 1, infra.

Other antibodies of the invention include amino acids that have been mutated, yet have at least 60, 70, 80, 85, 90 or 95 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full length heavy chain, and the full length light chain of the antibodies that specifically bind to a LOX-1 protein (e.g., human and cynomolgus monkey LOX-1). Such nucleic acid sequences can be optimized for expression in mammalian cells (for example, Table 1 shows the optimized nucleic acid sequences for the heavy chain and light chain of antibodies of the invention).

TABLE 1

Examples of LOX-1 Antibodies, Fabs and LOX-1 Proteins.

| Sequence Description | Sequence Identifier (SEQ ID NO:) | Amino acid or polynucleotide sequence |
| --- | --- | --- |
| Human LOX-1 full-length protein sequence (NCBI Reference Sequence: NM_002543.3) | 1 | MTFDDLKIQTVKDQPDEKSNGKKAKGLQFLYSPWWCLAA ATLGVLCLGLVVTIMVLGMQLSQVSDLLTQEQANLTHQK KKLEGQISARQQAEEASQESENELKEMIETLARKLNEKS KEQMELHHQNLNLQETLKRVANCSAPCPQDWIWHGENCY LFSSGSFNWEKSQEKCLSLDAKLLKINSTADLDFIQQAI SYSSFPFWMGLSRRNPSYPWLWEDGSPLMPHLFRVRGAV SQTYPSGTCAYIQRGAVYAENCILAAFSICQKKANLRAQ |
| Human LOX-1 full-length nucleotide sequence (NCBI Reference Sequence: NM_002543.3) | 2 | ATGACTTTTGATGACCTAAAGATCCAGACTGTGAAGGAC CAGCCTGATGAGAAGTCAAATGGAAAAAAAGCTAAAGGT CTTCAGTTTCTTTACTCTCCATGGTGGTGCCTGGCTGCT GCGACTCTAGGGGTCCTTTGCCTGGGATTAGTAGTGACC ATTATGGTGCTGGGCATGCAATTATCCCAGGTGTCTGAC CTCCTAACACAAGAGCAAGCAAACCTAACTCACCAGAAA AAGAAACTGGAGGGACAGATCTCAGCCCGGCAACAAGCA GAAGAAGCTTCACAGGAGTCAGAAAACGAACTCAAGGAA ATGATAGAAACCCTTGCTCGGAAGCTGAATGAGAAATCC AAAGAGCAAATGGAACTTCACCACCAGAATCTGAATCTC CAAGAAACACTGAAGAGAGTAGCAAATTGTTCAGCTCCT TGTCCGCAAGACTGGATCTGGCATGGAGAAAACTGTTAC CTATTTTCCTCGGGCTCATTTAACTGGGAAAAGAGCCAA GAGAAGTGCTTGTCTTTGGATGCCAAGTTGCTGAAAATT AATAGCACAGCTGATCTGGACTTCATCCAGCAAGCAATT TCCTATTCCAGTTTTCCATTCTGGATGGGCTGTCTCGG AGGAACCCCAGCTACCCATGGCTCTGGGAGGACGGTTCT CCTTTGATGCCCCACTTATTTAGAGTCCGAGGCGCTGTC TCCCAGACATACCCTTCAGGTACCTGTGCATATATACAA CGAGGAGCTGTTTATGCGGAAAACTGCATTTTAGCTGCC TTCAGTATATGTCAGAAGAAGGCAAACCTAAGAGCACAG |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| MOR21435 HCDR1 (Kabat) | 3 | DYAIS |
| HCDR2 (Kabat) | 4 | GIVPIVGTANYAQKFQG |
| HCDR3 (Kabat) | 5 | DSSTSYYYYFDY |
| HCDR1 (Chothia) | 6 | GGTFSDY |
| HCDR2 (Chothia) | 7 | VPIVGT |
| HCDR3 (Chothia) | 8 | DSSTSYYYYFDY |
| VH | 9 | QVQLVQSGAEVKKPGSSVKVSCKASGGTFSDYAISWVRQ APGQGLEWMGGIVPIVGTANYAQKFQGRVTITADESTST AYMELSSLRSEDTAVYYCARDSSTSYYYYFDYWGQGTLV TVSS |
| DNA encoding VH | 10 | caggtgcaattggtgcagagcggtgccgaagtgaaaaaa ccgggcagcagcgtgaaagttagctgcaaagcatccgga gggacgttttctgactacgctatctcttgggtgcgccag gccccgggccagggcctcgagtggatgggcggtatcgtt ccgatcgttggcactgcgaactacgcccagaaatttcag ggccgggtgaccattaccgccgatgaaagcaccagcacc gcctatatggaactgagcagcctgcgcagcgaagatacg gccgtgtattattgcgcgcgtgactcttctacttcttac tactactactacttcgattactggggccaaggcaccctggtg actgttagctca |
| Heavy Chain | 11 | QVQLVQSGAEVKKPGSSVKVSCKASGGTFSDYAISWVRQ APGQGLEWMGGIVPIVGTANYAQKFQGRVTITADESTST AYMELSSLRSEDTAVYYCARDSSTSYYYYFDYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKRVEPKSCDKTHTCPPCP APEAAGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALPAPIEKTISKAKGQPREPQ VYTLPPSREEMTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| DNA encoding Heavy Chain | 12 | caggtgcaattggtgcagagcggtgccgaagtgaaaaaa ccgggcagcagcgtgaaagttagctgcaaagcatccgga gggacgttttctgactacgctatctcttgggtgcgccag gccccgggccagggcctcgagtggatgggcggtatcgtt ccgatcgttggcactgcgaactacgcccagaaatttcag ggccgggtgaccattaccgccgatgaaagcaccagcacc gcctatatggaactgagcagcctgcgcagcgaagatacg gccgtgtattattgcgcgcgtgactcttctacttcttac tactactactacttcgattactggggccaaggcaccctggtg actgttagctcagcctccaccaagggtccatcggtcttc cccctggcaccctcctccaagagcacctctgggggcaca gcggccctgggctgcctggtcaaggactacttccccgaa ccggtgacggtgtcgtggaactcaggcgccctgaccagc ggcgtgcacaccttcccggctgtcctacagtcctcagga ctctactccctcagcagcgtggtgaccgtgccctccagc agcttgggcacccagacctacatctgcaacgtgaatcac aagcccagcaacaccaaggtggacaagagagttgagccc aaatcttgtgacaaaactcacacatgcccaccgtgccca gcacctgaagcagcggggggaccgtcagtcttcctcttc cccccaaaacccaaggacaccctcatgatctcccggacc cctgaggtcacatgcgtggtggtggacgtgagccacgaa gaccctgaggtcaagttcaactggtacgtggacggcgtg gaggtgcataatgccaagacaaagccgcggaggagcag tacaacagcacgtaccgggtggtcagcgtcctcaccgtc ctgcaccaggactggctgaatggcaaggagtacaagtgc aaggtctccaacaaagcccctcccagccccatcgagaaa accatctccaaagccaaagggcagccccgagaaccacag gtgtacaccctgcccccatcccgggaggagatgaccaag aaccaggtcagcctgacctgcctggtcaaaggcttctat cccagcgacatcgccgtggagtgggagagcaatgggcag ccggagaacaactacaagaccacgcctcccgtgctggac tccgacggctccttcttcctctacagcaagctcaccgtg |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | gacaagagcaggtggcagcaggggaacgtcttctcatgc tccgtgatgcatgaggctctgcacaaccactacacgcag aagagcctctccctgtctccgggtaaa |
| LCDR1 (Kabat) | 13 | RASQDINSWLA |
| LCDR2 (Kabat) | 14 | QASNLQS |
| LCDR3 (Kabat) | 15 | QQMWQFPIT |
| LCDR1 (Chothia) | 16 | SQDINSW |
| LCDR2 (Chothia) | 17 | QAS |
| LCDR3 (Chothia) | 18 | MWQFPI |
| VL | 19 | DIQMTQSPSSLSASVGDRVTITCRASQDINSWLAWYQQK PGKAPKLLIYQASNLQSGVPSRFSGSGSGTDFTLTISSL QPEDFATYYCQQMWQFPITFGQGTKVEIK |
| DNA encoding VL | 20 | gatatccagatgacccagagcccgagcagcctgagcgcc agcgtgggcgatcgcgtgaccattacctgcagagccagc caggacattaactcttggctggcttggtaccagcagaaa ccggggcaaagcgccgaaactattaatctaccaggcttct aacctgcaaagcggcgtgccgagccgctttagcggcagc ggatccggcaccgatttcaccctgaccattagctctctg caaccggaagactttgcgacctattattgccagcagatg tggcagttcccgatcacctttggccagggcacgaaagtt gaaattaaa |
| Light Chain | 21 | DIQMTQSPSSLSASVGDRVTITCRASQDINSWLAWYQQK PGKAPKLLIYQASNLQSGVPSRFSGSGSGTDFTLTISSL QPEDFATYYCQQMWQFPITFGQGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| DNA encoding Light Chain | 22 | gatatccagatgacccagagcccgagcagcctgagcgcc agcgtgggcgatcgcgtgaccattacctgcagagccagc caggacattaactcttggctggcttggtaccagcagaaa ccggggcaaagcgccgaaactattaatctaccaggcttct aacctgcaaagcggcgtgccgagccgctttagcggcagc ggatccggcaccgatttcaccctgaccattagctctctg caaccggaagactttgcgacctattattgccagcagatg tggcagttcccgatcacctttggccagggcacgaaagtt gaaattaaacgtacggtggccgctcccagcgtgttcatc ttccccccagcgacgagcagctgaagagcggcaccgcc agcgtggtgtgcctgctgaacaacttctaccccgggag gccaaggtgcagtggaaggtggacaacgccctgcagagc ggcaacagccaggaaagcgtcaccgagcaggacagcaag gactccacctacagcctgagcagcaccctgaccctgagc aaggccgactacgagaagcacaaggtgtacgcctgcgag gtgacccaccagggcctgtccagccccgtgaccaagagc ttcaaccggggcgagtgt |
| MOR20159 HCDR1 (Kabat) | 23 | DYAIS |
| HCDR2 (Kabat) | 24 | GIVPIVGTANYAQKFQG |
| HCDR3 (Kabat) | 25 | DSSTSYYYYFDY |
| HCDR1 (Chothia) | 26 | GGTFSDY |
| HCDR2 (Chothia) | 27 | VPIVGT |
| HCDR3 (Chothia) | 28 | DSSTSYYYYFDY |
| VH | 29 | QVQLVQSGAEVKKPGSSVKVSCKASGGTFSDYAISWVRQ APGQGLEWMGGIVPIVGTANYAQKFQGRVTITADESTST AYMELSSLRSEDTAVYYCARDSSTSYYYYFDYWGQGTLV TVSS |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| DNA encoding VH | 30 | caggtgcaattggtgcagagcggtgccgaagtgaaaaaa ccgggcagcagcgtgaaagttagctgcaaagcatccgga gggacgttttctgactacgctatctcttgggtgcgccag gccccgggccagggcctcgagtggatgggcggtatcgtt ccgatcgttggcactgcgaactacgcccagaaatttcag ggccgggtgaccattaccgccgataaagcaccagcacc gcctatatggaactgagcagcctgcgcagcgaagatacg gccgtgtattattgcgcgcgtgactcttctacttcttac tactactacttcgattactggggccaaggcaccctggtg actgttagctca |
| Heavy Chain | 31 | QVQLVQSGAEVKKPGSSVKVSCKASGGTFSDYAISWVRQ APGQGLEWMGGIVPIVGTANYAQKFQGRVTITADESTST AYMELSSLRSEDTAVYYCARDSSTSYYYYFDYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKRVEPKSCDKTHTCPPCP APEAAGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALPAPIEKTISKAKGQPREPQ VYTLPPSREEMTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| DNA encoding Heavy Chain | 32 | caggtgcaattggtgcagagcggtgccgaagtgaaaaaa ccgggcagcagcgtgaaagttagctgcaaagcatccgga gggacgttttctgactacgctatctcttgggtgcgccag gccccgggccagggcctcgagtggatgggcggtatcgtt ccgatcgttggcactgcgaactacgcccagaaatttcag ggccgggtgaccattaccgccgataaagcaccagcacc gcctatatggaactgagcagcctgcgcagcgaagatacg gccgtgtattattgcgcgcgtgactcttctacttcttac tactactacttcgattactggggccaaggcaccctggtg actgttagctcagcctccaccaagggtccatcggtcttc cccctggcaccctcctccaagagcacctctggggcaca gcggccctgggctgcctggtcaaggactacttccccgaa ccggtgacggtgtcgtggaactcaggcgccctgaccagc ggcgtgcacaccttcccggctgtcctacagtcctcagga ctctactccctcagcagcgtggtgaccgtgccctccagc agcttgggcacccagacctacatctgcaacgtgaatcac aagcccagcaacaccaaggtggacaagagagttgagccc aaatcttgtgacaaaactcacacatgcccaccgtgccca gcacctgaagcagcggggggaccgtcagtcttcctcttc cccccaaaacccaaggacaccctcatgatctcccggacc cctgaggtcacatgcgtggtggtggacgtgagccacgaa gaccctgaggtcaagttcaactggtacgtggacggcgtg gaggtgcataatgccaagacaaagccgcgggaggagcag tacaacagcacgtaccgggtggtcagcgtcctcaccgtc ctgcaccaggactggctgaatggcaaggagtacaagtgc aaggtctccaacaaagcccccagccccatcgagaaa accatctccaaagccaaagggcagccccgagaaccacag gtgtacaccctgcccccatcccgggaggagatgaccaag aaccaggtcagcctgacctgcctggtcaaaggcttctat cccagcgacatcgccgtggagtgggagagcaatgggcag ccggagaacaactacaagaccacgcctcccgtgctggac tccgacggctccttcttcctctacagcaagctcaccgtg gacaagagcaggtggcagcaggggaacgtcttctcatgc tccgtgatgcatgaggctctgcacaaccactacacgcag aagagcctctccctgtctccgggtaaa |
| LCDR1 (Kabat) | 33 | RASQDINSWLA |
| LCDR2 (Kabat) | 34 | QASNLQS |
| LCDR3 (Kabat) | 35 | QQIDHTPFT |
| LCDR1 (Chothia) | 36 | SQDINSW |
| LCDR2 (Chothia) | 37 | QAS |
| LCDR3 (Chothia) | 38 | IDHTPF |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| VL | 39 | DIQMTQSPSSLSASVGDRVTITCRASQDINSWLAWYQQK PGKAPKLLIYQASNLQSGVPSRFSGSGSGTDFTLTISSL QPEDFATYYCQQIDHTPFTFGQGTKVEIK |
| DNA encoding VL | 40 | gatatccagatgacccagagcccgagcagcctgagcgcc agcgtgggcgatcgcgtgaccattacctgcagagccagc caggacattaactcttggctggcttggtaccagcagaaa ccgggcaaagcgccgaaactattaatctaccaggcttct aacctgcaaagcggcgtgccgagccgctttagcggcagc ggatccggcaccgatttcaccctgaccattagctctctg caaccggaagactttgcgacctattattgccagcagatc gaccatactccgttcacctttggccagggcacgaaagtt gaaattaaa |
| Light Chain | 41 | DIQMTQSPSSLSASVGDRVTITCRASQDINSWLAWYQQK PGKAPKLLIYQASNLQSGVPSRFSGSGSGTDFTLTISSL QPEDFATYYCQQIDHTPFTFGQGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVIKSFNRGEC |
| DNA encoding Light Chain | 42 | gatatccagatgacccagagcccgagcagcctgagcgcc agcgtgggcgatcgcgtgaccattacctgcagagccagc caggacattaactcttggctggcttggtaccagcagaaa ccgggcaaagcgccgaaactattaatctaccaggcttct aacctgcaaagcggcgtgccgagccgctttagcggcagc ggatccggcaccgatttcaccctgaccattagctctctg caaccggaagactttgcgacctattattgccagcagatc gaccatactccgttcacctttggccagggcacgaaagtt gaaattaaacgtacggtggccgctcccagcgtgttcatc ttcccccccagcgacgagcagctgaagagcggcaccgcc agcgtggtgtgcctgctgaacaacttctaccccgggag gccaaggtgcagtggaaggtggacaacgccctgcagagc ggcaacagccaggaaagcgtcaccgagcaggacagcaag gactccacctacagcctgagcagcaccctgaccctgagc aaggccgactacgagaagcacaaggtgtacgcctgcgag gtgacccaccagggcctgtccagccccgtgaccaagagc ttcaaccggggcgagtgt |
| MOR22031 HCDR1 (Kabat) | 43 | DYAIS |
| HCDR2 (Kabat) | 44 | GIMPISGAPYYAQKFQG |
| HCDR3 (Kabat) | 45 | DSSTSYYYYFDY |
| HCDR1 (Chothia) | 46 | GGTFSDY |
| HCDR2 (Chothia) | 47 | MPISGA |
| HCDR3 (Chothia) | 48 | DSSTSYYYYFDY |
| VH | 49 | QVQLVQSGAEVKKPGSSVKVSCKASGGTFSDYAISWVRQ APGQGLEWMGGIMPISGAPYYAQKFQGRVTITADESTST AYMELSSERSEDTAVYYCARDSSTSYYYYFDYWGQGTLV TVSS |
| DNA encoding VH | 50 | caggtgcaattggtgcagagcggtgccgaagtgaaaaaa ccggggcagcagcgtgaaagttagctgcaaagcatccga gggacgttttctgactacgctatctcttgggtgcgccag gcccccgggccagggcctcgagtggatgggcggtatcatg ccgatctctggcgctccgtactacgcccagaaatttcag ggccgggtgaccattaccgccgatgaaagcaccagcacc gcctatatggaactgagcagcctgcgcagcgaagatacg gccgtgtattattgcgcgcgtgactcttctacttcttac tactacttcgattactggggccaaggcacccctggtg actgttagctca |
| Heavy Chain | 51 | QVQLVQSGAEVKKPGSSVKVSCKASGGTFSDYAISWVRQ APGQGLEWMGGIMPISGAPYYAQKFQGRVTITADESTST AYMELSSLRSEDTAVYYCARDSSTSYYYYFDYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKRVEPKSCDKTHTCPPCP |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | APEAAGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALPAPIEKTISKAKGQPREPQ VYTLPPSREEMTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| DNA encoding Heavy Chain | 52 | caggtgcaattggtgcagagcggtgccgaagtgaaaaaa ccgggcagcagcgtgaaagttagctgcaaagcatccgga gggacgttttctgactacgctatctcttgggtgcgccag gccccgggccagggcctcgagtggatgggcggtatcatg ccgatctctggcgctccgtactacgcccagaaatttcag ggccgggtgaccattaccgccgatgaaagcaccagcacc gcctatatggaactgagcagcctgcgcagcgaagatacg gccgtgtattattgcgcgcgtgactcttctacttcttac tactacttcgattactggggccaaggcaccctggtg actgttagctcagcctccaccaagggtccatcggtcttc ccctggcaccctcctccaagagcacctctgggggcaca gcggccctgggctgcctggtcaaggactacttccccgaa ccggtgacggtgtcgtggaactcaggcgccctgaccagc ggcgtgcacaccttcccggctgtcctacagtcctcagga ctctactccctcagcagcgtggtgaccgtgccctccagc agcttgggcacccagacctacatctgcaacgtgaatcac aagcccagcaacaccaaggtggacaagagagttgagccc aaatcttgtgacaaaactcacacatgcccaccgtgccca gcacctgaagcagcggggggaccgtcagtcttcctcttc ccccaaaacccaaggacaccctcatgatctcccggacc cctgaggtcacatgcgtggtggtggacgtgagccacgaa gaccctgaggtcaagttcaactggtacgtggacggcgtg gaggtgcataatgccaagacaaagccgcgggaggagcag tacaacagcacgtaccgggtggtcagcgtcctcaccgtc ctgcaccaggactggctgaatggcaaggagtacaagtgc aaggtctccaacaaagccctcccagcccccatcgagaaa accatctccaaagccaaagggcagccccgagaaccacag gtgtacaccctgcccccatcccgggaggagatgaccaag aaccaggtcagcctgacctgcctggtcaaaggcttctat cccagcgacatcgccgtggagtgggagagcaatgggcag ccggagaacaactacaagaccacgcctcccgtgctggac tccgacggctccttcttcctctacagcaagctcaccgtg gacaagagcaggtggcagcaggggaacgtcttctcatgc tccgtgatgcatgaggctctgcacaaccactacacgcag aagagcctctccctgtctccgggtaaa |
| LCDR1 (Kabat) | 53 | RASQDISSWLA |
| LCDR2 (Kabat) | 54 | QASNLQS |
| LCDR3 (Kabat) | 55 | QQIDHTPFT |
| LCDR1 (Chothia) | 56 | SQDISSW |
| LCDR2 (Chothia) | 57 | QAS |
| LCDR3 (Chothia) | 58 | IDHTPF |
| VL | 59 | DIQMTQSPSSLSASVGDRVTITCRASQDISSWLAWYQQK PGKAPKLLIYQASNLQSGVPSRFSGSGSGTDFTLTISSL QPEDFATYYCQQIDHTPFTFGQGTKVEIK |
| DNA encoding VL | 60 | gatatccagatgacccagagcccgagcagcctgagcgcc agcgtgggcgatcgcgtgaccattacctgcagagccagc caggacattagctcttggctggcttggtaccagcagaaa ccgggcaaagcgccgaaactattaatctaccaggcttct aacctgcaaagcggcgtgccgagccgctttagcggcagc ggatccggcaccgatttcaccctgaccattagctctctg caaccggaagactttgcgacctattattgccagcagatc gaccatactccgttcacctttggccagggcacgaaagtt gaaattaaa |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| Light Chain | 61 | DIQMTQSPSSLSASVGDRVTITCRASQDISSWLAWYQQK PGKAPKLLIYQASNLQSGVPSRFSGSGSGTDFTLTISSL QPEDFATYYCQQIDHTPFTFGQGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| DNA encoding Light Chain | 62 | gatatccagatgacccagagcccgagcagcctgagcgcc agcgtgggcgatcgcgtgaccattacctgcagagccagc caggacattagctcttggctggcttggtaccagcagaaa ccgggcaaagcgccgaaactattaatctaccaggcttct aacctgcaaagcggcgtgccgagccgctttagcggcagc ggatccggcaccgatttcaccctgaccattagctctctg caaccggaagactttgcgacctattattgccagcagatc gaccatactccgttcacctttggccagggcacgaaagtt gaaattaaacgtacggtggccgctcccagcgtgttcatc ttcccccccagcgacgagcagctgaagagcggcaccgcc agcgtggtgtgcctgctgaacaacttctacccccgggag gccaaggtcagtggaaggtggacaacgccctgcagagc ggcaacagccaggaaagcgtcaccgagcaggacagcaag gactccacctacagcctgagcagcaccctgaccctgagc aaggccgactacgagaagcacaaggtgtacgcctgcgag gtgacccaccagggcctgtccagccccgtgaccaagagc ttcaaccggggcgagtgt |
| MOR22034 HCDR1 (Kabat) | 63 | DYAIS |
| HCDR2 (Kabat) | 64 | GIVPIVGTANYAQKFQG |
| HCDR3 (Kabat) | 65 | DSSTSYYYYFDY |
| HCDR1 (Chothia) | 66 | GGTFSDY |
| HCDR2 (Chothia) | 67 | VPIVGT |
| HCDR3 (Chothia) | 68 | DSSTSYYYYFDY |
| VH | 69 | QVQLVQSGAEVKKPGSSVKVSCKASGGTFSDYAISWVRQ APGQGLEWMGGIVPIVGTANYAQKFQGRVTITADESTST AYMELSSLRSEDTAVYYCARDSSTSYYYYFDYWGQGTLV TVSS |
| DNA encoding VH | 70 | caggtgcaattggtgcagagcggtgccgaagtgaaaaaa ccgggcagcagcgtgaaagttagctgcaaagcatccgga gggacgttttctgactacgctatctcttgggtgcgccag gccccgggccagggcctcgagtggatgggcggtatcgtt ccgatcgttggcactgcgaactacgcccagaaatttcag ggccgggtgaccattaccgccgatgaaagcaccagcacc gcctatatggaactgagcagcctgcgcagcgaagatacg gccgtgtattattgcgcgcgtgactcttctacttcttac tactactacttcgattactggggccaaggcacccctggtg actgttagctca |
| Heavy Chain | 71 | QVQLVQSGAEVKKPGSSVKVSCKASGGTFSDYAISWVRQ APGQGLEWMGGIVPIVGTANYAQKFQGRVTITADESTST AYMELSSLRSEDTAVYYCARDSSTSYYYYFDYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKRVEPKSCDKTHTCPPCP APEAAGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALPAPIEKTISKAKGQPREPQ VYTLPPSREEMTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| DNA encoding Heavy Chain | 72 | caggtgcaattggtgcagagcggtgccgaagtgaaaaaa ccgggcagcagcgtgaaagttagctgcaaagcatccgga gggacgttttctgactacgctatctcttgggtgcgccag gccccgggccagggcctcgagtggatgggcggtatcgtt ccgatcgttggcactgcgaactacgcccagaaatttcag ggccgggtgaccattaccgccgatgaaagcaccagcacc gcctatatggaactgagcagcctgcgcagcgaagatacg |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | gccgtgtattattgcgcgcgtgactcttctacttcttac<br>tactactacttcgattactggggccaaggcaccctggtg<br>actgttagctcagcctccaccaagggtccatcggtcttc<br>cccctggcaccctcctccaagagcacctctgggggcaca<br>gcggccctgggctgcctggtcaaggactacttccccgaa<br>ccggtgacggtgtcgtggaactcaggcgccctgaccagc<br>ggcgtgcacaccttcccggctgtcctacagtcctcagga<br>ctctactccctcagcagcgtggtgaccgtgccctccagc<br>agcttgggcacccagacctacatctgcaacgtgaatcac<br>aagcccagcaacaccaaggtggacaagagagttgagccc<br>aaatcttgtgacaaaactcacacatgcccaccgtgccca<br>gcacctgaagcagcgggggaccgtcagtcttcctcttc<br>cccccaaaacccaaggacaccctcatgatctcccggacc<br>cctgaggtcacatgcgtggtggtggacgtgagccacgaa<br>gaccctgaggtcaagttcaactggtacgtggacggcgtg<br>gaggtgcataatgccaagacaaagccgcgggaggagcag<br>tacaacagcacgtaccgggtggtcagcgtcctcaccgtc<br>ctgcaccaggactggctgaatggcaaggagtacaagtgc<br>aaggtctccaacaaagccctcccagccccatcgagaaa<br>accatctccaaagccaaagggcagccccgagaaccacag<br>gtgtacaccctgcccccatcccgggaggagatgaccaag<br>aaccaggtcagcctgacctgcctggtcaaaggcttctat<br>cccagcgacatcgccgtggagtgggagagcaatgggcag<br>ccggagaacaactacaagaccacgcctcccgtgctggac<br>tccgacggctccttcttcctctacagcaagctcaccgtg<br>gacaagagcaggtggcagcaggggaacgtcttctcatgc<br>tccgtgatgcatgaggctctgcacaaccactacacgcag<br>aagagcctctccctgtctccgggtaaa |
| LCDR1 (Kabat) | 73 | RASQDISSWLA |
| LCDR2 (Kabat) | 74 | QASNLQS |
| LCDR3 (Kabat) | 75 | QQMWQFPIT |
| LCDR1 (Chothia) | 76 | SQDISSW |
| LCDR2 (Chothia) | 77 | QAS |
| LCDR3 (Chothia) | 78 | MWQFPI |
| VL | 79 | DIQMTQSPSSLSASVGDRVTITCRASQDISSWLAWYQQK<br>PGKAPKLLIYQASNLQSGVPSRFSGSGSGTDFTLTISSL<br>QPEDFATYYCQQMWQFPITFGQGTKVEIK |
| DNA encoding VL | 80 | gatatccagatgacccagagcccgagcagcctgagcgcc<br>agcgtgggcgatcgcgtgaccattacctgcagagccagc<br>caggacattagctctttggctggcttggtaccagcagaaa<br>ccggggcaaagcgccgaaactattaatctaccaggcttct<br>aacctgcaaagcggcgtgccgagccgctttagcggcagc<br>ggatccggcaccgatttcaccctgaccattagctctctg<br>caaccggaagactttgcgacctattattgccagcagatg<br>tggcagttcccgatcacctttggcagggcacgaaagtt<br>gaaattaaa |
| Light Chain | 81 | DIQMTQSPSSLSASVGDRVTITCRASQDISSWLAWYQQK<br>PGKAPKLLIYQASNLQSGVPSRFSGSGSGTDFTLTISSL<br>QPEDFATYYCQQMWQFPITFGQGTKVEIKRTVAAPSVFI<br>FPPSDEQLKSGTASVVCLLNNFYPREAKVQWKVDNALQS<br>GNSQESVTEQDSKDSTYSLSSILTLSKADYEKHKVYACE<br>VTHQGLSSPVTKSFNRGEC |
| DNA encoding Light Chain | 82 | gatatccagatgacccagagcccgagcagcctgagcgcc<br>agcgtgggcgatcgcgtgaccattacctgcagagccagc<br>caggacattagctctttggctggcttggtaccagcagaaa<br>ccggggcaaagcgccgaaactattaatctaccaggcttct<br>aacctgcaaagcggcgtgccgagccgctttagcggcagc<br>ggatccggcaccgatttcaccctgaccattagctctctg<br>caaccggaagactttgcgacctattattgccagcagatg<br>tggcagttcccgatcacctttggcagggcacgaaagtt<br>gaaattaaacgtacggtggccgctcccagcgtgttcatc<br>ttccccccagcgacgagcagctgaagagcggcaccgcc<br>agcgtggtgtgcctgctgaacaacttctaccccggggag<br>gccaaggtgcagtggaaggtggacaacgccctgcagagc |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
| --- | --- | --- |
| | | ggcaacagccaggaaagcgtcaccgagcaggacagcaag<br>gactccacctacagcctgagcagcaccctgaccctgagc<br>aaggccgactacgagaagcacaaggtgtacgcctgcgag<br>gtgacccacagggcctgtccagccccgtgaccaagagc<br>ttcaaccggggcgagtgt |
| MOR21433<br>HCDR1 (Kabat) | 83 | DYAIS |
| HCDR2 (Kabat) | 84 | GIMPISGAPYYAQKFQG |
| HCDR3 (Kabat) | 85 | DSSTSYYYYFDY |
| HCDR1 (Chothia) | 86 | GGTFSDY |
| HCDR2 (Chothis) | 87 | MPISGA |
| HCDR3 (Chothia) | 88 | DSSTSYYYFDY |
| VH | 89 | QVQLVQSGAEVKKPGSSVKVSCKASGGTFSDYAISWVRQ<br>APGQGLEWMGGIMPISGAPYYAQKFQGRVTITADESTST<br>AYMELSSLRSEDTAVYYCARDSSTSYYYYFDYWGQGTLV<br>TVSS |
| DNA encoding VH | 90 | caggtgcaattggtgcagagcggtgccgaagtgaaaaaa<br>ccgggcagcagcgtgaaagttagctgcaaagcatccgga<br>gggacgttttctgactacgctatctcttgggtgcgccag<br>gccccgggccagggcctcgagtggatgggcggtatcatg<br>ccgatctctggcgctccgtactacgcccagaaatttcag<br>ggccgggtgaccattaccgccgatgaaagcaccagcacc<br>gcctatatggaactgagcagcctgcgcagcgaagatacg<br>gccgtgtattattgcgcgcgtgactcttctacttcttac<br>tactactacttcgattactggggccaaggcacc ctggtg<br>actgttagctca |
| Heavy Chain | 91 | QVQLVQSGAEVKKPGSSVKVSCKASGGTFSDYAISWVRQ<br>APGQGLEWMGGIMPISGAPYYAQKFQGRVTITADESTST<br>AYMELSSLRSEDTAVYYCARDSSTSYYYYFDYWGQGTLV<br>TVSSASTKGPSVFPLAPSSKSTSGGTAALGCLVKDYFPE<br>PVTVSWNSGALTSGVHTFPAVLQSSGLYSLSSVVTVPSS<br>SLGTQTYICNVNHKPSNTKVDKRVEPKSCDKTHTCPPCP<br>APEAAGGPSVFLFPPKPKDTLMISRTPEVTCVVVDVSHE<br>DPEVKFNWYVDGVEVHNAKTKPREEQYNSTYRVVSVLTV<br>LHQDWLNGKEYKCKVSNKALPAPIEKTISKAKGQPREPQ<br>VYTLPPSREEMTKNQVSLTCLVKGFYPSDIAVEWESNGQ<br>PENNYKTTPPVLDSDGSFFLYSKLTVDKSRWQQGNVFSC<br>SVMHEALHNHYTQKSLSLSPGK |
| DNA encoding Heavy Chain | 92 | caggtgcaattggtgcagagcggtgccgaagtgaaaaaa<br>ccgggcagcagcgtgaaagttagctgcaaagcatccgga<br>gggacgttttctgactacgctatctcttgggtgcgccag<br>gccccgggccagggcctcgagtggatgggcggtatcatg<br>ccgatctctggcgctccgtactacgcccagaaatttcag<br>ggccgggtgaccattaccgccgatgaaagcaccagcacc<br>gcctatatggaactgagcagcctgcgcagcgaagatacg<br>gccgtgtattattgcgcgcgtgactcttctacttcttac<br>tactactacttcgattactggggccaaggcaccctggtg<br>actgttagctcagcctccaccaagggtccatcggtcttc<br>cccctggcaccctcctccaagagcacctctgggggcaca<br>gcggccctgggctgcctggtcaaggactacttccccgaa<br>ccggtgacggtgtcgtggaactcaggcgccctgaccagc<br>ggcgtgcacaccttcccggctgtcctacagtcctcagga<br>ctctactccctcagcagcgtggtgaccgtgccctccagc<br>agcttgggcacccagacctacatctgcaacgtgaatcac<br>aagcccagcaacaccaaggtggacaagagagttgagccc<br>aaatcttgtgacaaaactcacacatgcccaccgtgccca<br>gcacctgaagcagcggggggaccgtcagtcttcctcttc<br>cccccaaaacccaaggacaccctcatgatctcccggacc<br>cctgaggtcacatgcgtggtggtggacgtgagccacgaa<br>gaccctgaggtcaagttcaactggtacgtggacggcgtg<br>gaggtgcataatgccaagacaaagccgcgggaggagcag<br>tacaacagcacgtaccgggtggtcagcgtcctcaccgtc<br>ctgcaccaggactggctgaatggcaaggagtacaagtgc<br>aaggtctccaacaaagcccctcccagcccccatcgagaaa |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | accatctccaaagccaaagggcagccccgagaaccacag gtgtacaccctgcccccatcccgggaggagatgaccaag aaccaggtcagcctgacctgcctggtcaaaggcttctat cccagcgacatcgccgtggagtgggagagcaatgggcag ccggagaacaactacaagaccacgcctcccgtgctggac tccgacggctccttcttcctctacagcaagctcaccgtg gacaagagcaggtggcagcaggggaacgtcttctcatgc tccgtgatgcatgaggctctgcacaaccactacacgcag aagagcctctccctgtctccgggtaaa |
| LCDR1 (Kabat) | 93 | RASQDINSWLA |
| LCDR2 (Kabat) | 94 | QASNLQS |
| LCDR3 (Kabat) | 95 | QQIDHTPFT |
| LCDR1 (Chothia) | 96 | SQDINSW |
| LCDR2 (Chothia) | 97 | QAS |
| LCDR3 (Chothia) | 98 | IDHTPF |
| VL | 99 | DIQMTQSPSSLSASVGDRVTITCRASQDINSWLAWYQQK PGKAPKLLIYQASNLQSGVPSRFSGSGSGTDFTLTISSL QPEDFATYYCQQIDHTPFTFGQGTKVEIK |
| DNA encoding VL | 100 | gatatccagatgacccagagcccgagcagcctgagcgcc agcgtgggcgatcgcgtgaccattacctgcagagccagc caggacattaactcttggctggcttggtaccagcagaaa ccgggcaaagcgccgaaactattaatctaccaggcttct aacctgcaaagcggcgtgccgagccgctttagcggcagc ggatccggcaccgatttcaccctgaccattagctctctg caaccggaagactttgcgacctattattgccagcagatc gaccatactccgttcacctttggccagggcacgaaagtt gaaattaaa |
| Light Chain | 101 | DIQMTQSPSSLSASVGDRVTITCRASQDINSWLAWYQQK PGKAPKLLIYQASNLQSGVPSRFSGSGSGTDFTLTISSL QPEDFATYYCQQIDHTPFTFGQGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| DNA encoding Light Chain | 102 | Gatatccagatgacccagagcccgagcagcctgagcgcc agcgtgggcgatcgcgtgaccattacctgcagagccagc caggacattaactcttggctggcttggtaccagcagaaa ccgggcaaagcgccgaaactattaatctaccaggcttct aacctgcaaagcggcgtgccgagccgctttagcggcagc ggatccggcaccgatttcaccctgaccattagctctctg caaccggaagactttgcgacctattattgccagcagatc gaccatactccgttcacctttggccagggcacgaaagtt gaaattaaacgtacggtggccgctcccagcgtgttcatc ttccccccagcgacgagcagctgaagagcggcaccgcc agcgtggtgtgcctgctgaacaacttctaccccggag gccaaggtgcagtggaaggtggacaacgccctgcagagc ggcaacagccaggaaagcgtcaccgagcaggacagcaag gactccacctacagcctgagcagcaccctgaccctgagc aaggccgactacgagaagcacaaggtgtacgcctgcgag gtgacccaccagggcctgtccagcccgtgaccaagagc ttcaaccggggcgagtgt |
| MOR21452 HCDR1 (Kabat) | 103 | SYALS |
| HCDR2 (Kabat) | 104 | RTKHENEGYTTWYAASVKG |
| HCDR3 (Kabat) | 105 | DFWADHYYYFDY |
| HCDR1 (Chothia) | 106 | GFTFSSY |
| HCDR2 (Chothia) | 107 | KHENEGYT |
| HCDR3 (Chothia) | 108 | DFWADHYYYFDY |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| VH | 109 | QVQLVESGGGLVKPGGSLRLSCAASGFTFSSYALSWVRQ APGKGLEWVGRTKHENEGYTTWYAASVKGRFTISRDDSK NTLYLQMNSLKTEDTAVYYCARDFWADHYYYFDYWGQGT LVTVSS |
| DNA encoding VH | 110 | caggtgcaattggtggaaagcggcggtggcctggtgaaa ccaggcggcagcctgcgcctgagctgcgccgcctccgga ttcaccttttcttcttacgctctgtcttgggtgcgccag gccccgggcaaaggtctcgagtgggtgggccgtactaaa catgaaaacgaaggctacactacttggtatgccgcctct gtgaaaggccgctttaccattagccgcgatgattcgaaa aacaccctgtatctgcaaatgaacagcctgaaaaccgaa gatacggccgtgtattattgcgcgcgtgacttctgggct gaccattactacttcgattactggggccaaggcacc ctggtgactgttagctca |
| Heavy Chain | 111 | QVQLVESGGGLVKPGGSLRLSCAASGFTFSSYALSWVRQ APGKGLEWVGRTKHENEGYTTWYAASVKGRFTISRDDSK NTLYLQMNSLKTEDTAVYYCARDFWADHYYYFDYWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCPP CPAPEAAGGPSVFLFPPKPKDTLMISRTPEVTCVVVDVS HEDPEVKFNWYVDGVEVHNAKTKPREEQYNSTYRVVSVL TVLHQDWLNGKEYKCKVSNKALPAPIEKTISKAKGQPRE PQVYTLPPSREEMTKNQVSLTCLVKGFYPSDIAVEWESN GQPENNYKTTPPVLDSDGSFFLYSKLTVDKSRWQQGNVF SCSVMHEALHNHYTQKSLSLSPGK |
| DNA encoding Heavy Chain | 112 | Caggtgcaattggtggaaagcggcggtggcctggtgaaa ccaggcggcagcctgcgcctgagctgcgccgcctccgga ttcaccttttcttcttacgctctgtcttgggtgcgccag gccccgggcaaaggtctcgagtgggtgggccgtactaaa catgaaaacgaaggctacactacttggtatgccgcctct gtgaaaggccgctttaccattagccgcgatgattcgaaa aacaccctgtatctgcaaatgaacagcctgaaaaccgaa gatacggccgtgtattattgcgcgcgtgacttctgggct gaccattactacttcgattactggggccaaggcacc ctggtgactgttagctcagcctccaccaagggtccatcg gtcttccccctggcaccctcctccaagagcacctctggg ggcacagcggccctgggctgcctggtcaaggactacttc cccgaaccggtgacggtgtcgtggaactcaggcgccctg accagcggcgtgcacaccttcccggctgtcctacagtcc tcaggactctactccctcagcagcgtggtgaccgtgccc tccagcagcttgggcacccagacctacatctgcaacgtg aatcacaagcccagcaacaccaaggtggacaagagagtt gagcccaaatcttgtgacaaaactcacacatgcccaccg tgcccagcacctgaagcagcggggggaccgtcagtcttc ctcttccccccaaaacccaaggacaccctcatgatctcc cggacccctgaggtcacatgcgtggtggtggacgtgagc cacgaagaccctgaggtcaagttcaactggtacgtggac ggcgtggaggtgcataatgccaagacaaagccgcgggag gagcagtacaacagcacgtaccgggtggtcagcgtcctc accgtcctgcaccaggactggctgaatggcaaggagtac aagtgcaaggtctccaacaaagccctcccagcccccatc gagaaaaccatctccaaagccaaagggcagccccgagaa ccacaggtgtacaccctgcccccatcccgggaggagatg accaagaaccaggtcagcctgacctgcctggtcaaaggc ttctatcccagcgacatcgccgtggagtgggagagcaat gggcagccggagaacaactacaagaccacgcctcccgtg ctggactccgacggctccttcttcctctacagcaagctc accgtggacaagagcaggtggcagcaggggaacgtcttc tcatgctccgtgatgcatgaggctctgcacaaccactac acgcagaagagcctctccctgtctccgggtaaa |
| LCDR1 (Kabat) | 113 | TGTSSDVGYINYVN |
| LCDR2 (Kabat) | 114 | EVSNRPS |
| LCDR3 (Kabat) | 115 | ASWDWYDNVV |
| LCDR1 (Chothia) | 116 | TSSDVGYINY |
| LCDR2 (Chothia) | 117 | EVS |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
| --- | --- | --- |
| LCDR3 (Chothia) | 118 | WDWYDNV |
| VL | 119 | DIALTQPASVSGSPGQSITISCTGTSSDVGYINYVNWYQ QHPGKAPKLMIYEVSNRPSGVSNRFSGSKSGNTASLTIS GLQAEDEADYYCASWDWYDNVVFGGGTKLTVL |
| DNA encoding VL | 120 | gatatcgcgctgacccagccggcgagcgtgagcggtagc ccgggccagagcattaccattagctgcaccggcaccagc agcgatgtgggctacatcaactacgtgaactggtaccag cagcatccgggcaaggcgccgaaactgatgatctacgaa gtttctaaccgtccgagcggcgtgagcaaccgttttagc ggatccaaaagcggcaacaccgcgagcctgaccattagc ggcctgcaagcggaagacgaagcggattattactgcgct tcttgggactggtacgacaacgttgtgtttggcggcggc acgaagttaaccgtccta |
| Light Chain | 121 | DIALTQPASVSGSPGQSITISCTGTSSDVGYINYVNWYQ QHPGKAPKLMIYEVSNRPSGVSNRFSGSKSGNTASLTIS GLQAEDEADYYCASWDWYDNVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA encoding Light Chain | 122 | gatatcgcgctgacccagccggcgagcgtgagcggtagc ccgggccagagcattaccattagctgcaccggcaccagc agcgatgtgggctacatcaactacgtgaactggtaccag cagcatccgggcaaggcgccgaaactgatgatctacgaa gtttctaaccgtccgagcggcgtgagcaaccgttttagc ggatccaaaagcggcaacaccgcgagcctgaccattagc ggcctgcaagcggaagacgaagcggattattactgcgct tcttgggactggtacgacaacgttgtgtttggcggcggc acgaagttaaccgtcctaggtcagcccaaggctgccccc tcggtcactctgttcccgccctcctctgaggagcttcaa gccaacaaggccacactggtgtgtctcataagtgacttc tacccgggagccgcgacagtggcctggaaggcagatagc agccccgtcaaggcgggagtggagaccaccacaccctcc aaacaaagcaacaacaagtacgcggccagcagctatctg agcctgacgcctgagcagcggaagtcccacagaagctac agctgccaggtcacgcatgaagggagcaccgtggagaag acagtggcccctacagaatgttca |
| MOR21453 HCDR1 (Kabat) | 123 | SYALS |
| HCDR2 (Kabat) | 124 | RIKLINKGYTTWYAASVKG |
| HCDR3 (Kabat) | 125 | DFWADHYYYFDY |
| HCDR1 (Chothia) | 126 | GFTFSSY |
| HCDR2 (Chothia) | 127 | KLINKGYT |
| HCDR3 (Chothia) | 128 | DFWADHYYYFDY |
| VH | 129 | QVQLVESGGGLVKPGGSLRLSCAASGFTFSSYALSWVRQ APGKGLEWVGRIKLINKGYTTWYAASVKGRFTISRDDSK NTLYLQMNSLKTEDTAVYYCARDFWADHYYYFDYWGQGT LVTVSS |
| DNA encoding VH | 130 | caggtgcaattggtggaaagcggcggtggcctggtgaaa ccaggcggcagcctgcgcctgagctgcgccgcctccgga ttcacctttcttcttacgctctgtcttgggtgcgccag gcccgggcaaaggtctcgagtgggtgggccgtatcaaa ctgatcaacaaaggctacactacttggtatgccgcctct gtgaaaggccgctttaccattagccgcgatgattcgaaa aacaccctgtatctgcaaatgaacagcctgaaaaccgaa gatacggccgtgtattattgcgcgcgtgacttctggct gaccattactactacttcgattactggggccaaggcacc ctggtgactgttagctca |
| Heavy Chain | 131 | QVQLVESGGGLVKPGGSLRLSCAASGFTFSSYALSWVRQ APGKGLEWVGRIKLINKGYTTWYAASVKGRFTISRDDSK NTLYLQMNSLKTEDTAVYYCARDFWADHYYYFDYWGQGT |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCPP CPAPEAAGGPSVFLFPPKPKDTLMISRTPEVTCVVVDVS HEDPEVKFNWYVDGVEVHNAKTKPREEQYNSTYRVVSVL TVLHQDWLNGKEYKCKVSNKALPAPIEKTISKAKGQPRE PQVYTLPPSREEMTKNQVSLTCLVKGFYPSDIAVEWESN GQPENNYKTTPPVLDSDGSFFLYSKLTVDKSRWQQGNVF SCSVMHEALHNHYTQKSLSLSPGK |
| DNA encoding Heavy Chain | 132 | caggtgcaattggtggaaagcggcggtggcctggtgaaa ccaggcggcagcctgcgcctgagctgcgccgcctccgga ttcacctttcttcttacgctctgtcttgggtgcgccag gccccgggcaaaggtctcgagtgggtgggccgtatcaaa ctgatcaacaaaggctacactacttggtatgccgcctct gtgaaaggccgctttaccattagccgcgatgattcgaaa aacaccctgtatctgcaaatgaacagcctgaaaaccgaa gatacggccgtgtattattgcgcgcgtgacttctgggct gaccattactactacttcgattactggggccaaggcacc ctggtgactgttagctcagcctccaccaagggtccatcg gtcttccccctggcaccctcctccaagagcacctctggg ggcacagcggccctgggctgcctggtcaaggactacttc cccgaaccggtgacggtgtcgtggaactcaggcgccctg accagcggcgtgcacaccttcccggctgtcctacagtcc tcaggactctactccctcagcagcgtggtgaccgtgccc tccagcagcttgggcacccagacctacatctgcaacgtg aatcacaagcccagcaacaccaaggtggacaagagagtt gagcccaaatcttgtgacaaaactcacacatgcccaccg tgcccagcacctgaagcagcgggggggaccgtcagtcttc ctcttccccccaaaacccaaggacaccctcatgatctcc cggacccctgaggtcacatgcgtggtggtggacgtgagc cacgaagaccctgaggtcaagttcaactggtacgtggac ggcgtggaggtgcataatgccaagacaaagccgcgggag gagcagtacaacagcacgtaccgggtggtcagcgtcctc accgtcctgcaccaggactggctgaatggcaaggagtac aagtgcaaggtctccaacaaagcccctcccagcccccatc gagaaaaccatctccaaagccaaagggcagccccgagaa ccacaggtgtacaccctgcccccatcccgggaggagatg accaagaaccaggtcagcctgacctgcctggtcaaaggc ttctatcccagcgacatcgccgtggagtgggagagcaat gggcagccggagaacaactacaagaccacgcctcccgtg ctggactccgacggctccttcttcctctacagcaagctc accgtggacaagagcaggtggcagcaggggaacgtcttc tcatgctccgtgatgcatgaggctctgcacaaccactac acgcagaagagcctctccctgtctccgggtaaa |
| LCDR1 (Kabat) | 133 | TGTSSDVGYINYVN |
| LCDR2 (Kabat) | 134 | EVSNRPS |
| LCDR3 (Kabat) | 135 | ASWDWYDNVV |
| LCDR1 (Chothia) | 136 | TSSDVGYINY |
| LCDR2 (Chothia) | 137 | EVS |
| LCDR3 (Chothia) | 138 | WDWYDNV |
| VL | 139 | DIALTQPASVSGSPGQSITISCTGTSSDVGYINYVNWYQ QHPGKAPKLMIYEVSNRPSGVSNRFSGSKSGNTASLTIS GLQAEDEADYYCASWDWYDNVVFGGGTKLTVL |
| DNA encoding VL | 140 | gatatcgcgctgacccagccggcgagcgtgagcggtagc ccgggccagagcattaccattagctgcaccggcaccagc agcgatgtgggctacatcaactacgtgaactggtaccag cagcatccgggcaaggcgccgaaactgatgatctacgaa gtttctaaccgtccgagcggcgtgagcaaccgttttagc ggatccaaaagcggcaacaccgcgagcctgaccattagc ggcctgcaagcggaagacgaagcggattattactgcgct cttgggactggtacgacaacgttgtgtttggcggcggc acgaagttaaccgtccta |
| Light Chain | 141 | DIALTQPASVSGSPGQSITISCTGTSSDVGYINYVNWYQ QHPGKAPKLMIYEVSNRPSGVSNRFSGSKSGNTASLTIS |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | GLQAEDEADYYCASWDWYDNVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA encoding Light Chain | 142 | gatatcgcgctgacccagccggcgagcgtgagcggtagc ccgggccagagcattaccattagctgcaccggcaccagc agcgatgtgggctacatcaactacgtgaactggtaccag cagcatccgggcaaggcgccgaaactgatgatctacgaa gtttctaaccgtccgagcggcgtgagcaaccgttttagc ggatccaaaagcggcaacaccgcgagcctgaccattagc ggcctgcaagcggaagacgaagcggattattactgcgct tcttgggactggtacgacaacgttgtgtttggcggcggc acgaagttaaccgtcctaggtcagcccaaggctgccccc tcggtcactctgttcccgccctcctctgaggagcttcaa gccaacaaggccacactggtgtgtctcataagtgacttc tacccgggagccgtgacagtggcctggaaggcagatagc agccccgtcaaggcgggagtggagaccaccacaccctcc aaacaaagcaacaacaagtacgcggccagcagctatctg agcctgacgcctgagcagtggaagtcccacagaagctac agctgccaggtcacgcatgaagggagcaccgtggagaag acagtggcccctacagaatgttca |
| MOR21460 HCDR1 (Kabat) | 143 | DYALH |
| HCDR2 (Kabat) | 144 | VISYQGGFIYYADSVKG |
| HCDR3 (Kabat) | 145 | SPGLTSYHDS |
| HCDR1 (Chothia) | 146 | GFTFSDY |
| HCDR2 (Chothia) | 147 | SYQGGF |
| HCDR3 (Chothia) | 148 | SPGLTSYHDS |
| VH | 149 | QVQLLESGGGLVQPGGSLRLSCAASGFTFSDYALHWVRQ APGKGLEWVSVISYQGGFIYYADSVKGRFTISRDNSKNT LYLQMNSLRAEDTAVYYCARSPGLTSYHDSWGQGTLVTV SS |
| DNA encoding VH | 150 | caggtgcaattgctggaaagcggcggtggcctggtgcag ccgggtggcagcctgcgtctgagctgcgcggcgtccgga ttcacctttctgactacgctctgcattgggtgcgccag gccccgggcaaaggtctcgagtgggtttccgttatctct taccagggcggtttcatctactatgcggatagcgtgaaa ggccgctttaccatcagccgcgataattcgaaaaacacc ctgtatctgcaaatgaacagcctgcgtgcggaagatacg gccgtgtattattgcgcgcgttctccgggtctgacttct taccatgattcttggggccaaggcaccctggtgactgtt agctca |
| Heavy Chain | 151 | QVQLLESGGGLVQPGGSLRLSCAASGFTFSDYALHWVRQ APGKGLEWVSVISYQGGFIYYADSVKGRFTISRDNSKNT LYLQMNSLRAEDTAVYYCARSPGLTSYHDSWGQGTLVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |
| DNA encoding Heavy Chain | 152 | Caggtgcaattgctggaaagcggcggtggcctggtgcag ccgggtggcagcctgcgtctgagctgcgcggcgtccgga ttcacctttctgactacgctctgcattgggtgcgccag gccccgggcaaaggtctcgagtgggtttccgttatctct taccagggcggtttcatctactatgcggatagcgtgaaa ggccgctttaccatcagccgcgataattcgaaaaacacc ctgtatctgcaaatgaacagcctgcgtgcggaagatacg gccgtgtattattgcgcgcgttctccgggtctgacttct taccatgattcttggggccaaggcaccctggtgactgtt |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | agctcagcctccaccaagggtccatcggtcttcccctg<br>gcaccctcctccaagagcacctctgggggcacagcggcc<br>ctgggctgcctggtcaaggactacttccccgaaccggtg<br>acggtgtcgtggaactcaggcgccctgaccagcggcgtg<br>cacaccttcccggctgtcctacagtcctcaggactctac<br>tccctcagcagcgtggtgaccgtgccctccagcagcttg<br>ggcacccagacctacatctgcaacgtgaatcacaagccc<br>agcaacaccaaggtggacaagagagttgagcccaaatct<br>tgtgacaaaactcacacatgcccaccgtgcccagcacct<br>gaagcagcggggggaccgtcagtcttcctcttccccca<br>aaacccaaggacaccctcatgatctcccggacccctgag<br>gtcacatgcgtggtggtggacgtgagccacgaagaccct<br>gaggtcaagttcaactggtacgtggacggcgtggaggtg<br>cataatgccaagacaaagccgcgggaggagcagtacaac<br>agcacgtaccgggtggtcagcgtcctcaccgtcctgcac<br>caggactggctgaatggcaaggagtacaagtgcaaggtc<br>tccaacaaagccctcccagcccccatcgagaaaaccatc<br>tccaaagccaaagggcagccccgagaaccacaggtgtac<br>accctgccccatcccgggaggagatgaccaagaaccag<br>gtcagcctgacctgcctggtcaaaggcttctatcccagc<br>gacatcgccgtggagtgggagagcaatgggcagccggag<br>aacaactacaagaccacgcctcccgtgctggactccgac<br>ggctccttcttcctctacagcaagctcaccgtggacaag<br>agcaggtggcagcaggggaacgtcttctcatgctccgtg<br>atgcatgaggctctgcacaaccactacacgcagaagagc<br>ctctccctgtctccgggtaaa |
| LCDR1 (Kabat) | 153 | SGSSSNIGSNYVS |
| LCDR2 (Kabat) | 154 | SNSHRPS |
| LCDR3 (Kabat) | 155 | QSWDYESERVV |
| LCDR1 (Chothia) | 156 | SSSNIGSNY |
| LCDR2 (Chothia) | 157 | SNS |
| LCDR3 (Chothia) | 158 | WDYESERV |
| VL | 159 | DIVLTQPPSVSGAPGQRVTISCSGSSSNIGSNYVSWYQQ<br>LPGTAPKLLIHSNSHRPSGVPDRFSGSKSGTSASLAITG<br>LQAEDEADYYCQSWDYESERVVFGGGTKLTVL |
| DNA encoding VL | 160 | gatatcgtgctgacccagccgccgagcgtgagcggtgca<br>ccggggccagcgcgtgaccattagctgtagcggcagcagc<br>agcaacattggttctaactacgtgtcttggtaccagcag<br>ctgccgggcacggcgccgaaactgctgatccattctaac<br>tctcatcgcccgagcggcgtgccggatcgctttagcgga<br>tccaaaagcggcaccagcgccagcctggcgattaccggc<br>ctgcaagcagaagacgaagcggattattactgccagtct<br>tgggactacgaatctgaacgtgttgtgtttggcggcggc<br>acgaagttaaccgtccta |
| Light Chain | 161 | DIVLTQPPSVSGAPGQRVTISCSGSSSNIGSNYVSWYQQ<br>LPGTAPKLLIHSNSHRPSGVPDRFSGSKSGTSASLAITG<br>LQAEDEADYYCQSWDYESERVVFGGGTKLTVLGQPKAAP<br>SVTLFPPSSEELQANKATLVCLISDFYPGAVTVAWKADS<br>SPVKAGVETTTPSKQSNNKYAASSYLSLTPEQWKSHRSY<br>SCQVTHEGSTVEKTVAPTECS |
| DNA encoding Light Chain | 162 | gatatcgtgctgacccagccgccgagcgtgagcggtgca<br>ccggggccagcgcgtgaccattagctgtagcggcagcagc<br>agcaacattggttctaactacgtgtcttggtaccagcag<br>ctgccgggcacggcgccgaaactgctgatccattctaac<br>tctcatcgcccgagcggcgtgccggatcgctttagcgga<br>tccaaaagcggcaccagcgccagcctggcgattaccggc<br>ctgcaagcagaagacgaagcggattattactgccagtct<br>tgggactacgaatctgaacgtgttgtgtttggcggcggc<br>acgaagttaaccgtcctaggtcagcccaaggctgccccc<br>tcggtcactctgttcccgccctcctctgaggagcttcaa<br>gccaacaaggccacactggtgtgtctcataagtgacttc<br>tacccgggagccgtgacagtggcctggaaggcagatagc<br>agccccgtcaaggcgggagtggagaccaccacaccctcc<br>aaacaaagcaacaacaagtacgcggccagcagctatctg |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | agcctgacgcctgagcagtggaagtcccacagaagctac<br>agctgccaggtcacgcatgaagggagcaccgtggagaag<br>acagtggcccctacagaatgttca |
| MOR21468<br>HCDR1 (Kabat) | 163 | DYALH |
| HCDR2 (Kabat) | 164 | VISYAGGFKFYADSVKG |
| HCDR3 (Kabat) | 165 | SPGLTSYHDS |
| HCDR1 (Chothia) | 166 | GFTFSDY |
| HCDR2 (Chothia) | 167 | SYAGGF |
| HCDR3 (Chothia) | 168 | SPGLTSYHDS |
| VH | 169 | QVQLLESGGGLVQPGGSLRLSCAASGFTFSDYALHWVRQ<br>APGKGLEWVSVISYAGGFKFYADSVKGRFTISRDNSKNT<br>LYLQMNSLRAEDTAVYYCARSPGLTSYHDSWGQGTLVTV<br>SS |
| DNA encoding VH | 170 | caggtgcaattgctggaaagcggcggtggcctggtgcag<br>ccgggtggcagcctgcgtctgagctgcgcggcgtccgga<br>ttcaccttttctgactacgctctgcattgggtgcgccag<br>gccccgggcaaaggtctcgagtgggtttccgttatctct<br>tacgctggcggtttcaaattctatgcggatagcgtgaaa<br>ggccgctttaccatcagccgcgataattcgaaaaacacc<br>ctgtatctgcaaatgaacagcctgcgtgcggaagatacg<br>gccgtgtattattgcgcgcgttctccgggtctgacttct<br>taccatgattcttggggccaaggcaccctggtgactgtt<br>agctca |
| Heavy Chain | 171 | QVQLLESGGGLVQPGGSLRLSCAASGFTFSDYALHWVRQ<br>APGKGLEWVSVISYAGGFKFYADSVKGRFTISRDNSKNT<br>LYLQMNSLRAEDTAVYYCARSPGLTSYHDSWGQGTLVTV<br>SSASTKGPSVFPLAPSSKSTSGGTAALGCLVKDYFPEPV<br>TVSWNSGALTSGVHTFPAVLQSSGLYSLSSVVTVPSSSL<br>GTQTYICNVNHKPSNTKVDKRVEPKSCDKTHTCPPCPAP<br>EAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAKGQPREPQVY<br>TLPPSREEMTKNQVSLTCLVKGFYPSDIAVEWESNGQPE<br>NNYKTTPPVLDSDGSFFLYSKLTVDKSRWQQGNVFSCSV<br>MHEALHNHYTQKSLSLSPGK |
| DNA encoding Heavy Chain | 172 | caggtgcaattgctggaaagcggcggtggcctggtgcag<br>ccgggtggcagcctgcgtctgagctgcgcggcgtccgga<br>ttcaccttttctgactacgctctgcattgggtgcgccag<br>gccccgggcaaaggtctcgagtgggtttccgttatctct<br>tacgctggcggtttcaaattctatgcggatagcgtgaaa<br>ggccgctttaccatcagccgcgataattcgaaaaacacc<br>ctgtatctgcaaatgaacagcctgcgtgcggaagatacg<br>gccgtgtattattgcgcgcgttctccgggtctgacttct<br>taccatgattcttggggccaaggcaccctggtgactgtt<br>agctcagcctccaccaagggtccatcggtcttccccctg<br>gcaccctcctccaagagcacctctggggggcacagcggcc<br>ctgggctgcctggtcaaggactacttccccgaaccggtg<br>acggtgtcgtggaactcaggcgccctgaccagcggcgtg<br>cacaccttcccggctgtcctacagtcctcaggactctac<br>tccctcagcagcgtggtgaccgtgccctccagcagcttg<br>ggcacccagacctacatctgcaacgtgaatcacaagccc<br>agcaacaccaaggtggacaagagagttgagcccaaatct<br>tgtgacaaaactcacacatgcccaccgtgcccagcacct<br>gaagcagcggggggaccgtcagtcttcctcttccccca<br>aaacccaaggacaccctcatgatctcccggacccctgag<br>gtcacatgcgtggtggtggacgtgagccacgaagaccct<br>gaggtcaagttcaactggtacgtggacggcgtggaggtg<br>cataatgccaagacaaagccgcgggaggagcagtacaac<br>agcacgtaccgggtggtcagcgtcctcaccgtcctgcac<br>caggactggctgaatggcaaggagtacaagtgcaaggtc<br>tccaacaaagccctcccagcccccatcgagaaaaccatc<br>tccaaagccaaagggcagccccgagaaccacaggtgtac<br>accctgcccccatcccgggaggagatgaccaagaaccag |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | gtcagcctgacctgcctggtcaaaggcttctatcccagc gacatcgccgtggagtgggagagcaatgggcagccggag aacaactacaagaccacgcctcccgtgctggactccgac ggctccttcttcctctacagcaagctcaccgtggacaag agcaggtggcagcaggggaacgtcttctcatgctccgtg atgcatgaggctctgcacaaccactacacgcagaagagc ctctccctgtctccgggtaaa |
| LCDR1 (Kabat) | 173 | SGSSSNIGSNYVS |
| LCDR2 (Kabat) | 174 | SNSHRPS |
| LCDR3 (Kabat) | 175 | QSWDYESERVV |
| LCDR1 (Chothia) | 176 | SSSNIGSNY |
| LCDR2 (Chothia) | 177 | SNS |
| LCDR3 (Chothia) | 178 | WDYESERV |
| VL | 179 | DIVLTQPPSVSGAPGQRVTISCSGSSSNIGSNYVSWYQQ LPGTAPKLLIHSNSHRPSGVPDRFSGSKSGTSASLAITG LQAEDEADYYCQSWDYESERVVFGGGTKLTVL |
| DNA encoding VL | 180 | gatatcgtgctgacccagccgccgagcgtgagcggtgca ccggggccagcgcgtgaccattagctgtagcggcagcagc agcaacattggttctaactacgtgtcttggtaccagcag ctgccggggcacggcgccgaaactgctgatccattctaac tctcatcgcccgagcggcgtgccggatcgctttagcgga tccaaaagcggcaccagcgccagcctggcgattaccggc ctgcaagcagaagacgaagcggattattactgccagtct tgggactacgaatctgaacgtgttgtgtttggcggcggc acgaagttaaccgtccta |
| Light Chain | 181 | DIVLTQPPSVSGAPGQRVTISCSGSSSNIGSNYVSWYQQ LPGTAPKLLIHSNSHRPSGVPDRFSGSKSGTSASLAITG LQAEDEADYYCQSWDYESERVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA encoding Light Chain | 182 | gatatcgtgctgacccagccgccgagcgtgagcggtgca ccggggccagcgcgtgaccattagctgtagcggcagcagc agcaacattggttctaactacgtgtcttggtaccagcag ctgccggggcacggcgccgaaactgctgatccattctaac tctcatcgcccgagcggcgtgccggatcgctttagcgga tccaaaagcggcaccagcgccagcctggcgattaccggc ctgcaagcagaagacgaagcggattattactgccagtct tgggactacgaatctgaacgtgttgtgtttggcggcggc acgaagttaaccgtcctaggtcagcccaaggctgccccc tcggtcactctgttcccgccctcctctgaggagcttcaa gccaacaaggccacactggtgtgtctcataagtgacttc tacccgggagccgtgacagtggcctggaaggcagatagc agccccgtcaaggcgggagtggagaccaccacaccctcc aaacaaagcaacaacaagtacgcggccagcagctatctg agcctgacgcctgagcagtggaagtcccacagaagctac agctgccaggtcacgcatgaagggagcaccgtggagaag acagtggcccctacagaatgttca |
| MOR20052 HCDR1 (Kabat) | 183 | DYAIS |
| HCDR2 (Kabat) | 184 | GIIPGFGQANYAQKFQG |
| HCDR3 (Kabat) | 185 | EPSPLYGPYSDYVMDP |
| HCDR1 (Chothia) | 186 | GGTFSDY |
| HCDR2 (Chothia) | 187 | IPGFGQ |
| HCDR3 (Chothia) | 188 | EPSPLYGPYSDYVMDP |
| VH | 189 | QVQLVQSGAEVKKPGSSVKVSCKASGGTFSDYAISWVRQ APGQGLEWMGGIIPGFGQANYAQKFQGRVTITADESTST |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | AYMELSSLRSEDTAVYYCAREPSPLYGPYSDYVMDPWGQ<br>GTLVTVSS |
| DNA encoding VH | 190 | caggtgcaattggtgcagagcggtgccgaagtgaaaaaa<br>ccgggcagcagcgtgaaagttagctgcaaagcatccgga<br>gggacgttttctgactacgctatctcttgggtgcgccag<br>gccccgggccagggcctcgagtggatgggcggtatcatc<br>ccggtttcggccaggcgaactacgcccagaaatttcag<br>ggccgggtgaccattaccgccgatgaaagcaccagcacc<br>gcctatatggaactgagcagcctgcgcagcgaagatacg<br>gccgtgtattattgcgcgcgtgaaccgtctccgctgtac<br>ggtccgtactctgactacgttatggatccgtggggccaa<br>ggcaccctggtgactgttagctca |
| Heavy Chain | 191 | QVQLVQSGAEVKKPGSSVKVSCKASGGTFSDYAISWVRQ<br>APGQGLEWMGGIIPGFGQANYAQKFQGRVTITADESTST<br>AYMELSSLRSEDTAVYYCAREPSPLYGPYSDYVMDPWGQ<br>GTLVTVSSASTKGPSVFPLAPSSKSTSGGTAALGCLVKD<br>YFPEPVTVSWNSGALTSGVHTFPAVLQSSGLYSLSSVVT<br>VPSSSLGTQTYICNVNHKPSNTKVDKRVEPKSCDKTHTC<br>PPCPAPEAAGGPSVFLFPPKPKDTLMISRTPEVTCVVVD<br>VSHEDPEVKFNWYVDGVEVHNAKTKPREEQYNSTYRVVS<br>VLTVLHQDWLNGKEYKCKVSNKALPAPIEKTISKAKGQP<br>REPQVYTLPPSREEMTKNQVSLTCLVKGFYPSDIAVEWE<br>SNGQPENNYKTTPPVLDSDGSFFLYSKLTVDKSRWQQGN<br>VFSCSVMHEALHNHYTQKSLSLSPGK |
| DNA encoding Heavy Chain | 192 | caggtgcaattggtgcagagcggtgccgaagtgaaaaaa<br>ccgggcagcagcgtgaaagttagctgcaaagcatccgga<br>gggacgttttctgactacgctatctcttgggtgcgccag<br>gccccgggccagggcctcgagtggatgggcggtatcatc<br>ccggtttcggccaggcgaactacgcccagaaatttcag<br>ggccgggtgaccattaccgccgatgaaagcaccagcacc<br>gcctatatggaactgagcagcctgcgcagcgaagatacg<br>gccgtgtattattgcgcgcgtgaaccgtctccgctgtac<br>ggtccgtactctgactacgttatggatccgtggggccaa<br>ggcaccctggtgactgttagctcagcctccaccaagggt<br>ccatcggtcttccccctggcaccctcctccaagagcacc<br>tccgggggcacagcggccctgggctgcctggtcaaggac<br>tacttccccgaaccggtgacggtgtcgtggaactcaggc<br>gccctgaccagcggcgtgcacaccttcccggctgtccta<br>cagtcctcaggactctactccctcagcagcgtggtgacc<br>gtgccctccagcagcttgggcacccagacctacatctgc<br>aacgtgaatcacaagcccagcaacaccaaggtggacaag<br>agagttgagcccaaatcttgtgacaaaactcacacatgc<br>ccaccgtgcccagcacctgaagcagcggggggaccgtca<br>gtcttcctcttccccccaaaacccaaggacaccctcatg<br>atctcccggacccctgaggtcacatgcgtggtggtggac<br>gtgagccacgaagaccctgaggtcaagttcaactggtac<br>gtggacggcgtggaggtgcataacgccaagacaaagccg<br>cgggaggagcagtacaacagcacgtaccgggtggtcagc<br>gtcctcaccgtcctgcaccaggactggctgaatggcaag<br>gagtacaagtgcaaggtctccaacaaagcccctcccagcc<br>cccatcgagaaaaccatctccaaagccaaagggcagccc<br>cgagaaccacaggtgtacaccctgcccccatcccgggag<br>gagatgaccaagaaccaggtcagcctgacctgcctggtc<br>aaaggcttctatcccagcgacatcgccgtggagtgggag<br>agcaatgggcagccggagaacaactacaagaccacgcct<br>cccgtgctggactccgacggctccttcttcctctacagc<br>aagctcaccgtggacaagagcaggtggcagcaggggaac<br>gtcttctcatgctccgtgatgcatgaggctctgcacaac<br>cactacacgcagaagagcctctccctgtctccgggtaaa |
| LCDR1 (Kabat) | 193 | TGTSSDVGYFNFVS |
| LCDR2 (Kabat) | 194 | DVSNRPS |
| LCDR3 (Kabat) | 195 | ASYGWDSSWV |
| LCDR1 (Chothia) | 196 | TSSDVGYFNF |
| LCDR2 (Chothia) | 197 | DVS |
| LCDR3 (Chothia) | 198 | YGWDSSW |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| VL | 199 | DIALTQPASVSGSPGQSITISCTGTSSDVGYFNFVSWYQ QHPGKAPKLMIYDVSNRPSGVSNRFSGSKSGNTASLTIS GLQAEDEADYYCASYGWDSSWVFGGGTKLTVL |
| DNA encoding VL | 200 | gatatcgcgctgacccagccggcgagcgtgagcggtagc ccggggccagagcattaccattagctgcaccggcaccagc agcgatgtgggctacttcaacttcgtgtcttggtaccag cagcatccgggcaaggcgccgaaactgatgatctacgac gtttctaaccgtccgagcggcgtgagcaaccgttttagc ggatccaaaagcggcaacaccgcgagcctgaccattagc ggcctgcaagcggaagacgaagcggattattactgcgct tcttacggttgggactcttcttgggtgttcggcggcggc acgaagttaaccgtccta |
| Light Chain | 201 | DIALTQPASVSGSPGQSITISCTGTSSDVGYFNFVSWYQ QHPGKAPKLMIYDVSNRPSGVSNRFSGSKSGNTASLTIS GLQAEDEADYYCASYGWDSSWVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA encoding Light Chain | 202 | gatatcgcgctgacccagccggcgagcgtgagcggtagc ccggggccagagcattaccattagctgcaccggcaccagc agcgatgtgggctacttcaacttcgtgtcttggtaccag cagcatccgggcaaggcgccgaaactgatgatctacgac gtttctaaccgtccgagcggcgtgagcaaccgttttagc ggatccaaaagcggcaacaccgcgagcctgaccattagc ggcctgcaagcggaagacgaagcggattattactgcgct tcttacggttgggactcttcttgggtgttcggcggcggc acgaagttaaccgtcctaggtcagcccaaggctgccccc tcggtcactctgttcccgccctcctctgaggagcttcaa gccaacaaggccacactggtgtgtctcataagtgacttc tacccgggagccgtgacagtggcctggaaggcagatagc agccccgtcaaggcgggagtggagaccaccacaccctcc aaacaaagcaacaacaagtacgcggccagcagctatctg agcctgacgcctgagcagtggaagtcccacagaagctac agctgccaggtcacgcatgaagggagcaccgtggagaag acagtggcccctacagaatgttca |
| MOR20133 HCDR1 (Kabat) | 203 | NYWIA |
| HCDR2 (Kabat) | 204 | RIFPGDSTTTYSPSFQG |
| HCDR3 (Kabat) | 205 | GKRGATHPTQYEGWEVYGFDP |
| HCDR1 (Chothia) | 206 | GYSFTNY |
| HCDR2 (Chothia) | 207 | FPGDST |
| HCDR3 (Chothia) | 208 | GKRGATHPTQYEGWEVYGFDP |
| VH | 209 | QVQLVQSGAEVKKPGESLKISCKGSGYSFTNYWIAWVRQ MPGKGLEWMGRIFPGDSTTTYSPSFQGQVTISADKSIST AYLQWSSLKASDTAMYYCARGKRGATHPTQYEGWEVYGF DPWGQGTLVTVSS |
| DNA encoding VH | 210 | caggtgcaattggtgcagagcggtgcggaagtgaaaaaa ccgggcgaaagcctgaaaattagctgcaaaggctccgga tatagcttcactaactactggattgcttgggtgcgccag atgccgggcaaaggtctcgagtggatgggccgtatcttc ccgggtgacagcactaccacttatagcccgagctttcag ggccaggtgaccattagcgcggataaaagcatcagcacc gcgtatctgcaatggagcagcctgaaagcgagcgatacc gcgatgtattattgcgcgcgtggtaaacgtggtgctact catccgactcagtacgaaggttgggaagtttacggtttc gatccgtggggccaaggcaccctggtgactgttagtca |
| Heavy Chain | 211 | QVQLVQSGAEVKKPGESLKISCKGSGYSFTNYWIAWVRQ MPGKGLEWMGRIFPGDSTTTYSPSFQGQVTISADKSIST AYLQWSSLKASDTAMYYCARGKRGATHPTQYEGWEVYGF DPWGQGTLVTVSSASTKGPSVFPLAPSSKSTSGGTAALG CLVKDYFPEPVTVSWNSGALTSGVHTFPAVLQSSGLYSL |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | SSVVTVPSSSLGTQTYICNVNHKPSNTKVDKRVEPKSCD KTHTCPPCPAPEAAGGPSVFLFPPKPKDTLMISRTPEVT CVVVDVSHEDPEVKFNWYVDGVEVHNAKTKPREEQYNST YRVVSVLTVLHQDWLNGKEYKCKVSNKALPAPIEKTISK AKGQPREPQVYTLPPSREEMTKNQVSLTCLVKGFYPSDI AVEWESNGQPENNYKTTPPVLDSDGSFFLYSKLTVDKSR WQQGNVFSCSVMHEALHNHYTQKSLSLSPGK |
| DNA encoding Heavy Chain | 212 | caggtgcaattggtgcagagcggtgcggaagtgaaaaaa ccgggcgaaagcctgaaaattagctgcaaaggctccgga tatagcttcactaactactggattgcttgggtgcgccag atgccgggcaaaggtctcgagtggatgggccgtatcttc ccgggtgacagcactaccacttatagcccgagctttcag ggccaggtgaccattagcgcggataaaagcatcagcacc gcgtatctgcaatggagcagcctgaaagcgagcgatacc gcgatgtattattgcgcgcgtggtaaacgtggtgctact catccgactcagtacgaaggttgggaagtttacggtttc gatccgtggggccaaggcaccctggtgactgttagctca gcctccaccaagggtccatcggtcttcccctggcaccc tcctccaagagcacctctggggcacagcggccctgggc tgcctggtcaaggactacttccccgaaccggtgacggtg tcgtggaactcaggcgccctgaccagcggcgtgcacacc ttcccggctgtcctacagtcctcaggactctactccctc agcagcgtggtgaccgtgccctccagcagcttgggcacc cagacctacatctgcaacgtgaatcacaagcccagcaac accaaggtggacaagagagttgagcccaaatcttgtgac aaaactcacacatgcccaccgtgcccagcacctgaagca gcgggggaccgtcagtcttcctcttccccccaaaaccc aaggacacccctcatgatctcccggacccctgaggtcaca tgcgtggtggtggacgtgagccacgaagaccctgaggtc aagttcaactggtacgtggacggcgtggaggtgcataat gccaagacaaagccgcgggaggagcagtacaacagcacg taccgggtggtcagcgtcctcaccgtcctgcaccaggac tggctgaatggcaaggagtacaagtgcaaggtctccaac aaagccctcccagccccatcgagaaaaccatctccaaa gccaaagggcagccccgagaaccacaggtgtacaccctg cccccatcccgggaggagatgaccaagaaccaggtcagc ctgacctgcctggtcaaaggcttctatcccagcgacatc gccgtggagtgggagagcaatgggcagccggagaacaac tacaagaccacgcctcccgtgctggactccgacggctcc ttcttcctctacagcaagctcaccgtggacaagagcagg tggcagcaggggaacgtcttctcatgctccgtgatgcat gaggctctgcacaaccactacacgcagaagagcctctcc ctgtctccgggtaaa |
| LCDR1 (Kabat) | 213 | SGDALGGKYAS |
| LCDR2 (Kabat) | 214 | DDNKRPS |
| LCDR3 (Kabat) | 215 | QSWAFYSGV |
| LCDR1 (Chothia) | 216 | DALGGKY |
| LCDR2 (Chothia) | 217 | DDN |
| LCDR3 (Chothia) | 218 | WAFYSG |
| VL | 219 | DIELTQPPSVSVSPGQTASITCSGDALGGKYASWYQQKP GQAPVLVIYDDNKRPSGIPERFSGSNSGNTATLTISGTQ AEDEADYYCQSWAFYSGVFGGGTKLTVL |
| DNA encoding VL | 220 | gatatcgaactgacccagccgccgagcgtgagcgtgagc ccgggccagaccgcgagcattacctgtagcggcgatgct ctgggtggtaaatacgcttcttggtaccagcagaaaccg ggccaggcgccggtgctggtgatctacgacgacaacaaa cgtccgagcggcatcccggaacgttttagcggatccaac agcggcaacaccgcgaccctgaccattagcggcacccag gcggaagacgaagcggattattactgccagtcttgggct ttctactctggtgtgtttggcggcggcacgaagttaacc gtccta |
| Light Chain | 221 | DIELTQPPSVSVSPGQTASITCSGDALGGKYASWYQQKP GQAPVLVIYDDNKRPSGIPERFSGSNSGNTATLTISGTQ AEDEADYYCQSWAFYSGVFGGGTKLTVLGQPKAAPSVTL |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | FPPSSEELQANKATLVCLISDFYPGAVTVAWKADSSPVK AGVETTTPSKQSNNKYAASSYLSLTPEQWKSHRSYSCQV THEGSTVEKTVAPTECS |
| DNA encoding Light Chain | 222 | gatatcgaactgacccagccgccgagcgtgagcgtgagc ccgggccagaccgcgagcattacctgtagcggcgatgct ctgggtggtaaatacgcttcttggtaccagcagaaaccg ggccaggcgccggtgctggtgatctacgacgacaacaaa cgtccgagcggcatcccggaacgttttagcggatccaac agcggcaacaccgcgaccctgaccattagcggcacccag gcggaagacgaagcggattattactgccagtcttgggct ttctactctggtgtgtttggcggcggcacgaagttaacc gtcctaggtcagcccaaggctgccccctcggtcactctg ttcccgccctcctctgaggagcttcaagccaacaaggcc acactggtgtgtctcataagtgacttctacccgggagcc gtgacagtggcctggaaggcagatagcagccccgtcaag gcgggagtggagaccaccacaccctccaaacaaagcaac aacaagtacgcggccagcagctatctgagcctgacgcct gagcagtggaagtcccacagaagctacagctgccaggtc acgcatgaagggagcaccgtggagaagacagtggcccct acagaatgttca |
| MOR20144 HCDR1 (Kabat) | 223 | DYALH |
| HCDR2 (Kabat) | 224 | VISYSGGYTYYADSVKG |
| HCDR3 (Kabat) | 225 | SPGLTSYHDS |
| HCDR1 (Chothia) | 226 | GFTFSDY |
| HCDR2 (Chothia) | 227 | SYSGGY |
| HCDR3 (Chothia) | 228 | SPGLTSYHDS |
| VH | 229 | QVQLLESGGGLVQPGGSLRLSCAASGFTFSDYALHWVRQ APGKGLEWVSVISYSGGYTYYADSVKGRFTISRDNSKNT LYLQMNSLRAEDTAVYYCARSPGLTSYHDSWGQGTLVTV SS |
| DNA encoding VH | 230 | caggtgcaattgctggaaagcggcggtggcctggtgcag ccgggtggcagcctgcgtctgagctgcgcggcgtccgga ttcaccttttctgactacgctctgcattgggtgcgccag gccccgggcaaaggtctcgagtgggtttccgttatctct tactctggtggttacacctactatgcggatagcgtgaaa ggccgctttaccatcagccgcgataattcgaaaaacacc ctgtatctgcaaatgaacagcctgcgtgcggaagatacg gccgtgtattattgcgcgcgttctccgggtctgacttct taccatgattcttggggccaaggcaccctggtgactgtt agctca |
| Heavy Chain | 231 | QVQLLESGGGLVQPGGSLRLSCAASGFTFSDYALHWVRQ APGKGLEWVSVISYSGGYTYYADSVKGRFTISRDNSKNT LYLQMNSLRAEDTAVYYCARSPGLTSYHDSWGQGTLVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |
| DNA encoding Heavy Chain | 232 | caggtgcaattgctggaaagcggcggtggcctggtgcag ccgggtggcagcctgcgtctgagctgcgcggcgtccgga ttcaccttttctgactacgctctgcattgggtgcgccag gccccgggcaaaggtctcgagtgggtttccgttatctct tactctggtggttacacctactatgcggatagcgtgaaa ggccgctttaccatcagccgcgataattcgaaaaacacc ctgtatctgcaaatgaacagcctgcgtgcggaagatacg gccgtgtattattgcgcgcgttctccgggtctgacttct taccatgattcttggggccaaggcaccctggtgactgtt agctcagcctccaccaagggtccatcggtcttccccctg |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | gcaccctcctccaagagcacctctgggggcacagcggcc<br>ctgggctgcctggtcaaggactacttccccgaaccggtg<br>acggtgtcgtggaactcaggcgccctgaccagcggcgtg<br>cacaccttcccggctgtcctacagtcctcaggactctac<br>tccctcagcagcgtggtgaccgtgccctcagcagcttg<br>ggcacccagacctacatctgcaacgtgaatcacaagccc<br>agcaacaccaaggtggacaagagagttgagcccaaatct<br>tgtgacaaaactcacacatgcccaccgtgcccagcacct<br>gaagcagcggggggaccgtcagtcttcctcttcccccca<br>aaacccaaggacaccctcatgatctcccggacccctgag<br>gtcacatgcgtggtggtggacgtgagccacgaagaccct<br>gaggtcaagttcaactggtacgtggacggcgtggaggtg<br>cataatgccaagacaaagccgcgggaggagcagtacaac<br>agcacgtaccgggtggtcagcgtcctcaccgtcctgcac<br>caggactggctgaatggcaaggagtacaagtgcaaggtc<br>tccaacaaagcccccagcccccatcgagaaaaccatc<br>tccaaagccaaagggcagccccgagaaccacaggtgtac<br>accctgcccccatcccgggaggagatgaccaagaaccag<br>gtcagcctgacctgcctggtcaaaggcttctatcccagc<br>gacatcgccgtggagtgggagagcaatgggcagccggag<br>aacaactacaagaccacgcctcccgtgctggactccgac<br>ggctccttcttcctctacagcaagctcaccgtggacaag<br>agcaggtggcagcaggggaacgtcttctcatgctccgtg<br>atgcatgaggctctgcacaaccactacacgcagaagagc<br>ctctccctgtctccgggtaaa |
| LCDR1 (Kabat) | 233 | SGSSSNIGSNYVS |
| LCDR2 (Kabat) | 234 | SNSHRPS |
| LCDR3 (Kabat) | 235 | QSWDYESERVV |
| LCDR1 (Chothia) | 236 | SSSNIGSNY |
| LCDR2 (Chothia) | 237 | SNS |
| LCDR3 (Chothia) | 238 | WDYESERV |
| VL | 239 | DIVLTQPPSVSGAPGQRVTISCSGSSSNIGSNYVSWYQQ<br>LPGTAPKLLIHSNSHRPSGVPDRFSGSKSGTSASLAITG<br>LQAEDEADYYCQSWDYESERVVFGGGTKLTVL |
| DNA encoding VL | 240 | gatatcgtgctgacccagccgccgagcgtgagcggtgca<br>ccgggccagcgcgtgaccattagctgtagcggcagcagc<br>agcaacattggttctaactacgtgtcttggtaccagcag<br>ctgccgggcacggcgccgaaactgctgatccattctaac<br>tctcatcgcccgagcggcgtgccggatcgctttagcgga<br>tccaaaagcggcaccagcgccagcctggcgattaccggc<br>ctgcaagcagaagacgaagcggattattactgccagtct<br>tgggactacgaatctgaacgtgttgtgtttggcggcggc<br>acgaagttaaccgtccta |
| Light Chain | 241 | DIVLTQPPSVSGAPGQRVTISCSGSSSNIGSNYVSWYQQ<br>LPGTAPKLLIHSNSHRPSGVPDRFSGSKSGTSASLAITG<br>LQAEDEADYYCQSWDYESERVVFGGGTKLTVLGQPKAAP<br>SVTLFPPSSEELQANKATLVCLISDFYPGAVTVAWKADS<br>SPVKAGVETTTPSKQSNNKYAASSYLSLTPEQWKSHRSY<br>SCQVTHEGSTVEKTVAPTECS |
| DNA encoding Light Chain | 242 | gatatcgtgctgacccagccgccgagcgtgagcggtgca<br>ccgggccagcgcgtgaccattagctgtagcggcagcagc<br>agcaacattggttctaactacgtgtcttggtaccagcag<br>ctgccgggcacggcgccgaaactgctgatccattctaac<br>tctcatcgcccgagcggcgtgccggatcgctttagcgga<br>tccaaaagcggcaccagcgccagcctggcgattaccggc<br>ctgcaagcagaagacgaagcggattattactgccagtct<br>tgggactacgaatctgaacgtgttgtgtttggcggcggc<br>acgaagttaaccgtcctaggtcagcccaaggctgccccc<br>tcggtcactctgttcccgccctcctctgaggagcttcaa<br>gccaacaaggccacactggtgtgtctcataagtgacttc<br>tacccgggagccgtgacagtggcctggaaggcagatagc<br>agccccgtcaaggcgggagtggagaccaccacaccctcc<br>aaacaaagcaacaacaagtacgcggccagcagctatctg<br>agcctgacgcctgagcagtggaagtcccacagaagctac |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
| --- | --- | --- |
| | | agctgccaggtcacgcatgaagggagcaccgtggagaag<br>acagtggcccctacagaatgttca |
| MOR20148<br>HCDR1 (Kabat) | 243 | SGAAMH |
| HCDR2 (Kabat) | 244 | GISSFSSSTDYADSVKG |
| HCDR3 (Kabat) | 245 | NFKYAMDY |
| HCDR1 (Chothia) | 246 | GFTFRSGA |
| HCDR2 (Chothia) | 247 | SSFSSS |
| HCDR3 (Chothia) | 248 | NFKYAMDY |
| VH | 249 | QVQLLESGGGLVQSGGSLRLSCAASGFTFRSGAAMHWVR<br>QAPGKGLEWVSGISSFSSSTDYADSVKGRFTISRDNSKN<br>TLYLQMNSLRAEDTAVYYCARNFKYAMDYWGQGTLVTVSS |
| DNA encoding VH | 250 | caggtgcaattgctggaaagcggcggtggcctggtgcag<br>tcgggtggcagcctgcgtctgagctgcgcggcgtccgga<br>ttcaccttcgttctggtgctgctatgcattgggtgcgc<br>caggcccccgggcaaaggtctcgagtgggtttccggtatc<br>tcttctttctcttcttctaccgactatgcggatagcgtg<br>aaaggccgctttaccatcagccgcgataattcgaaaaac<br>accctgtatctgcaaatgaacagcctgcgtgcggaagat<br>acggccgtgtattattgcgcgcgtaacttcaaatacgct<br>atggattactggggccaaggcaccctggtgactgttagc<br>tca |
| Heavy Chain | 251 | QVQLLESGGGLVQSGGSLRLSCAASGFTFRSGAAMHWVR<br>QAPGKGLEWVSGISSFSSSTDYADSVKGRFTISRDNSKN<br>TLYLQMNSLRAEDTAVYYCARNFKYAMDYWGQGTLVTVS<br>SASTKGPSVFPLAPSSKSTSGGTAALGCLVKDYFPEPVT<br>VSWNSGALTSGVHTFPAVLQSSGLYSLSSVVTVPSSSLG<br>TQTYICNVNHKPSNTKVDKRVEPKSCDKTHTCPPCPAPE<br>AAGGPSVFLFPPKPKDTLMTSRTPEVTCVVVDVSHEDPE<br>VKFNWYVDGVEVHNAKTKPREEQYNSTYRVVSVLTVLHQ<br>DWLNGKEYKCKVSNKALPAPIEKTISKAKGQPREPQVYT<br>LPPSREEMTKNQVSLTCLVKGFYPSDIAVEWESNGQPEN<br>NYKTTPPVLDSDGSFFLYSKLTVDKSRWQQGNVFSCSVM<br>HEALHNHYTQKSLSLSPGK |
| DNA encoding Heavy Chain | 252 | caggtgcaattgctggaaagcggcggtggcctggtgcag<br>tcgggtggcagcctgcgtctgagctgcgcggcgtccgga<br>ttcaccttcgttctggtgctgctatgcattgggtgcgc<br>caggcccccgggcaaaggtctcgagtgggtttccggtatc<br>tcttctttctcttcttctaccgactatgcggatagcgtg<br>aaaggccgctttaccatcagccgcgataattcgaaaaac<br>accctgtatctgcaaatgaacagcctgcgtgcggaagat<br>acggccgtgtattattgcgcgcgtaacttcaaatacgct<br>atggattactggggccaaggcaccctggtgactgttagc<br>tcagcctccaccaagggtccatcggtcttccccctggca<br>ccctcctccaagagcacctctgggggcacagcggccctg<br>ggctgcctggtcaaggactacttccccgaaccggtgacg<br>gtgtcgtggaactcaggcgccctgaccagcggcgtgcac<br>accttcccggctgtcctacagtcctcaggactctactcc<br>ctcagcagcgtggtgaccgtgccctccagcagcttgggc<br>acccagacctacatctgcaacgtgaatcacaagcccagc<br>aacaccaaggtggacaagagagttgagcccaaatcttgt<br>gacaaaactcacacatgcccaccgtgcccagcacctgaa<br>gcagcggggggaccgtcagtcttcctcttccccccaaaa<br>cccaaggacaccctcatgatctcccggacccctgaggtc<br>acatgcgtggtggtggacgtgagccacgaagaccctgag<br>gtcaagttcaactggtacgtggacggcgtggaggtgcat<br>aatgccaagacaaagccgcgggaggagcagtacaacagc<br>acgtaccgggtggtcagcgtcctcaccgtcctgcaccag<br>gactggctgaatggcaaggagtacaagtgcaaggtctcc<br>aacaaagcccctcccagcccccatcgagaaaaccatctcc<br>aaagccaaagggcagccccgagaaccacaggtgtacacc<br>ctgcccccatcccgggaggagatgaccaagaaccaggtc<br>agcctgacctgcctggtcaaaggcttctatcccagcgac<br>atcgccgtggagtgggagagcaatgggcagccggagaac |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | aactacaagaccacgcctcccgtgctggactccgacggc tccttcttcctctacagcaagctcaccgtggacaagagc aggtggcagcaggggaacgtcttctcatgctccgtgatg catgaggctctgcacaaccactacacgcagaagagcctc tccctgtctccgggtaaa |
| LCDR1 (Kabat) | 253 | TGTSSDVGSINYVS |
| LCDR2 (Kabat) | 254 | AVSYRPS |
| LCDR3 (Kabat) | 255 | QVWDWRSDSRV |
| LCDR1 (Chothia) | 256 | TSSDVGSINY |
| LCDR2 (Chothia) | 257 | AVS |
| LCDR3 (Chothia) | 258 | WDWRSDSR |
| VL | 259 | DIALTQPASVSGSPGQSITISCTGTSSDVGSINYVSWYQ QHPGKAPKMIYAVSYRPSGVSNRFSGSKSGNTASLTISG LQAEDEADYYCQVWDWRSDSRVFGGGTKLTVL |
| DNA encoding VL | 260 | gatatcgcgctgacccagccggcgagcgtgagcggtagc ccggggccagagcattaccattagctgcaccggcaccagc agcgatgtgggctctatcaactacgtgtcttggtaccag cagcatccgggcaaggcgccgaaaatgatctacgctgtt tcttaccgtccgagcggcgtgagcaaccgttttagcgga tccaaaagcggcaacaccgcgagcctgaccattagcggc ctgcaagcggaagacgaagcggattattactgccaggtt tgggactggcgttctgactctcgtgtgtttggcggcggc acgaagttaaccgtccta |
| Light Chain | 261 | DIALTQPASVSGSPGQSITISCTGTSSDVGSINYVSWYQ QHPGKAPKMIYAVSYRPSGVSNRFSGSKSGNTASLTISG LQAEDEADYYCQVWDWRSDSRVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA encoding Light Chain | 262 | gatatcgcgctgacccagccggcgagcgtgagcggtagc ccggggccagagcattaccattagctgcaccggcaccagc agcgatgtgggctctatcaactacgtgtcttggtaccag cagcatccgggcaaggcgccgaaaatgatctacgctgtt tcttaccgtccgagcggcgtgagcaaccgttttagcgga tccaaaagcggcaacaccgcgagcctgaccattagcggc ctgcaagcggaagacgaagcggattattactgccaggtt tgggactggcgttctgactctcgtgtgtttggcggcggc acgaagttaaccgtcctaggtcagcccaaggctgccccc tcggtcactctgttcccgccctcctctgaggagcttcaa gccaacaaggccacactggtgtgtctcataagtgacttc tacccgggagccgtgacagtggcctggaaggcagatagc agccccgtcaaggcgggagtggagaccaccacaccctcc aaacaaagcaacaacaagtacgcggccagcagctatctg agcctgacgcctgagcagtggaagtcccacagaagctac agctgccaggtcacgcatgaagggagcaccgtggagaag acagtggcccctacagaatgttca |
| MOR20151 HCDR1 (Kabat) | 263 | SYALS |
| HCDR2 (Kabat) | 264 | RIKSKTMGGTSDYAAPVKG |
| HCDR3 (Kabat) | 265 | DFWADHYYYFDY |
| HCDR1 (Chothia) | 266 | GFTFSSY |
| HCDR2 (Chothia) | 267 | KSKTMGGT |
| HCDR3 (Chothia) | 268 | DFWADHYYYFDY |
| VH | 269 | QVQLVESGGGLVKPGGSLRLSCAASGFTFSSYALSWVRQ APGKGLEWVGRIKSKTMGGTSDYAAPVKGRFTISRDDSK NTLYLQMNSLKTEDTAVYYCARDFWADHYYYFDYWGQGT LVTVSS |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| DNA encoding VH | 270 | caggtgcaattggtggaaagcggcggtggcctggtgaaa ccaggcggcagcctgcgcctgagctgcgccgcctccgga ttcaccttttcttcttacgctctgtcttgggtgcgccag gccccgggcaaaggtctcgagtgggtgggccgtatcaaa tctaaaactatgggtggtacttctgactatgccgcccca gtgaaaggccgctttaccattagccgcgatgattcgaaa aacaccctgtatctgcaaatgaacagcctgaaaaccgaa gatacggccgtgtattattgcgcgcgtgacttctgggct gaccattactacttcgattactggggccaaggcacc ctggtgactgttagctca |
| Heavy Chain | 271 | QVQLVESGGGLVKPGGSLRLSCAASGFTFSSYALSWVRQ APGKGLEWVGRIKSKTMGGTSDYAAPVKGRFTISRDDSK NTLYLQMNSLKTEDTAVYYCARDFWADHYYYFDYWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCPP CPAPEAAGGPSVFLFPPKPKDILMISRTPEVTCVVVDVS HEDPEVKFNWYVDGVEVHNAKTKPREEQYNSTYRVVSVL TVLHQDWLNGKEYKCKVSNKALPAPIEKTISKAKGQPRE PQVYTLPPSREEMTKNQVSLTCLVKGFYPSDIAVEWESN GQPENNYKTTPPVLDSDGSFFLYSKLTVDKSRWQQGNVF SCSVMHEALHNHYTQKSLSLSPGK |
| DNA encoding Heavy Chain | 272 | caggtgcaattggtggaaagcggcggtggcctggtgaaa ccaggcggcagcctgcgcctgagctgcgccgcctccgga ttcaccttttcttcttacgctctgtcttgggtgcgccag gccccgggcaaaggtctcgagtgggtgggccgtatcaaa tctaaaactatgggtggtacttctgactatgccgcccca gtgaaaggccgctttaccattagccgcgatgattcgaaa aacaccctgtatctgcaaatgaacagcctgaaaaccgaa gatacggccgtgtattattgcgcgcgtgacttctgggct gaccattactacttcgattactggggccaaggcacc ctggtgactgttagctcagcctccaccaagggtccatcg gtcttccccctggcaccctcctccaagagcacctctggg ggcacagcggccctgggctgcctggtcaaggactacttc cccgaaccggtgacggtgtcgtggaactcaggcgccctg accagcggcgtgcacaccttcccggctgtcctacagtcc tcaggactctactccctcagcagcgtggtgaccgtgccc tccagcagcttgggcacccagacctacatctgcaacgtg aatcacaagcccagcaacaccaaggtggacaagagagtt gagcccaaatcttgtgacaaaactcacacatgcccaccg tgcccagcacctgaagcagcggggggaccgtcagtcttc ctcttccccccaaaacccaaggacaccctcatgatctcc cggacccctgaggtcacatgcgtggtggtggacgtgagc cacgaagaccctgaggtcaagttcaactggtacgtggac ggcgtggaggtgcataatgccaagacaaagccgcgggag gagcagtacaacagcacgtaccgggtggtcagcgtcctc accgtcctgcaccaggactggctgaatggcaaggagtac aagtgcaaggtctccaacaaagccctcccagcccccatc gagaaaaccatctccaaagccaaagggcagccccgagaa ccacaggtgtacaccctgcccccatcccgggaggagatg accaagaaccaggtcagcctgacctgcctggtcaaaggc ttctatcccagcgacatcgccgtggagtgggagagcaat gggcagccggagaacaactacaagaccacgcctcccgtg ctggactccgacggctccttcttcctctacagcaagctc accgtggacaagagcaggtggcagcaggggaacgtcttc tcatgctccgtgatgcatgaggctctgcacaaccactac acgcagaagagcctctccctgtctccgggtaaa |
| LCDR1 (Kabat) | 273 | TGTSSDVGYINYVN |
| LCDR2 (Kabat) | 274 | EVSNRPS |
| LCDR3 (Kabat) | 275 | ASWDWYDNVV |
| LCDR1 (Chothia) | 276 | TSSDVGYINY |
| LCDR2 (Chothia) | 277 | EVS |
| LCDR3 (Chothia) | 278 | WDWYDNV |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| VL | 279 | DIALTQPASVSGSPGQSITISCTGTSSDVGYINYVNWYQ QHPGKAPKLMIYEVSNRPSGVSNRFSGSKSGNTASLTIS GLQAEDEADYYCASWDWYDNVVFGGGTKLTVL |
| DNA encoding VL | 280 | gatatcgcgctgacccagccggcgagcgtgagcggtagc ccgggccagagcattaccattagctgcaccggcaccagc agcgatgtgggctacatcaactacgtgaactggtaccag cagcatccgggcaaggcgccgaaactgatgatctacgaa gtttctaaccgtccgagcggcgtgagcaaccgttttagc ggatccaaaagcggcaacaccgcgagcctgaccattagc ggcctgcaagcggaagacgaagcggattattactgcgct tcttgggactggtacgacaacgttgtgtttggcggcggc acgaagttaaccgtccta |
| Light Chain | 281 | DIALTQPASVSGSPGQSITISCTGTSSDVGYINYVNWYQ QHPGKAPKLMIYEVSNRPSGVSNRFSGSKSGNTASLTIS GLQAEDEADYYCASWDWYDNVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA encoding Light Chain | 282 | gatatcgcgctgacccagccggcgagcgtgagcggtagc ccgggccagagcattaccattagctgcaccggcaccagc agcgatgtgggctacatcaactacgtgaactggtaccag cagcatccgggcaaggcgccgaaactgatgatctacgaa gtttctaaccgtccgagcggcgtgagcaaccgttttagc ggatccaaaagcggcaacaccgcgagcctgaccattagc ggcctgcaagcggaagacgaagcggattattactgcgct tcttgggactggtacgacaacgttgtgtttggcggcggc acgaagttaaccgtcctaggtcagcccaaggctgccccc tcggtcactctgttcccgccctcctctgaggagcttcaa gccaacaaggccacactggtgtgtctcataagtgacttc tacccgggagccgtgacagtggcctggaaggcagatagc agccccgtcaaggcgggagtggagaccaccacaccctcc aaacaaagcaacaacaagtacgcggccagcagctatctg agcctgacgcctgagcagtggaagtcccacagaagctac agctgccaggtcacgcatgaagggagcaccgtggagaag acagtggcccctacagaatgttca |
| MOR20152 HCDR1 (Kabat) | 283 | SYAIS |
| HCDR2 (Kabat) | 284 | RIIPIFGGANYAQKFQG |
| HCDR3 (Kabat) | 285 | DPLYRSDYYYHWFDF |
| HCDR1 (Chothia) | 286 | GGTFSSY |
| HCDR2 (Chothia) | 287 | IPIFGG |
| HCDR3 (Chothia) | 288 | DPLYRSDYYYHWFDF |
| VH | 289 | QVQLVQSGAEVKKPGSSVKVSCKASGGTFSSYAISWVRQ APGQGLEWMGRIIPIFGGANYAQKFQGRVTITADESTST AYMELSSLRSEDTAVYYCARDPLYRSDYYYHWFDFWGQG TLVTVSS |
| DNA encoding VH | 290 | caggtgcaattggtgcagagcggtgccgaagtgaaaaaa ccgggcagcagcgtgaaagttagctgcaaagcatccgga gggacgttttcttcttacgctatctcttgggtgcgccag gcccccgggccagggcctcgagtggatgggccgtatcatc ccgatcttcggcggtgcgaactacgcccagaaatttcag ggccgggtgaccattaccgccgatgaaagcaccagcacc gcctatatggaactgagcagcctgcgcagcgaagatacg gccgtgtattattgcgcgcgtgacccgctgtaccgttct gactactactaccattggttcgatttctggggccaaggc accctggtgactgttagctca |
| Heavy Chain | 291 | QVQLVQSGAEVKKPGSSVKVSCKASGGTFSSYAISWVRQ APGQGLEWMGRIIPIFGGANYAQKFQGRVTITADESTST AYMELSSLRSEDTAVYYCARDPLYRSDYYYHWFDFWGQG TLVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKRVEPKSCDKTHTCP |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | PCPAPEAAGGPSVFLFPPKPKDTLMISRTPEVTCVVVDV SHEDPEVKFNWYVDGVEVHNAKTKPREEQYNSTYRVVSV LTVLHQDWLNGKEYKCKVSNKALPAPIEKTISKAKGQPR EPQVYTLPPSREEMTKNQVSLTCLVKGFYPSDIAVEWES NGQPENNYKTTPPVLDSDGSFFLYSKLTVDKSRWQQGNV FSCSVMHEALHNHYTQKSLSLSPGK |
| DNA encoding Heavy Chain | 292 | caggtgcaattggtgcagagcggtgccgaagtgaaaaaa ccgggcagcagcgtgaaagttagctgcaaagcatccgga gggacgttttcttcttacgctatctcttgggtgcgccag gccccgggccagggcctcgagtggatgggccgtatcatc ccgatcttcggcggtgcgaactacgcccagaaatttcag ggccgggtgaccattaccgccgatgaaagcaccagcacc gcctatatggaactgagcagcctgcgcagcgaagatacg gccgtgtattattgcgcgcgtgacccgctgtaccgttct gactactaccattggttcgatttctgggccaaggc accctggtgactgttagctcagcctccaccaagggtcca tcggtcttccccctggcaccctcctccaagagcacctct ggggcacagcggccctgggctgcctggtcaaggactac ttccccgaaccggtgacggtgtcgtggaactcaggcgcc ctgaccagcggcgtgcacaccttcccggctgtcctacag tcctcaggactctactccctcagcagcgtggtgaccgtg ccctccagcagcttgggcacccagacctacatctgcaac gtgaatcacaagcccagcaacaccaaggtggacaagaga gttgagcccaaatcttgtgacaaaactcacacatgccca ccgtgcccagcacctgaagcagcggggggaccgtcagtc ttcctcttccccccaaaacccaaggacaccctcatgatc tcccggacccctgaggtcacatgcgtggtggtggacgtg agccacgaagaccctgaggtcaagttcaactggtacgtg gacggcgtggaggtgcataatgccaagacacagccgcgg gaggagcagtacaacagcacgtaccgggtggtcagcgtc ctcaccgtcctgcaccaggactggctgaatggcaaggag tacaagtgcaaggtctccaacaaagcccctcccagccccc atcgagaaaaccatctccaaagccaaagggcagccccga gaaccacaggtgtacaccctgcccccatcccgggaggag atgaccaagaaccaggtcagcctgacctgcctggtcaaa ggcttctatcccagcgacatcgccgtggagtgggagagc aatgggcagccggagaacaactacaagaccacgcctccc gtgctggactccgacggctccttcttcctctacagcaag ctcaccgtggacaagagcaggtggcagcaggggaacgtc ttctcatgctccgtgatgcatgaggctctgcacaaccac tacacgcagaagagcctctccctgtctccgggtaaa |
| LCDR1 (Kabat) | 293 | TGTSSDVGNFNYVS |
| LCDR2 (Kabat) | 294 | GVNNRPS |
| LCDR3 (Kabat) | 295 | AAYGWALDEVV |
| LCDR1 (Chothia) | 296 | TSSDVGNFNY |
| LCDR2 (Chothia) | 297 | GVN |
| LCDR3 (Chothia) | 298 | YGWALDEV |
| VL | 299 | DIALTQPASVSGSPGQSITISCTGTSSDVGNFNYVSWYQ QHPGKAPKLMIYGVNNRPSGVSNRFSGSKSGNTASLTIS GLQAEDEADYYCAAYGWALDEVVFGGGTKLTVL |
| DNA encoding VL | 300 | gatatcgcgctgacccagccggcgagcgtgagcggtagc ccgggccagagcattaccattagctgcaccggcaccagc agcgatgtgggcaacttcaactacgtgtcttggtaccag cagcatccgggcaaggcgccgaaactgatgatctacggt gtcaacaaccgtccgagcggcgtgagcaaccgttttagc ggatccaaaagcggcaacaccgcgagcctgaccattagc ggcctgcaagcggaagacgaagcggattattactgcct gcttacggttgggctctggacgaagtcgtgtttggcggc ggcacgaagttaaccgtccta |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| Light Chain | 301 | DIALTQPASVSGSPGQSITISCTGTSSDVGNFNYVSWYQ QHPGKAPKLMIYGVNNRPSGVSNRFSGSKSGNTASLTIS GLQAEDEADYYCAAYCWALDEVVFGGGTKLTVLGQPKAA PSVTLFPPSSEELQANKATLVCLISDFYPGAVTVAWKAD SSPVKAGVETTTPSKQSNNKYAASSYLSLTPEQWKSHRS YSCQVTHEGSTVEKTVAPTECS |
| DNA encoding Light Chain | 302 | gatatcgcgctgacccagccggcgagcgtgagcggtagc ccggggccagagcattaccattagctgcaccggcaccagc agcgatgtgggcaacttcaactacgtgtcttggtaccag cagcatccgggcaaggcgccgaaactgatgatctacggt gtcaacaaccgtccgagcggcgtgagcaaccgttttagc ggatccaaaagcggcaacaccgcgagcctgaccattagc ggcctgcaagcggaagacgaagcggattattactgcgct gcttacggttgcgctctggacgaagttgtgtttggcggc ggcacgaagttaaccgtcctaggtcagcccaaggctgcc ccctcggtcactctgttcccgcctcctctgaggagctt caagccaacaaggccacactggtgtgtctcataagtgac ttctacccgggagccgtgacagtggcctggaaggcagat agcagccccgtcaaggcgggagtggagaccaccacaccc tccaaacaaagcaacaacaagtacgcggccagcagctat ctgagcctgacgcctgagcagtggaagtcccacagaagc tacagctgccaggccacgcatgaagggagcaccgtggag aagacagtggcccctacagaatgttca |
| MOR022025 HCDR1 (Kabat) | 303 | DYALH |
| HCDR2 (Kabat) | 304 | VISYQGGFIYYADSVKG |
| HCDR3 (Kabat) | 305 | SPGLTSYHDS |
| HCDR1 (Chothia) | 306 | GFTFSDY |
| HCDR2 (Chothia) | 307 | SYQGGF |
| HCDR3 (Chothia) | 308 | SPGLTSYHDS |
| VH | 309 | QVQLLESGGGLVQPGGSLRLSCAASGFTFSDYALHWVRQ APGKGLEWVSVISYQGGFIYYADSVKGRFTISRDNSKNT LYLQMNSLRAEDTAVYYCARSPGLTSYHDSWGQGTLVTV SS |
| DNA encoding VH | 310 | caggtgcaattgctggaaagcggcggtggcctggtgcag ccgggtggcagcctgcgtctgagctgcgcggcgtccgga ttcacctttctgactacgctctgcattgggtgcgccag gccccgggcaaaggtctcgagtgggtttccgttatctct taccagggcggtttcatctactatgcggatagcgtgaaa ggccgctttaccatcagccgcgataattcgaaaaacacc ctgtatctgcaaatgaacagcctgcgtgcggaagatacg gccgtgtattattgcgcgcgttctccgggtctgacttct taccatgattcttgggccaaggcaccctggtgactgtt agctca |
| Heavy Chain | 311 | QVQLLESGGGLVQPGGSLRLSCAASGFTFSDYALHWVRQ APGKGLEWVSVISYQGGFIYYADSVKGRFTISRDNSKNT LYLQMNSLRAEDTAVYYCARSPGLTSYHDSWGQGTLVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSREEMTKNQVSLICLVKGFYPSDIAVEWESNGQPE NNYKTTPPVLDSDGSFFLYSKLTVDKSRWQQGNVFSCSV MHEALHNHYTQKSLSLSPGK |
| DNA encoding Heavy Chain | 312 | caggtgcaattgctggaaagcggcggtggcctggtgcag ccgggtggcagcctgcgtctgagctgcgcggcgtccgga ttcacctttctgactacgctctgcattgggtgcgccag gccccgggcaaaggtctcgagtgggtttccgttatctct taccagggcggtttcatctactatgcggatagcgtgaaa ggccgctttaccatcagccgcgataattcgaaaaacacc ctgtatctgcaaatgaacagcctgcgtgcggaagatacg |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | gccgtgtattattgcgcgcgttctccgggtctgacttct<br>taccatgattcttggggccaaggcaccctggtgactgtt<br>agctcagcctccaccaagggtccatcggtcttcccctg<br>gcaccctcctccaagagcacctctgggggcacagcggcc<br>ctgggctgcctggtcaaggactacttccccgaaccggtg<br>acggtgtcgtggaactcaggcgccctgaccagcggcgtg<br>cacaccttcccggctgtcctacagtcctcaggactctac<br>tccctcagcagcgtggtgaccgtgccctccagcagcttg<br>ggcacccagacctacatctgcaacgtgaatcacaagccc<br>agcaacaccaaggtggacaagagagttgagcccaaatct<br>tgtgacaaaactcacacatgcccaccgtgcccagcacct<br>gaagcagcggggggaccgtcagtcttcctcttcccccca<br>aaacccaaggacaccctcatgatctcccggacccctgag<br>gtcacatgcgtggtggtggacgtgagccacgaagaccct<br>gaggtcaagttcaactggtacgtggacggcgtggaggtg<br>cataatgccaagacaaagccgcgggaggagcagtacaac<br>agcacgtaccgggtggtcagcgtcctcaccgtcctgcac<br>caggactggctgaatggcaaggagtacaagtgcaaggtc<br>tccaacaaagccctcccagcccccatcgagaaaaccatc<br>tccaaagccaaagggcagccccgagaaccacaggtgtac<br>accctgcccccatcccgggaggagatgaccaagaaccag<br>gtcagcctgacctgcctggtcaaaggcttctatcccagc<br>gacatcgccgtggagtgggagagcaatgggcagccggag<br>aacaactacaagaccacgcctcccgtgctggactccgac<br>ggctccttcttcctctacagcaagctcaccgtggacasg<br>agcaggtggcagcaggggaacgtcttctcatgctccgtg<br>atgcatgaggctctgcacaaccactacacgcagaagagc<br>ctctccctgtctccgggtaaa |
| LCDR1 (Kabat) | 313 | SGSSSNIGSNYVS |
| LCDR2 (Kabat) | 314 | STSHRPS |
| LCDR3 (Kabat) | 315 | QSWDYESERVV |
| LCDR1 (Chothia) | 316 | SSSNIGSNY |
| LCDR2 (Chothia) | 317 | STS |
| LCDR3 (Chothia) | 318 | WDYESERV |
| VL | 319 | QSVLTQPPSVSGAPGQRVTISCSGSSSNTGSNYVSWYQQ<br>LPGTAPKLLIHSTSHRPSGVPDRFSGSKSGTSASLAITG<br>LQAEDSADYYCQSWDVESERVVFGGGTKLTVL |
| DNA encoding VL | 320 | cagagcgtgctgacccagccgccgagcgtgagcggtgca<br>ccggggccagcgcgtgaccattagctgtagcggcagcagc<br>agcaacattggttctaactacgtgtcttggtaccagcag<br>ctgccggggcacggcgccgaaactgctgatccattctacc<br>tctcatcgcccgagcggcgtgccggatcgctttagcgga<br>tccaaaagcggcaccagcgccagcctggcgattaccggc<br>ctgcaagcagaagacgaagcggattattactgccagtct<br>tgggactacgaatctgaacgtgttgtgtttggcggcggc<br>acgaagttaaccgtccta |
| Light Chain | 321 | QSVLTQPPSVSGAPGQRVTISCSGSSSNIGSNYVSWYQQ<br>LPGTAPKLLIHSTSHRPSGVPDRFSGSKSGTSASLAITG<br>LQAEDEADYYCQSWDYESERVVFGGGTKLTVLGQPKAAP<br>SVTLFPPSSEELQANKATLVCLISDFYPGAVTVAWKADS<br>SPVKAGVETTTPSKQSNNKYAASSYLSLTPEQWKSHRSY<br>SCQVTHEGSTVEKTVAPTECS |
| DNA encoding Light Chain | 322 | cagagcgtgctgacccagccgccgagcgtgagcggtgca<br>ccggggccagcgcgtgaccattagctgtagcggcagcagc<br>agcaacattggttctaactacgtgtcttggtaccagcag<br>ctgccggggcacggcgccgaaactgctgatccattctacc<br>tctcatcgcccgagcggcgtgccggatcgctttagcgga<br>tccaaaagcggcaccagcgccagcctggcgattaccggc<br>ctgcaagcagaagacgaagcggattattactgccagtct<br>tgggactacgaatctgaacgtgttgtgtttggcggcggc<br>acgaagttaaccgtcctaggtcagcccaaggctgccccc<br>tcggtcactctgttcccgcccctcctctgaggagcttcaa<br>gccaacaaggccacactggtgtgtctcataagtgacttc<br>tacccgggagccgtgacagtggcctggaaggcagatagc |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | agccccgtcaaggcgggagtggagaccaccacaccctcc<br>aaacaaagcaacaacaagtacgcggccagcagctatctg<br>agcctgacgcctgagcagtggaagtcccacagaagctac<br>agctgccaggtcacgcatgagggagcaccgtggagaag<br>acagtggcccctacagaatgttca |
| MOR22028<br>HCDR1 (Kabat) | 323 | DYALH |
| HCDR2 (Kabat) | 324 | VISYAGGFKFYADSVKG |
| HCDR3 (Kabat) | 325 | SPGLTSYHDS |
| HCDR1 (Chothia) | 326 | GFTFSDY |
| HCDR2 (Chothia) | 327 | SYAGGF |
| HCDR3 (Chothia) | 328 | SPGLTSYHDS |
| VH | 329 | QVQLLESGGGLVQPGGSLRLSCAASGFTFSDYALHWVRQ<br>APGKGLEWVSVISYAGGFKFYADSVKGRFTISRDNSKNT<br>LYLQMNSLRAEDTAVYYCARSPGLTSYHDSWGQGTLVTV<br>SS |
| DNA encoding VH | 330 | caggtgcaattgctggaaagcggcggtggcctggtgcag<br>ccgggtggcagcctgcgtctgagctgcgcggcgtccgga<br>ttcacctttctgactacgctctgcattgggtgcgccag<br>gccccgggcaaaggtctcgagtgggtttccgttatctct<br>tacgctggcggtttcaaattctatgcggatagcgtgaaa<br>ggccgctttaccatcagccgcgataattcgaaaaacacc<br>ctgtatctgcaaatgaacagcctgcgtgcggaagatacg<br>gccgtgtattattgcgcgcgttctccgggtctgacttct<br>taccatgattcttggggccaaggcaccctggtgactgtt<br>agctca |
| Heavy Chain | 331 | QVQLLESGGGLVQPGGSLRLSCAASGFTFSDYALHWVRQ<br>APGKGLEWVSVISYAGGFKFYADSVKGRFTISRDNSKNT<br>LYLQMNSLRAEDTAVYYCARSPGLTSYHDSWGQGTLVTV<br>SSASTKGPSVFPLAPSSKSTSGGTAALGCLVKDYFPEPV<br>TVSWNSGALTSGVHTFPAVLQSSGLYSLSSVVTVPSSSL<br>GTQTYICNVNHKPSNTKVDKRVEPKSCDKTHTCPPCPAP<br>EAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAKGQPREPQVY<br>TLPPSREEMTKNQVSLTCLVKGFYPSDIAVEWESNGQPE<br>NNYKTTPPVLDSDGSFFLYSKLTVDKSRWQQGNVFSCSV<br>MHEALHNHYTQKSLSLSPGK |
| DNA encoding Heavy<br>Chain | 332 | caggtgcaattgctggaaagcggcggtggcctggtgcag<br>ccgggtggcagcctgcgtctgagctgcgcggcgtccgga<br>ttcacctttctgactacgctctgcattgggtgcgccag<br>gccccgggcaaaggtctcgagtgggtttccgttatctct<br>tacgctggcggtttcaaattctatgcggatagcgtgaaa<br>ggccgctttaccatcagccgcgataattcgaaaaacacc<br>ctgtatctgcaaatgaacagcctgcgtgcggaagatacg<br>gccgtgtattattgcgcgcgttctccgggtctgacttct<br>taccatgattcttggggccaaggcaccctggtgactgtt<br>agctcagcctccaccaagggtccatcggtcttccccctg<br>gcaccctcctccaagagcacctctgggggcacagcggcc<br>ctgggctgcctggtcaaggactacttccccgaaccggtg<br>acggtgtcgtggaactcaggcgccctgaccagcggcgtg<br>cacaccttcccggctgtcctacagtcctcaggactctac<br>tccctcagcagcgtggtgaccgtgccctcagcagcttg<br>ggcacccagacctacatctgcaacgtgaatcacaagccc<br>agcaacaccaaggtggacaagagagttgagcccaaatct<br>tgtgacaaaactcacacatgcccaccgtgcccagcacct<br>gaagcagcggggggaccgtcagtcttcctcttccccca<br>aaacccaaggacaccctcatgatctcccggacccctgag<br>gtcacatgcgtggtggtggacgtgagccacgaagaccct<br>gaggtcaagttcaactggtacgtggacggcgtggaggtg<br>cataatgccaagacaaagccgagggaggagcagtacaac<br>agcacgtaccgggtggtcagcgtcctcaccgtcctgcac<br>caggactggctgaatggcaaggagtacaagtgcaaggtc<br>tccaacaaagccctcccagcccccatcgagaaaaccatc |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
| --- | --- | --- |
| | | tccaaagccaaagggcagccccgagaaccacaggtgtac accctgcccccatcccggggaggagatgaccaagaaccag gtcagcctgacctgcctggtcaaaggcttctatcccagc gacatcgccgtggagtgggagagcaatgggcagccggag aacaactacaagaccacgcctcccgtgctggactccgac ggctccttcttcctctacagcaagctcaccgtggacaag agcaggtggcagcaggggaacgtcttctcatgctccgtg atgcatgaggctctgcacaaccactacacgcagaagagc ctctccctgtctccgggtaaa |
| LCDR1 (Kabat) | 333 | SGSSSNIGSNYVS |
| LCDR2 (Kabat) | 334 | SSSHRPS |
| LCDR3 (Kabat) | 335 | QSWDYESERVV |
| LCDR1 (Chothia) | 336 | SSSNIGSNY |
| LCDR2 (Chothia) | 337 | SSS |
| LCDR3 (Chothia) | 338 | WDYESERV |
| VL | 339 | QSVLTQPPSVSGAPGQRVTISCSGSSSNIGSNYVSWYQQ LPGTAPKLLIHSSSHRPSGVPDRFSGSKSGTSASLAITG LQAEDEADYYCQSWDYESERVVFGGGTKLTVL |
| DNA encoding VL | 340 | cagagcgtgctgacccagccgccgagcgtgagcggtgca ccgggccagcgcgtgaccattagctgtagcggcagcagc agcaacattggttctaactacgtgtcttggtaccagcag ctgccgggcacggcgccgaaactgctgatccattctagc tctcatcgcccgagcggcgtgccggatcgctttagcgga tccaaaagcggcaccagcgccagcctggcgattaccggc ctgcaagcagaagacgaagcggattattactgccagtct tgggactacgaatctgaacgtgttgtgtttggcggcggc acgaagttaaccgtccta |
| Light Chain | 341 | QSVLTQPPSVSGAPGQRVTISCSGSSSNIGSNYVSWYQQ LPGTAPKLLIHSSSHRPSGVPDRFSGSKSGTSASLAITG LQAEDEADYYCQSWDYESERVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA encoding Light Chain | 342 | cagagcgtgctgacccagccgccgagcgtgagcggtgca ccgggccagcgcgtgaccattagctgtagcggcagcagc agcaacattggttctaactacgtgtcttggtaccagcag ctgccgggcacggcgccgaaactgctgatccattctagc tctcatcgcccgagcggcgtgccggatcgctttagcgga tccaaaagcggcaccagcgccagcctggcgattaccggc ctgcaagcagaagacgaagcggattattactgccagtct tgggactacgaatctgaacgtgttgtgtttggcggcggc acgaagttaaccgtcctaggtcagcccaaggctgccccc tcggtcactctgttcccgccctcctctgaggagcttcaa gccaacaaggccacactggtgtgtctcataagtgacttc tacccgggagccgtgacagtggcctggaaggcagatagc agccccgtcaaggcgggagtggagaccaccacccctcc aaacaaagcaacaacaagtacgcggccagcagctatctg agcctgacgcctgagcagtggaagtcccacagaagctac agctgccaggtcacgcatgaagggagcaccgtggagaag acagtggcccctacagaatgttca |
| MOR22029 HCDR1 (Kabat) | 343 | SYALS |
| HCDR2 (Kabat) | 344 | RTKHENEGYTTWYAASVKG |
| HCDR3 (Kabat) | 345 | DFWADHYYYFDY |
| HCDR1 (Chothia) | 346 | GFTFSSY |
| HCDR2 (Chothia) | 347 | KHENEGYT |
| HCDR3 (Chothia) | 348 | DFWADHYYYFDY |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| VH | 349 | QVQLVESGGGLVKPGGSLRLSCAASGFTFSSYALSWVRQ APGKGLEWVGRTKHENEGYTTWYAASVKGRFTISRDDSK NTLYLQMNSLKTEDTAVYYCARDFWADHYYYFDYWGQGT LVTVSS |
| DNA encoding VH | 350 | caggtgcaattggtggaaagcggcggtggcctggtgaaa ccaggcggcagcctgcgcctgagctgcgccgcctccgga ttcacctttttcttcttacgctctgtcttgggtgcgccag gccccgggcaaaggtctcgagtgggtgggccgtactaaa catgaaaacgaaggctacactacttggtatgccgcctct gtgaaaggccgctttaccattagccgcgatgattcgaaa aacaccctgtatctgcaaatgaacagcctgaaaaccgaa gatacggccgtgtattattgcgcgcgtgacttctgggct gaccattactacttcgattactggggccaaggcacc ctggtgactgttagctca |
| Heavy Chain | 351 | QVQLVESGGGLVKPGGSLRLSCAASGFTFSSYALSWVRQ APGKGLEWVGRTKHENEGYTTWYAASVKGRFTISRDDSK NTLYLQMNSLKTEDTAVYYCARDFWADHYYYFDYWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCPP CPAPEAAGGPSVFLFPPKPKDTLMISRTPEVTCVVVDVS HEDPEVKFNWYVDGVEVHNAKTKPREEQYNSTYRVVSVL TVLHQDWLNGKEYKCKVSNKALPAPIEKTISKAKGQPRE PQVYTLPPSREEMTKNQVSLTCLVKGFYPSDIAVEWESN GQPENNYKTTPPVLDSDGSFFLYSKLTVDKSRWQQGNVF SCSVMHEALHNHYTQKSLSLSPGK |
| DNA encoding Heavy Chain | 352 | caggtgcaattggtggaaagcggcggtggcctggtgaaa ccaggcggcagcctgcgcctgagctgcgccgcctccgga ttcacctttttcttcttacgctctgtcttgggtgcgccag gccccgggcaaaggtctcgagtgggtgggccgtactaaa catgaaaacgaaggctacactacttggtatgccgcctct gtgaaaggccgctttaccattagccgcgatgattcgaaa aacaccctgtatctgcaaatgaacagcctgaaaaccgaa gatacggccgtgtattattgcgcgcgtgacttctgggct gaccattactacttcgattactggggccaaggcacc ctggtgactgttagctcagcctccaccaagggtccatcg gtcttccccctggcaccctcctccaagagcacctctggg ggcacagcggccctgggctgcctggtcaaggactacttc cccgaaccggtgacggtgtcgtggaactcaggcgccctg accagcggcgtgcacaccttcccggctgtcctacagtcc tcaggactctactccctcagcagcgtggtgaccgtgccc tccagcagcttgggcacccagacctacatctgcaacgtg aatcacaagcccagcaacaccaaggtggacaagagagtt gagcccaaatcttgtgacaaaactcacacatgcccaccg tgcccagcacctgaagcagcggggggaccgtcagtcttc ctcttccccccaaaacccaaggacaccctcatgatctcc cggacccctgaggtcacatgcgtggtggtggacgtgagc cacgaagaccctgaggtcaagttcaactggtacgtggac ggcgtggaggtgcataatgccaagacaaagccgcgggag gagcagtacaacagcacgtaccgggtggtcagcgtcctc accgtcctgcaccaggactggctgaatggcaaggagtac aagtgcaaggtctccaacaaagccctcccagcccccatc gagaaaaccatctccaaagccaaagggcagccccgagaa ccacaggtgtacaccctgcccccatcccgggaggagatg accaagaaccaggtcagcctgacctgcctggtcaaaggc ttctatcccagcgacatcgccgtggagtgggagagcaat gggcagccggagaacaactacaagaccacgcctcccgtg ctggactccgacggctccttcttcctctacagcaagctc accgtggacaagagcaggtggcagcaggggaacgtcttc tcatgctccgtgatgcatgaggctctgcacaaccactac acgcagaagagcctctccctgtctccgggtaaa |
| LCDR1 (Kabat) | 353 | TGTSSDVGYINYVN |
| LCDR2 (Kabat) | 354 | EVSNRPS |
| LCDR3 (Kabat) | 355 | ASWDWYDNVV |
| LCDR1 (Chothia) | 356 | TSSDVGYINY |
| LCDR2 (Chothia) | 357 | EVS |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| LCDR3 (Chothia) | 358 | WDWYDNV |
| VL | 359 | QSALTQPASVSGSPGQSITISCTGSSDVGYINYVNWYQ QHPGKAPKLMIYEVSNRPSGVSNRFSGSKSGNTASLTIS GLQAEDEADYYCASWDWYDNVVFGGGTKLTVL |
| DNA encoding VL | 360 | cagagcgcgctgacccagccggcgagcgtgagcggtagc ccggggccagagcattaccattagctgcaccggcaccag agcgatgtgggctacatcaactacgtgaactggtaccag cagcatccgggcaaggcgccgaaactgatgatctacgaa gtttctaaccgtccgagcggcgtgagcaaccgttttagc ggatccaaaagcggcaacaccgcgagcctgaccattagc ggcctgcaagcggaagacgaagcggattattactgcgct tcttgggactggtacgacaacgttgtgtttggcggcggc acgaagttaaccgtccta |
| Light Chain | 361 | QSALTQPASVSGSPGQSITISCTGTSSDVGYINYVNWYQ QHPGKAPKLMIYEVSNRPSGVSNRFSGSKSGNTASLTIS GLQAEDEADYYCASWDWYDNVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA encoding Light Chain | 362 | cagagcgcgctgacccagccggcgagcgtgagcggtagc ccggggccagagcattaccattagctgcaccggcaccag agcgatgtgggctacatcaactacgtgaactggtaccag cagcatccgggcaaggcgccgaaactgatgatctacgaa gtttctaaccgtccgagcggcgtgagcaaccgttttagc ggatccaaaagcggcaacaccgcgagcctgaccattagc ggcctgcaagcggaagacgaagcggattattactgcgct tcttgggactggtacgacaacgttgtgtttggcggcggc acgaagttaaccgtcctaggtcagcccaaggctgccccc tcggtcactctgttcccgccctcctctgaggagcttcaa gccaacaaggccacactggtgtgtctcataagtgacttc tacccgggagccgtgacagtggcctggaaggcagatagc agccccgtcaaggcgggagtggagaccaccacaccctcc aaacaaagcaacaacaagtacgcggccagcagctatctg agcctgacgcctgagcagtggaagtcccacagaagctac agctgccaggtcacgcatgaagggagcaccgtggagaag acagtggcccctacagaatgttca |
| MOR22030 HCDR1 (Kabat) | 363 | SYALS |
| HCDR2 (Kabat) | 364 | RIKLINKGYTTWYAASVKG |
| HCDR3 (Kabat) | 365 | DFWADHYYYFDY |
| HCDR1 (Chothia) | 366 | GFTFSSY |
| HCDR2 (Chothia) | 367 | KLINKGYT |
| HCDR3 (Chothia) | 368 | DFWADHYYYFDY |
| VH | 369 | QVQLVESGGGLVKPGGSLRLSCAASGFTFSSYALSWVRQ APGKGLEWVGRIKLINKGYTTWYAASVKGRFTISRDDSK NTLYLQMNSLKTEDTAVYYCARDFWADHYYYFDYWGQGT LVTVSS |
| DNA encoding VH | 370 | caggtgcaattggtggaaagcggcggtggcctggtgaaa ccaggcggcagcctgcgcctgagctgcgccgcctccgga ttcacctttttcttcttacgctctgtcttgggtgcgcag gccccgggcaaaggtctcgagtgggtgggccgtatcaaa ctgatcaacaaaggctacactacttggtatgccgcctct gtgaaaggccgctttaccattagccgcgatgattcgaaa aacaccctgtatctgcaaatgaacagcctgaaaaccgaa gatacggccgtgtattattgcgcgcgtgacttctggct gaccattactactacttcgattactggggccaaggcacc ctggtgactgttagctca |
| Heavy Chain | 371 | QVQLVESGGGLVKPGGSLRLSCAASGFTFSSYALSWVRQ APGKGLEWVGRIKLINKGYTTWYAASVKGRFTISRDDSK NTLYLQMNSLKTEDTAVYYCARDFWADHYYYFDYWGQGT |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCPP CPAPEAAGGPSVFLFPPKPKDTLMISRTPEVTCVVVDVS HEDPEVKFNWYVDGVEVHNAKTKPREEQYNSTYRVVSVL TVLHQDWLNGKEYKCKVSNKALPAPIEKTISKAKGQPRE PQVYTLPPSREEMTKNQVSLTCLVKGFYPSDIAVEWESN GQPENNYKTTPPVLDSDGSFFLYSKLTVDKSRWQQGNVF SCSVMHEALHNHYTQKSLSLSPGK |
| DNA encoding Heavy Chain | 372 | caggtgcaattggtggaaagcggcggtggcctggtgaaa ccaggcggcagcctgcgcctgagctgcgccgcctccgga ttcaccttttcttcttacgctctgtcttgggtgcgccag gccccgggcaaaggtctcgagtgggtgggccgtatcaaa ctgatcaacaaaggctacactacttggtatgccgcctct gtgaaaggccgctttaccattagccgcgatgattcgaaa aacaccctgtatctgcaaatgaacagcctgaaaaccgaa gatacggccgtgtattattgcgcgcgtgacttctgggct gaccattactactacttcgattactggggccaaggcacc ctggtgactgttagctcagcctccaccaagggtccatcg gtcttccccctggcaccctcctccaagagcacctctggg ggcacagcggccctgggctgcctggtcaaggactacttc cccgaaccggtgacggtgtcgtggaactcaggcgccctg accagcggcgtgcacaccttcccggctgtcctacagtcc tcaggactctactccctcagcagcgtggtgaccgtgccc tccagcagcttgggcacccagacctacatctgcaacgtg aatcacaagcccagcaacaccaaggtggacaagagagtt gagcccaaatcttgtgacaaaactcacacatgcccaccg tgcccagcacctgaagcagcggggggaccgtcagtcttc ctcttccccccaaaacccaaggacaccctcatgatctcc cggacccctgaggtcacatgcgtggtggtggacgtgagc cacgaagaccctgaggtcaagttcaactggtacgtggac ggcgtggaggtgcataatgccaagacaaagccgcgggag gagcagtacaacagcacgtaccgggtggtcagcgtcctc accgtcctgcaccaggactggctgaatggcaaggagtac aagtgcaaggtctccaacaaagcccteccagcccccate gagaaaaccatctccaaagccaaagggcagccccgagaa ccacaggtgtacaccctgcccccatcccgggaggagatg accaagaaccaggtcagcctgacctgcctggtcaaaggc ttctatcccagcgacatcgccgtggagtgggagagcaat gggcagccggagaacaactacaagaccacgcctcccgtg ctggactccgacggctccttcttcctctacagcaagctc accgtggacaagagcaggtggcagcaggggaacgtcttc tcatgctccgtgatgcatgaggctctgcacaaccactac acgcagaagagcctctccctgtctccgggtaaa |
| LCDR1 (Kabat) | 373 | TGTSSDVGYINYVN |
| LCDR2 (Kabat) | 374 | EVSNRPS |
| LCDR3 (Kabat) | 375 | ASWDWYDNVV |
| LCDR1 (Chothia) | 376 | TSSDVGYINY |
| LCDR2 (Chothia) | 377 | EVS |
| LCDR3 (Chothia) | 378 | WDWYDNV |
| VL | 379 | QSALTQPASVSCSPGQSITISCTGTSSDVGYINYVNWYQ QHPGKAPKLMIYEVSNRPSGVSNRFSGSKSGNTASLTIS GLQAEDEADYYCASWDWYDNVVFGGGTKLTVL |
| DNA encoding VL | 380 | cagagcgcgctgacccagccggcgagcgtgagcggtagc ccgggccagagcattaccattagctgcaccggcaccagc agcgatgtgggctacatcaactacgtgaactggtaccag cagcatccgggcaaggcgccgaaactgatgatctacgaa gtttctaaccgtccgagcggcgtgagcaaccgtttttagc ggatccaaaagcggcaacaccgcgagcctgaccattagc ggcctgcaagcggaagacgaagcggattattactgcgct tcttgggactggtacgacaacgttgtgtttggcggcggc acgaagttaaccgtccta |
| Light Chain | 381 | QSALTQPASVSGSPGQSITISCTGTSSDVGYINYVNWYQ QHPGKAPKLMIYEVSNRPSGVSNRFSGSKSGNTASLTIS |

TABLE 1-continued

Examples of LOX-1 Antibodies, Fabs and LOX-1 Proteins.

| Sequence Description | Sequence Identifier (SEQ ID NO:) | Amino acid or polynucleotide sequence |
|---|---|---|
| | | GLQAEDEADYYCASWDWYDNVVFGGGTKLTVLGQPKAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| DNA encoding Light Chain | 382 | cagagcgcgctgacccagccggcgagcgtgagcggtagc ccgggccagagcattaccattagctgcaccggcaccagc agcgatgtgggctacatcaactacgtgaactggtaccag cagcatccgggcaaggcgccgaaactgatgatctacgaa gtttctaaccgtccgagcggcgtgagcaaccgttttagc ggatccaaaagcggcaacaccgcgagcctgaccattagc ggcctgcaagcggaagacgaagcggattattactgcgct tcttgggactggtacgacaacgttgtgtttggcggcggc acgaagttaaccgtcctaggtcagcccaaggctgccccc tcggtcactctgttcccgcctcctctgaggagcttcaa gccaacaaggccacactggtgtgtctcataagtgacttc tacccgggagccgtgacagtggcctggaaggcagatagc agccccgtcaaggcgggagtggagaccaccacacctcc aaacaaagcaacaacaagtacgcggccagcagctatctg agcctgacgcctgagcagtggaagtcccacagaagctac agctgccaggtcacgcatgaagggagcaccgtggagaag acagtggcccctacagaatgttca |

Other antibodies of the invention include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen binding activity.

Since each of these antibodies can bind to LOX-1, the VH, VL, full length light chain, and full length heavy chain sequences (amino acid sequences and the nucleotide sequences encoding the amino acid sequences) can be "mixed and matched" to create other LOX-1-binding antibodies of the invention. Such "mixed and matched" LOX-1-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

Accordingly, in one aspect, the invention provides an isolated antibody or antigen binding region thereof having: a heavy chain variable domain comprising an amino acid sequence selected from the group consisting of SEQ ID NOs: 9, 29, 49, 69, 89, 109, 129, 149, 169, 189, 209, 229, 249, 269, 289, 309, 329, 349, and 369, and a light chain variable domain comprising an amino acid sequence selected from the group consisting of SEQ ID NOs: 24, 44, 64, 84, and 104, wherein the antibody specifically binds to LOX-1 (e.g., human and cynomolgus monkey LOX-1).

More specifically, in certain aspects, the invention provides an isolated antibody or antigen binding region thereof having a heavy chain variable domain and a light chain variable domain comprising amino acid sequences selected from SEQ ID NOs: 14 and 24; 34 and 44; 54 and 64; 74 and 84; or 94 and 104, respectively.

In another aspect, the invention provides (i) an isolated antibody having: a full length heavy chain comprising an amino acid sequence that has been optimized for expression in a mammalian cell selected from the group consisting of SEQ ID NOs: 11, 31, 51, 71, 91, 111, 131, 151, 171, 191, 211, 231, 251, 271, 291, 311, 331, 351, or 371, and a full length light chain comprising an amino acid sequence that has been optimized for expression in a mammalian cell selected from the group consisting of SEQ ID NOs: 21, 41, 61, 81, 101, 121, 141, 161, 181, 201, 221, 241, 261, 281, 301, 321, 341, 361, or 381; or (ii) a functional protein comprising an antigen binding portion thereof. More specifically, in certain aspects, the invention provides an isolated antibody or antigen binding region thereof having a heavy chain and a light chain comprising amino acid sequences selected from SEQ ID NOs: 14 and 24; 34 and 44; 54 and 64; 74 and 84; or 94 and 104, respectively.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme).

For example, under Kabat, the CDR amino acid residues of antibody MOR21435 in the heavy chain variable domain (VH) are numbered 31-35 (HCDR1), 50-66 (HCDR2), and 99-110 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-30 (HCDR1), 52-57 (HCDR2), and 99-110 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-66 (HCDR2), and 99-110 (HCDR3) in human VH and amino acid residues 24-34 (LCDR1), 50-56 (LCDR2), and 89-97 (LCDR3) in human VL.

In another aspect, the present invention provides LOX-1 binding antibodies that comprise the heavy chain and light chain CDR1s, CDR2s, and CDR3s as described in Table 1, or combinations thereof. The amino acid sequences of the VH CDR1s of the antibodies are shown in SEQ ID NOs: 3, 23, 43, 63, 83, 103, 123, 143, 163, 183, 203, 223, 243, 263, 283, 303, 323, 343, and 363. The amino acid sequences of the VH CDR2s of the antibodies and are shown in SEQ ID NOs: 4, 24, 44, 64, 84, 104, 124, 144, 164, 184, 204, 224, 244, 264, 284, 304, 324, 344, and 364. The amino acid sequences of the VH CDR3s of the antibodies are shown in SEQ ID NOs: 5, 25, 45, 65, 85, 105, 125, 145, 165, 185, 205, 225, 245, 265, 285, 305, 325, 345, and 365. The amino acid sequences of the VL CDR1s of the antibodies are shown in SEQ ID NOs: 13, 33, 53, 73, 93, 113, 133, 153, 173, 193, 213, 233, 253, 273, 293, 313, 333, 353, and 373. The amino acid sequences of the VL CDR2s of the antibodies are shown in SEQ ID NOs: 14, 34, 54, 74, 94, 114, 134, 154, 174, 194, 214, 234, 254, 274, 294, 314, 334, 354, and 374. The amino acid sequences of the VL CDR3s of the antibodies are shown in SEQ ID NOs: 15, 35, 55, 75, 95, 115, 135, 155, 175, 195, 215, 235, 255, 275, 295, 315, 335, 355, and 375. These CDR regions are delineated using the Kabat system.

Alternatively, as defined using the Chothia system (Al-Lazikani et al., (1997) JMB 273, 927-948), the amino acid sequences of the VH CDR1s of the antibodies are shown in SEQ ID NOs: 6, 26, 46, 66, 86, 106, 126, 146, 166, 186, 206, 226, 246, 266, 286, 306, 326, 346, and 366. The amino acid sequences of the VH CDR2s of the antibodies and are shown in SEQ ID NOs: 7, 27, 47, 67, 87, 107, 127, 147, 167, 187, 207, 227, 247, 267, 287, 307, 327, 347, and 367. The amino acid sequences of the VH CDR3s of the antibodies are shown in SEQ ID NOs: 8, 28, 48, 68, 88, 108, 128, 148, 168, 188, 208, 228, 248, 268, 288, 308, 328, 348, and 368. The amino acid sequences of the VL CDR1s of the antibodies are shown in SEQ ID NOs: 16, 36, 56, 76, 96, 116, 136, 156, 176, 196, 216, 236, 256, 276, 296, 316, 336, 356, and 376. The amino acid sequences of the VL CDR2s of the antibodies are shown in SEQ ID NOs: 17, 37, 57, 77, 97, 117, 137, 157, 177, 197, 217, 237, 257, 277, 297, 317, 337, 357, and 377. The amino acid sequences of the VL CDR3s of the antibodies are shown in SEQ ID NOs: 18, 38, 58, 78, 98, 118, 138, 158, 178, 198, 218, 238, 258, 278, 298, 318, 338, 358, and 378.

Given that each of these antibodies can bind to LOX-1 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody preferably contains a VH CDR1, 2 and 3 and a VL CDR1, 2 and 3 to create other LOX-1 binding molecules of the invention. Such "mixed and matched" LOX-1 binding antibodies can be tested using the binding assays known in the art and those described in the Examples (e.g., ELISAs, SET, BIA-CORE™). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention. In addition to the foregoing, in one embodiment, the antigen binding fragments of the antibodies described herein can comprise a VH CDR1, 2, and 3, or a VL CDR 1, 2, and 3, wherein the fragment binds to LOX-1 as a single variable domain.

In certain embodiments of the invention, the antibodies or antigen binding fragments thereof may have the heavy and light chain sequences of the Fabs described in Table 1. More specifically, the antibody or antigen binding fragments thereof may have the heavy and light sequence of MOR21435, MOR20159, MOR22031, MOR22034, MOR21452, MOR21453, MOR21460, MOR21468, MOR20052, MOR20133, MOR20144, MOR20148, MOR20151, MOR20152, MOR022025, MOR22028, MOR22029, and MOR22030.

In other embodiments of the invention the antibody or antigen binding fragment in that specifically binds LOX-1 comprises a heavy chain variable region CDR1, a heavy chain variable region CDR2, a heavy chain variable region CDR3, a light chain variable region CDR1, a light chain variable region CDR2, and a light chain variable region CDR3 as defined by Kabat and described in Table 1. In still other embodiments of the invention the antibody or antigen binding fragment in that specifically binds LOX-1 comprises a heavy chain variable region CDR1, a heavy chain variable region CDR2, a heavy chain variable region CDR3, a light chain variable region CDR1, a light chain variable region CDR2, and a light chain variable region CDR3 as defined by Chothia and described in Table 1.

In a specific embodiment, the invention includes an antibody that specifically binds to LOX-1 comprising a heavy chain variable region CDR1 of SEQ ID NO: 3; a heavy chain variable region CDR2 of SEQ ID NO: 4; a heavy chain variable region CDR3 of SEQ ID NO: 5; a light chain variable region CDR1 of SEQ ID NO: 13; a light chain variable region CDR2 of SEQ ID NO: 14; and a light chain variable region CDR3 of SEQ ID NO: 15.

In a specific embodiment, the invention includes an antibody that specifically binds to LOX-1 comprising a heavy chain variable region CDR1 of SEQ ID NO: 23; a heavy chain variable region CDR2 of SEQ ID NO: 24; a heavy chain variable region CDR3 of SEQ ID NO: 25; a light chain variable region CDR1 of SEQ ID NO: 33; a light chain variable region CDR2 of SEQ ID NO: 34; and a light chain variable region CDR3 of SEQ ID NO: 35.

In a specific embodiment, the invention includes an antibody that specifically binds to LOX-1 comprising a heavy chain variable region CDR1 of SEQ ID NO: 43; a heavy chain variable region CDR2 of SEQ ID NO: 44; a heavy chain variable region CDR3 of SEQ ID NO: 45; a light chain variable region CDR1 of SEQ ID NO: 53; a light chain variable region CDR2 of SEQ ID NO: 54; and a light chain variable region CDR3 of SEQ ID NO: 55.

In a specific embodiment, the invention includes an antibody that specifically binds to LOX-1 comprising a heavy chain variable region CDR1 of SEQ ID NO: 63; a heavy chain variable region CDR2 of SEQ ID NO: 64; a heavy chain variable region CDR3 of SEQ ID NO: 65; a light chain variable region CDR1 of SEQ ID NO: 73; a light chain variable region CDR2 of SEQ ID NO: 74; and a light chain variable region CDR3 of SEQ ID NO: 75.

In a specific embodiment, the invention includes an antibody that specifically binds to LOX-1 comprising a heavy chain variable region CDR1 of SEQ ID NO: 83; a heavy chain variable region CDR2 of SEQ ID NO: 84; a heavy chain variable region CDR3 of SEQ ID NO: 85; a light chain variable region CDR1 of SEQ ID NO: 93; a light chain variable region CDR2 of SEQ ID NO: 94; and a light chain variable region CDR3 of SEQ ID NO: 95.

In a specific embodiment, the invention includes an antibody that specifically binds to LOX-1 comprising a heavy chain variable region CDR1 of SEQ ID NO: 103; a heavy chain variable region CDR2 of SEQ ID NO: 104; a heavy chain variable region CDR3 of SEQ ID NO: 105; a light chain variable region CDR1 of SEQ ID NO: 113; a light chain variable region CDR2 of SEQ ID NO: 114; and a light chain variable region CDR3 of SEQ ID NO: 115.

In a specific embodiment, the invention includes an antibody that specifically binds to LOX-1 comprising a heavy chain variable region CDR1 of SEQ ID NO: 123; a heavy chain variable region CDR2 of SEQ ID NO: 124; a heavy chain variable region CDR3 of SEQ ID NO: 125; a light chain variable region CDR1 of SEQ ID NO: 133; a light chain variable region CDR2 of SEQ ID NO: 134; and a light chain variable region CDR3 of SEQ ID NO: 135.

In a specific embodiment, the invention includes an antibody that specifically binds to LOX-1 comprising a heavy chain variable region CDR1 of SEQ ID NO: 143; a heavy chain variable region CDR2 of SEQ ID NO: 144; a heavy chain variable region CDR3 of SEQ ID NO: 145; a light chain variable region CDR1 of SEQ ID NO: 153; a light chain variable region CDR2 of SEQ ID NO: 154; and a light chain variable region CDR3 of SEQ ID NO: 155.

In a specific embodiment, the invention includes an antibody that specifically binds to LOX-1 comprising a heavy chain variable region CDR1 of SEQ ID NO: 163; a heavy chain variable region CDR2 of SEQ ID NO: 164; a heavy chain variable region CDR3 of SEQ ID NO: 165; a light chain variable region CDR1 of SEQ ID NO: 173; a light chain variable region CDR2 of SEQ ID NO: 174; and a light chain variable region CDR3 of SEQ ID NO: 175.

In a specific embodiment, the invention includes an antibody that specifically binds to LOX-1 comprising a heavy chain variable region CDR1 of SEQ ID NO: 183; a heavy chain variable region CDR2 of SEQ ID NO: 184; a heavy chain variable region CDR3 of SEQ ID NO: 185; a light chain variable region CDR1 of SEQ ID NO: 193; a light chain variable region CDR2 of SEQ ID NO: 194; and a light chain variable region CDR3 of SEQ ID NO: 195.

In a specific embodiment, the invention includes an antibody that specifically binds to LOX-1 comprising a heavy chain variable region CDR1 of SEQ ID NO: 203; a heavy chain variable region CDR2 of SEQ ID NO: 204; a heavy chain variable region CDR3 of SEQ ID NO: 205; a light chain variable region CDR1 of SEQ ID NO: 213; a light chain variable region CDR2 of SEQ ID NO: 214; and a light chain variable region CDR3 of SEQ ID NO: 215.

In a specific embodiment, the invention includes an antibody that specifically binds to LOX-1 comprising a heavy chain variable region CDR1 of SEQ ID NO: 223; a heavy chain variable region CDR2 of SEQ ID NO: 224; a heavy chain variable region CDR3 of SEQ ID NO: 225; a light chain variable region CDR1 of SEQ ID NO: 233; a light chain variable region CDR2 of SEQ ID NO: 234; and a light chain variable region CDR3 of SEQ ID NO: 235.

In a specific embodiment, the invention includes an antibody that specifically binds to LOX-1 comprising a heavy chain variable region CDR1 of SEQ ID NO: 243; a heavy chain variable region CDR2 of SEQ ID NO: 244; a heavy chain variable region CDR3 of SEQ ID NO: 245; a light chain variable region CDR1 of SEQ ID NO: 253; a light chain variable region CDR2 of SEQ ID NO: 254; and a light chain variable region CDR3 of SEQ ID NO: 255.

In a specific embodiment, the invention includes an antibody that specifically binds to LOX-1 comprising a heavy chain variable region CDR1 of SEQ ID NO: 263; a heavy chain variable region CDR2 of SEQ ID NO: 264; a heavy chain variable region CDR3 of SEQ ID NO: 265; a light chain variable region CDR1 of SEQ ID NO: 273; a light chain variable region CDR2 of SEQ ID NO: 274; and a light chain variable region CDR3 of SEQ ID NO: 275.

In a specific embodiment, the invention includes an antibody that specifically binds to LOX-1 comprising a heavy chain variable region CDR1 of SEQ ID NO: 283; a heavy chain variable region CDR2 of SEQ ID NO: 284; a heavy chain variable region CDR3 of SEQ ID NO: 285; a light chain variable region CDR1 of SEQ ID NO: 293; a light chain variable region CDR2 of SEQ ID NO: 294; and a light chain variable region CDR3 of SEQ ID NO: 295.

In a specific embodiment, the invention includes an antibody that specifically binds to LOX-1 comprising a heavy chain variable region CDR1 of SEQ ID NO: 303; a heavy chain variable region CDR2 of SEQ ID NO: 304; a heavy chain variable region CDR3 of SEQ ID NO: 305; a light chain variable region CDR1 of SEQ ID NO: 313; a light chain variable region CDR2 of SEQ ID NO: 314; and a light chain variable region CDR3 of SEQ ID NO: 315.

In a specific embodiment, the invention includes an antibody that specifically binds to LOX-1 comprising a heavy chain variable region CDR1 of SEQ ID NO: 323; a heavy chain variable region CDR2 of SEQ ID NO: 324; a heavy chain variable region CDR3 of SEQ ID NO: 325; a light chain variable region CDR1 of SEQ ID NO: 333; a light chain variable region CDR2 of SEQ ID NO: 334; and a light chain variable region CDR3 of SEQ ID NO: 335.

In a specific embodiment, the invention includes an antibody that specifically binds to LOX-1 comprising a heavy chain variable region CDR1 of SEQ ID NO: 343; a heavy chain variable region CDR2 of SEQ ID NO: 344; a heavy chain variable region CDR3 of SEQ ID NO: 345; a light chain variable region CDR1 of SEQ ID NO: 353; a light chain variable region CDR2 of SEQ ID NO: 354; and a light chain variable region CDR3 of SEQ ID NO: 355.

In a specific embodiment, the invention includes an antibody that specifically binds to LOX-1 comprising a heavy chain variable region CDR1 of SEQ ID NO: 363; a heavy chain variable region CDR2 of SEQ ID NO: 364; a heavy chain variable region CDR3 of SEQ ID NO: 365; a light chain variable region CDR1 of SEQ ID NO: 373; a light chain variable region CDR2 of SEQ ID NO: 374; and a light chain variable region CDR3 of SEQ ID NO: 375.

In a specific embodiment, the invention includes an antibody that specifically binds to LOX-1 comprising a heavy chain variable region CDR1 of SEQ ID NO: 6; a heavy chain variable region CDR2 of SEQ ID NO: 7; a heavy chain variable region CDR3 of SEQ ID NO: 8; a light chain variable region CDR1 of SEQ ID NO: 16; a light chain variable region CDR2 of SEQ ID NO: 17; and a light chain variable region CDR3 of SEQ ID NO: 18.

In a specific embodiment, the invention includes an antibody that specifically binds to LOX-1 comprising a heavy chain variable region CDR1 of SEQ ID NO: 26; a heavy chain variable region CDR2 of SEQ ID NO: 27; a heavy chain variable region CDR3 of SEQ ID NO: 28; a light chain variable region CDR1 of SEQ ID NO: 36; a light chain variable region CDR2 of SEQ ID NO: 37; and a light chain variable region CDR3 of SEQ ID NO: 38.

In a specific embodiment, the invention includes an antibody that specifically binds to LOX-1 comprising a heavy chain variable region CDR1 of SEQ ID NO: 46; a heavy chain variable region CDR2 of SEQ ID NO: 47; a heavy chain variable region CDR3 of SEQ ID NO: 48; a light chain variable region CDR1 of SEQ ID NO: 56; a light chain variable region CDR2 of SEQ ID NO: 57; and a light chain variable region CDR3 of SEQ ID NO: 58.

In a specific embodiment, the invention includes an antibody that specifically binds to LOX-1 comprising a heavy chain variable region CDR1 of SEQ ID NO: 66; a heavy chain variable region CDR2 of SEQ ID NO: 67; a heavy chain variable region CDR3 of SEQ ID NO: 68; a light chain variable region CDR1 of SEQ ID NO: 76; a light chain variable region CDR2 of SEQ ID NO: 77; and a light chain variable region CDR3 of SEQ ID NO: 78.

In a specific embodiment, the invention includes an antibody that specifically binds to LOX-1 comprising a heavy chain variable region CDR1 of SEQ ID NO: 86; a heavy chain variable region CDR2 of SEQ ID NO: 87; a heavy chain variable region CDR3 of SEQ ID NO: 88; a light chain variable region CDR1 of SEQ ID NO: 96; a light chain variable region CDR2 of SEQ ID NO: 97; and a light chain variable region CDR3 of SEQ ID NO: 98.

In a specific embodiment, the invention includes an antibody that specifically binds to LOX-1 comprising a heavy chain variable region CDR1 of SEQ ID NO: 106; a heavy chain variable region CDR2 of SEQ ID NO: 107; a heavy chain variable region CDR3 of SEQ ID NO: 108; a light chain variable region CDR1 of SEQ ID NO: 116; a light chain variable region CDR2 of SEQ ID NO: 117; and a light chain variable region CDR3 of SEQ ID NO: 118.

In a specific embodiment, the invention includes an antibody that specifically binds to LOX-1 comprising a heavy chain variable region CDR1 of SEQ ID NO: 126; a heavy chain variable region CDR2 of SEQ ID NO: 127; a heavy chain variable region CDR3 of SEQ ID NO: 128; a light chain variable region CDR1 of SEQ ID NO: 136; a light chain variable region CDR2 of SEQ ID NO: 137; and a light chain variable region CDR3 of SEQ ID NO: 138.

In a specific embodiment, the invention includes an antibody that specifically binds to LOX-1 comprising a heavy chain variable region CDR1 of SEQ ID NO: 146; a heavy chain variable region CDR2 of SEQ ID NO: 147; a heavy chain variable region CDR3 of SEQ ID NO: 148; a light chain variable region CDR1 of SEQ ID NO: 156; a light chain variable region CDR2 of SEQ ID NO: 157; and a light chain variable region CDR3 of SEQ ID NO: 158.

In a specific embodiment, the invention includes an antibody that specifically binds to LOX-1 comprising a heavy chain variable region CDR1 of SEQ ID NO: 166; a heavy chain variable region CDR2 of SEQ ID NO: 167; a heavy chain variable region CDR3 of SEQ ID NO: 168; a light chain variable region CDR1 of SEQ ID NO: 176; a light chain variable region CDR2 of SEQ ID NO: 177; and a light chain variable region CDR3 of SEQ ID NO: 178.

In a specific embodiment, the invention includes an antibody that specifically binds to LOX-1 comprising a heavy chain variable region CDR1 of SEQ ID NO: 186; a heavy chain variable region CDR2 of SEQ ID NO: 187; a heavy chain variable region CDR3 of SEQ ID NO: 188; a light chain variable region CDR1 of SEQ ID NO: 196; a light chain variable region CDR2 of SEQ ID NO: 197; and a light chain variable region CDR3 of SEQ ID NO: 198.

In a specific embodiment, the invention includes an antibody that specifically binds to LOX-1 comprising a heavy chain variable region CDR1 of SEQ ID NO: 206; a heavy chain variable region CDR2 of SEQ ID NO: 207; a heavy chain variable region CDR3 of SEQ ID NO: 208; a light chain variable region CDR1 of SEQ ID NO: 216; a light chain variable region CDR2 of SEQ ID NO: 217; and a light chain variable region CDR3 of SEQ ID NO: 218.

In a specific embodiment, the invention includes an antibody that specifically binds to LOX-1 comprising a heavy chain variable region CDR1 of SEQ ID NO: 226; a heavy chain variable region CDR2 of SEQ ID NO: 227; a heavy chain variable region CDR3 of SEQ ID NO: 228; a light chain variable region CDR1 of SEQ ID NO: 236; a light chain variable region CDR2 of SEQ ID NO: 237; and a light chain variable region CDR3 of SEQ ID NO: 238.

In a specific embodiment, the invention includes an antibody that specifically binds to LOX-1 comprising a heavy chain variable region CDR1 of SEQ ID NO: 246; a heavy chain variable region CDR2 of SEQ ID NO: 247; a heavy chain variable region CDR3 of SEQ ID NO: 248; a light chain variable region CDR1 of SEQ ID NO: 256; a light chain variable region CDR2 of SEQ ID NO: 257; and a light chain variable region CDR3 of SEQ ID NO: 258.

In a specific embodiment, the invention includes an antibody that specifically binds to LOX-1 comprising a heavy chain variable region CDR1 of SEQ ID NO: 266; a heavy chain variable region CDR2 of SEQ ID NO: 267; a heavy chain variable region CDR3 of SEQ ID NO: 268; a light chain variable region CDR1 of SEQ ID NO: 276; a light chain variable region CDR2 of SEQ ID NO: 277; and a light chain variable region CDR3 of SEQ ID NO: 278.

In a specific embodiment, the invention includes an antibody that specifically binds to LOX-1 comprising a heavy chain variable region CDR1 of SEQ ID NO: 286; a heavy chain variable region CDR2 of SEQ ID NO: 287; a heavy chain variable region CDR3 of SEQ ID NO: 288; a light chain variable region CDR1 of SEQ ID NO: 296; a light chain variable region CDR2 of SEQ ID NO: 297; and a light chain variable region CDR3 of SEQ ID NO: 298.

In a specific embodiment, the invention includes an antibody that specifically binds to LOX-1 comprising a heavy chain variable region CDR1 of SEQ ID NO: 306; a heavy chain variable region CDR2 of SEQ ID NO: 307; a heavy chain variable region CDR3 of SEQ ID NO: 308; a light chain variable region CDR1 of SEQ ID NO: 316; a light chain variable region CDR2 of SEQ ID NO: 317; and a light chain variable region CDR3 of SEQ ID NO: 318.

In a specific embodiment, the invention includes an antibody that specifically binds to LOX-1 comprising a heavy chain variable region CDR1 of SEQ ID NO: 326; a heavy chain variable region CDR2 of SEQ ID NO: 327; a heavy chain variable region CDR3 of SEQ ID NO: 328; a light chain variable region CDR1 of SEQ ID NO: 336; a light chain variable region CDR2 of SEQ ID NO: 337; and a light chain variable region CDR3 of SEQ ID NO: 338.

In a specific embodiment, the invention includes an antibody that specifically binds to LOX-1 comprising a heavy chain variable region CDR1 of SEQ ID NO: 346; a heavy chain variable region CDR2 of SEQ ID NO: 347; a heavy chain variable region CDR3 of SEQ ID NO: 348; a light chain variable region CDR1 of SEQ ID NO: 356; a light chain variable region CDR2 of SEQ ID NO: 357; and a light chain variable region CDR3 of SEQ ID NO: 358.

In a specific embodiment, the invention includes an antibody that specifically binds to LOX-1 comprising a heavy chain variable region CDR1 of SEQ ID NO: 366; a heavy chain variable region CDR2 of SEQ ID NO: 367; a heavy chain variable region CDR3 of SEQ ID NO: 368; a light chain variable region CDR1 of SEQ ID NO: 376; a light chain variable region CDR2 of SEQ ID NO: 377; and a light chain variable region CDR3 of SEQ ID NO: 378.

In certain embodiments, the invention includes antibodies or antigen binding fragments that specifically bind to LOX-1 as described in Table 1. In a preferred embodiment, the antibody, or antigen binding fragment, that binds LOX-1 is MOR21435, MOR20159, MOR22031, MOR22034, MOR21433, MOR21452, MOR21453, MOR21460, MOR21468, MOR20052, MOR20133, MOR20144, MOR20148, MOR20151, MOR20152, MOR022025, MOR22028, MOR22029, and MOR22030.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene.

Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described below, as well as DP47 and DPK9.

Homologous Antibodies

In yet another embodiment, the present invention provides an antibody, or an antigen binding fragment thereof, comprising amino acid sequences that are homologous to the sequences described in Table 1, and the antibody binds to a LOX-1 protein (e.g., human and cynomolgus monkey LOX-1), and retains the desired functional properties of those antibodies described in Table 1.

For example, the invention provides an isolated antibody, or a functional antigen binding fragment thereof, comprising a heavy chain variable domain and a light chain variable domain, wherein the heavy chain variable domain comprises an amino acid sequence that is at least 80%, at least 90%, or at least 95% identical to an amino acid sequence selected from the group consisting of SEQ ID NOs: 9, 29, 49, 69, 89, 109, 129, 149, 169, 189, 209, 229, 249, 269, 289, 309, 329, 349, and 369; the light chain variable domain comprises an amino acid sequence that is at least 80%, at least 90%, or at least 95% identical to an amino acid sequence selected from the group consisting of SEQ ID NOs: 19, 39, 59, 79, 99, 119, 139, 159, 179, 199, 219, 239, 259, 279, 299, 319, 339, 359, and 379; and the antibody specifically binds to LOX-1 (e.g., human and cynomolgus monkey LOX-1). In certain aspects of the invention the heavy and light chain sequences further comprise HCDR1, HCDR2, HCDR3, LCDR1, LCDR2, and LCDR3 sequences as defined by Kabat, for example SEQ ID NOs: 8, 9, 10, 18, 19, and 20, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 11, 12, 13, 21, 22, and 23, respectively.

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except for an amino acid substitution in no more than 1, 2, 3, 4 or 5 amino acid positions. An antibody having VH and VL regions having high (i.e., 80% or greater) identity to the VH and VL regions of those described in Table 1 can be obtained by mutagenesis (e.g., site-directed or PCR-mediated mutagenesis) of nucleic acid molecules encoding SEQ ID NOs: 10, 30, 50, 70, 90, 110, 130, 150, 170, 190, 210, 230, 250, 270, 290, 310, 330, 350, or 370 and SEQ ID NOs: 20, 40, 60, 80, 100, 120, 140, 160, 180, 200, 220, 240, 260, 280, 300, 320, 340, 360, or 380, respectively, followed by testing of the encoded altered antibody for retained function using the functional assays described herein.

In other embodiments, the full length heavy chain and/or full length light chain amino acid sequences may be 50% 60%, 70%, 80%, 90%, 95%, 96%, 97%, 98% or 99% identical to the sequences set forth in Table 1. An antibody having a full length heavy chain and full length light chain having high (i.e., 80% or greater) identity to the full length heavy chains of any of SEQ ID NOs: 11, 31, 51, 71, 91, 111, 131, 151, 171, 191, 211, 231, 251, 271, 291, 311, 331, 351, or 371, and full length light chains of any of SEQ ID NOs: 21, 41, 61, 81, 101, 121, 141, 161, 181, 201, 221, 241, 261, 281, 301, 321, 341, 361, or 381, can be obtained by mutagenesis (e.g., site-directed or PCR-mediated mutagenesis) of nucleic acid molecules encoding such polypeptides, followed by testing of the encoded altered antibody for retained function using the functional assays described herein.

In other embodiments, the full length heavy chain and/or full length light chain nucleotide sequences may be 60%, 70%, 80%, 90%, 95%, 96%, 97%, 98% or 99% identical to the sequences set forth in Table 1.

In other embodiments, the variable regions of heavy chain and/or the variable regions of light chain nucleotide sequences may be 60%, 70%, 80%, 90%, 95%, 96%, 97%, 98% or 99% identical to the sequences set forth in Table 1.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the LOX-1-binding antibodies of the invention.

Accordingly, the invention provides an isolated antibody, or an antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 3, 23, 43, 63, 83, 103, 123, 143, 163, 183, 203, 223, 243, 263, 283, 303, 323, 343, and 363, and conservative modifications thereof; the heavy chain variable region CDR2 amino acid sequences are selected from the group consisting of SEQ ID NOs: 4, 24, 44, 64, 84, 104, 124, 144, 164, 184, 204, 224, 244, 264, 284, 304, 324, 344, and 364, and conservative modifications thereof; the heavy chain variable region CDR3 amino acid sequences are selected from the group consisting of SEQ ID NOs: 5, 25, 45, 65, 85, 105, 125, 145, 165, 185, 205, 225, 245, 265, 285, 305, 325, 345, and 365, and conservative modifications thereof; the light chain variable regions CDR1 amino acid sequences are selected from the group consisting of SEQ ID NOs: 13, 33, 53, 73, 93, 113, 133, 153, 173, 193, 213, 233, 253, 273, 293, 313, 333, 353, and 373, and conservative modifications thereof; the light chain variable regions CDR2 amino acid sequences are selected from the group consisting of SEQ ID NOs: 14, 34, 54, 74, 94, 114, 134, 154, 174, 194, 214, 234, 254, 274, 294, 314, 334, 354, and 374, and conservative modifications thereof; the light chain variable regions of CDR3 amino acid sequences are selected from the group consisting of SEQ ID NOs: 15, 35, 55, 75, 95, 115, 135, 155, 175, 195, 215, 235, 255, 275, 295, 315, 335, 355, and 375, and conservative modifications thereof; and the antibody or antigen binding fragments thereof specifically binds to LOX-1.

In other embodiments, the antibody of the invention is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the LOX-1 binding antibodies of the invention. Accordingly, the invention provides an isolated antibody optimized for expression in a mammalian cell consisting of a full length heavy chain and a full length light chain wherein the full length heavy chain has amino acid sequences selected from the group of SEQ ID NOs: 11, 31, 51, 71, 91, 111, 131, 151, 171, 191, 211, 231, 251, 271, 291, 311, 331, 351, or 371, and conservative modifications thereof; and the full length light chain has amino acid sequences selected from the group of SEQ ID NOs: 21, 41, 61, 81, 101, 121, 141, 161, 181, 201, 221, 241, 261, 281, 301, 321, 341, 361, or 381, and conservative modifications thereof; and the antibody specifically binds to LOX-1 (e.g., human and cynomolgus monkey LOX-1).

Antibodies that Bind to the Same Epitope

The present invention provides antibodies that bind to the same epitope as the LOX-1 binding antibodies described in Table 1. Additional antibodies can therefore be identified based on their ability to compete (e.g., to competitively inhibit the binding of, in a statistically significant manner) with other antibodies of the invention in LOX-1 binding assays (such as those described in the Examples). The ability of a test antibody to inhibit the binding of antibodies of the present invention to a LOX-1 protein demonstrates that the test antibody can compete with that antibody for binding to LOX-1; such an antibody may, according to non-limiting theory, bind to the same or a related (e.g., a structurally similar or spatially proximal) epitope on the LOX-1 protein as the antibody with which it competes. In a certain embodiment, the antibody that binds to the same epitope on LOX-1 as the antibodies of the present invention is a human monoclonal antibody. Such human monoclonal antibodies can be prepared and isolated as described herein. As used herein, an antibody "competes" for binding when the competing antibody inhibits LOX-1 binding of an antibody or antigen binding fragment of the invention by more than 50% (for example, 80%, 85%, 90%, 95%, 98% or 99%) in the presence of an equimolar concentration of competing antibody.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated antibody, or an antigen binding fragment thereof, comprising a heavy chain variable region comprising CDR1 sequences having an amino acid sequence selected from the group consisting of SEQ ID NOs: 3, 23, 43, 63, 83, 103, 123, 143, 163, 183, 203, 223, 243, 263, 283, 303, 323, 343, and 363; CDR2 sequences having an amino acid sequence selected from the group consisting of SEQ ID NOs: 4, 24, 44, 64, 84, 104, 124, 144, 164, 184, 204, 224, 244, 264, 284, 304, 324, 344, and 364; CDR3 sequences having an amino acid sequence selected from the group consisting of SEQ ID NOs: 5, 25, 45, 65, 85, 105, 125, 145, 165, 185, 205, 225, 245, 265, 285, 305, 325, 345, and 365, respectively; and a light chain variable region having CDR1 sequences having an amino acid sequence selected from the group consisting of SEQ ID NOs: 13, 33, 53, 73, 93, 113, 133, 153, 173, 193, 213, 233, 253, 273, 293, 313, 333, 353, and 373; CDR2 sequences having an amino acid sequence selected from the group consisting of SEQ ID NOs: 14, 34, 54, 74, 94, 114, 134, 154, 174, 194, 214, 234, 254, 274, 294, 314, 334, 354, and 374; and CDR3 sequences consisting of an amino acid sequence selected from the group consisting of SEQ ID NOs: 15, 35, 55, 75, 95, 115, 135, 155, 175, 195, 215, 235, 255, 275, 295, 315, 335, 355, and 375, respectively. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al). Frameworks that can be utilized as scaffolds on which to build the antibodies and antigen binding fragments described herein include, but are not limited to VH1A, VH1B, VH3, Vk1, VI2, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the invention relates to isolated LOX-1 binding antibodies, or antigen binding fragments thereof, comprising a heavy chain variable region comprising an amino acid sequence selected from the group consisting of SEQ ID NOs: 9, 29, 49, 69, 89, 109, 129, 149, 169, 189, 209, 229, 249, 269, 289, 309, 329, 349, and 369, or an amino acid sequence having one, two, three, four or five amino acid substitutions, deletions or additions in the framework region of such sequences, and further comprising a light chain variable region having an amino acid sequence selected from the group consisting of SEQ ID NOs: 19, 39, 59, 79, 99, 119, 139, 159, 179, 199, 219, 239, 259, 279, 299, 319, 339, 359, and 379, or an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated LOX-1-binding antibodies, or antigen binding fragments thereof, consisting of a heavy chain variable region having a VH CDR1 region consisting of an amino acid sequence selected from the group having SEQ ID NOs: 3, 23, 43, 63, 83, 103, 123, 143, 163, 183, 203, 223, 243, 263, 283, 303, 323, 343, and 363 or an amino acid sequence having one, two, three, four or five amino acid substitutions, deletions or additions as compared to SEQ ID NOs: 3, 23, 43, 63, 83, 103, 123, 143, 163, 183, 203, 223, 243, 263, 283, 303, 323, 343, and 363; a VH CDR2 region having an amino acid sequence selected from the group consisting of SEQ ID NOs: 4, 24, 44, 64, 84, 104, 124, 144, 164, 184, 204, 224, 244, 264, 284, 304, 324, 344, and 364 or an amino acid sequence having one, two, three, four or five amino acid substitutions, deletions or additions as compared to SEQ ID NOs: 4, 24, 44, 64, 84, 104, 124, 144, 164, 184, 204, 224, 244, 264, 284, 304, 324, 344, and 364; a VH CDR3 region having an amino acid sequence selected from the group consisting of SEQ ID NOs: 5, 25, 45, 65, 85, 105, 125, 145, 165, 185, 205, 225, 245, 265, 285, 305, 325, 345, and 365, or an amino acid sequence having one, two, three, four or five amino acid substitutions, deletions or additions as compared to SEQ ID NOs: 5, 25, 45, 65, 85, 105, 125, 145, 165, 185, 205, 225, 245, 265, 285, 305, 325, 345, and 365; a VL CDR1 region having an amino acid sequence selected from the group consisting of SEQ ID NOs: 13, 33, 53, 73, 93, 113, 133, 153, 173, 193, 213, 233, 253, 273, 293, 313, 333, 353, and 373, or an amino acid sequence having one, two, three, four or five amino acid substitutions, deletions or additions as compared to SEQ ID NOs: 13, 33, 53, 73, 93, 113, 133, 153, 173, 193, 213, 233, 253, 273, 293, 313, 333, 353, and 373; a VL CDR2 region having an amino acid sequence selected from the group consisting of SEQ ID NOs: 14, 34, 54, 74, 94, 114, 134, 154, 174, 194, 214, 234, 254, 274, 294, 314, 334, 354, and 374, or an amino acid sequence having one, two, three, four or five amino acid substitutions, deletions or additions as compared to SEQ ID NOs: 14, 34, 54, 74, 94, 114, 134, 154, 174, 194, 214, 234, 254, 274, 294, 314, 334, 354, and 374; and a VL CDR3 region having an amino acid sequence selected from the group consisting of SEQ ID NOs: 15, 35, 55, 75, 95, 115, 135, 155, 175, 195, 215, 235, 255, 275, 295, 315, 335, 355, and 375, or an amino acid sequence having one, two, three, four or five amino acid substitutions, deletions or additions as compared to SEQ ID NOs: 15, 35, 55, 75, 95, 115, 135, 155, 175, 195, 215, 235, 255, 275, 295, 315, 335, 355, and 375.

Accordingly, in another embodiment, the invention provides isolated LOX-1-binding antibodies, or antigen binding fragments thereof, consisting of a heavy chain variable region having a VH CDR1 region consisting of an amino acid sequence selected from the group having SEQ ID NOs: 6, 26, 46, 66, 86, 106, 126, 146, 166, 186, 206, 226, 246, 266, 286, 306, 326, 346, and 366 or an amino acid sequence having one, two, three, four or five amino acid substitutions, deletions or additions as compared to SEQ ID NOs: 6, 26, 46, 66, 86, 106, 126, 146, 166, 186, 206, 226, 246, 266, 286, 306, 326, 346, and 366; a VH CDR2 region having an amino acid sequence selected from the group consisting of SEQ ID NOs: 7, 27, 47, 67, 87, 107, 127, 147, 167, 187, 207, 227, 247, 267, 287, 307, 327, 347, and 367 or an amino acid sequence having one, two, three, four or five amino acid substitutions, deletions or additions as compared to SEQ ID NOs: 7, 27, 47, 67, 87, 107, 127, 147, 167, 187, 207, 227, 247, 267, 287, 307, 327, 347, and 367; a VH CDR3 region having an amino acid sequence selected from the group consisting of SEQ ID NOs: 8, 28, 48, 68, 88, 108, 128, 148, 168, 188, 208, 228, 248, 268, 288, 308, 328, 348, and 368, or an amino acid sequence having one, two, three, four or five amino acid substitutions, deletions or additions as compared to SEQ ID NOs: 8, 28, 48, 68, 88, 108, 128, 148, 168, 188, 208, 228, 248, 268, 288, 308, 328, 348, and 368; a VL CDR1 region having an amino acid sequence selected from the group consisting of SEQ ID NOs: 16, 36, 56, 76, 96, 116, 136, 156, 176, 196, 216, 236, 256, 276, 296, 316, 336, 356, and 376, or an amino acid sequence having one, two, three, four or five amino acid substitutions, deletions or additions as compared to SEQ ID NOs: 16, 36, 56, 76, 96, 116, 136, 156, 176, 196, 216, 236, 256, 276, 296, 316, 336, 356, and 376; a VL CDR2 region having an amino acid sequence selected from the group consisting of SEQ ID NOs: 17, 37, 57, 77, 97, 117, 137, 157, 177, 197, 217, 237, 257, 277, 297, 317, 337, 357, and 377, or an amino acid sequence having one, two, three, four or five amino acid substitutions, deletions or additions as compared to SEQ ID NOs: 17, 37, 57, 77, 97, 117, 137, 157, 177, 197, 217, 237, 257, 277, 297, 317, 337, 357, and 377; and a VL CDR3 region having an amino acid sequence selected from the group consisting of SEQ ID NOs: 18, 38, 58, 78, 98, 118, 138, 158, 178, 198, 218, 238, 258, 278, 298, 318, 338, 358, and 378, or an amino acid sequence having one, two, three, four or five amino acid substitutions, deletions or additions as compared to SEQ ID NOs: 18, 38, 58, 78, 98, 118, 138, 158, 178, 198, 218, 238, 258, 278, 298, 318, 338, 358, and 378.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to LOX-1. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target LOX-1 protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The present invention provides fully human antibodies that specifically bind to a LOX-1 protein. Compared to the chimeric or humanized antibodies, the human LOX-1-binding antibodies of the invention have further reduced antigenicity when administered to human subjects.

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for LOX-1. In certain embodiments herein, the camelid antibody or nanobody is naturally produced in the camelid animal, i.e., is produced by the camelid following immunization with LOX-1 or a peptide fragment thereof, using techniques described herein for other antibodies. Alternatively, the LOX-1-binding camelid nanobody is engineered, i.e., produced by selection for example from a library of phage displaying appropriately mutagenized camelid nanobody proteins using panning procedures with LOX-1 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising a LOX-1-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for LOX-1 and a second binding specificity for a second target epitope. For example, the second target epitope is another epitope of LOX-1 different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al, 1993 Proc. Natl. Acad. Sci. USA 90:6444-6448; Poljak et al, 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the invention are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-l-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies of the invention binding to LOX-1. The antigen-binding portions can be linked together via protein fusion or covalent or non covalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fc or hinge region.

Trimerizing domain are described for example in Borean patent EP 1 012 280B1. Pentamerizing modules are described for example in PCT/EP97/05897.

Antibodies with Extended Half Life

The present invention provides for antibodies that specifically bind to LOX-1 protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vive can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vive or have a longer half life in vivo. The techniques are well-known in the art, see, e.g., International Publication Nos. WO 93/15199, WO 93/15200, and WO 01/77137; and European Patent No. EP 413,622. In addition, in the context of a bispecific antibody as described above, the specificities of the antibody can be designed such that one binding domain of the antibody binds to LOX-1 while a second binding domain of the antibody binds to serum albumin, preferably HSA.

The strategies for increasing half life is especially useful in nanobodies, fibronectin-based binders, and other antibodies or proteins for which increased in vivo half life is desired.

Antibody Conjugates

The present invention provides antibodies or fragments thereof that specifically bind to a LOX-1 protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a LOX-1 protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al, 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbeliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and noradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alphemitters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N",N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et at (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et at (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies of the Invention

Nucleic Acids Encoding the Antibodies

The invention provides substantially purified nucleic acid molecules which encode polypeptides comprising segments or domains of the LOX-1-binding antibody chains described above. Some of the nucleic acids of the invention comprise the nucleotide sequence encoding the heavy chain variable region shown in SEQ ID NO: 10, 30, 50, 70, 90, 110, 130, 150, 170, 190, 210, 230, 250, 270, 290, 310, 330, 350, or 370, and/or the nucleotide sequence encoding the light chain variable region shown in SEQ ID NO: 20, 40, 60, 80, 100, 120, 140, 160, 180, 200, 220, 240, 260, 280, 300, 320, 340, 360, or 380. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting LOX-1 antigen binding capacity.

Also provided in the invention are polynucleotides which encode at least one CDR region and usually all three CDR regions from the heavy or light chain of the LOX-1-binding antibody set forth above. Some other polynucleotides encode all or substantially all of the variable region sequence of the heavy chain and/or the light chain of the LOX-1-binding antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a heavy chain sequence that is substantially identical (e.g., at least 80%, 90%, or 99%) to the heavy chain sequence set forth in SEQ ID NO: 11, 31, 51, 71, 91, 111, 131, 151, 171, 191, 211, 231, 251, 271, 291, 311, 331, 351, or 371. Some other nucleic acid sequences comprising nucleotide encoding a light chain sequence that is substantially identical (e.g., at least 80%, 90%, or 99%) to the light chain sequence set forth in SEQ ID NO: 21, 41, 61, 81, 101, 121, 141, 161, 181, 201, 221, 241, 261, 281, 301, 321, 341, 361, or 381.

The polynucleotide sequences can be produced by de novo solid-phase DNA synthesis or by PCR mutagenesis of an existing sequence (e.g., sequences as described in the Examples below) encoding a LOX-1-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al, PCR Methods and Applications 1:17, 1991.

Also provided in the invention are expression vectors and host cells for producing the LOX-1-binding antibodies described above. Various expression vectors can be employed to express the polynucleotides encoding the LOX-1-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the LOX-1-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a LOX-1-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a LOX-1-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted LOX-1-binding antibody sequences. More often, the inserted LOX-1-binding antibody sequences are linked to a signal sequences before inclusion in the vector. Vectors to be used to receive sequences encoding LOX-1-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the LOX-1-binding antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express LOX-1-binding polypeptides of the invention. Insect cells in combination with baculovirus vectors can also be used.

In some preferred embodiments, mammalian host cells are used to express and produce the LOX-1-binding polypeptides of the present invention. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, and transformed B-cells. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences.

These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et at, supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express LOX-1-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germine sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chem. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the LOX-1-binding antibodies having VH and VL sequences or full length heavy and light chain sequences shown herein can be used to create new LOX-1-binding antibodies by modifying full length heavy chain and/or light chain sequences, VH and/or VL sequences, or the constant region(s) attached thereto. Thus, in another aspect of the invention, the structural features of a LOX-1-binding antibody of the invention are used to create structurally related LOX-1-binding antibodies that retain at least one functional property of the antibodies of the invention, such as binding to human LOX-1 and also inhibiting one or more functional properties of LOX-1 (e.g., inhibit LOX-1 binding to the LOX-1 receptor, inhibit LOX-1-dependent cell proliferation).

For example, one or more CDR regions of the antibodies of the present invention, or mutations thereof, can be combined recombinantly with known framework regions and/or other CDRs to create additional, recombinantly-engineered, LOX-1-binding antibodies of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing a LOX-1-binding antibody consisting of a heavy chain variable region antibody sequence having a CDR1 sequence selected from the group consisting of SEQ ID NOs: 3, 23, 43, 63, 83, 103, 123, 143, 163, 183, 203, 223, 243, 263, 283, 303, 323, 343, and 363, a CDR2 sequence selected from the group consisting of SEQ ID NOs: 4, 24, 44, 64, 84, 104, 124, 144, 164, 184, 204, 224, 244, 264, 284, 304, 324, 344, and 364, and/or a CDR3 sequence selected from the group consisting of SEQ ID NOs: 5, 25, 45, 65, 85, 105, 125, 145, 165, 185, 205, 225, 245, 265, 285, 305, 325, 345, and 365; and a light chain variable region antibody sequence having a CDR1 sequence selected from the group consisting of SEQ ID NOs: 13, 33, 53, 73, 93, 113, 133, 153, 173, 193, 213, 233, 253, 273, 293, 313, 333, 353, and 373, a CDR2 sequence selected from the group consisting of SEQ ID NOs: 14, 34, 54, 74, 94, 114, 134, 154, 174, 194, 214, 234, 254, 274, 294, 314, 334, 354, and 374, and/or a CDR3 sequence selected from the group consisting of SEQ ID NOs: 15, 35, 55, 75, 95, 115, 135, 155, 175, 195, 215, 235, 255, 275, 295, 315, 335, 355, and 375; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a LOX-1-binding antibody consisting of a heavy chain variable region antibody sequence having a CDR1 sequence selected from the group consisting of SEQ ID NOs: 6, 26, 46, 66, 86, 106, 126, 146, 166, 186, 206, 226, 246, 266, 286, 306, 326, 346, and 366, a CDR2 sequence selected from the group consisting of SEQ ID NOs: 7, 27, 47, 67, 87, 107, 127, 147, 167, 187, 207, 227, 247, 267, 287, 307, 327, 347, and 367, and/or a CDR3 sequence selected from the group consisting of SEQ ID NOs: 8, 28, 48, 68, 88, 108, 128, 148, 168, 188, 208, 228, 248, 268, 288, 308, 328, 348, and 368; and a light chain variable region antibody sequence having a CDR1 sequence selected from the group consisting of SEQ ID NOs: 16, 36, 56, 76, 96, 116, 136, 156, 176, 196, 216, 236, 256, 276, 296, 316, 336, 356, and 376, a CDR2 sequence selected from the group consisting of SEQ ID NOs: 17, 37, 57, 77, 97, 117, 137, 157, 177, 197, 217, 237, 257, 277, 297, 317, 337, 357, and 377, and/or a CDR3 sequence selected from the group consisting of SEQ ID NOs: 18, 38, 58, 78, 98, 118, 138, 158, 178, 198, 218, 238, 258, 278, 298, 318, 338, 358, and 378; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a LOX-1-binding antibody optimized for expression in a mammalian cell consisting of: a full length heavy chain antibody sequence having a sequence selected from the group of SEQ ID NOs: 11, 31, 51, 71, 91, 111, 131, 151, 171, 191, 211, 231, 251, 271, 291, 311, 331, 351, or 371; and a full length light chain antibody sequence having a sequence selected from the group of 21, 41, 61, 81, 101, 121, 141, 161, 181, 201, 221, 241, 261, 281, 301, 321, 341, 361, or 381; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the LOX-1-binding antibodies described herein, which functional properties include, but are not limited to, specifically binding to human, cynomolgus, rat, and/or mouse LOX-1; and the antibody inhibit LOX-1-dependent cell proliferation in a F36E and/or Ba/F3-LOX-1R cell proliferation assay.

In certain embodiments of the methods of engineering antibodies of the invention, mutations can be introduced randomly or selectively along all or part of an LOX-1-binding antibody coding sequence and the resulting modified LOX-1-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments of the invention antibodies have been engineered to remove sites of deamidation. Deamidation is known to cause structural and functional changes in a peptide or protein. Deamindation can result in decreased bioactivity, as well as alterations in pharmacokinetics and antigenicity of the protein pharmaceutical. (*Anal Chem.* 2005 Mar. 1; 77(5):1432-9).

In certain embodiments of the invention the antibodies have been engineered to increase pI and improve their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-LOX-1 antibodies, or Fabs, of the invention improved their solubility, enabling the antibodies to be formulated at higher concentrations (>100 mg/ml). Formulation of the antibodies at high concentrations (e.g. >100 mg/ml) offers the advantage of being able to administer higher doses of the antibodies into eyes of patients via intravitreal injections, which in turn may enable reduced dosing frequency, a significant advantage for treatment of chronic diseases including cardiovascular disorderss. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

The functional properties of the altered antibodies can be assessed using standard assays available in the art and/or described herein, such as those set forth in the Examples (e.g., ELISAs).

Prophylactic and Therapeutic Uses

Antibodies that binds LOX-1 as described herein, can be used at a therapeutically useful concentration for the treatment of a disease or disorder associated with increased LOX-1 levels and/or activity by administering to a subject in need thereof an effective amount of the antibodies or antigen binding fragments of the invention. The present invention provides a method of treating LOX-1-associated cardiovascular disorders by administering to a subject in need thereof an effective amount of the antibodies of the invention. The present invention provides a method of treating LOX-1-associated cardiovascular disorders by administering to a subject in need thereof an effective amount of the antibodies of the invention.

The antibodies of the invention can be used, inter alia, to prevent treat, prevent, and improve LOX-1 associated conditions or disorders, including but not limited to cardiovascular disorders, endothelial cell dysfunction, endothelial cell disorders, atherosclerosis, arteriosclerosis, hypertension, hyperlipidemia, hypercholesterolemia, diabetes mellitus, nitric oxide deficiency, myocardial infarction, vascular oxidative stress, myocardial ischemia, ischemia-reperfusion, sepsis, diabetic nephropathy, renal disease, cardiomyopathy, heart failure, peripheral artery disease, coronary heart disease, claudication (e.g., intermittent claudication, Rutherford Class II/III Claudication), peripheral artery disease (PAD), angina (e.g., refractory angina), coronary artery disease (CAD)(e.g., due to atherosclerosis of the arteries feeding the heart), stroke, and abnormal endothelium-dependent vasodilation.

Treatment and/or prevention of cardiovascular disorders, e.g., LOX-1-associated cardiovascular disorders, can be determined by a health care professional using clinically relevant measurements of vascular function. Treatment of LOX-1-associated cardiovascular disorders means any action (e.g., administration of an anti-LOX-1 antibody described herein) that results in, or is contemplated to result in, the improvement or preservation of vascular function, vascular anatomy and/or hemodynamic parameters. In addition, prevention as it relates to conditions or disorders associated with cardiovascular disorders means any action (e.g., administration of an anti-LOX-1 antibody described herein) that prevents or slows a worsening in vascular function, and/or a cardiovascular disorders parameter, as defined herein, in a patient at risk for said worsening.

As oxLDLs and soluble LOX-1 levels are both increased in stable angina and acute ischemic syndromes, the anti-LOX-1 antibodies of the invention are expected to inhibit vascular oxidative stress, reduce myocardial ischemia and improve angina and exercise tolerance; said antibodies have the potential to become the first disease-modifying anti-anginal treatment available.

The efficacy of said therapeutic administration may be measured by a serial assessment of frequency and duration of transient ischemic events (ambulatory ECG monitoring) and angina (Seattle angina questionnaire), and serial exercise tolerance testing with perfusion imaging option. Efficacy may also be measured by use of biomarkers such as plasma oxLDL, soluble LOX-1, and oxidative stress biomarkers (F2-isoprostanes, malondialdehyde, myeloperoxidase).

"Claudication," as used herein, includes severe claudication and other like terms, and describes a mobility impairment and high unmet medical need. Claudication is a condition characterized by lower extremity ischemia, causing muscle fatigue, pain on exertion relieved by rest, limited mobility, and reduced quality of life, and is caused by atherosclerosis and abnormal (e.g., impaired) endothelium-dependent vasodilation. Its prevalence in the US is 8-12 million patients. Among patients with intermittent claudication, 7% will undergo lower extremity bypass surgery, 4% will require major amputations, and 16% will develop worsening claudication. Cardiovascular events, such as myocardial infarction and stroke, occur in 20% of severe claudication sufferers over 5 years. The current therapy is surgical, and treatment through less invasive means, such as the administration of the anti-LOX-1 antibodies of the invention, would represent an enormous therapeutic breakthrough.

The efficacy of said therapeutic administration may be measured by a serial assessment of exercise-induced claudication (plantar flexion and treadmill), with endpoints to include time to onset of pain, exercise duration, and walking distance. Efficacy may also be measured by use of mechanistic biomarkers such as plasma oxLDL and soluble LOX-1; oxidative stress biomarkers (F2-isoprostanes, malondialdehyde, myeloperoxidase); exercise-induced changes in lower extremity flow and muscle O2 saturation.

Another high unmet medical need for which the anti-LOX-1 antibodies of the invention would be therapeutically useful is refractory angina. Angina recurs in afflicated subjects despite optimum medical therapy (e.g., administration of long acting beta-blocker, nitrate, and calcium channel blocker), with no option for revascularization. Refractory angina is a condition marked by chest pain due to ischemia of the heart muscle, generally due to obstruction or spasm of the coronary arteries (e.g., from coronary artery disease), with debilitating symptoms, very limited physical activity and poor quality of life. The 1-1.8 million patients refractory angina sufferers in the US experience increased cardiovascular mortality at a rate of 10% per year; at least 100,000 new refractory angina cases arise per year.

The antibodies of the invention can also be used in combination with other agents for the prevention, treatment, or improvement of LOX-1 associated disorders. For example, statin therapies may be used in combination with the LOX-1 antibodies and antigen binding fragments of the invention for the treatment of patients with cardiovascular disorders.

Pharmaceutical Compositions

The invention provides pharmaceutical compositions comprising the LOX-1-binding antibodies (intact or binding fragments) formulated together with a pharmaceutically acceptable carrier. The compositions can additionally contain one or more other therapeutic agents that are suitable for treating or preventing, for example, cardiovascular disorders. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravitreal, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e., antibody, bispeciic and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the LOX-1-binding antibody is employed in the pharmaceutical compositions of the invention. The LOX-1-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of a cardiovascular disorders described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. For intravitreal administration with an antibody, the dosage may range from 0.1 mg/eye to 5 mg/eye. For example, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, or 5.0 mg/ml. An exemplary treatment regime entails systemic administration once per every two weeks or once a month or once every 3 to 6 months. An exemplary treatment regime entails systemic administration once per every two weeks or once a month or once every 3 to 6 months, or as needed (PRN).

Antibody is usually administered on multiple occasions. Intervals between single dosages can be weekly, monthly or yearly. Intervals can also be irregular as indicated by measuring blood levels of LOX-1-binding antibody in the patient. In addition alternative dosing intervals can be determined by a physician and administered monthly or as necessary to be efficacious. In some methods of systemic administration, dosage is adjusted to achieve a plasma antibody concentration of 1-1000 µg/ml and in some methods 25-500 µg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the invention will be readily apparent to one of ordinary skill in the art and are encompassed by the appended claims.

Example 1

Preparation of Purified Recombinant Human Soluble LOX-1 for Use as an Antigen

A nucleic acid sequence encoding the extracellular domain (amino acid residues 61-273) of human LOX-1 polypeptide with N-terminal signal peptide from human CD33, purification tag (EFHR), and BirA biotinylation sequence (GLNDIFEAQKIEWHE) (SEQ ID NO: 384) was subcloned into the mammalian cell expression vector pRS5a. The resulting plasmid, pRS5a_APP-Avi-human-sLOX-1(61-273), was transiently transfected into HEK293T cells using standard polyethylenimine (PEI) transfection methods. Cells were propagated in suspension culture in Novartis medium M11V3 (Bioconcept) and transfection was carried out at $1.4\times10^6$ cells/ml final cell concentration in 5 liters media using a Wave Bioreactor.

Five hours after transfection, 5 liters of ExCell VPRO serum-free media (Sigma) was added. Cells were grown at 37° C. and 5% $CO_2$ for 10 days. Cells were then harvested by centrifugation, followed by filtration with a 0.22 micron sterile filer. The clarified supernatant was passed over a 20 mL anti-APP affinity resin (Novartis proprietary) equilibrated with PBS. The column was washed with PBS until baseline absorbance at 280 nm was reached. The column was then washed with 10 column volumes of PBS containing 1% Triton X-100 and 0.3% tri-n-butylphosphate, followed by 25 column volumes PBS. The sLOX-1 protein was then eluted with 50 mM sodium citrate, pH 3.0, and the fractions were neutralized with 1/10$^{th}$ volume of 1M Tris, pH 9.0. Relevant fractions were pooled and exhaustively dialyzed against PBS, then aliquoted and flash frozen in liquid nitrogen. Analytical sizing analysis showed the purified soluble LOX-1 protein material to be >95% dimer form, which is the expected form of this protein.

Example 2

Preparation of Human LOX-1 Transfected HEK293 Cells

To test the binding specificity and functional activity of anti-LOX1 specific antibodies, HEK293 cells stably overexpressing human LOX-1 were generated. Using standard Lipofectamine 2000 transfection methods, HEK293-6E cells were transfected with a mammalian expression plasmid encoding full-length human LOX-1 cDNA and hygromycin resistance. Transfected cultures were evaluated for surface expression of LOX-1 by flow cytometry on day three post transfection and then subjected to hygromycin selection (200 μg/ml) to enrich for stably expressing cells. Clonal populations were obtained by two sequential rounds of limiting dilution and expression was confirmed by flow cytometry. Only clones maintaining stable LOX-1 expression for more than four weeks in culture were selected and used in subsequent antibody characterization assays.

Example 3

Human Fab Phage Library Panning

The phagemid library is based on the HuCAL® concept (Knappik et al., 2000) and employs the CysDisplay® technology for displaying the Fab on the phage surface (Lohning, 2001).

Capture Panning Against LOX-1: For capture panning, the antigen LOX-1 was immobilized on a 96-well Maxisorp™ plate via a capture antibody directed against the APP-Avi tag fused to the antigen (mouse anti-APP tag capture antibody prepared at Novartis, batch code ACE21514). For phage selection, an appropriate number (dependent on the number of sub-library pools) of wells of a 96-well Maxisorp™ plate were coated with capture antibody overnight at 4° C. and afterwards an antigen solution was added and incubated for at least 1 hour at room temperature. For each panning, about $4 \times 10^{13}$ HuCAL PLATINUM® phage-antibodies were blocked with milk powder and BSA. Additional blocking reagents were added to the blocking buffer to avoid selection of antibodies against the tag or the capture antibody (unrelated Protein-His-APP-Avi and mouse gamma-globulin). After the blocking procedure, the pro-blocked phage mix was added to each antigen coated and blocked well and incubated. Afterwards, unspecific bound phage were washed off by several washing steps. For elution of specifically bound phage, DTT was added to the wells for 10 min at RT. The DTT eluate was transferred into E. coli TG1. The mix of E. coli TG1 and DTT eluate was incubated for 45 min in a water bath at 37° C. for phage infection. The bacterial pellets were resuspended in growth medium, plated on LB/Cam agar plates and incubated overnight. Colonies were scraped off the plates and were used for phage rescue, polyclonal amplification of selected clones, and phage production. With purified phage the next panning round was started. The second and third round of capture panning was performed according to the protocol of the first round except for more stringent washing conditions.

Carboxy Bead Panning Against LOX-1: Prior to a bead-based penning, the antigen was immobilized on carboxy beads (Dynabeads® M-270 Carboxylic Acid, Invitrogen) according to the manufacturer's protocol. In brief, the activation of the carboxy beads was performed with a carbodiimide in presence of NHS followed by coupling of the antigen LOX-1 (amine containing), resulting in a stable amide bond between the bead and the antigen. Per phage pool, $1 \times 10^7$ antigen coated beads were blocked using PBS/, Tween20 and milk powder. In parallel, for each panning HuCAL PLATINUM® phage-antibodies were blocked with an equal volume of PBS, Tween20 and milk powder. Then, $1 \times 10^7$ blocked antigen-coated beads were added to the pre-adsorbed and blocked phage particles and incubated at room temperature. Phage particles bound to the antigen coated beads were collected with a magnetic separator. Unspecific bound phage were washed off by several washing steps and specifically bound phage were eluted from antigen coated beads using DTT. The DTT eluate was then transferred into E. coli TG1 and the mix of TG1 and DTT eluate was incubated at 37° C. for phage infection. The bacterial pellets were resuspended in growth medium, plated on LB/Cam agar plates and incubated. Colonies were scraped off the plates and were used for phage rescue, polyclonal amplification of selected clones, and phage production. With purified phage the next panning round was started. The second and third round of bead-based panning was performed according to the protocol of the first round except for more stringent washing conditions.

Solution Panning Against LOX-1 with Streptavidin-Coupled Magnetic Beads: Prior to solution panning, the antigen was biotinylated and retention of activity of the biotinylated LOX-1 antigen was confirmed. During solution panning, the Fab displaying phage and the biotinylated antigen were incubated in solution which facilitated the accessibility of the antigen to the phage. For each phage pool, streptavidin beads (Dynabeads® M-280 Streptavidin; Invitrogen) were blocked in 1× Chemiblocker. In parallel, for each panning, about $4 \times 10^{13}$ HuCAL PLATINUM® phage-antibodies were blocked with an equal volume of 2× Chemiblocker/Tween20. Then, 100 nM biotinylated antigen LOX-1 was added to the pre-adsorbed and blocked phage particles and incubated at RT on a rotator. The phage-antigen complexes were captured using 2 mg blocked Streptavidin beads and phage particles bound to the Streptavidin beads were collected with a magnetic separator. Unspecific bound phage were washed off by several washing steps using PBS, Tween20 and PBS and specifically bound phage were eluted from Streptavidin beads using DDT. The DTT eluate was then transferred into E. coli TG1 and the mix of TG1 and DTT eluate was incubated at 37° C. for phage infection. The bacterial pellets were resuspended in growth medium, plated on LB/Cam agar plates and incubated o/n. Colonies were scraped off the plates and were used for phage rescue, polyclonal amplification of selected clones, and phage production. With purified phage the next panning round was started. The second and third round of the solution panning was performed according to the protocol of the first round except for more stringent washing conditions.

Whole Cell Panning Against LOX-1: For each panning, about $4 \times 10^{13}$ HuCAL PLATINUM® phage-antibodies were blocked in FCS. In parallel, target cells expressing antigen LOX-1 and adsorption cells without expression of antigen LOX-1 per phage pool were resuspended and blocked using FCS. The blocked target cells were spun down, resuspended in the pre-blocked phage particles and incubated. The phage-cell complexes were washed three times. Elution of specifically bound phage from target cells was performed by acidic elution. After centrifugation, the supernatant (eluate) was neutralized by adding unbuffered Tris. After an adsorption step, the supernatant was used for infection of *E. coli* TG1 culture and incubated at 37° C. for phage infection. The bacterial pellets were resuspended in growth medium, plated on LB/Cam agar plates and incubated o/n. Colonies were scraped off the plates and were used for phage rescue and phage amplification. Amplified phage were used for the next panning round. The second and third round of the whole cell panning was performed according to the protocol of the first round except for more stringent washing conditions.

Differential Whole Cell Panning Against LOX-1: In the differential whole cell panning, the alternating selections on LOX-1 expressing cells and purified LOX-1 protein were performed according to the procedures described above. Two different strategies were applied: either 2 rounds (1st and 3rd round; cells-protein-cells) or one round (2nd round; protein-cells-protein) of selection on cells.

Affinity Maturation Pannings: To increase affinity and biological activity of selected antibody fragments, light chain CDR3 (L-CDR3) and heavy chain CDR2 (H-CDR2) regions were optimized in parallel by cassette mutagenesis using trinucleotide directed mutagenesis (Virnekas et al., 1994), while the framework regions were kept constant. Prior to cloning for affinity maturation, parental Fab fragments were transferred from the corresponding expression vector pM®x11 into the CysDisplay® vector pMORPH®30.

For optimizing L-CDR3 of parental Fab fragments the L-CDR3, framework and the constant region of the light chains were replaced by a repertoire of diversified L-CDR3s together with framework 4 and the constant domain by subcloning. In a second library set the H-CDR2 was diversified, while the connecting framework regions were kept constant. This library size ensured coverage of the theoretical diversity. Amplification of the library was performed as described elsewhere (Rauchenberger et al., 2003). For quality control single clones were randomly picked and sequenced.

For the selection of affinity improved binders phage derived from maturation libraries were subjected to three rounds of solution pannings using LOX-1. Stringency was increased by lowering the antigen concentration in each panning round (Low et al., 1996) combined with more stringent washing steps.

Example 4

IgG Expression and Purification

In order to express full length IgG, variable domain fragments of heavy (VH) and light chains (VL) were subcloned from Fab expression vectors into an appropriate pMorph®_hIg vector for human IgG1f_LALA. Restriction enzymes MfeI, BlpI were used for subcloning of the VH domain fragment and EcoRV, BsiWI, HpaI for subcloning of the VL domain fragment into pMorph®4 vector. RapCLONE® was performed to convert Fab clones into the IgG format.

Eukaryotic HKB11 cells were transfected with pMORPH14 eucaryotic expression vector DNA encoding both heavy and light chains of IgGs. Cell culture supernatant was harvested on day 3 or 7 post transfection and subjected to standard Protein A affinity chromatography (MabSelect SURE, GE Healthcare). All samples were sterile filtered (0.2 μm pore size). Purity of IgG was analyzed under denaturing, reducing and non-reducing conditions using a Labchip System (Caliper GXII, Perkin Elmer) or on SDS-PAGE. Protein concentrations were determined by UV-spectrophotometry and HP-SEC was performed to analyze IgG preparations in native state.

Example 5

Fab and IgG Inhibition of OxLDL or MDA-LDL Binding to LOX-1

Purified APP-Avi-soluble human soluble LOX-1(61-273) protein prepared as described in Example 1 was biotinylated as follows: purified soluble LOX-1 protein (8-10 mg) in 50 mM Bicine pH 8.3 buffer at a final concentration of approximately 1 mg/mL was incubated in the presence of 10 mM ATP, 10 mM magnesium acetate, 0.1 mM biotin, and BirA biotin ligase (Avidity) at 30° C. for 1 hr and then placed at 4° C. overnight. The protein was then purified using a S200 Superdex 16/60 column equilibrated with PBS. Relevant fractions were pooled and the protein was concentrated to approximately 1 mg/mL concentration, aliquoted, and flash frozen in liquid nitrogen. Percent biotinylation was assessed by mass spectrometry peptide mapping of unbiotinylated and biotinylated samples. Typically, the biotinylation yield was >95%, and unbiotinylated material was not detected. Analytical sizing analysis showed the biotinylated material to be 100% dimer form, which is the expected form of this protein.

NeutrAvidin 384 well plates were coated with 2.5 μg/ml biotinylated LOX-1 diluted in PBS. After blocking with 25% Block Ace (AbD Serotec, Cat#BUF029) in PBS, purified Fabs or IgGs diluted in PBS/1% BSA were added. Subsequently OxLDL (copper-sulfate oxidized LDL, Kalen Biomedical #770202) or MDA-LDL (Academy Biomedical, #20P-MD-L102) ligand diluted in PBS/1% BSA were allowed to bind to coated LOX-1. Secondary antibody (HRP conjugated sheep anti ApoB IgG; The Binding Site) diluted 1:1,000 in PBS/1% BSA was added followed by addition of TMB substrate (Thermo Scientific). After 10 minutes 1M H2SO4 was added and absorbance was determined at 450 nm. During early screenings, Fab fragments were also tested in this oxLDL binding assay using Fab-containing crude *E. coli* lysates.

Example 6

Fab and IgG Inhibition of AGE-BSA Binding to LOX-1

Purified APP-Avi-soluble human soluble LOX-1(61-273) protein prepared as described in Example 1 was biotinylated as described in Example 5. NeutrAvidin 384 well plates were coated with 5 μg/ml biotinylated LOX-1 diluted in bicarbonate buffer (Thermo Scientific). After blocking with PBS/2% BSA/0.1% Tween20/0.1% TritonX-100, purified Fabs or IgGs diluted in PBS/2% BSA/0.1% Tween20/0.1% TritonX-100 were added. Subsequently AGE-BSA ligand (R&D Systems, #BT4127) diluted in PBS/2% BSA/0.1% Tween20/0.1% TritonX-100 was allowed to bind to coated LOX-1. Streptavidin-HRP (R&D Systems) diluted 1:200 in PBS/2% BSA/0.1% Tween20/0.1% TritonX-100 was added followed by addition of TMB substrate (Thermo Scientific). After 10 minutes 1M $H_2SO_4$ was added and absorbance was determined at 450 nm. Assay performance was affected by the type of BSA used for blocking and diluent solutions. For optimal assay performance, BSA from Sigma (catalog #A4503) was used.

Example 7

LOX-1 Antibody Inhibition of OxLDL Binding to LOX-1 Protein

Figure 1B:
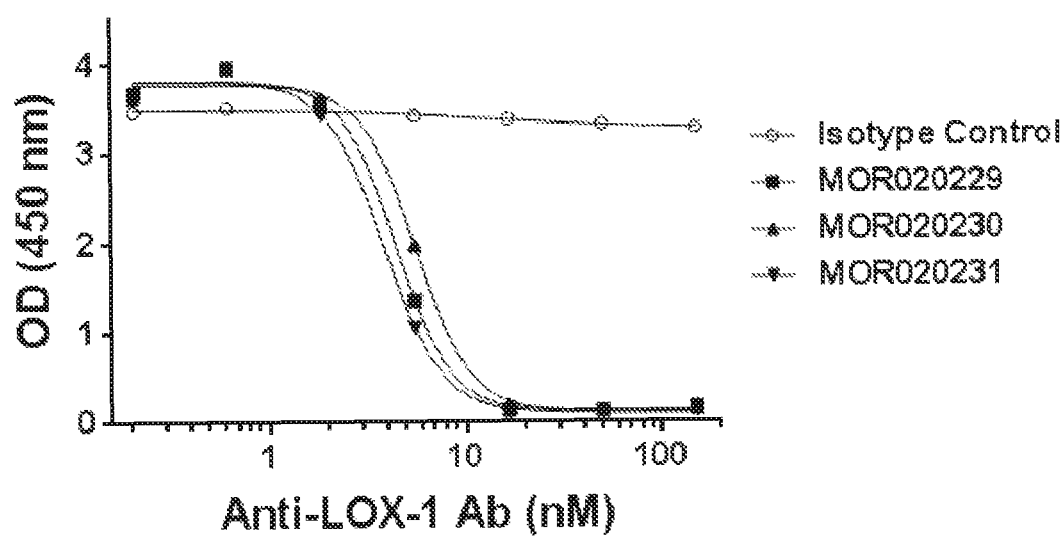

The ability of LOX-1 antibodies to inhibit oxLDL binding to LOX-1 protein was determined using the method described in Example 4. In addition to "high binding OxLDL" from Kalen Biomedical (catalog number 770212-7), which is generated by copper sulfate mediated oxidation of LDL, two other forms of modified LDL were tested in this assay: malondialdehyde modified LDL (Academy Bio-Medical Co. catalog number 20P-MD-L105) and hypochlorite modified LDL. Hypochlorite modified LDL was prepared according to the following procedure. Human LDL (Kalen Biomedical catalog number 770200-4) was diluted with PBS to a final concentration of 0.25 mg/mL. Sodium hypochlorite (NaOCl, JT Baker catalog number 9416-01) was then added to 0.1 mM final concentration. The solution was incubated at room temperate for 4 hours, then quenched by adding L-methionine to a final concentration of reaction by adding 5 μl of 100 mM Mehionine per 200 μl total volume. Representative data showing inhibition of copper sulfate oxidized LDL (oxLDL) binding to LOX-1 by LOX-1 antibodies is shown in FIGS. 1A-1B, and described in Tables 3, 5, and 7.

Example 8

LOX-1 Antibody Inhibition of OxLDL Binding to LOX-1/HEK293 Cells

The huLOX-1/HEK293 cells were maintained in DMEM containing 10% FBS and 1% Penicillin-Streptomycin as an adherent monolayer in T flasks containing 20 ml culture medium per 75 cm$^2$ surface area. The cells were incubated in a humidified incubator at 5% $CO_2$ and 37° C., and sub-cultivated every 2-3 days. To passage the cells, the culture medium is removed, and the monolayer is washed once with 10-20 ml pre-warmed PBS. After washing, 1 ml of pre-warmed TrypLE Express is added, and the cells were incubated at 37° C. for 5 min. Pre-warmed fresh culture medium was then added.

Figure 2A:
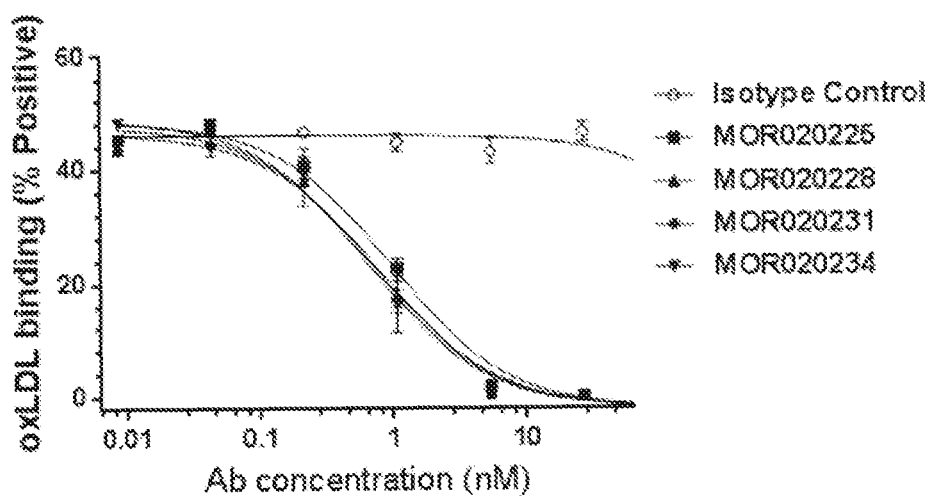
FIGS. 2A-2B depict LOX-1 antibodies inhibiting dil-labeled OxLDL binding to human LOX-1 transfected HEK293 cells.
Figure 2B:
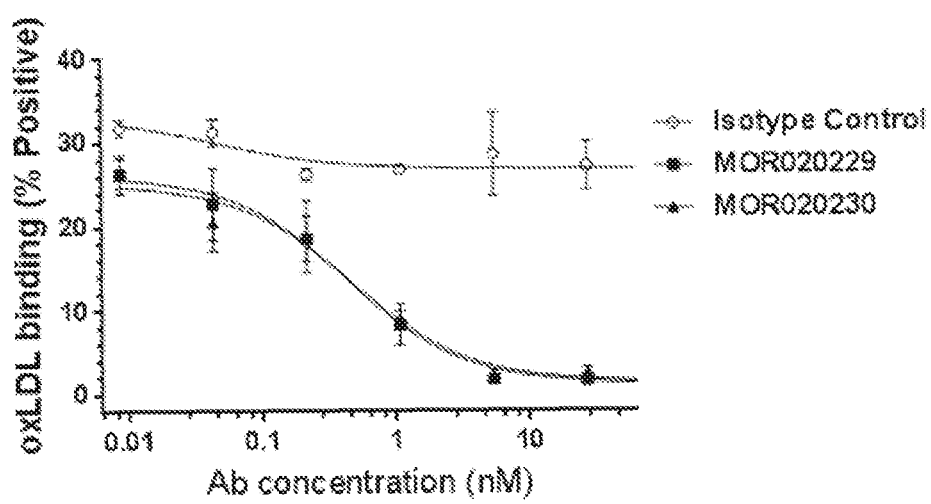
Figure 3:
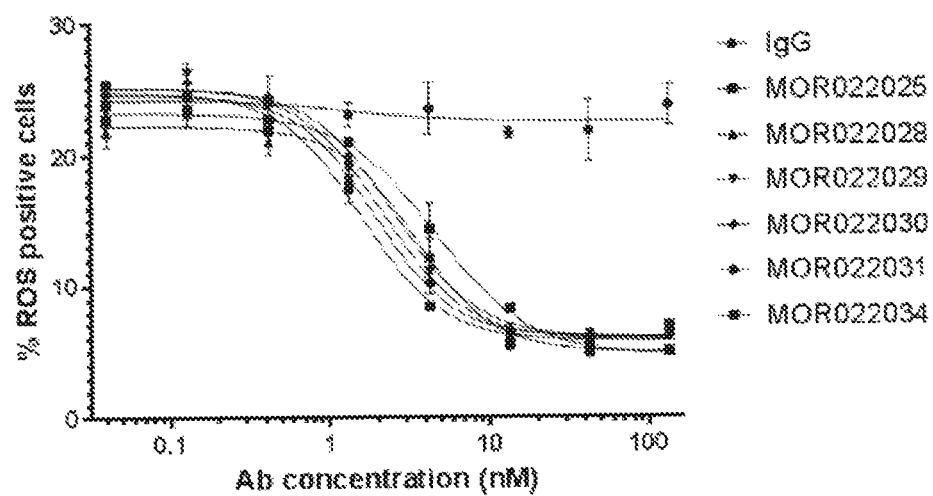
FIG. 3 depicts a dose response curve of LOX-1 antibody inhibition of oxLDL induced reactive oxygen species (ROS) production in human LOX-1 transfected HEK293 cells.
Figure 4A:
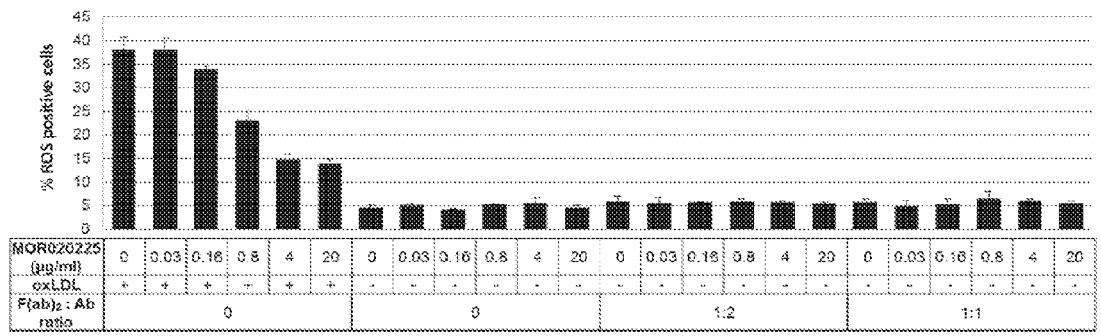
FIGS. 4A-4G demonstrate that LOX-1 antibodies inhibit oxLDL induced reactive oxygen species (ROS) production in human LOX-1 transfected HEK293 cells similar to the results shown in FIG. 3. In the absence of oxLDL, LOX-1 antibodies (antibodies alone or antibodies cross-linked using an anti-human IgG Fab$_2$) do not induce ROS production in LOX-1 transfected HEK293 cells.
Figure 4B:
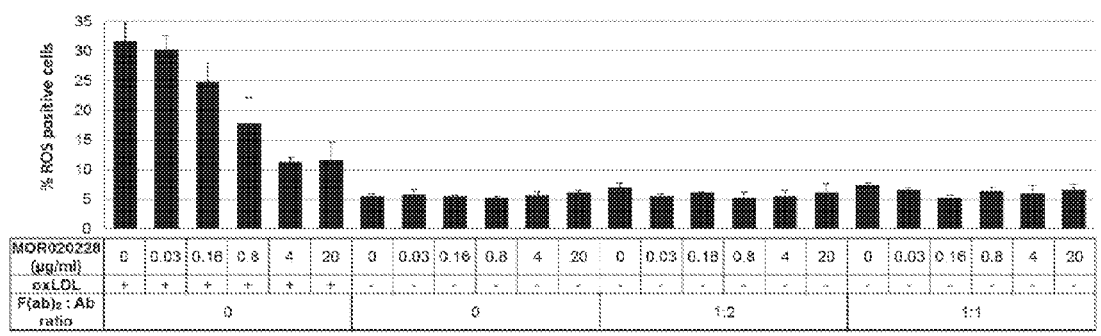
Figure 4C:
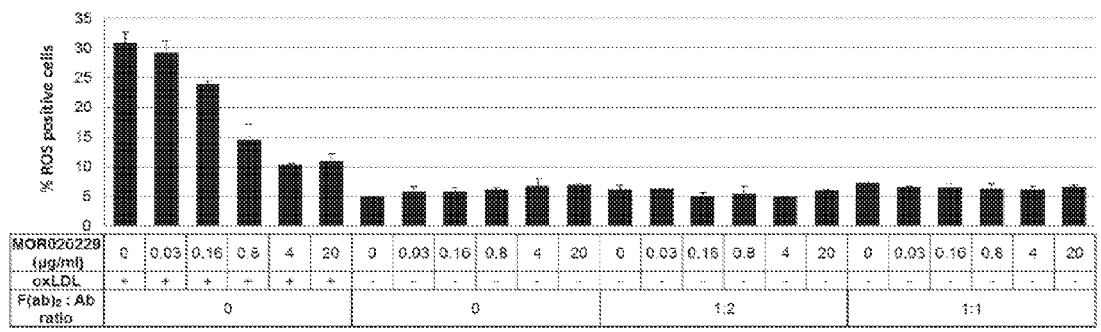
Figure 4D:
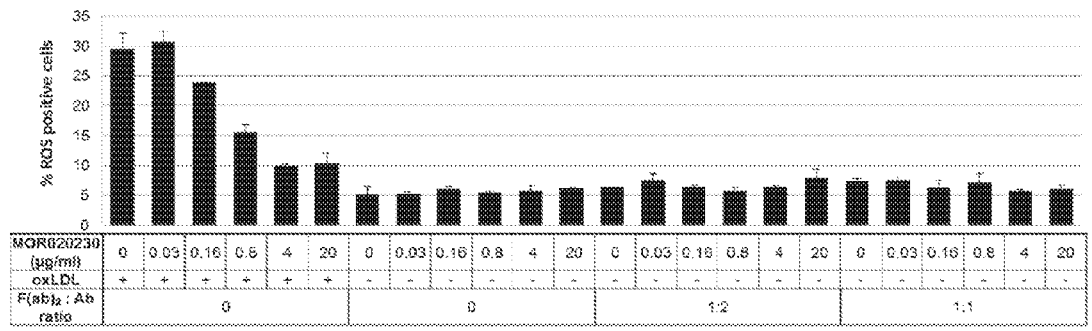
Figure 4E:
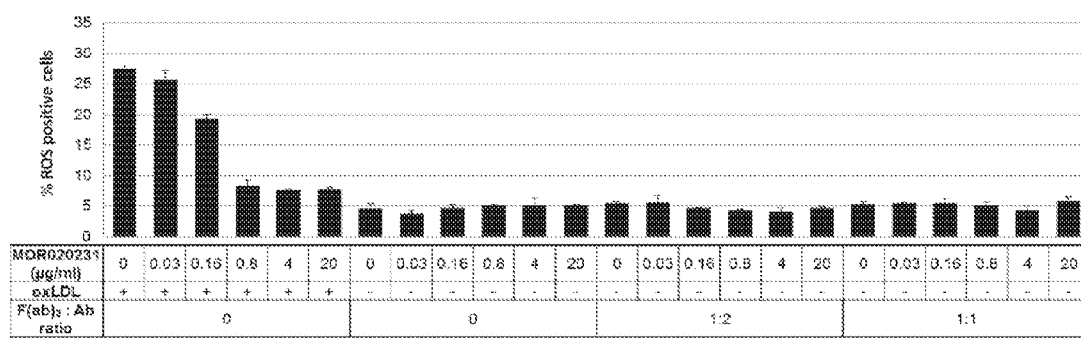
Figure 4F:
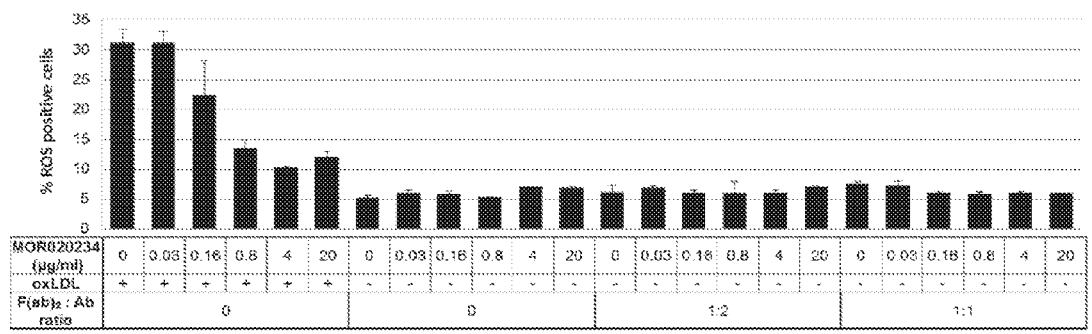
Figure 4G:
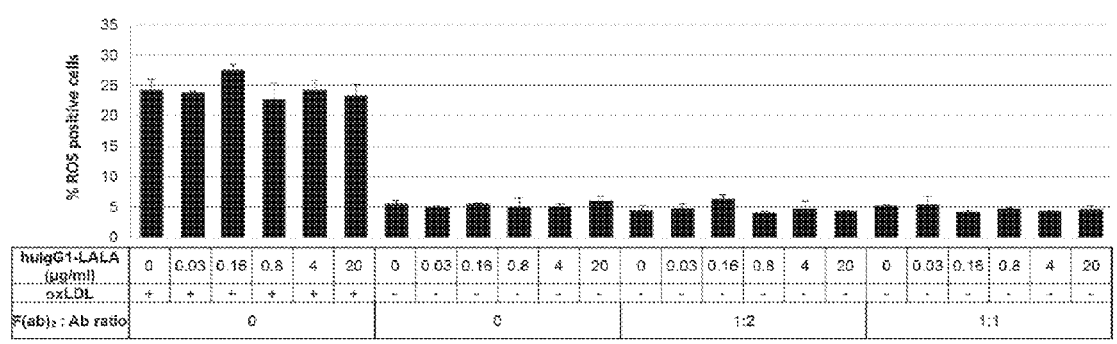

The huLOX-1/HEK293 cells were resuspended at $1 \times 10^6$ cells/mL and seeded 50 μL per well into a 96-well V-bottom plate ($5 \times 10^4$ cells per well). LOX-1 or irrelevant control antibodies in assay medium (DMEM+10% FBS) were then added to the cells. Typical final antibody concentrations ranged from 0.006 μg/mL to 20 μg/mL. The cells were incubated at 37° C. for 1 hour, then washed twice with warm HBSS. DiI-oxLDL (human diI-labeled "High Oxidized" LDL, Kalen Biomedical, catalog number 770262-9; DiI is 1,1'-dioctadecyl-3,3,3',3'-tetramethylindocarbocyanine perchlorate) in 50 ul assay medium was then added to a final concentration 30 to 100 μg/mL. The cells were then incubated at 37° C. for 2 hours, and then washed twice with FACS buffer (2% FBS in PBS). Cells were then analyzed for intensity of Di-I fluorescence by flow cytometry, as depicted in FIGS. 2A-2B and Table 3.

Example 9

OxLDL Induced Reactive Oxygen Species (ROS) Production Assay

LOX-1 antibodies or irrelevant control antibodies were incubated at 2× final concentration either alone or in the presence of a (Fab)$_2$ cross-linker (polyclonal goat anti-human IgG Fc (Fab)$_2$, Abcam catalog number ab98526)) in 0.05 mL assay medium (DMEM+10% FBS) and incubated at room temperature for 15 min. The (Fab)$_2$ cross-linker to LOX-1 antibody ratio was varied and included 1:1 and 1:2 ratios. In dose response experiments with LOX-1 or control antibody alone (without cross-linker), antibody concentrations ranging from 0.005 μg/mL to 20 μg/mL were used. In experiments comparing antibody alone to antibody with cross-linker, antibody concentrations ranging from 0.03 μg/mL to 20 μg/mL were used.

Cells expressing human LOX-1 (huLOX1/HEK293) were dissociated using TrypLE Express (Invitrogen catalog number 12605-010) and washed once with PBS. The cells were then resuspended at $2 \times 10^6$ cells/mL in assay medium (DMEM+10% FBS) and seeded at 50 μl/well ($1 \times 10^5$ cells/well) into a 96-well V-bottom plate (Costar catalog number 3894). 50 μl/well of LOX-1 (or control) antibody solution with or without cross-linking Fab (prepared as described above) was added and the mixture was incubated for 15 min at 37° C. OxLDL (0.1 mL/well in assay buffer, "High oxLDL" from Kalen, catalog number 770252-7) was added to a final concentration of 25 μg/mL, and the resulting mixture was incubated for 100 min at 37° C. H2DCFDA was diluted in assay medium and 0.1 mL/well added to a final concentration of 5-10 μM, and the mixture incubated for 15 min at 37° C. The cells were then washed once with 200 μl/well of HBSS containing calcium and magnesium, once with 200 μl/well of cold FACS buffer (2% FBS in PBS), and the cells were resuspended in 50-100 μL/well of cold FACS buffer. The fluorescence generated as a result of H2DCFDA oxidation was measured using a flow cytometer (excitation: 488 nm, emission: 500/530 nm). Exemplary results are shown in FIGS. 3 and 4A-4G, and Tables 4, 5 and 6.

Example 10

LOX-1 Antibodies Bind to Endogenous LOX-1 on Human Neutrophils

LOX-1 antibodies MOR20225, MOR20228, MOR20229, MOR20230, MOR20231, MOR20234 and an isotype-matched control antibody were biotinylated using a kit from Thermo Scientific (EZ-Link Micro NHS-PEO4-Biotinylation Kit; Thermo Scientific catalog number 21955). Briefly, the antibody in PBS buffer was incubated with a 50-fold molar excess of NHS-biotin reagent at room temperature for 60 min. The biotinylated antibody was then separated from excess biotinylation reagent using a desalting spin column equilibrated in PBS and used according to the manufacturer's instructions (Zeba Desalt Spin Column 7K MWCO, Thermo Scientific catalog number 89882). The concentration of the biotinylated antibody was determined based on measurement of its absorbance at 280 nm.

Neutrophils were isolated from human blood samples obtained from healthy donors. Briefly, human whole blood was collected in a vial containing EDTA. To 10 mL of the blood sample, 10 mL of Sedimentation Buffer (3% dextran, 0.9% sodium chloride) was added, and the resulting solution was gently mixed and allowed to stand at room temperature for 20 minutes. The top layer comprising leukocyte-rich plasma was centrifuged at 1200 rpm (250×g) for 10 minutes at 4° C. The supernatant was discarded, and the cell pellet immediately resuspended in 10 mL of 0.9% sodium chloride at room temperature. The resulting cell suspension was carefully transferred to a 50-mL conical tube containing 10 mL Ficoll-Paque, layering the cell suspension on top of the Ficoll-Paque, and the tube was then centrifuged at 1400 rpm (400×g) for 30 minutes at room temperature with no brake. The top layer was then discarded. To the resulting cell pellet, 10 mL 0.2% ice-cold sodium chloride was added, and the mixture was incubated for exactly 30 seconds to lyse red blood cells; and 10 mL of ice-cold 1.6% sodium chloride was then added to restore isotonicity. The cell suspension was then centrifuged at 1200 rpm (250×g) for 5 minutes. The supernatant was discarded, and the red blood cell lysis procedure repeated once more. The resulting cell pellet was resuspended in FACS buffer (2 mM EDTA, 1% BSA, and 0.2% sodium azide in PBS) at a cell density of 2×10$^6$ cells/mL.

Figure 5:
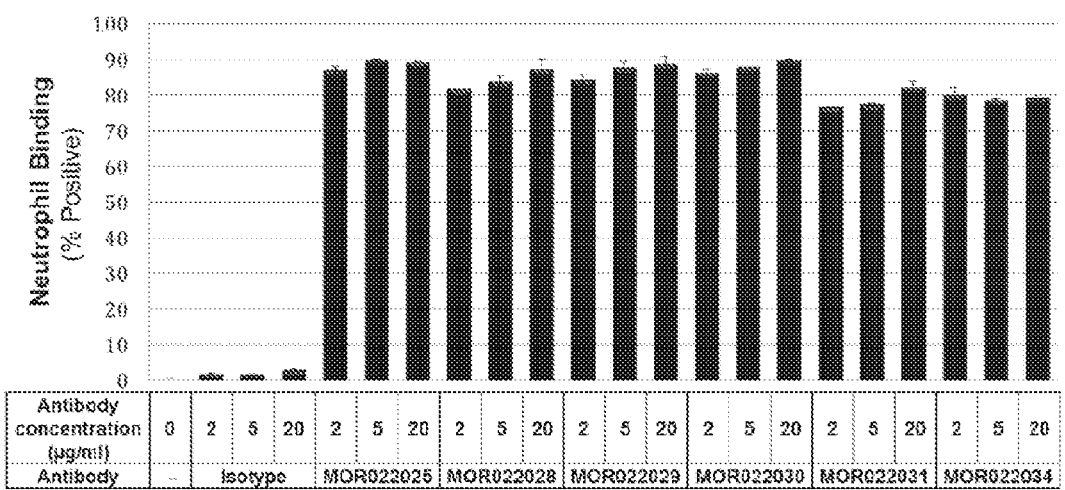

The cell suspension containing freshly isolated human neutrophils was transferred (50 μL/well) to wells of a 96-well V-bottom plate (1×10$^5$ cells/well) (Costar, catalog number 3894). Blocking buffer (4% normal rabbit serum diluted in FACS buffer (2 mM EDTA, 1% BSA, and 0.2% sodium azide in PBS) (50 μl/well) was added and the plate was incubated on ice for 30 minutes. Biotinylated LOX-1 antibody or biotinylated isotype control antibody in FACS buffer was added to the wells to final concentrations of 2, 5 and 20 μg/ml, and the plate was incubated on ice for 30 minutes. The plate was then centrifuged at 1200 rpm (250-300×g) for 3 minutes and supernatant was discarded. The cells were washed twice with 0.2 mL FACS buffer, and then 0.1 mL of PE-straptavidin (BD Pharmingen catalog number 554061) diluted at 1:250 in FACS buffer was added, and the plate was incubated on ice for 30 minutes. The plate was then centrifuged again, supernatant discarded, and the cells washed twice with 0.2 mL FACS buffer. Cells were then resuspended in 0.05 mL of fixing buffer (FACS buffer with 2% paraformaldehyde) and analyzed using a FACS instrument. The LOX-1 antibodies were found to bind to human neutrophils; in contrast, binding of the isotype control antibody to human neutrophils was not detected (FIG. 5).

Example 11

Preparation of Purified Recombinant Cynomolgus Monkey Soluble LOX-1 for Use in LOX-1 Antibody Binding Assays To determine the nucleotide and amino acid sequences of cynomolgus monkey LOX-1, total RNAs were extracted from organs obtained from 3 individual monkeys: 3 organs from one individual from Zyagen/GW, and 12 organs from 2 individuals from Covance, Inc. The total RNAs were then used for PCR amplification, using primers from the untranslated region which were designed according to public databases (Uniprot, NCBI). Standard sequencing methods were used to determine the nucleic acid sequences of the amplified LOX-1 mRNAs. Within the extracellular domain of cynomolgus monkey LOX-1 (corresponding to amino acids 61-273), the cynomolgus LOX-1 amino acid sequences derived from the 3 individual monkeys were identical.

A nucleic acid sequence encoding the extracellular domain (amino acid residues 61-273) of cynomolgus monkey LOX-1 polypeptide with N-terminal signal peptide from human CD33, purification tag (EFHR), and BirA biotinylation sequence (GLNDIFEAQKIEWHE) (SEQ ID NO 385; Table 2) was subcloned into the mammalian cell expression vector pRS5a. Expression and purification of cynomolgus monkey soluble LOX-1 was carried out using the same methods described for human soluble LOX-1 in Example 1. The amino acid sequence of mature APP-Avi-soluble cynomolgus monkey LOX-1(61-273) is shown in Table 2. For some experiments, cynomolgus monkey soluble LOX-1 protein was biotinylated using the same method described for human soluble LOX-1 in Example 5.

TABLE 2

SEQ ID 385: Amino Acid Sequence of mature APP-Avi-soluble cynomolgus monkey LOX-1(61273) (APP and Avi tags underlined)

EFRHGLNDIFEAQKIEWHESQVSNLLKQQQTNLTHQKNKLEGQISARQ

QAEEASQESQNELKEMIETLAWKLNEKSKEQMELHHQNLNLQETLKRV

ANCSAPCPQDWIWHEENCYLFSTGSFNWEKSQEKCLSLDAKLLKINST

ADLDFIQQAISYSSFPFWMGLSRRNPSYPWLWEDGSPLMPHLFRIRGA

VSQTYPSGTCAYITQRGAVYAENCILAAFSICQKKANLRAQ

Example 12

Antibody Dissociation Constant Determination by Solution Equilibrium Titration (SET) Assay Affinity determination for anti-LOX-1 IgGs using Solution Equilibrium Titration (SET) was basically performed as described in the literature (Friguet et al., 1985 J Immunol Methods 77: 305-319). The assays were performed in a 96-well polypropylene plate (Thermo Scientific, Catalog no. AB-1127) using a constant concentration of LOX-1 antibody mixed with different concentrations of non-biotinylated human or cynomolgus monkey LOX-1 protein and incubated at 22° C. for 14 hours with constant shaking (300 rpm).

On a pre-blocked MSD plate (Meso Scale Discovery, catalog no. L21SA) biotinylated human or cynomolgus monkey soluble LOX-1 protein was immobilized and washed afterwards. The equilibrium binding reactions were then applied to the MSD plate with immobilized LOX-1 and incubated for 30 min. The unbound material was removed by washing the plate, and the captured antibody was detected by adding Sulfo-tagged goat anti-human IgG (Meso Scale Discovery, catalog no. R3AJ-1). After incubation and washing 1×MSD read buffer T(Meso Scale Discovery, catalog no. R92TC-2) was added and the plate was developed using a Sector Imager 6000 (Meso Scale Discovery). The data were transferred to Excel for analysis and plotted using GraphPad Prism v5. The $K_D$ values were determined by fitting the data to the following equation:

$$Y=(Bmax/(CAb/2))*((CAb/2)-((((((CAg+CAb)+KD)/2)-((((((CAg+CAb)+KD)^2)/4)-(CAg*CAb))^0.5)^2)/(2*CAb))),$$

where Bmax is the signal when no LOX-1 protein is present in solution, CAb is the constant concentration of LOX-1 antibody in solution, CAg is the concentration of soluble LOX-1 in solution, and KD is the equilibrium binding constant.

TABLE 3

Characterization data for LOX-1 IgG antibodies (antibodies after removal of potential post-translational modification sites and/or germlining)

| MOR# | Human sLOX-1 KD by SET (pM) | Cyno sLOX-1 KD by SET | oxLDL human sLOX-1 binding inhibition ELISA (IC50, nM) | diI-OxLDL binding to LOX-1 transfected HEK cells (IC50, nM) |
|---|---|---|---|---|
| MOR20225 | 0.3 | 0.7 | 11 | 1.0 |
| MOR20228 | 0.6 | 0.5 | 9 | 0.7 |
| MOR20229 | 10 | 7 | 4 | 0.4 |
| MOR20230 | 4 | 7 | 6 | 0.5 |
| MOR20231 | 3 | 4 | 4 | 0.8 |
| MOR20234 | 5 | 5 | 10 | 0.6 |

TABLE 4

LOX-1 antibodies inhibit oxLDL induced reactive oxygen species (ROS) production in human LOX-1 transfected HEK293 cells (table with IC50 values), with no evidence for LOX-1 agonist activity (antibody alone or antibody + cross-linking Fab₂)

| Sequence MOR# | Inhibition of ROS generation (IC50, nM) | LOX-1 agonism (antibody alone) | LOX-1 agonism (antibody + anti-human Fab2 at 1:2 Fab2 to antibody molar ratio) | LOX-1 agonism (antibody + anti-human Fab2 at 1:1 Fab2 to antibody molar ratio) |
|---|---|---|---|---|
| MOR20225 | 4.6 | No | No | No |
| MOR20228 | 3.5 | No | No | No |
| MOR20229 | 2.2 | No | No | No |
| MOR20230 | 2.5 | No | No | No |
| MOR20231 | 1.9 | No | No | No |
| MOR20234 | 1.6 | No | No | No |

TABLE 5

Examples of LOX-1 Antibodies (IgG antibodies prior to affinity maturation)

| Sequence MOR# | HC framework | LC framework | OxLDL/Human sLOX-1 binding assay (IC$_{50}$, nM) | Human sLOX-1 affinity by SET (K$_D$, pM) | Antagonist activity at 20 ug/mL? | Absence of agonist activity at 20 ug/mL? (Ab alone or when cross-linked) |
|---|---|---|---|---|---|---|
| MOR020052 | VH1A | lambda-2 | 12 | 500 | Yes | Yes |
| MOR020133 | VH5 | lambda-3 | 6 | 144 | Yes | Yes |
| MOR020144 | VH3_23 | lambda-1 | 5 | 0.2 | Yes | Yes |
| MOR020148 | VH3_23 | lambda-2 | 9 | 6500 | Yes | Yes |
| MOR020151 | VH3_15 | lambda-2 | 7 | 270 | Yes | Yes |
| MOR020152 | VH1A | lambda-2 | 5 | 1.4 | Yes | Yes |
| MOR020159 | VH1A | kappa-1 | 5 | 560 | Yes | Yes |

TABLE 6

Examples of LOX-1 Antibodies (IgG antibodies after affinity maturation)

| MOR# | Parental Sequence MOR# | Sequence Parental change | Sequence changed from Parental change in CDR | Sequence of changed CDR | SEQ ID NO. | Human sLOX-1 KD by SET (pM) | Antagonist activity at 20 ug/mL? | Absence of agonist activity at 20 ug/mL? (Ab alone or when cross-linked) |
|---|---|---|---|---|---|---|---|---|
| MOR021448 | MOR20052 | | HCDR2 | MGRVIRPYYGWTEYAQKFQG | 386 | 0.3 | Yes | Yes |
| MOR021449 | MOR20052 | | HCDR2 | MGGIQPGFAGAWYAQKFQG | 387 | 0.3 | Yes | Yes |
| MOR021450 | MOR20052 | | HCDR2 | MGAIMPKFAGWPQYAQKFQG | 388 | nd | nd | nd |
| MOR021443 | MOR20133 | | HCDR2 | MGRIFPGKSETSYSPSFQG | 389 | 75 | Yes | Yes |
| MOR021444 | MOR20133 | | HCDR2 | MGRIEPLSSTTEYSPSFQG | 390 | 35 | Yes | Yes |

TABLE 6-continued

Examples of LOX-1 Antibodies (IgG antibodies after affinity maturation)

| MOR# | Parental Sequence MOR# | Sequence change in Parental | Sequence of changed CDR | SEQ ID NO. | Human sLOX-1 KD by SET (pM) | Human LOX-1/HEK cell ROS assay Antagonist activity at 20 ug/mL? | Absence of agonist activity at 20 ug/mL? (Ab alone or when cross-linked) |
|---|---|---|---|---|---|---|---|
| MOR021445 | MOR20133 | HCDR2 | MGAIRPEWSETKYSPSFQG | 391 | 30 | Yes | Yes |
| MOR021458 | MOR20144 | HCDR2 | VSSISYVGGFIYYADSVKG | 392 | 0.6 | Yes | Yes |
| MOR021459 | MOR20144 | HCDR2 | VSVISYVGGFKFYADSVKG | 393 | 0.4 | Yes | Yes |
| MOR021460 | MOR20144 | HCDR2 | VSVISYQGGFIYYADSVKG | 394 | 0.3 | Yes | Yes |
| MOR021461 | MOR20144 | HCDR2 | VSVISYAGGFTYYADSVKG | 395 | 0.2 | Yes | Yes |
| MOR021462 | MOR20144 | HCDR2 | VSGISYQGGFIFYADSVKG | 396 | 0.9 | Yes | Yes |
| MOR021463 | MOR20144 | HCDR2 | VSVISYMGGFKYYADSVKG | 397 | 1.3 | Yes | Yes |
| MOR021464 | MOR20144 | HCDR2 | VSLISYQGGFKYYADSVKG | 398 | nd | nd | nd |
| MOR021465 | MOR20144 | HCDR2 | VSVISYQGAFIYYADSVKG | 399 | 1.6 | Yes | Yes |
| MOR021466 | MOR20144 | HCDR2 | VSVISYMGGFKFYADSVKG | 400 | 0.6 | Yes | Yes |
| MOR021467 | MOR20144 | HCDR2 | VSVISYQGGFTFYADSVKG | 401 | 0.9 | Yes | Yes |
| MOR021468 | MOR20144 | HCDR2 | VSVISYAGGFKFYADSVKG | 402 | 0.65 | Yes | Yes |
| MOR021469 | MOR20144 | HCDR2 | VSAISYQGGFIFYADSVKG | 403 | 1 | Yes | Yes |
| MOR021470 | MOR20144 | HCDR2 | VSVISYAGAFTYYADSVKG | 404 | 0.5 | Yes | Yes |
| MOR021553 | MOR20148 | HCDR2 | VSSIEYFGSATLYADSVKG | 405 | 6 | Yes | Yes |
| MOR021452 | MOR20151 | HCDR2 | VGRTKHENEGYTTWYAASVKG | 406 | 7.5 | Yes | Yes |
| MOR021453 | MOR20151 | HCDR2 | VGRIKLINKGYTTWYAASVKG | 407 | 4 | Yes | Yes |
| MOR021454 | MOR20151 | HCDR2 | VGRIRHYKWGGTTEYAAPVKG | 408 | 0.7 | Yes | Yes |
| MOR021456 | MOR20151 | HCDR2 | VGRIRYWPDGYTTHYAASVKG | 409 | 2 | Yes | Yes |
| MOR021457 | MOR20151 | HCDR2 | VGRTRMWTVGYTTHYAASVKG | 410 | 1 | Yes | Yes |
| MOR021451 | MOR20152 | HCDR2 | MGRIVPGFVYTSYAQKFQG | 411 | 0.1 | Yes | Yes |
| MOR021455 | MOR20152 | HCDR2 | MGRIIPQWAGTPEYAQKFQG | 412 | 0.3 | Yes | Yes |

TABLE 6-continued

Examples of LOX-1 Antibodies (IgG antibodies after affinity maturation)

| MOR# | Parental Sequence MOR# | Sequence change in | Sequence of changed CDR | SEQ ID NO. | Human sLOX-1 KD by SET (pM) | Antagonist activity at 20 ug/mL? | Absence of agonist activity at 20 ug/mL? (Ab alone or when cross-linked) |
|---|---|---|---|---|---|---|---|
| MOR021433 | MOR20159 | HCDR2 | MGGIMPISGAPYYAQKFQG | 413 | 2.5 | Yes | Yes |
| MOR021434 | MOR20159 | HCDR2 | MGGIVPILGAANYAQKFQG | 414 | 7 | Yes | Yes |
| MOR021435 | MOR20159 | LCDR3 | QQMWQFPI | 415 | 6 | Yes | Yes |
| MOR021436 | MOR20159 | LCDR3 | QQMQTSLI | 416 | 4 | Yes | Yes |
| MOR021437 | MOR20159 | LCDR3 | QQMKISLI | 417 | 4 | Yes | Yes |
| MOR021438 | MOR20159 | LCDR3 | QQMHRHPI | 418 | 2 | Yes | Yes |
| MOR021439 | MOR20159 | LCDR3 | QQMHRFPM | 419 | 3 | Yes | Yes |
| MOR021440 | MOR20159 | LCDR3 | QQMQESLL | 420 | 6 | Yes | Yes |
| MOR021441 | MOR20159 | LCDR3 | QQMKTFPI | 421 | 3 | Yes | Yes |
| MOR021442 | MOR20159 | LCDR3 | QQMHRLPV | 422 | 4 | Yes | Yes |

TABLE 7

Examples of LOX-1 Antibodies (additional characterization of some of the affinity-matured IgG antibodies)

| Sequence MOR# | Parent Sequence | HC framework | LG framework | Human sLOX-1 KD by SET (pM) | Cyno sLOX-1 KD by SET | oxLDL human sLOX-1 binding inhibition ELISA (IC50, nM) | AGE-BSA human sLOX-1 binding inhibition ELISA (IC50, nM) |
|---|---|---|---|---|---|---|---|
| MOR21460 | MOR20144 | VH3_23 | lambda-1 | 0.3 | 0.7 | 4.0 | 2.1 |
| MOR21468 | MOR20144 | | | 0.6 | 0.5 | 4.8 | 2.4 |
| MOR21452 | MOR20151 | VH3_15 | lambda-2 | 10 | 7 | 3.2 | 2.2 |
| MOR21453 | MOR20151 | | | 4 | 7 | 2.6 | 1.6 |
| MOR21433 | MOR20159 | VH1A | kappa-2 | 3 | 4 | 2.9 | 1.4 |
| MOR21435 | MOR20159 | | | 5 | 5 | 2.8 | 1.7 |

TABLE 8

Examples of LOX-1 Antibodies and Fabs (changes made to some of the antibodies to remove potential post-translational modification sites and/or restore the N-terminal sequence of the light chain to human germline sequence)

| MOR# | Parent Sequence | HC framework | LC framework | Germlining | PTM Site Removal |
|---|---|---|---|---|---|
| MOR022025 | MOR21460 | VH3_23 | lambda-1 | VL D1Q, I2S | LCDR2 N51T |
| MOR022028 | MOR21468 | | | | LCDR 2N51S |
| MOR022029 | MOR21452 | VH3_15 | lambda-2 | VL D1Q, I2S | none |
| MOR022030 | MOR21453 | | | | LCDR1 N30S |
| MOR022031 | MOR21433 | VH1A | kappa-2 | no | LCDR1 N30S |
| MOR022034 | MOR21435 | | | | |

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The invention claimed is:

1. A method of treating a subject afflicted with a lectin-type oxidized low density lipoprotein receptor 1 (LOX-1)-disorder that is a cardiovascular disorder, the method comprising administering to the subject an effective amount of an isolated antibody or antigen binding fragment thereof comprising a variable heavy chain (VH) comprising the amino acid sequence of SEQ ID NO:309; and a variable light chain (VL) comprising the amino acid sequence of SEQ ID NO:319.

2. The method of claim 1, wherein the subject is afflicted with one or more of intermittent claudication and Rutherford Class II/III Claudication.

3. The method of claim 1, wherein the subject is afflicted with angina.

4. The method of claim 1, wherein the antibody or fragment thereof comprises a heavy chain comprising the amino acid sequence of SEQ ID NO:311 and a light chain comprising the amino acid sequence of SEQ ID NO:321.

5. The method of claim 1, wherein the antibody is a monoclonal antibody.

6. The method of claim 1, wherein the antibody is a human antibody.

7. A method of treating a subject afflicted with a LOX-1-disorder that is a cardiovascular disorder, the method comprising administering to the subject an effective amount of an isolated antibody or antigen binding fragment thereof comprising a VH comprising complementarity determining regions HCDR1, HCDR2, and HCDR3 and a VL comprising complementarity determining regions LCDR1, LCDR2, and LCDR3, wherein the HCDR1 comprises the amino acid sequence of SEQ ID NO:303; the HCDR2 comprises the amino acid sequence of SEQ ID NO:304; the HCDR3 comprises the amino acid sequence of SEQ ID NO:305; the LCDR1 comprises the amino acid sequence of SEQ ID NO:313; the LCDR2 comprises the amino acid sequence of SEQ ID NO:314; and the LCDR3 comprises the amino acid sequence of SEQ ID NO:315.

8. The method of claim 7, wherein the VH comprises an amino acid sequence that is at least 90% identical to the amino acid sequence of SEQ ID NO:309, and wherein the VL comprises an amino acid sequence that is at least 90% identical to the amino acid sequence of SEQ ID NO:319.

9. The method of claim 7, wherein the VH comprises an amino acid sequence that is at least 95% identical to the amino acid sequence of SEQ ID NO:309, and wherein the VL comprises an amino acid sequence that is at least 95% identical to the amino acid sequence of SEQ ID NO:319.

10. The method of claim 7, wherein the VH comprises the amino acid sequence of SEQ ID NO:309.

11. The method of claim 7, wherein the VL comprises the amino acid sequence of SEQ ID NO:319.

12. The method of claim 7, wherein the antibody is a monoclonal antibody.

13. The method of claim 7, wherein the antibody is a human antibody.

14. The method of claim 7, wherein the antibody or fragment thereof is a single chain antibody, Fab fragment, Fv fragment, F(ab)2 fragment, or scFv fragment.

15. The method of claim 7, wherein the antibody or fragment thereof is an IgG1 isotype.

16. The method of claim 7, wherein the subject is afflicted with one or more of intermittent claudication and Rutherford Class II/III Claudication.

17. The method of claim 7, wherein the subject is afflicted with angina.

18. A method of treating a subject afflicted with a LOX-1-disorder that is a cardiovascular disorder, the method comprising administering to the subject an effective amount of an isolated antibody or antigen binding fragment thereof comprising a VH comprising complementarity determining regions HCDR1, HCDR2, and HCDR3, and a VL comprising complementarity determining regions LCDR1, LCDR2, and LCDR3, wherein the HCDR1 comprises the amino acid sequence of SEQ ID NO:306; the HCDR2 comprises the amino acid sequence of SEQ ID NO:307; the HCDR3 comprises the amino acid sequence of SEQ ID NO:308; the LCDR1 comprises the amino acid sequence of SEQ ID NO:316; the LCDR2 comprises the amino acid sequence of SEQ ID NO:317; and the LCDR3 comprises the amino acid sequence of SEQ ID NO:318.

19. The method of claim 18, wherein the VH comprises an amino acid sequence that is at least 90% identical to the amino acid sequence of SEQ ID NO:309, and wherein the VL comprises an amino acid sequence that is at least 90% identical to the amino acid sequence of SEQ ID NO:319.

20. The method of claim 18, wherein the VH comprises an amino acid sequence that is at least 95% identical to the amino acid sequence of SEQ ID NO:309, and wherein the VL comprises an amino acid sequence that is at least 95% identical to the amino acid sequence of SEQ ID NO:319.

21. The method of claim 18, wherein the VH comprises the amino acid sequence of SEQ ID NO:309.

22. The method of claim 18, wherein the VL comprises the amino acid sequence of SEQ ID NO:319.

23. The method of claim 18, wherein the antibody is a monoclonal antibody.

24. The method of claim 18, wherein the antibody is a human antibody.

25. The method of claim 18, wherein the antibody or fragment thereof is a single chain antibody, Fab fragment, Fv fragment, F(ab)2 fragment, or scFv fragment.

26. The method of claim 18, wherein the antibody or fragment thereof is an IgG1 isotype.

27. The method of claim 18, wherein the subject is afflicted with one or more of intermittent claudication and Rutherford Class II/III Claudication.

28. The method of claim 18, wherein the subject is afflicted with angina.

* * * * *